United States Patent
Dixon et al.

(10) Patent No.: US 10,807,948 B2
(45) Date of Patent: Oct. 20, 2020

(54) AROMATIC COMPOUNDS AND USES THEREOF

(71) Applicant: PELOTON THERAPEUTICS, INC., Dallas, TX (US)

(72) Inventors: Darryl David Dixon, Somerset, NJ (US); Jonas Grina, Coppell, TX (US); John A. Josey, Dallas, TX (US); James P. Rizzi, Irving, TX (US); Stephen T. Schlachter, Dallas, TX (US); Eli M. Wallace, Richardson, TX (US); Bin Wang, Dallas, TX (US); Paul Wehn, Dallas, TX (US); Rui Xu, Dallas, TX (US); Hanbiao Yang, Coppell, TX (US)

(73) Assignee: PELOTON THERAPEUTICS, INC., Dallas, TX (US)

( * ) Notice: Subject to any disclaimer, the term of this patent is extended or adjusted under 35 U.S.C. 154(b) by 0 days.

(21) Appl. No.: 15/556,153

(22) PCT Filed: Mar. 4, 2016

(86) PCT No.: PCT/US2016/021060
§ 371 (c)(1),
(2) Date: Sep. 6, 2017

(87) PCT Pub. No.: WO2016/144825
PCT Pub. Date: Sep. 15, 2016

(65) Prior Publication Data
US 2018/0162807 A1    Jun. 14, 2018

Related U.S. Application Data

(60) Provisional application No. 62/131,793, filed on Mar. 11, 2015, provisional application No. 62/131,809, filed on Mar. 11, 2015.

(51) Int. Cl.
*C07C 317/22* (2006.01)
*C07C 317/24* (2006.01)
(Continued)

(52) U.S. Cl.
CPC ............ *C07C 317/22* (2013.01); *A61P 35/00* (2018.01); *C07C 43/23* (2013.01); *C07C 43/295* (2013.01); *C07C 217/58* (2013.01); *C07C 235/40* (2013.01); *C07C 251/42* (2013.01); *C07C 255/47* (2013.01); *C07C 255/54* (2013.01); *C07C 317/24* (2013.01); *C07C 317/32* (2013.01); *C07C 317/36* (2013.01); *C07C 317/38* (2013.01); *C07C 317/44* (2013.01); *C07C 317/46* (2013.01); *C07C 323/65* (2013.01); *C07D 207/12* (2013.01); *C07D 207/48* (2013.01); *C07D 209/12* (2013.01); *C07D 211/42* (2013.01); *C07D 211/44* (2013.01); *C07D 211/76* (2013.01); *C07D 211/94* (2013.01); *C07D 211/96* (2013.01); *C07D 213/30* (2013.01); *C07D 213/52* (2013.01); *C07D 213/74* (2013.01); *C07D 213/85* (2013.01); *C07D 213/89* (2013.01); *C07D 221/04* (2013.01); *C07D 231/14* (2013.01); *C07D 231/56* (2013.01); *C07D 249/04* (2013.01); *C07D 249/08* (2013.01); *C07D 265/30* (2013.01); *C07D 295/096* (2013.01); *C07D 305/06* (2013.01); *C07D 305/08* (2013.01); *C07D 305/14* (2013.01); *C07D 307/20* (2013.01); *C07D 307/52* (2013.01); *C07D 309/10* (2013.01); *C07D 309/14* (2013.01); *C07D 333/20* (2013.01); *C07D 335/02* (2013.01); *C07C 2601/02* (2017.05); *C07C 2601/04* (2017.05); *C07C 2601/08* (2017.05); *C07C 2601/14* (2017.05); *C07C 2601/16* (2017.05); *C07C 2602/08* (2017.05)

(58) Field of Classification Search
CPC .. C07C 317/22; C07D 305/08; C07D 265/30; C07D 213/89; A61P 35/00
See application file for complete search history.

(56) References Cited

U.S. PATENT DOCUMENTS 4,214,103 A    7/1980    Garman et al.
4,364,875 A    12/1982   Sehring et al.
(Continued)

FOREIGN PATENT DOCUMENTS

CA    1264763 A      1/1990
CN    101058535 A    10/2007
(Continued)

OTHER PUBLICATIONS

Zaragoza Dorwald, Side Reactions in Organic Synthesis, 2005, Wiley-VCH Verlag GmbH & Co. KGaA, Weinheim, Preface. p. IX. (Year: 2005).*
STN, CHEMCATS, RN 950051-37-3, Oct. 2007. (Year: 2007).*
Al-Kaabi, et al. Studies on fused 2(1H)-pyridinethiones: new routes for the synthesis of fused 1H-pyrazolo[3,4-b]pyridines and fused thieno[2,3-b]pyridines. Restrived from SN. Database accession No. 1992:633914.
Anonymous: "A Phase 1, Dose-Escalation Trial of PT2385 Tablets in Patients With Advanced Clear Cell Renal Cell Carcinoma—Full Text View—Clinical Trials.gov", Nov. 19, 2014 (Nov. 19, 2014), XP55486644.
Banker et al. Modern Pharmaceutics. 3rd ed. Marcel Dekker, New York.p. 596 (1996).
(Continued)

*Primary Examiner* — Paul A Zucker
(74) *Attorney, Agent, or Firm* — Wilson Sonsini Goodrich & Rosati

(57) ABSTRACT

Disclosed herein are substituted indane derivatives useful as HIF-2α inhibitors. Pharmaceutical compositions comprising said indane derivatives and methods of using said indane derivatives for treating proliferative diseases, such as renal cell carcinoma and von Hippel-Lindau disease, and other conditions associated with HIF-2α activity are also disclosed.

18 Claims, 5 Drawing Sheets

(51) Int. Cl.

| | | |
|---|---|---|
| C07C 255/47 | (2006.01) | |
| C07C 255/54 | (2006.01) | |
| C07C 317/36 | (2006.01) | |
| C07C 317/38 | (2006.01) | |
| C07C 317/44 | (2006.01) | |
| C07C 43/23 | (2006.01) | |
| C07C 217/58 | (2006.01) | |
| C07C 43/295 | (2006.01) | |
| C07C 35/00 | (2006.01) | |
| C07C 323/65 | (2006.01) | |
| C07C 317/32 | (2006.01) | |
| C07C 317/46 | (2006.01) | |
| C07D 213/74 | (2006.01) | |
| C07D 309/10 | (2006.01) | |
| C07D 213/85 | (2006.01) | |
| C07D 309/14 | (2006.01) | |
| C07D 221/04 | (2006.01) | |
| C07D 335/02 | (2006.01) | |
| C07D 249/04 | (2006.01) | |
| C07D 249/08 | (2006.01) | |
| C07D 231/14 | (2006.01) | |
| C07D 333/20 | (2006.01) | |
| C07D 231/56 | (2006.01) | |
| C07C 235/40 | (2006.01) | |
| C07D 207/12 | (2006.01) | |
| C07C 251/42 | (2006.01) | |
| C07D 207/48 | (2006.01) | |
| C07D 209/12 | (2006.01) | |
| C07D 211/42 | (2006.01) | |
| C07D 295/096 | (2006.01) | |
| C07D 211/44 | (2006.01) | |
| C07D 211/76 | (2006.01) | |
| C07D 211/96 | (2006.01) | |
| C07D 213/30 | (2006.01) | |
| C07D 213/52 | (2006.01) | |
| C07D 305/06 | (2006.01) | |
| C07D 305/14 | (2006.01) | |
| C07D 307/20 | (2006.01) | |
| C07D 307/52 | (2006.01) | |
| A61P 35/00 | (2006.01) | |
| C07D 211/94 | (2006.01) | |
| C07D 213/89 | (2006.01) | |
| C07D 265/30 | (2006.01) | |
| C07D 305/08 | (2006.01) | |

(56) References Cited

U.S. PATENT DOCUMENTS

| | | | |
|---|---|---|---|
| 4,426,385 A | 1/1984 | Cain | |
| 4,505,929 A | 3/1985 | Markley et al. | |
| 4,665,097 A | 5/1987 | Cain | |
| 4,705,955 A | 11/1987 | Mileikowsky | |
| 5,059,609 A | 10/1991 | Eggler et al. | |
| 5,644,024 A | 7/1997 | Abrecht et al. | |
| 8,003,656 B2 | 8/2011 | Bakthavatchalam et al. | |
| 9,796,697 B2 | 10/2017 | Wehn et al. | |
| 9,884,843 B2 | 2/2018 | Dixon et al. | |
| 9,896,418 B2* | 2/2018 | Dixon | C07C 255/56 |
| 9,908,845 B2* | 3/2018 | Dixon | C07C 255/56 |
| 9,969,689 B2* | 5/2018 | Dixon | C07C 255/56 |
| 10,144,711 B2 | 12/2018 | Dixon et al. | |
| 10,155,726 B2 | 12/2018 | Wehn et al. | |
| 2005/0070474 A1 | 3/2005 | Krissansen et al. | |
| 2005/0085541 A1 | 4/2005 | Shiohara et al. | |
| 2006/0058361 A1 | 3/2006 | Fliri et al. | |
| 2006/0128790 A1 | 6/2006 | Chu et al. | |
| 2007/0088053 A1 | 4/2007 | Mirzadegan et al. | |
| 2007/0155726 A1 | 7/2007 | Arnaiz et al. | |
| 2007/0244071 A1 | 10/2007 | Dennis et al. | |
| 2007/0265332 A1 | 11/2007 | Ge et al. | |
| 2008/0070928 A1 | 3/2008 | Nonoshita et al. | |
| 2008/0312313 A1 | 12/2008 | Carballido Herrera et al. | |
| 2009/0286812 A1 | 11/2009 | Erickson et al. | |
| 2009/0325961 A1 | 12/2009 | Duan et al. | |
| 2010/0029694 A1 | 2/2010 | Herold et al. | |
| 2010/0048537 A1 | 2/2010 | Matsuoka et al. | |
| 2010/0168110 A1 | 7/2010 | Chhipa et al. | |
| 2011/0054173 A1 | 3/2011 | Brewster et al. | |
| 2012/0295937 A1 | 11/2012 | Linehan et al. | |
| 2013/0116275 A1 | 5/2013 | Van Meir et al. | |
| 2013/0137746 A1 | 5/2013 | Govek et al. | |
| 2014/0057914 A1 | 2/2014 | Jones et al. | |
| 2014/0073634 A1 | 3/2014 | Jones et al. | |
| 2014/0128365 A1 | 5/2014 | Robl et al. | |
| 2014/0148462 A1 | 5/2014 | Eckhardt et al. | |
| 2014/0163025 A1 | 6/2014 | Eckhardt et al. | |
| 2014/0200218 A1 | 7/2014 | Bellingham et al. | |
| 2014/0371319 A1 | 12/2014 | Kazuta et al. | |
| 2016/0250216 A1 | 9/2016 | Bruick et al. | |
| 2016/0251307 A1* | 9/2016 | Dixon | C07C 255/56 514/344 |
| 2016/0368893 A1 | 12/2016 | Dixon et al. | |
| 2017/0217891 A1 | 8/2017 | Dixon et al. | |
| 2017/0217892 A1 | 8/2017 | Dixon et al. | |
| 2018/0140569 A1 | 5/2018 | Josey et al. | |
| 2018/0155279 A1 | 6/2018 | Dixon et al. | |
| 2018/0177754 A1 | 6/2018 | Josey et al. | |

FOREIGN PATENT DOCUMENTS

| | | | |
|---|---|---|---|
| DE | 705530 C | 4/1941 | |
| DE | 2423972 A1 | 1/1975 | |
| DE | 3239449 A1 | 5/1983 | |
| DE | 3209878 A1 | 9/1983 | |
| EP | 0027555 A1 | 4/1981 | |
| EP | 2599774 A1 | 6/2013 | |
| FR | 1574139 A | 7/1969 | |
| GB | 2017087 A | 10/1979 | |
| JP | S4872169 A | 9/1973 | |
| JP | S5655357 A | 5/1981 | |
| JP | S57169449 A | 10/1982 | |
| JP | S58124758 A | 7/1983 | |
| JP | S58170736 A | 10/1983 | |
| JP | S6351363 A | 3/1988 | |
| JP | 2012515156 A | 7/2012 | |
| JP | 2013523710 A | 6/2013 | |
| JP | 2013523803 A | 6/2013 | |
| WO | WO-9324434 A1 | 12/1993 | |
| WO | WO-9842671 A1 | 10/1998 | |
| WO | WO-0116097 A1 | 3/2001 | |
| WO | WO-02086497 A2 | 10/2002 | |
| WO | WO-2004113303 A1 | 12/2004 | |
| WO | WO-2005063738 A1 | 7/2005 | |
| WO | WO-2006027684 A1 | 3/2006 | |
| WO | WO-2006083781 A1 | 8/2006 | |
| WO | WO-2006125972 A1 | 11/2006 | |
| WO | WO-2007071441 A1 | 6/2007 | |
| WO | WO-2007099423 A1 | 9/2007 | |
| WO | WO-2008157273 A1 | 12/2008 | |
| WO | WO-2009093133 A1 | 7/2009 | |
| WO | WO-2009109477 A1 * | 9/2009 | C07D 401/12 |
| WO | WO-2010058032 A2 | 5/2010 | |
| WO | WO-2010068794 A2 | 6/2010 | |
| WO | WO-2010079443 A1 | 7/2010 | |
| WO | WO-2010103438 A1 | 9/2010 | |
| WO | WO-2010137620 A1 | 12/2010 | |
| WO | WO-2010141956 A2 | 12/2010 | |
| WO | WO-2011105603 A1 | 9/2011 | |
| WO | WO-2011121366 A1 | 10/2011 | |
| WO | WO-2011124930 A1 | 10/2011 | |
| WO | WO-2012123129 A1 | 9/2012 | |
| WO | WO-2012170442 A1 | 12/2012 | |
| WO | WO-2013011033 A1 | 1/2013 | |
| WO | WO-2013040863 A1 | 3/2013 | |
| WO | WO-2013057101 A1 | 4/2013 | |
| WO | WO-2013064984 A1 | 5/2013 | |

(56) References Cited

FOREIGN PATENT DOCUMENTS

| WO | WO-2013110433 | A1 | 8/2013 | | |
|---|---|---|---|---|---|
| WO | WO-2013133325 | A1 | 9/2013 | | |
| WO | WO-2014078479 | A2 | 5/2014 | | |
| WO | WO-2014086712 | A1 | * | 6/2014 | ........... A61K 31/343 |
| WO | WO-2015035223 | A1 | 3/2015 | | |
| WO | WO-2015095048 | A1 | 6/2015 | | |
| WO | WO-2016144825 | A1 | 9/2016 | | |
| WO | WO-2016144826 | A1 | 9/2016 | | |
| WO | WO-2016145032 | A1 | 9/2016 | | |
| WO | WO-2016145045 | A1 | 9/2016 | | |
| WO | WO-2016145236 | A1 | 9/2016 | | |
| WO | WO-2016168510 | A1 | 10/2016 | | |

OTHER PUBLICATIONS

Bundgaard, Design of Prodrugs, chapter 1, p. 1. (Year: 1985).
Catozzi, et al. Synthesis of the Louisianin Alkaloid Family via a 1,2,4-Triazine Inverse-Electron-Demand Diels-Alder Approach. Journal of Organic Chemistry. vol. 74, No. 21, Nov. 6, 2009, pp. 8343-8354.
Dittmar, et al. (4+2)-Cycloadditionen Der 1.2.4-Triazine-Ein Neuer Weg Zu 4-H-Acepinen. Tetrahedron Letters. El Sevier. Amsterdamn, NL, No. 59, Jan. 1, 1969, pp. 5171-5174.
European search report with written opinion dated Jul. 16, 2018 for EP application No. 16762264.
Freeman. Reaction of Cyanoacetamide and Some 2-Acylcyclanones. Jan. 1, 1969. pp. 3670-3672.
Gewald, et al. Reaktion von methylenaktiven Nitrilen und Cyanamid mit acylierten Enaminen//Reaction of Methylene Active Nitriles and Cyanamide with Acylated Enamines. Journal Fur Praktische Chemie: Practical Applications and Applied Chemistry: Covering All Aspects of Applied Chemistry, Wiley, DE, vol. 324, No. 6, Jan. 1, 1982, pp. 933-941.
Kozhevnikov, et al. Synthesis of Cyclometallated Platinum Complexes with Substituted Thienylpyridines and Detailed Characterization of Their Luminescence Properties. Inorganic Chemistry, vol. 48, No. 9, Apr. 1, 2009, pp. 4179-4189.
Lone, et al. A Substrate-Free Activity-Based Protein Profiling Screen for the Discovery of Selective PREPL Inhibitors. Journal of the American Chemical Society. vol. 133, No. 30, Aug. 3, 2011 (Aug. 3, 2011), pp. 11665-11674, XP55486936.
Luke, et al. PD-1 pathway inhibitors: The next generation of immunotherapy for advanced melanoma. Oncotarget. Feb. 2015; 6(6): 3479-3492.
McLean, et al. The "inverse electron-demand" Diels-Alder reaction in polymer synthesis. Part 3. Model Diels-Alder reactions of some bis(1,2,4-triazines) with dienophiles and some bis-dienophiles with heterocyclic dienes. XP002782445, retrieved from STN, Database accession No. 1996:608859.
Navarro, et al. American Association for Cancer Research (AACR)—106th Annual Meeting. Philadelphia, Pennsylvania, USA—Apr. 18-22, 2015. Drugs of the Future. vol. 40, No. 5, May 205, p. 341, XP55272384.
Notice of Allowance dated Aug. 13, 2018 for U.S. Appl. No. 15/805,390.
Office action dated Jun. 26, 2018 for U.S. Appl. No. 15/553,570.
Office action dated Jul. 3, 2018 for U.S. Appl. No. 15/556,607.
Office action dated Aug. 16, 2018 for U.S. Appl. No. 15/564,348.
Platonov, et al. Thermolytic reactions of polyfluoroorganic compounds. XXI. Thermolytic reations of hexafluorobenzene and pentafluoropyridine with potassium fluoride and poly(tetrafluoroethylene). XP002782444. Chemical Abstracts Service, Columbus, Ohio, US. Retrieved from STN. Database accession No. 1979:6196.
Prelog, et al. Helvetica Chimica Acta (1946), 29, 1163-9.
Schroder, et al. Non-steroidal anti-inflammatory agents. 6. Anti-inflammatory methanesulfonamides I. European Journal of Medicinal Chemistry, 1982, vol. 17, No. 1, p. 35-42.
Seki, et al. 6,7-Dihydro-5H-2-pyrindines. Retrieved from STN. Database accession No. 1974:3400.
Silverman et al. Chapter 8: Prodrugs and drug delivery systems. In: The Organic Chemistry of Drug Design and Drug Action. San Diego: Academic Press, Inc. p. 352-401 (1992).
Small, W. and Donnelly, E.D. Leibel and Phillips textbook of Radiation oncology. JAMA. 2012; 307(1):93.
U.S. Appl. No. 15/805,390 Office Action dated Apr. 3, 2018.
Vanneman, et al. Combining immunotherapy and targeted therapies in cancer treatment. Nat Rev Cancer. Mar. 22, 2012;12(4):237-51. doi: 10.1038/nrc3237.
Winter, et al. The Vinylogous Mannich Reaction: An Efficient Access to Substituted Nicotinonitriles. SYNLETT, No. 13, Jan. 1, 2003, pp. 1959-1964.
"Wolff, (ed.), Burger's Medicinal Chemistry and Drug Discovery, Fifth Edition, vol. 1: Principles and Practice, San Diego, California, John Wiley & Sons, 1994, pp. 975-977. (4 pages)".
Akincioglu, et al. Novel sulfamides as potential carbonic anhydrase isoenzymes inhibitors. Bioorg Med Chem. Mar. 15, 2013;21(6):1379-85. doi: 10.1016/j.bmc.2013.01.019. Epub Jan. 22, 2013.
Bertout, et al. HIF2alpha inhibition promotes p53 pathway activity, tumor cell death, and radiation responses. Proc Natl Acad Sci U S A. Aug. 25, 2009;106(34):14391-6. doi: 10.1073/pnas.0907357106. Epub Aug. 12, 2009.
Bhatt, et al. Hypoxia-inducible factor-2alpha: effect on radiation sensitivity and differential regulation by an mTOR inhibitor. BJU Int. Aug. 2008;102(3):358-63. doi: 10.1111/j.1464-410X.2008.07558. x. Epub Apr. 3, 2008.
Cardoso, et al. Identification of Cys255 in HIF-1α as a novel site for development of covalent inhibitors of HIF-1α/ARNT PasB domain protein-protein interaction. Protein Sci. Dec. 2012;21(12):1885-96. doi: 10.1002/pro.2172. Epub Nov. 9, 2012.
Carew, et al. ELR510444 inhibits tumor growth and angiogenesis by abrogating HIF activity and disrupting microtubules in renal cell carcinoma. PLoS One. 2012;7(1):e31120. doi: 10.1371/journal.pone. 0031120. Epub Jan. 25, 2012.
CAS Registry No. 1050878-94-8 (Sep. 2008).
CAS Registry No. 1062399-04-05 (Oct. 2008).
CAS Registry No. 1090604-08-2 (Dec. 2008).
CAS Registry No. 1119387-77-7 (Mar. 2009).
CAS Registry No. 1147778-06-0 (May 2009).
CAS Registry No. 1386280-55-2 (Aug. 2012).
CAS Registry No. 81614-92-8. (Nov. 1984).
CAS Registry No. 879353-79-4 (Apr. 2006).
CAS Registry No. 903274-78-2 (Aug. 2006).
CAS Registry No. 950051-37-3 (Oct. 2007).
CAS Registry No. 21081-71-0, Database Registry, Chemical Abstracts Services, [retrieved on Mar. 23, 2017], Published 1968.
Co-pending U.S. Appl. No. 15/553,570, filed Aug. 24, 2017.
Co-pending U.S. Appl. No. 15/556,248, filed Sep. 6, 2017.
Co-pending U.S. Appl. No. 15/556,607, filed Sep. 7, 2017.
Co-pending U.S. Appl. No. 15/556,609, filed Sep. 7, 2017.
Co-pending U.S. Appl. No. 15/564,348, filed Oct. 4, 2017.
Co-pending U.S. Appl. No. 15/805,390, filed Nov. 7, 2017.
European Search Report dated Mar. 29, 2017 for EP Application No. 14871152.6.
European Search Report dated Mar. 8, 2017 for EP Application No. 14842085.4.
Giatromanolaki, et al. Relation of hypoxia inducible factor 1 alpha and 2 alpha in operable non-small cell lung cancer to angiogenic/molecular profile of tumours and survival. Br J Cancer. Sep. 14, 2001;85(6):881-90.
Gordan, et al. HIF-2alpha promotes hypoxic cell proliferation by enhancing c-myc transcriptional activity. Cancer Cell. Apr. 2007;11(4):335-47.
He, et al. Downregulating hypoxia-inducible factor-2α improves the efficacy of doxorubicin in the treatment of hepatocellular carcinoma. Cancer Sci. Mar. 2012;103(3):528-34. doi: 10.1111/j.1349-7006.2011.02177.x. Epub Jan. 13, 2012.
Holmquist-Mengelbier, et al. Recruitment of HIF-1alpha and HIF-2alpha to common target genes is differentially regulated in neuroblastoma: HIF-2alpha promotes an aggressive phenotype. Cancer Cell. Nov. 2006;10(5):413-23.

(56) References Cited

OTHER PUBLICATIONS

Hu, et al. Differential roles of hypoxia-inducible factor 1alpha (HIF-1alpha) and HIF-2alpha in hypoxic gene regulation. Mol Cell Biol. Dec. 2003;23(24):9361-74.
Karoor, et al. Alveolar hypoxia promotes murine lung tumor growth through a VEGFR-2/EGFR-dependent mechanism. Cancer Prev Res (Phila). Aug. 2012;5(8):1061-71. doi: 10.1158/1940-6207.CAPR-12-0069-T. Epub Jun. 14, 2012.
Keith, et al. HIF1α and HIF2α: sibling rivalry in hypoxic tumour growth and progression. Nat Rev Cancer. Dec. 15, 2011;12(1):9-22. doi: 10.1038/nrc3183.
Key, et al. Principles of ligand binding within a completely buried cavity in HIF2alpha PAS-B. J Am Chem Soc. Dec. 9, 2009;131(48):17647-54. doi: 10.1021/ja9073062.
Kim, et al. HIF2alpha cooperates with RAS to promote lung tumorigenesis in mice. J Clin Invest. Aug. 2009;119(8):2160-70.
King, F.D., Biososteres, Conformational restriction, and pro-drugs-case history: An example of a conformational restriction approach. Med. Chem., Principle and Practice (1994), pp. 206-208.
Kondo, et a. Inhibition of HIF2alpha is sufficient to suppress pVHL-defective tumor growth. PLoS Biol. Dec. 2003;1(3):E83, 439-444. Epub Dec. 22, 2003.
Kondo, et al. Inhibition of HIF is necessary for tumor suppression by the von Hippel-Lindau protein. Cancer Cell. Apr. 2002;1(3):237-46.
Koshiji, et al. HIF-1alpha induces cell cycle arrest by functionally counteracting Myc. EMBO J. May 5, 2004;23(9):1949-56. Epub Apr. 8, 2004.
Lee, et al. Acriflavine inhibits HIF-1 dimerization, tumor growth, and vascularization. Proc Natl Acad Sci U S A. Oct. 20, 2009;106(42):17910-5. doi: 10.1073/pnas.0909353106. Epub Oct. 1, 2009.
Li et al. Hypoxia-inducible factors regulate tumorigenic capacity of glioma stem cells. Cancer Cell 15(6):501-513 (2009).
Lin, et al., Efficient in silico assay of inhibitors of hepatitis c virus RNA-dependent RNA polymerase by structure-based virtual screening and in vitro evaluation. ASSAY and drug development technologies. 9(3): Jun. 2011; pp. 290-298. XP55350132.
Maher, et al. von Hippel-Lindau disease: a clinical and scientific review. Eur J Hum Genet. Jun. 2011;19(6):617-23. doi: 10.1038/ejhg.2010.175. Epub Mar. 9, 2011.
Mandriota, et al. HIF activation identifies early lesions in VHL kidneys: evidence for site-specific tumor suppressor function in the nephron. Cancer Cell. Jun. 2002;1(5):459-68.
Maranchie, et al. The contribution of VHL substrate binding and HIF1-alpha to the phenotype of VHL loss in renal cell carcinoma. Cancer Cell. Apr. 2002;1(3):247-55.
Mazumdar, et al. HIF-2alpha deletion promotes Kras-driven lung tumor development. Proc Natl Acad Sci U S A. Aug. 10, 2010;107(32):14182-7. doi: 10.1073/pnas.1001296107. Epub Jul. 21, 2010.
Miranda, et al. A cyclic peptide inhibitor of HIF-1 heterodimerization that inhibits hypoxia signaling in cancer cells. J Am Chem Soc. Jul. 17, 2013;135(28):10418-25. doi: 10.1021/ja402993u. Epub Jul. 9, 2013.
Morrison and Boyd, Isotope Effects. Org. Chem., 3rd ed., (1974), pp. 353-356.
Nguyen, et al. Epigenetic regulation of hypoxia inducible factor in diseases and therapeutics. Arch Pharm Res. Mar. 2013;36(3):252-63. doi: 10.1007/s12272-013-0058-x. Epub Feb. 26, 2013.
Notice of Allowance dated Oct. 6, 2017 for U.S. Appl. No. 15/439,494.
Notice of Allowance dated Oct. 11, 2017 for U.S. Appl. No. 15/439,308.
Notice of Allowance dated Oct. 19, 2017 for U.S. Appl. No. 14/905,776.
Notice of Allowance dated Nov. 9, 2017 for U.S. Appl. No. 15/037,047.
Office Action dated Mar. 24, 2017 for U.S. Appl. No. 15/037,047.
Office Action dated Apr. 28, 2017 for U.S. Appl. No. 14/905,776.
Office Action dated Aug. 16, 2017 for U.S. Appl. No. 15/037,047.
Office Action dated Sep. 8, 2017 for U.S. Appl. No. 14/905,776.
Office Action dated Nov. 21, 2016 for U.S. Appl. No. 15/037,047.
Office Action dated Dec. 16, 2016 for U.S. Appl. No. 14/905,776.
Owens, et al. Smooth muscle cell hypertrophy versus hyperplasia in hypertension. Proc Natl Acad Sci U S A. Dec. 1981;78(12):7759-63.
Percy, et al. A gain-of-function mutation in the HIF2A gene in familial erythrocytosis. N Engl J Med. Jan. 10, 2008;358(2):162-8. doi: 10.1056/NEJMoa073123.
Percy, et al. Two new mutations in the HIF2A gene associated with erythrocytosis. Am J Hematol. Apr. 2012;87(4):439-42. doi: 10.1002/ajh.23123. Epub Feb. 24, 2012.
PubChem. Compound Summary for CID 21110550. 1-10. Create Date: Dec. 5, 2007. [retrieved on Jan. 20, 2015]. Retrieved from the Internet.<URL:http://pubchem.ncbi.nlm.nih.gov/compound/21110550>. entire document.
PubChem. Compound Summary for CID 825455. 1-11. Create Date: Jul. 9, 2005. [retrieved on Jan. 20, 2015]. Retrieved from the Internet.<URL:http://pubchem.ncbi.nlm.nih.gov/compound/825455>. entire document.
Raval, et al. Contrasting properties of hypoxia-inducible factor 1 (HIF-1) and HIF-2 in von Hippel-Lindau-associated renal cell carcinoma. Mol Cell Biol. Jul. 2005;25(13):5675-86.
Rogers, et al. Development of inhibitors of the PAS-B domain of the HIF-2α transcription factor. J Med Chem. Feb. 28, 2013;56(4):1739-47. doi: 10.1021/jm301847z. Epub Feb. 18, 2013.
Sakairi, et al. Synthesis and SAR studies of bicyclic amine series GPR119 agonists. Bioorganic & Medicinal Chemistry Letters. 2012; 22:5123-5128.
Scheuermann, et al. Allosteric inhibition of hypoxia inducible factor-2 with small molecules. Nat Chem Biol. Apr. 2013;9(4):271-6. doi: 10.1038/nchembio.1185. Epub Feb. 24, 2013.
Scheuermann, et al. Artificial ligand binding within the HIF2alpha PAS-B domain of the HIF2 transcription factor. Proc Natl Acad Sci U S A. Jan. 13, 2009;106(2):450-5. doi: 10.1073/pnas.0808092106. Epub Jan. 7, 2009.
Semenza. Hypoxia-inducible factors: mediators of cancer progression and targets for cancer therapy. Trends Pharmacol Sci. Apr. 2012;33(4):207-14. doi: 10.1016/j.tips.2012.01.005. Epub Mar. 6, 2012.
Shen, et al. The VHL/HIF axis in clear cell renal carcinoma. Semin Cancer Biol. Feb. 2013;23(1):18-25. doi: 10.1016/j.semcancer.2012.06.001. Epub Jun. 13, 2012.
Song et al., Synthesis and Biochemical Evaluation of Thiochromanone Thiosemicarbazone Analogues as Inhibitors of Cathepsin L ACS Med. Chem. Lett . . . (2012), vol. 3(6), pp. 450-453.
Svensson, et al., Bromination of bicyclic phenols with SO2 heterocyclic annelated rings, ACTA Pharmaceutica Suecica, Royal Pharmaceutical Institute, Sweden, vol. 12, No. 5-6, Jan. 1, 1975: pp. 401-406.
Talks, et al. The expression and distribution of the hypoxia-inducible factors HIF-1alpha and HIF-2alpha in normal human tissues, cancers, and tumor-associated macrophages. Am J Pathol. Aug. 2000;157(2):411-21.
Tan, et al. Identification of a novel small-molecule inhibitor of the hypoxia-inducible factor 1 pathway. Cancer Res. Jan. 15, 2005;65(2):605-12.
Vanharanta, et al. Epigenetic expansion of VHL-HIF signal output drives multiorgan metastasis in renal cancer. Nat Med. Jan. 2013;19(1):50-6. doi: 10.1038/nm.3029. Epub Dec. 9, 2012.
Xue, et al. Hypoxia-inducible factor-2α activation promotes colorectal cancer progression by dysregulating iron homeostasis. Cancer Res. May 1, 2012;72(9):2285-93. doi: 10.1158/0008-5472.CAN-11-3836. Epub Mar. 14, 2012.
Xue, et al. Hypoxia-inducible factor-2α is essential in activating the COX2/mPGES-1/PGE2 signaling axis in colon cancer. Carcinogenesis. Jan. 2013;34(1):163-9. doi: 10.1093/carcin/bgs313. Epub Oct. 5, 2012.
Zhuang, et al. Somatic HIF2A gain-of-function mutations in paraganglioma with polycythemia. N Engl J Med. Sep. 6, 2012;367(10):922-30. doi: 10.1056/NEJMoa1205119.
Zimmer, et al. Inhibition of hypoxia-inducible factor is sufficient for growth suppression of VHL−/− tumors. Mol Cancer Res. Feb. 2004;2(2):89-95.

(56) References Cited

OTHER PUBLICATIONS

Zimmer, et al. Small-molecule inhibitors of HIF-2a translation link its 5′UTR iron-responsive element to oxygen sensing. Mol Cell. Dec. 26, 2008;32(6):838-48. doi: 10.1016/j.molcel.2008.12.004.

Aftab, et al. Differential regulation of pulmonary vascular cell growth by hypoxia-inducible transcription factor-1α and hypoxia-inducible transcription factor-2α. Am J Respir Cell Mol Biol. Jul. 2013;49(1):78-85. doi: 10.1165/rcmb.2012-0107OC.

Biellmann, et al. Synthesis and reactions of [1,4-dihydropyridinecarboxylic acids]. Tetrahedron (1970), 26(20), 4799-808.

Brusselmans, et al. Heterozygous deficiency of hypoxia-inducible factor-2alpha protects mice against pulmonary hypertension and right ventricular dysfunction during prolonged hypoxia. J Clin Invest. May 2003;111(10):1519-27.

European search report with written opinion dated Aug. 24, 2018 for EP Application No. 16762394.

European search report with written opinion dated Nov. 22, 2018 for EP Application No. 18185557.

European search report with written opinion dated Nov. 22, 2018 for EP Application No. 18185565.

Neunhoeffer, et al. Cycloaddition reactions with azabenzenes. XVIII. Synthesis of [2]pyrindines. Heterocycles (1993), 35(2), 1089-101.

Notice of allowance dated Oct. 17, 2018 for U.S. Appl. No. 15/553,570.

Notice of allowance dated Dec. 13, 2018 for U.S. Appl. No. 15/556,607.

Office action dated Sep. 17, 2018 for U.S. Appl. No. 15/556,609.

Wenzel, et al. beta(2)-adrenoceptor antagonist ICI 118,551 decreases pulmonary vascular tone in mice via a G(i/o) protein/nitric oxide-coupled pathway. Hypertension. Jul. 2009;54(1):157-63. doi: 10.1161/HYPERTENSIONAHA.109.130468. Epub May 26, 2009.

Wigerup, et al. Therapeutic targeting of hypoxia and hypoxia-inducible factors in cancer. Pharmacol Ther. Aug. 2016;164:152-69. doi: 10.1016/j.pharmthera.2016.04.009. Epub Apr. 29, 2016.

\* cited by examiner

AROMATIC COMPOUNDS AND USES THEREOF

CROSS REFERENCE TO RELATED APPLICATIONS

This application is a National Stage Entry of PCT/US2016/021060, filed Mar. 4, 2016, which claims the benefit of U.S. Provisional Application No. 62/131,793, filed on Mar. 11, 2015, and U.S. Provisional Application No. 62/131,809, filed on Mar. 11, 2015, each incorporated herein by reference in its entirety.

BACKGROUND OF THE INVENTION

This invention was in part funded by a grant from Cancer Prevention Research Institute of Texas (Grant number R1009).

An adequate supply of oxygen to tissues is essential in maintaining mammalian cell function and physiology. A deficiency in oxygen supply to tissues is a characteristic of a number of pathophysiologic conditions in which there is insufficient blood flow to provide adequate oxygenation, for example, ischemic disorders, cancer, and atherosclerosis. The hypoxic (low oxygen) environment of tissues activates a signaling cascade that drives the induction or repression of the transcription of a multitude of genes implicated in events such as angiogenesis (neo-vascularization), glucose metabolism, and cell survival/death. A key to this hypoxic transcriptional response lies in the transcription factor, the hypoxia-inducible factors (HIF). HIFs are overexpressed in a vast array of cancers through hypoxia-dependent and independent mechanisms and expression is associated with poor patient prognosis.

HIFs consist of an oxygen-sensitive HIFα subunit and constitutively expressed HIFβ subunit. When HIFs are activated, the HIFα and HIFβ subunits assemble a functional heterodimer (the a subunit heterodimerizes with the β subunit). Both HIFα and HIFβ have two identical structural characteristics, a basic helix-loop-helix (bHLH) and PAS domains (PAS is an acronym referring to the first proteins, PER, ARNT, SIM, in which this motif was identified). There are three human HIFα subunits (HIF-1α, HIF-2α, and HIF-3α) that are oxygen sensitive. Among the three subunits, HIF-1α is the most ubiquitously expressed and induced by low oxygen concentrations in many cell types. HIF-2α is highly similar to HIF-1α in both structure and function, but exhibits more restricted tissue-specific expression, and might also be differentially regulated by nuclear translocation. HIF-3α also exhibits conservation with HIF-1α and HIF-2α in the HLH and PAS domains. HIFβ (also referred to as ARNT—Aryl Hydrocarbon Receptor Nuclear Translocator), the dimerization partner of the HIFα subunits, is constitutively expressed in all cell types and is not regulated by oxygen concentration.

SUMMARY OF THE INVENTION

The present disclosure addresses a need in the art by providing HIF-2α inhibitors as described herein.

In one aspect, the present invention provides a compound of Formula IV:

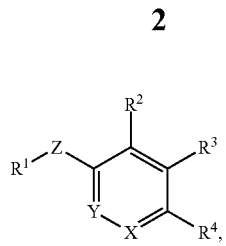
Formula IV or a pharmaceutically acceptable salt or prodrug thereof, wherein:

X is $CR^5$ or N;

Y is $CR^6$ or N;

Z is O, S, $CHR^7$, $NR^8$ or absent;

$R^1$ is alkyl, heteroalkyl, cycloalkyl, heterocycloalkyl, aryl, heteroaryl, acyl or cyano;

$R^2$ is nitro, carboxaldehyde, carboxyl, ester, amido, cyano, halo, sulfonyl, alkyl, alkenyl, alkynyl or heteroalkyl;

$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and $R^5$, $R^6$, $R^7$ and $R^8$ are independently hydrogen, halo, hydroxy, cyano, alkyl or alkoxy, wherein for a compound or salt of Formula IV, when Z is O, $R^1$ is alkyl, heteroalkyl, cycloalkyl, or heterocycloalkyl.

In one aspect, the present disclosure provides a compound of Formula I:

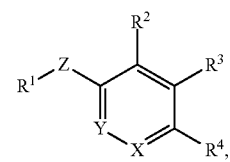
Formula I or a pharmaceutically acceptable salt or prodrug thereof, wherein:

X is $CR^5$ or N;

Y is $CR^6$ or N;

Z is S, $CHR^7$, $NR^8$ or absent;

$R^1$ is alkyl, heteroalkyl, cycloalkyl, heterocycloalkyl, aryl, heteroaryl, acyl or cyano;

$R^2$ is nitro, carboxaldehyde, carboxyl, ester, amido, cyano, halo, sulfonyl, alkyl, alkenyl, alkynyl or heteroalkyl;

$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and $R^5$, $R^6$, $R^7$ and $R^8$ are independently hydrogen, halo, hydroxy, cyano, alkyl or alkoxy.

In another aspect, the disclosure provides a compound of Formula I-A:

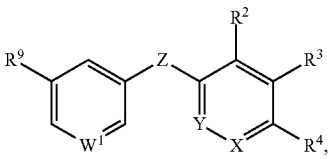

or a pharmaceutically acceptable salt or prodrug thereof, wherein:

X is $CR^5$ or N;
Y is $CR^6$ or N;
Z is S, $CHR^7$, $NR^8$ or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy.
$W^1$ is N or $CR^{10}$;
$R^9$ is cyano, halo, alkyl or alkoxy; and
$R^{10}$ is hydrogen, cyano, halo, alkyl or alkoxy.

In another aspect, the disclosure provides a compound of Formula I-B:

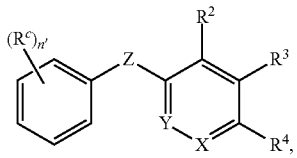

or a pharmaceutically acceptable salt or prodrug thereof, wherein:

X is $CR^5$ or N;
Y is $CR^6$ or N;
Z is S, $CHR^7$, $NR^8$ or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy.
$R^c$ is hydrogen, cyano, halo, alkyl or alkoxy; and
n' is 0, 1, 2, 3 or 4.

In yet another aspect, the invention provides a compound of Formula IV-C:

Formula IV-C

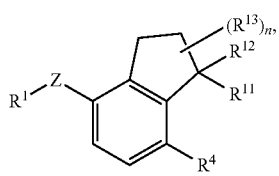

or a pharmaceutically acceptable salt or prodrug thereof, wherein:

Z is O, S, $CHR^7$, $NR^8$ or absent;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^7$ and $R^8$ are independently hydrogen, halo, hydroxy, cyano, alkyl or alkoxy;
$R^{11}$ is hydrogen, hydroxy, alkoxy or amino;
$R^{12}$ is hydrogen, alkyl, alkenyl or alkynyl; or $R^{11}$ and $R^{12}$ in combination form oxo or oxime;
each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and
n is 0, 1, 2, 3 or 4,
wherein for a compound or salt of Formula IV-C, when Z is O, $R^1$ is alkyl, heteroalkyl, cycloalkyl or heterocycloalkyl.

In yet another aspect, the disclosure provides a compound of Formula I-C:

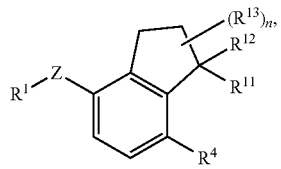

or a pharmaceutically acceptable salt or prodrug thereof, wherein:

Z is S, $CHR^7$, $NR^8$ or absent;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^7$ and $R^8$ are independently hydrogen, halo, hydroxy, cyano, alkyl or alkoxy;
$R^{11}$ is hydrogen, hydroxy, alkoxy or amino;
$R^{12}$ is hydrogen, alkyl, alkenyl or alkynyl; or $R^{11}$ and $R^{12}$ in combination form oxo or oxime;
each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and
n is 0, 1, 2, 3 or 4.

In some embodiments of compounds of Formula I-C or IV-C, $R^1$ is alkyl. In some embodiments, $R^1$ is cycloalkyl or heterocycloalkyl, such as cyclobutyl or cyclohexyl. In some embodiments, said cycloalkyl is selected from cyclobutyl, cyclopentyl, and cyclohexyl. In some embodiments, $R^1$ is phenyl, monocyclic heteroaryl or bicyclic heteroaryl. In some embodiments, $R^1$ is phenyl or pyridyl. In some embodiments, $R^1$ is substituted with at least one substituent selected from the group consisting of halo, $C_1$-$C_4$ alkyl, $C_1$-$C_4$ alkoxy and cyano. In some embodiments, $R^1$ is substituted with at least one fluoro.

In still other embodiments of compounds of Formula I-C or IV-C, $R^4$ is cyano, fluoroalkyl, sulfinyl, sulfonamidyl, sulfonyl or sulfoximinyl. In other embodiments, $R^4$ is fluoroalkyl or fluoroalkylsulfonyl. In some embodiments, $R^4$ is selected from the group consisting of —CF$_3$, —CN, —S(=O)CH$_3$, —S(=O)$_2$CH$_3$, —S(=O)$_2$CH$_2$F, —S(=O)$_2$CHF$_2$, and —S(=O)$_2$CF$_3$. In some other embodiments, R$^{11}$ is hydroxy or amino. In further embodiments, R$^{11}$ is hydroxy. In yet other embodiments, R$^{12}$ is hydrogen. In yet another embodiment, R$^{13}$ is fluoro and n is 1, 2 or 3.

In some embodiments of compounds of Formula I-C or IV-C, R$^4$ is cyano, fluoroalkyl, sulfinyl, sulfonamidyl, sulfonyl or sulfoximinyl; R$^{11}$ is hydroxy or amino; and R$^{12}$ is hydrogen. In still another embodiment, R$^4$ is fluoroalkyl; n is 0, 1, 2 or 3; R$^{11}$ is hydroxy; and R$^{12}$ is hydrogen. In yet another embodiment, R$^4$ is sulfonyl or fluoroalkylsulfonyl; n is 0, 1, 2 or 3; R$^{11}$ is hydroxy; and R$^{12}$ is hydrogen. In a further embodiment, R$^1$ is phenyl, pyridyl, cycloalkyl or heterocycloalkyl. In some embodiments, R$^{13}$ is fluoro and n is 1, 2 or 3. In some embodiments, Z is O; R$^1$ is cycloalkyl or alkyl; R$^4$ is sulfonyl, fluoroalkyl, halo, or cyano; R$^{11}$ is hydroxy; R$^{12}$ is hydrogen; R$^{13}$ is fluoro; and n is 1, 2, or 3.

In some other embodiments of compounds of Formula I-C or IV-C, Z is O. In yet another embodiment, Z is S. In some embodiments, Z is NR$^8$. In another embodiment, Z is CHR$^7$. In some embodiments, Z is absent.

In still another aspect, the invention provides a compound of Formula IV-D, IV-E, IV-F or IV-G:

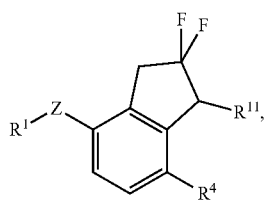

IV-D

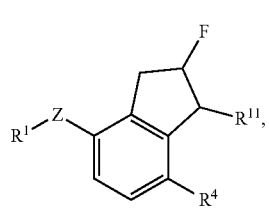

IV-E

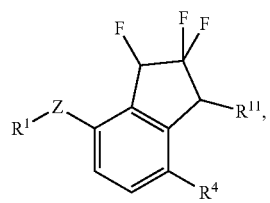

IV-F

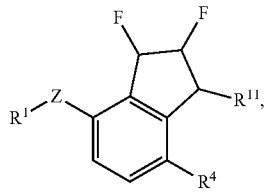

IV-G or a pharmaceutically acceptable salt or prodrug thereof, wherein:
Z is O, S, CHR$^7$, NR$^8$ or absent;
R$^1$ is alkyl, heteroalkyl, cycloalkyl, heterocycloalkyl, aryl or heteroaryl;
R$^4$ is nitro, halo, cyano, alkyl, cycloalkyl, heteroaryl, carboxyl, sulfinyl, sulfonamidyl, sulfonyl, sulfoximinyl or fluoroalkylsulfonyl;

R$^7$ and R$^8$ are independently hydrogen, halo, hydroxy, cyano, alkyl or alkoxy; and
R$^{11}$ is hydrogen, hydroxy, alkoxy or amino,
wherein for a compound or salt of Formula IV-D, IV-E, IV-F or IV-G, when Z is O, R$^1$ is alkyl, heteroalkyl, cycloalkyl or heterocycloalkyl.

In still another aspect, the disclosure provides a compound of Formula I-D, I-E, I-F or I-G:

I-D

I-E

I-F

I-G or a pharmaceutically acceptable salt or prodrug thereof, wherein:
Z is S, CHR$^7$, NR$^8$ or absent;
R$^1$ is alkyl, heteroalkyl, cycloalkyl, heterocycloalkyl, aryl or heteroaryl;
R$^4$ is nitro, halo, cyano, alkyl, cycloalkyl, heteroaryl, carboxyl, sulfinyl, sulfonamidyl, sulfonyl, sulfoximinyl or fluoroalkylsulfonyl; and
R$^7$ and R$^8$ are independently hydrogen, halo, hydroxy, cyano, alkyl or alkoxy; and
R$^{11}$ is hydrogen, hydroxy, alkoxy or amino.

In a further aspect, the invention provides a compound of Formula IV-H, IV-I, IV-J or IV-K:

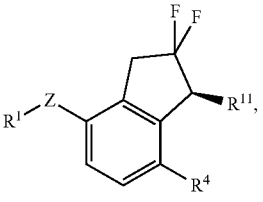

IV-H

-continued

IV-I
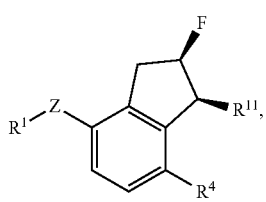

IV-J
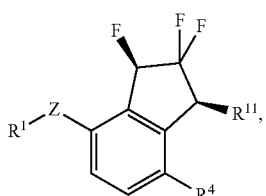

IV-K
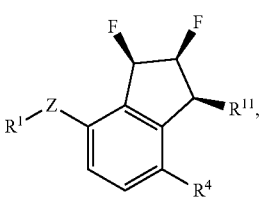

or a pharmaceutically acceptable salt or prodrug thereof, wherein:

Z is O, S, CHR$^7$, NR$^8$ or absent;

R$^1$ is alkyl, heteroalkyl, cycloalkyl, heterocycloalkyl, aryl or heteroaryl;

R$^4$ is nitro, halo, cyano, alkyl, cycloalkyl, heteroaryl, carboxyl, sulfinyl, sulfonamidyl, sulfonyl, sulfoximinyl or fluoroalkylsulfonyl;

R$^7$ and R$^8$ are independently hydrogen, halo, hydroxy, cyano, alkyl or alkoxy; and R$^{11}$ is hydroxy or amino, wherein for a compound or salt of Formula IV-H, IV-I, IV-J or IV-K, when Z is O, R$^1$ is alkyl, heteroalkyl, cycloalkyl or heterocycloalkyl.

In a further aspect, the disclosure provides a compound of Formula I-H, I-I, I-J or I-K:

I-H
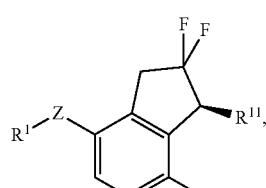

I-I
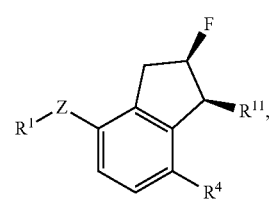

I-J
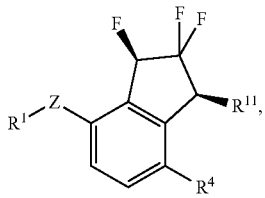

I-K
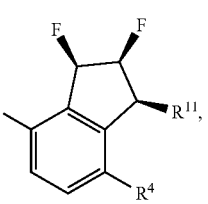

or a pharmaceutically acceptable salt or prodrug thereof, wherein:

Z is S, CHR$^7$, NR$^8$ or absent;

R$^1$ is alkyl, heteroalkyl, cycloalkyl, heterocycloalkyl, aryl or heteroaryl;

R$^4$ is nitro, halo, cyano, alkyl, cycloalkyl, heteroaryl, carboxyl, sulfinyl, sulfonamidyl, sulfonyl, sulfoximinyl or fluoroalkylsulfonyl; and R$^7$ and R$^8$ are independently hydrogen, halo, hydroxy, cyano, alkyl or alkoxy; and R$^{11}$ is hydroxy or amino.

In another aspect, the disclosure provides a compound of Formula II:

In one aspect, the present disclosure provides a compound having the structure of Formula II:

Formula II
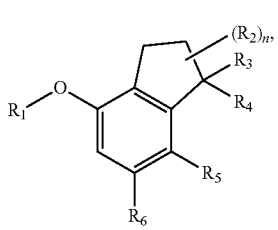

or a pharmaceutically acceptable salt thereof, wherein:

n is 1, 2, 3 or 4;

R$_1$ is cycloalkyl, alkyl, heteroalkyl or heterocycloalkyl;

each of R$_2$ is hydrogen, alkyl, hydroxy, or halo; or two R$_2$s and the atom(s) to which they are attached form a 3-8 membered cycloalkyl or heterocycloalkyl moiety;

R$_3$ is alkyl, hydrogen, or deuterium and R$_4$ is hydroxy, fluoro, alkylamino, alkoxy, amino, cyano, or amide; or R$_3$ and R$_4$ in combination form oxo or oxime;

R$_5$ is sulfonyl, sulfonamidyl, sulfinyl, sulfoximinyl, nitro, amide, halo, cyano, alkyl, or cycloalkyl; and R$_6$ is hydrogen, halo, or alkyl.

In some embodiments of compounds of Formula II, R$_1$ is alkyl. In some embodiments, said alkyl is substituted with at least one substituent selected from the group consisting of halo, C1-C4 alkyl, C1-C4 alkoxy, and cyano. In some embodiments, said alkyl is substituted with at least one fluoro.

In some embodiments of compounds of Formula II, R$_1$ is cycloalkyl, such as cyclobutyl, cyclopentyl or cyclohexyl. In some embodiments, said cyclobutyl, cyclopentyl or cyclohexyl is substituted with at least one substituent selected from the group consisting of halo, C1-C4 alkyl, C1-C4 alkoxy, and cyano. In some embodiments, said cyclobutyl, cyclopentyl or cyclohexyl is substituted with at least one fluoro.

In some embodiments of compounds of Formula II, n is 1, 2, or 3. In some embodiments, $R_2$ is fluoro. In some embodiments, $R_3$ is hydrogen. In some embodiments, $R_4$ is hydroxy. In some embodiments, $R_5$ is sulfonyl, alkyl, halo, or cyano. In some embodiments, $R_5$ is selected from the group consisting of —$CF_3$, —CN, —S(=O)$CH_3$, —S(=O)$_2CH_3$, —S(=O)$_2CH_2F$, —S(=O)$_2CHF_2$, and —S(=O)$_2CF_3$. In some embodiments, $R_6$ is hydrogen.

In some embodiments of compounds of Formula II, $R_1$ is cycloalkyl or alkyl; n is 1, 2, or 3; $R_2$ is fluoro; $R_3$ is hydrogen; $R_4$ is hydroxy; $R_5$ is sulfonyl, fluoroalkyl, halo, or cyano; and $R_6$ is hydrogen. In some embodiments, $R_5$ is sulfonyl, such as —S(=O)$_2CH_3$. In some embodiments, $R_5$ is fluoroalkyl, such as —$CF_3$.

In another aspect, the disclosure provides a compound having one of the formulae:

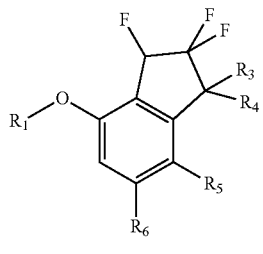

IIa

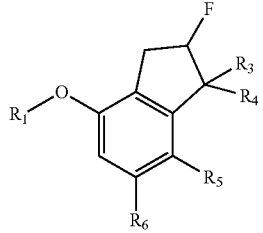

IIb

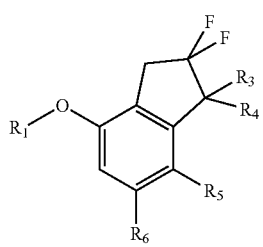

IIc

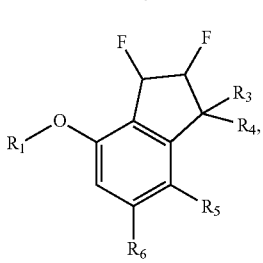

IId or a pharmaceutically acceptable salt thereof, wherein:
$R_1$ is cycloalkyl, alkyl, heteroalkyl or heterocycloalkyl;
$R_3$ is alkyl, hydrogen, or deuterium and $R_4$ is hydroxy, fluoro, alkylamino, alkoxy, amino, cyano, or amide; or $R_3$ and $R_4$ in combination form oxo or oxime;

$R_5$ is sulfonyl, sulfonamidyl, sulfinyl, sulfoximinyl, nitro, amide, halo, cyano, alkyl, or cycloalkyl; and $R_6$ is hydrogen, halo, or alkyl.

In another aspect, the present disclosure provides a compound having one of the formulae:

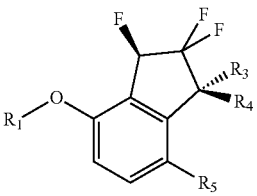

IIIa

IIIb

IIIc

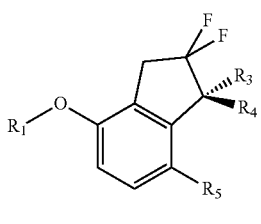

IIId or a pharmaceutically acceptable salt thereof, wherein:
$R_1$ is cycloalkyl, alkyl, heteroalkyl or heterocycloalkyl;
$R_3$ is hydrogen and $R_4$ is hydroxy, alkylamino, alkoxy, amino, or fluoro; or $R_3$ and $R_4$ in combination form oxo or oxime; and
$R_5$ is sulfonyl, sulfinyl, sulfonamidyl, sulfoximinyl, nitro, amide, halo, cyano, alkyl, or cycloalkyl.

In some embodiments of compounds of Formula IIa, IIb, IIc, IId, IIIa, IIIb, IIIc or IIId, $R_1$ is cycloalkyl, such as cyclobutyl, cyclopentyl or cyclohexyl. In some embodiments, said cyclobutyl, cyclopentyl or cyclohexyl is substituted with at least one fluoro. In some embodiments, $R_3$ is hydrogen. In some embodiments, $R_4$ is hydroxy. In some embodiments, $R_5$ is sulfonyl, fluoroalkyl, halo, or cyano. In some embodiments, $R_1$ is alkyl or cycloalkyl; $R_3$ is hydrogen; $R_4$ is hydroxy; and $R_5$ is sulfonyl, fluoroalkyl, halo, or cyano.

In yet another aspect, the present disclosure provides a pharmaceutical composition comprising a compound disclosed herein and a pharmaceutically acceptable carrier.

In still yet another aspect, the present disclosure provides a method for inhibiting HIF-2α signaling output, comprising contacting HIF-2α with an effective amount of a compound disclosed herein.

In another aspect, the present disclosure provides a method for inhibiting HIF-2a, comprising contacting HIF- 2α with an effective amount of a compound disclosed herein, wherein inhibition of HIF-2α is evidenced by a reduction of one or more biological effects selected from the group consisting of heterodimerization of HIF-2α to ARNT, HIF-2α target gene expression, VEGF gene expression, VEGF protein secretion, and the mRNA level of a HIF-2α-regulated gene.

In yet another aspect, the present disclosure provides a method for inhibiting HIF-2α, comprising contacting HIF-2α with an effective amount of a compound disclosed herein, thereby reducing the heterodimerization of HIF-2α to ARNT but not heterodimerization of HIF-1α to ARNT.

In practicing any of the methods described herein, the step of contacting may further comprise contacting a cell that expresses HIF-2α. In some other embodiments, the method further comprises administering a second therapeutic agent to the cell. In other embodiments, the contacting step of the method may take place in vivo. In another embodiment, the contacting step of the method may take place in vitro.

In some other aspects, the present disclosure provides a method for treating a condition associated with HIF-2α, comprising administering to a subject in need thereof an effective amount of a compound disclosed herein. In some embodiments, the present disclosure provides a method for treating a neoplastic condition in a subject, comprising administering to said subject a therapeutically effective amount of a pharmaceutical composition of a compound disclosed herein. In some embodiments, a method for treating renal cell carcinoma (RCC) in a subject, comprising administering to said subject a therapeutically effective amount of a pharmaceutical composition of a compound disclosed herein, is provided. In a further embodiment, said subject may be a human. In yet another embodiment, said renal cell carcinoma may be clear cell renal cell carcinoma (ccRCC).

In certain aspects, the present disclosure provides a method of treating von Hippel-Lindau (VHL) disease, comprising administering to a subject in need thereof an effective amount of a compound described herein.

In still another aspect, the present disclosure provides a kit comprising a pharmaceutical composition of a compound disclosed herein and instructions for using the composition to treat a subject suffering from renal cell carcinoma.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

FIG. 1 shows that Compound 95 treatment of renal cell carcinoma 786-O xenograft bearing mice reduced the mRNA levels of HIF-2α-regulated genes (PAI1, CCND1, VEGFA, and GLUT1) in tumor. Compound 95 had no significant effect on the mRNA level of non-HIF-2α-regulated gene (PGK1).

FIG. 2 shows that Compound 95 treatment of 786-O xenograft bearing mice reduced the plasma level of human VEGFA.

FIG. 3 shows that Compound 95 treatment of 786-O xenograft bearing mice as a single agent led to tumor growth inhibition and regression.

DETAILED DESCRIPTION OF THE INVENTION

Figure 1:
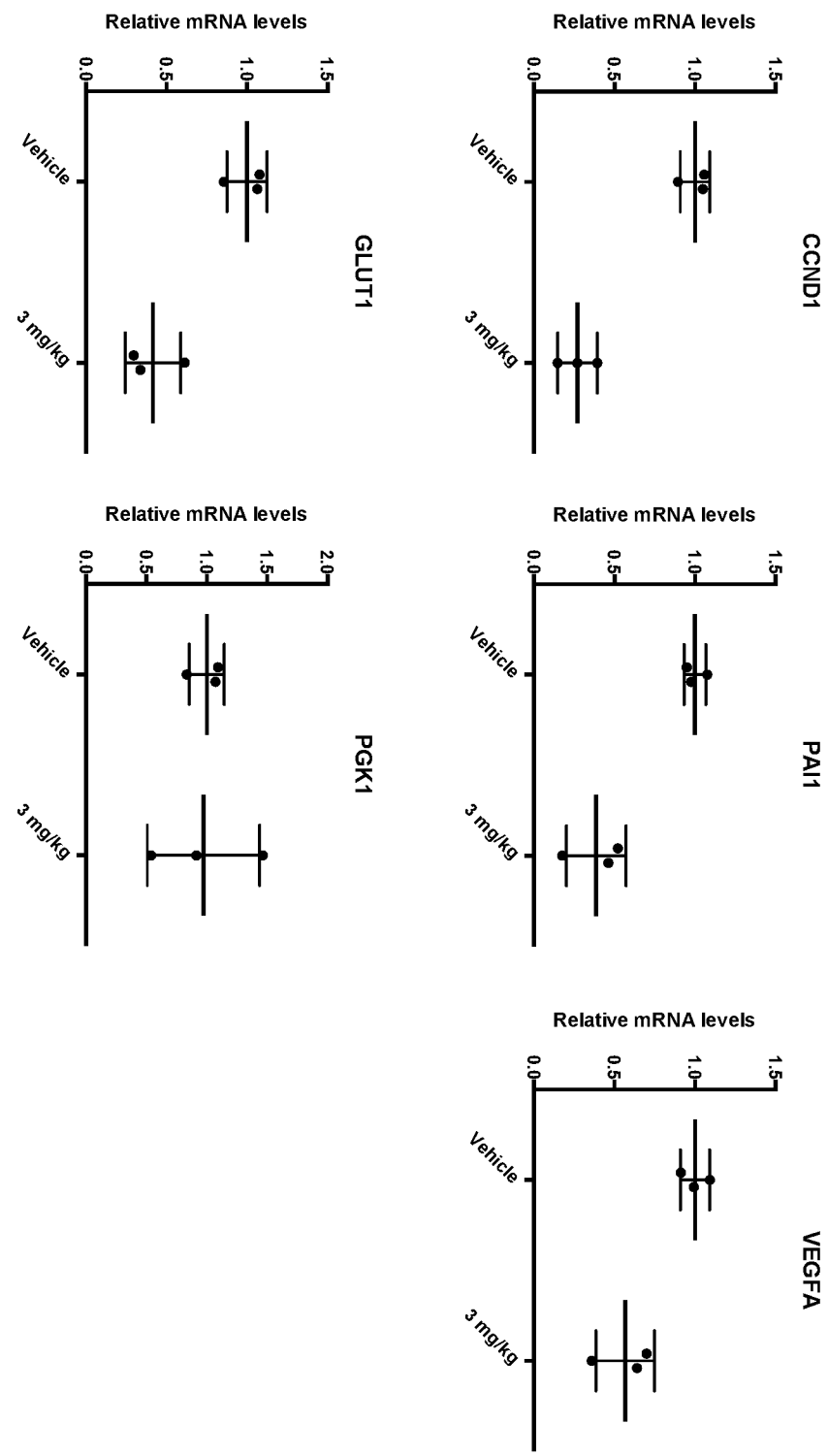
FIG. 1 shows treatment of renal cell carcinoma 786-O xenograft bearing mice at 0 mg/kg (denoted as "Vehicle") and 3 mg/kg of Compound 95 six times each at 12 hour intervals.
Figure 2:
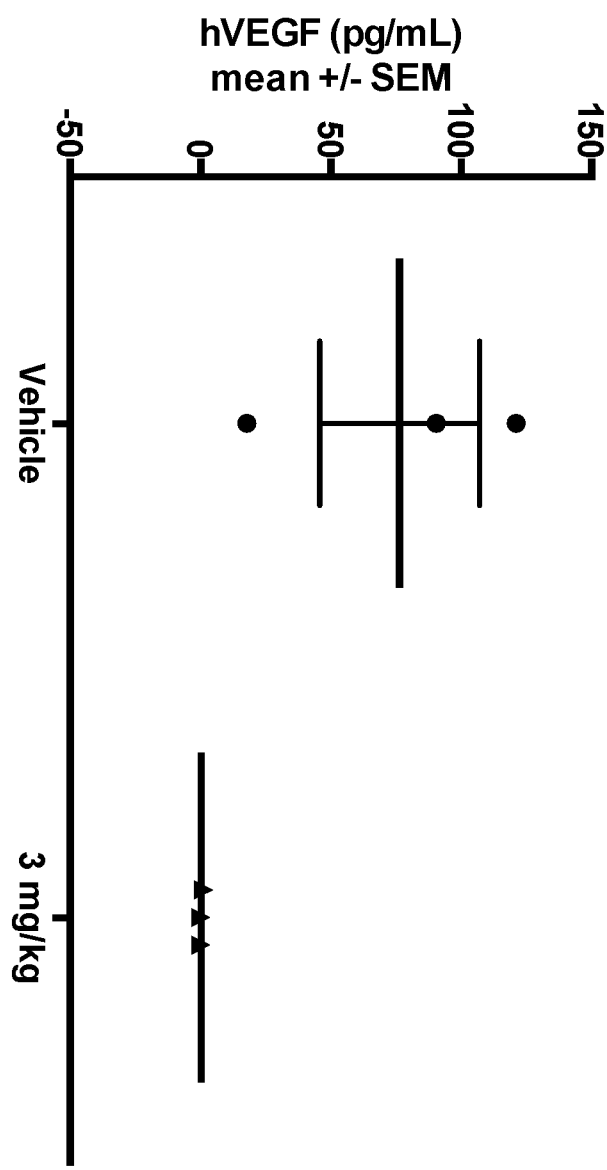
FIG. 2 shows human VEGF plasma levels of 786-O xenograft bearing mice after treating at 0 mg/kg (denoted as "Vehicle") and 3 mg/kg of Compound 95 six times each at 12 hour intervals.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oliopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The term "cell proliferation" refers to a phenomenon by which the cell number has changed as a result of division.

This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment", "treating", "palliating" and "ameliorating" are used interchangeably. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable" means that a chemical entity, such as a compound, a carrier, an additive or a salt, is acceptable for being administered to a subject.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

The term "selective inhibition" or "selectively inhibit" as applied to a biologically active agent refers to the agent's ability to selectively reduce the target signaling activity as compared to off-target signaling activity, via direct or indirect interaction with the target.

The term "subject" includes, but is not limited to, humans of any age group, e.g., a pediatric subject (e.g., infant, child or adolescent) or adult subject (e.g., young adult, middle-aged adult or senior adult)) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. The methods described herein can be useful in both human therapeutics and veterinary applications. In some embodiments, the patient is a mammal, and in some embodiments, the patient is human.

"Radiation therapy" or "radiation treatment" means exposing a patient, using routine methods and compositions known to the practitioner, to radiation emitters such as alpha-particle emitting radionucleotides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "HIF-2α" refers to a monomeric protein that contains several conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, including Endothelial PAS Domain Protein 1 (EPAS1), HIF-2A, PASD2, HIF-2-Alpha, HIF-2-Alpha, HLF, Hypoxia-Inducible Factor 2-Alpha, HIF-1alpha-Like Factor, and MOP2. As a member of the bHLH/PAS family of transcription factors, "HIF-2α" forms an active heterodimeric transcription factor complex by binding to the ARNT (also known as HIF-1β) protein through non-covalent interactions. In some embodiments, "HIF-2α" may refer to a fragment of the native protein. In some further embodiments, the fragment may include residues 239 to 348 of the native protein sequence.

The term "scintillation proximity assay" (SPA) refers to a homogeneous assay in which light is emitted when a radio-labeled ligand is brought into close proximity to a radio-sensitive bead. The assay typically contains a target protein that contains a tag (e.g., His Tag, Glutathione S-transferase Tag). The tag on the protein is used to bind the target protein to the scintillation bead. Radio-labeled ligand (e.g., labeled with tritium) that binds to the protein is now in close proximity to the bead, and when the radio-label (e.g., tritium) decays, the high energy particle hits the bead resulting in the emission of light that is detected by a detector, such as photomultiplier tube or CCD camera. When unlabeled ligands or compounds that bind to the protein are used in the assay, they displace the radio-labeled ligand, resulting in loss of signal. For a general reference describing the assay, see Park, et al. *Analytical Biochemistry* 269: 94-104, 1999.

"HIF-2α activity" as used herein has its ordinary meaning in the art. HIF-2α activity, for example, includes activation of gene transcription mediated by HIF-2α.

The term "inhibiting HIF-2α activity", as used herein, refers to slowing, reducing, altering, as well as completely eliminating and/or preventing HIF-2α activity.

The term "alkyl" refers to a straight or branched hydrocarbon chain radical comprising carbon and hydrogen atoms, containing no unsaturation, and having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl, (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "fluoroalkyl" refers to an alkyl group substituted with one or more fluorine atoms. In some embodiments, it is a $C_1$-$C_4$ alkyl group substituted with one or more fluorine atoms. Typical fluoroalkyl groups include, but are in no way limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

The term "alkenyl" refers to a straight or branched hydrocarbon chain radical group comprising carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., $C_2$-$C_8$ alkenyl). In other embodiments, an alkenyl comprises two to five carbon atoms (i.e., $C_2$-$C_5$ alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "alkynyl" refers to a straight or branched hydrocarbon chain radical group comprising carbon and hydrogen atoms, containing at least one triple bond, and having from two to ten carbon atoms (i.e., $C_2$-$C_{10}$ alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., $C_2$-$C_8$ alkynyl). In other embodiments, an alkynyl has two to five carbon atoms (i.e., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "aromatic" or "aryl" refers to an aromatic radical with six to ten ring atoms (i.e., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Aralkyl" or "arylalkyl" refers to an (aryl)alkyl- radical wherein the arylalkyl moiety is attached via the alkyl portion of the moiety. Aryl and alkyl are as disclosed herein and are optionally substituted by one or more of the substituents described as suitable substituents for aryl and alkyl, respectively.

The term "heteroaryl" or, alternatively, "heteroaromatic" refers to a 5- to 18-membered aromatic radical (i.e., $C_5$-$C_{18}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl. Examples of monocylic heteroaryls include, but are not limited to, imidazolyl, pyridinyl, pyrrolyl, pyrazinyl, pyrimidinyl, thiazolyl, furanyl and thienyl.

Substituted heteroaryl also includes ring systems substituted with one or more oxide substituents, such as pyridinyl N-oxides.

"Heteroarylalkyl" refers to a moiety having a heteroaryl moiety, as described herein, connected to an alkyl moiety, as described herein, wherein the connection to the remainder of the molecule is through the alkyl group. Heteroaryl and alkyl are as disclosed herein and are optionally substituted by one or more of the substituents described as suitable substituents for heteroaryl and alkyl, respectively.

The term "acyl" refers to a —C(=O)R radical, wherein R is alkyl, cycloalkyl, aryl, heteroaryl, heteroalkyl, or heterocycloalkyl, which are as described herein. The R group is attached to the parent structure through the carbonyl functionality. In some embodiments, it is a $C_1$-$C_{10}$ acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "halo", "halide", or alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" refer to haloalkyl and haloalkoxy groups, respectively, in which the halo is fluoro. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$. The alkyl part of the haloalkyl radical may be optionally substituted as defined above for an alkyl group.

The term "cyano" refers to a —CN radical.

The term "alkoxy" refers to an —O-alkyl radical, including from wherein alkyl is as described herein and contains 1 to 10 carbon atoms (i.e., $C_1$-$C_{10}$ alkoxy) of a straight, branched, or cyclic configuration and combinations thereof attached to the parent structure through an oxygen. Examples include methoxy, ethoxy, propoxy, isopropoxy, cyclopropyloxy, cyclohexyloxy and the like. Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. Unless stated otherwise specifically in the specification, an alkoxy moiety may be substituted by one or more of the substituents described as suitable substituents for an alkyl radical.

The term "sp$^3$ hybridized carbon" refers to a carbon atom that is bonded to four other atoms. sp$^3$ hybridization results from the combination of the s orbital and all three p orbitals in the second energy level of carbon. It results in four equivalent orbitals and the geometric arrangement of those four orbitals is tetrahedral.

The term "sulfonyl" refers to a —S(=O)$_2$R$^a$ radical, wherein R$^a$ is selected from the group consisting of alkyl, amino, cycloalkyl, aryl, heteroalkyl, heteroaryl (bonded through a ring carbon) and heterocycloalkyl (bonded through a ring carbon). Unless stated otherwise specifically in the specification, the R$^a$ group may be substituted by one or more of the substituents described as suitable substituents for an alkyl, an aryl or a heteroaryl radical.

The term "sulfoximinyl" refers to a —S(=O)(=NR$^a$)R$^b$ radical, wherein R$^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and R$^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R$^a$ and R$^b$ groups may be substituted by one or more of the substituents described as suitable substituents for an alkyl, an aryl or a heteroaryl radical.

"Sulfonamide," "sulfonamidyl" or "sulfonamido" refers to a —S(=O)$_2$N(R$^a$)$_2$ radical, wherein each R$^a$ is selected independently from the group consisting of hydrogen, alkyl, heteroalkyl, cycloalkyl, aryl, heteroaryl and heterocycloalkyl. The R$^a$ groups in —N(R$^a$)$_2$ of the —S(=O)$_2$—N(R$^a$)$_2$ radical may be taken together with the nitrogen to which it is attached to form a 4-, 5-, 6-, or 7-membered ring. In some embodiments, it is a $C_1$-$C_{10}$ sulfonamido, wherein each R$^a$ in sulfonamido contains 1 carbon, 2 carbons, 3 carbons or 4 carbons total. A sulfonamido group is optionally substituted by one or more of the substituents described for alkyl, cycloalkyl, aryl and heteroaryl, respectively.

The term "fluoroalkylsulfonyl" refers to a —S(=O)$_2$R$^a$ radical, wherein R$^a$ is fluoroalkyl. In some embodiments, R$^a$ is $C_1$-$C_4$ alkyl, substituted with one or more fluorines.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "heterocyclyl" or "heterocycloalkyl" refers to a stable 3- to 18-membered nonaromatic ring (e.g., $C_3$-$C_{18}$ heterocycloalkyl) radical that comprises two to twelve ring carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur and nitrogen, as well as combinations comprising at least one of the foregoing heteroatoms; the other ring, usually with 3 to 7 ring atoms, optionally contains 1-3 heteroatoms independently selected form oxygen, sulfur and nitrogen and is not aromatic.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, $C_3$-$C_4$ heteroalkyl has a chain length of 3-4 atoms. For example, a —CH$_2$OCH$_2$CH$_3$ radical is referred to as a "$C_4$ heteroalkyl", which includes the heteroatom in the atom chain length description. Connection to the rest of the molecule may be through either a heteroatom or a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amino" or "amine" refers to a —N(R$^a$)$_2$ radical group, where each R$^a$ is independently hydrogen, alkyl, heteroalkyl, fluoroalkyl, cycloalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ other than hydrogen, they can be combined with the nitrogen atom to form a 3-, 4-, 5-, 6-, 7- or 8-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "substituted amino" also refers to N-oxides of N(R$^a$)$_2$ as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "acyloxy" refers to a RC(=O)O— radical wherein R is alkyl, cycloalkyl, aryl, heteroalkyl, heteroaryl or heterocycloalkyl, which are as described herein. In some embodiments, it is a C$_1$-C$_4$ acyloxy radical, which refers to the total number of chain or ring atoms of the alkyl, cycloalkyl, aryl, heteroalkyl, heteroaryl or heterocycloalkyl portion of the acyloxy group plus the carbonyl carbon of acyl, i.e., the other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amide" or "amido" refers to a chemical moiety with formula —C(=O)N(R$^a$)$_2$ or —NR$^a$C(=O)R$^a$, wherein each of R$^a$ is independently selected from the group consisting of hydrogen, alkyl, cycloalkyl, aryl, heteroaryl (bonded through a ring carbon) and heterocycloalkyl. Two R$^a$s may optionally be taken together with the nitrogen to which it is attached to form a 4-10 membered ring. In some embodiments, it is a C$_1$-C$_4$ amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound having an amine or a carboxylic acid moiety, thereby forming a prodrug. Any amine, hydroxy or carboxyl side chain on the compounds described herein can be amidified. The procedures and specific groups to make such amides are known to those of skilled in the art and can readily be found in reference sources such as Wuts, Greene's Protective Groups in Organic Synthesis, 5$^{th}$ Ed., Wiley, New York, N.Y., 2014, which is incorporated herein by reference in its entirety.

"Carboxaldehyde" refers to a —C(=O)H radical.

"Carboxyl" refers to a —C(=O)OH radical.

"Ester" refers to a chemical radical of formula —C(=O)OR, where R is selected from the group consisting of alkyl, cycloalkyl, aryl, heteroaryl (bonded through a ring carbon) and heterocycloalkyl (bonded through a ring carbon). Any amine, hydroxy, or carboxyl side chain on the compounds described herein can be esterified. The procedures and specific groups to make such esters are known to those skilled in the art and can readily be found in reference sources such as Wuts, Greene's Protective Groups in Organic Synthesis, 5$^{th}$ Ed., Wiley, New York, N.Y., 2014, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Imino" refers to a =N—R$^a$ radical, wherein R$^a$ is hydrogen, alkyl, heteroalkyl, cycloalkyl, cyano, aryl, heterocycloalkyl or heteroaryl.

"Isocyanato" refers to a —NCO radical.

"Isothiocyanato" refers to a —NCS radical.

"Mercaptyl" refers to an —S(alkyl) or —SH radical.

"Methylene" refers to a =CH$_2$ radical.

"Hydroxy" refers to a —OH radical.

"Oxa" refers to a —O— radical.

"Oxo" refers to a =O radical.

"Nitro" refers to a —NO$_2$ radical.

"Oxime" refers to a =N(—OR) radical, where R is hydrogen or alkyl.

"Sulfinyl" refers to a —S(=O)R radical, where R is selected from the group consisting of alkyl, cycloalkyl, aryl, heteroalkyl, heteroaryl (bonded through a ring carbon) and heterocycloalkyl (bonded through a ring carbon). In some embodiments, R is fluoroalkyl.

"Sulfoxyl" refers to a —S(=O)$_2$OH radical.

"Sulfonate" refers to a —S(=O)$_2$OR radical, where R is selected from the group consisting of alkyl, cycloalkyl, aryl, heteroalkyl, heteroaryl (bonded through a ring carbon) and heteroalkyl (bonded through a ring carbon). The R group is optionally substituted by one or more of the substituents described for alkyl, heteroalkyl, cycloalkyl, heterocycloalkyl, aryl, and heteroaryl, respectively.

"Thiocyanato" refers to a —CNS radical.

"Thioxo" refers to a =S radical.

"Moiety" refers to a specific segment or functional group of a molecule. Chemical moieties are often recognized chemical entities embedded in or appended to a molecule.

"Substituted" means that the referenced group may be substituted with one or more additional group(s) individually and independently selected from acyl, alkyl, alkylaryl, heteroalkyl, cycloalkyl, aralkl, heterocycloalkyl, aryl, carbohydrate, carbonate, heteroaryl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamide, sulfoxyl, sulfonate, urea, and amino, including mono- and di-substituted amino groups and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Wuts, *Greene's Protective Groups in Organic Synthesis*, 5$^{th}$ Ed., Wiley, New York, N.Y., 2014.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*, Vol. 7, Wiley, ISBN-10: 0471495018, published on Mar. 14, 2001.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E- form (or cis- or trans- form). Furthermore, some chemical entities may exist in various tautomeric forms. Unless otherwise specified, chemical entities described herein are intended to include all Z-, E- and tautomeric forms as well.

The term "enantiomeric excess," as used herein, is the percent excess of one enantiomer compared to that of the other enantiomer in a mixture, and can be calculated using the following equation: enantiomeric excess=((R−S)/(R+S))×100=% (R*)−% (S*), wherein R and S are the number of moles of each enantiomer in the mixture, and R* and S* are the respective mole fractions of the enantiomers in the mixture. For example, for a mixture with 87% R enantiomer and 13% S enantiomer, the enantiomeric excess is 74%.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in Wuts, *Greene's Protective Groups in Organic Synthesis*, 5$^{th}$ Ed., Wiley, New York, N.Y., 2014. For example, a hydroxy protected form is where at least one of the hydroxy groups present in a compound is protected with a hydroxy protecting group. Likewise, amines and other reactive groups may similarly be protected.

"Solvate" refers to a compound in physical association with one or more molecules of a pharmaceutically acceptable solvent. It will be understood that the present chemical entities encompass the present chemical entities and solvates of the compound, as well as mixtures thereof.

"Solvent," "organic solvent," and "inert solvent" each means a solvent inert under the conditions of the reaction being described in conjunction therewith, including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Abbreviations used herein have their conventional meaning within the chemical and biological arts.

The following abbreviations and terms have the indicated meanings throughout:
DAST=Diethylaminosulfur trifluoride
DCM=Dichloromethane
MTBE=Methyl t-butyl ether
HATU=O-(7-azabenzotriazol-1-yl)-N,N,N',N'-tetramethyluronium hexafluorophosphate
NBS=N-Bromosuccinimide
NMP=N-Methyl-2-pyrrolidone
e.e. or ee=Enantiomeric excess
PPTS=Pyridinium p-toluenesulfonate
TLC=Thin Layer Chromatography
DMAP=4-Dimethylaminopyridine
DMF=N,N-Dimethylformamide When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E- forms (or cis- and trans- forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

When

" ⟍ "

is drawn across a bond, it denotes where a bond disconnection or attachment occurs. For example, in the chemical structure shown below,

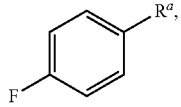

$R^a$ is attached to the para position of a fluorophenyl ring through a single bond. When $R^a$ is phenyl, it can also be drawn as,

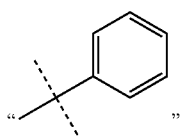

The waved line

means a bond with undefined stereochemistry. For example

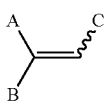

represents a mixture of

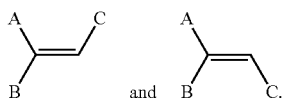

When a bond is drawn across a ring, it means substitution at a non-specific ring atom or position. For example, in the structure shown below,

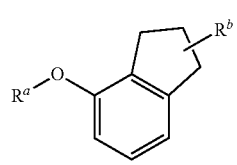

$R^b$ may be attached to any one of the —$CH_2$— in the five-membered ring.

When a bold bond

appears two or more times in the same chemical structure, a mixture of the two cis isomers of the compound is described. For example,

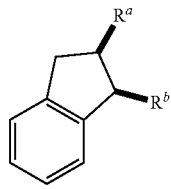

represents a mixture of the two isomers

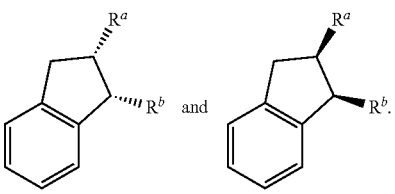

In one aspect, the present disclosure provides a compound of Formula I:

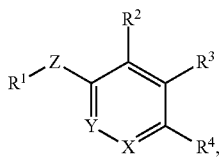

Formula I or a pharmaceutically acceptable salt or prodrug thereof, wherein:

X is $CR^5$ or N;
Y is $CR^6$ or N;
Z is S, $CHR^7$, $NR^8$ or absent;
$R^1$ is alkyl, heteroalkyl, cycloalkyl, heterocycloalkyl, aryl, heteroaryl, acyl or cyano;
$R^2$ is nitro, carboxaldehyde, carboxyl, ester, amido, cyano, halo, sulfonyl, alkyl, alkenyl, alkynyl or heteroalkyl;
$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and
$R^5$, $R^6$, $R^7$ and $R^8$ are independently hydrogen, halo, hydroxy, cyano, alkyl or alkoxy.

In some embodiments, for a compound of Formula I, $R^1$ is further selected from alkyl, heteroalkyl, cycloalkyl, cycloalkenyl, heterocycloalkyl, aryl, heteroaryl, acyl and cyano.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, the substituent(s) is selected from the group consisting of halo, $C_1$-$C_4$ alkyl, $C_1$-$C_4$ alkoxy and cyano.

In some embodiments, $R^1$ is bicyclic heteroaryl. In a further embodiment, the bicyclic heteroaryl is substituted with one or more substituents selected from the group consisting of halo, $C_1$-$C_4$ alkyl, $C_1$-$C_4$ alkoxy and cyano.

In some embodiments, $R^1$ is pyridyl N-oxide. In a further embodiment, the pyridyl N-oxide is substituted with one or more substituents selected from the group consisting of halo, $C_1$-$C_4$ alkyl, $C_1$-$C_4$ alkoxy and cyano.

In some embodiments, $R^1$ is

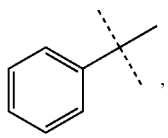

wherein the aryl ring may optionally be substituted with one or more substituents selected from the group consisting of cyano, halo, alkyl and alkoxy. In a further embodiment, the substituent(s) is selected from the group consisting of halo, $C_1$-$C_4$ alkyl, $C_1$-$C_4$ alkoxy and cyano.

In some embodiments, $R^1$ is

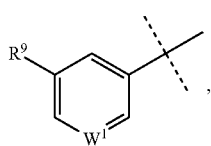

wherein $W^1$ is N or $CR^{10}$, $R^9$ is cyano, halo, alkyl or alkoxy, and $R^{10}$ is hydrogen, cyano, halo, alkyl or alkoxy. In a further embodiment, $R^9$ is cyano, halo, $C_1$-$C_4$ alkyl or $C_1$-$C_4$ alkoxy, and $R^{10}$ is hydrogen, cyano, halo, $C_1$-$C_4$ alkyl or $C_1$-$C_4$ alkoxy.

In some embodiments, $R^1$ is selected from the group consisting of:

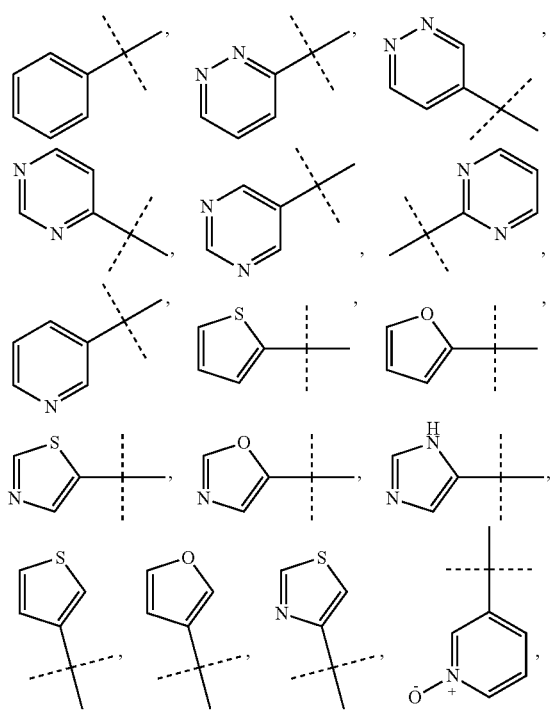

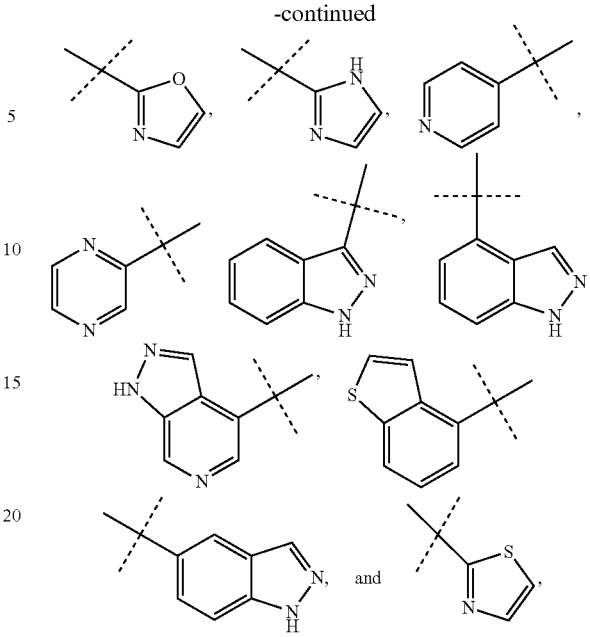

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

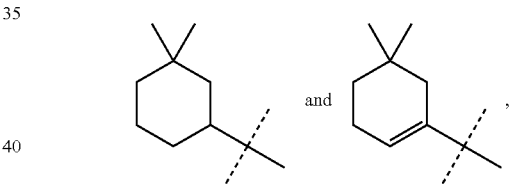

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, R¹ is selected from the group consisting of:

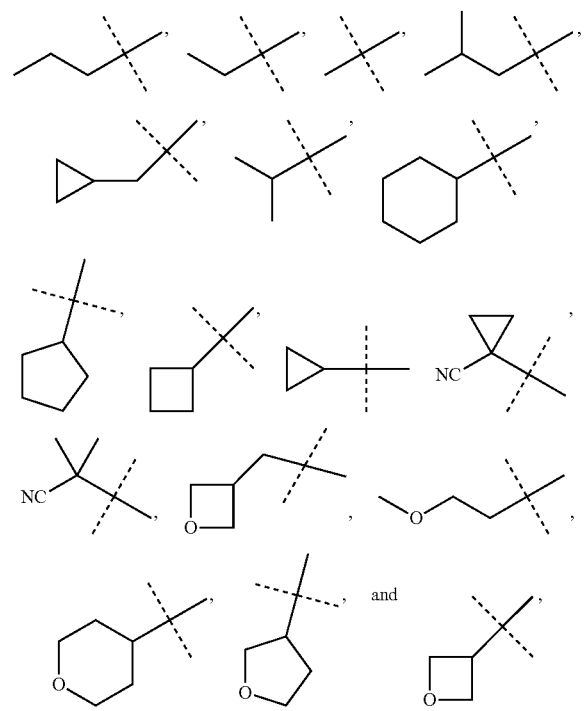

wherein each of the members may optionally be substituted with one or more substituents selected from the group consisting of cyano, halo, alkyl and alkoxy. In a further embodiment, the substituent(s) is selected from the group consisting of fluoro, C₁-C₄ alkyl, C₁-C₄ alkoxy and cyano.

In some embodiments, R² is cyano, halo or alkyl. In some embodiments, R² is halo or alkyl. In some embodiments, R² is fluoro, chloro, bromo or iodo. In some embodiments, R² is fluoroalkyl. In some further embodiments, R² is —CH₂F, —CHF₂ or —CF₃. In another embodiment, R² is hydrogen. In some other embodiments, R² is heteroalkyl, alkenyl or alkynyl.

In some embodiments, R³ is hydrogen, halo, cyano, alkyl, alkenyl, heteroalkyl or acyl; or R² and R³ taken together form a cyclic moiety. In a further embodiment, R³ is halo, cyano or alkyl. In yet a further embodiment, R³ is —(CH₂)ₙOH, wherein n is 1, 2 or 3. In still a further embodiment, R³ is —CH₂OH.

In some embodiments, R² and R³ taken together with the atoms to which they are attached form a 5- or 6-membered carbocycle with at least one sp³ hybridized carbon. Representative compounds with the carbocycle include, but are not limited to, the following:

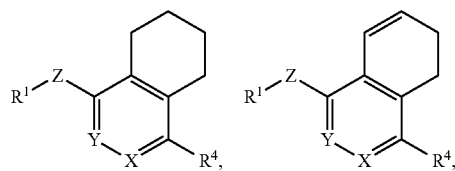

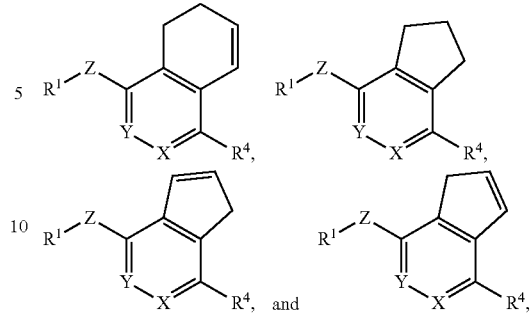

wherein the carbocycle formed by linking R² and R³ may be optionally substituted with fluoro, chloro, hydroxy, alkyl or heteroalkyl. In a further embodiment, the substituent(s) is selected from the group consisting of halo, C₁-C₄ alkyl, C₁-C₄ alkoxy and cyano. In yet other embodiments, the substituent(s) is cycloalkyl or heterocycloalkyl and shares one or more ring atoms with the carbocycle formed by linking R² and R³. In some embodiments, the substituent(s) is C₃-C₅ cycloalkyl or C₃-C₅ heterocycloalkyl. In other embodiments, the substituent is oxo.

In some embodiments, R² and R³ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, C₁-C₄ alkyl, C₁-C₄ alkoxy and cyano.

In some embodiments, R⁴ is halo, cyano, fluoroalkyl, sulfinyl, sulfonamidyl, sulfonyl, sulfoximinyl or fluoroalkylsulfonyl. In some embodiments, R⁴ is cyano, fluoroalkyl, sulfonamidyl, sulfinyl, sulfonyl or sulfoximinyl. In some embodiments, R⁴ is fluoroalkyl, sulfonamidyl, sulfonyl, sulfoximinyl or fluoroalkylsulfonyl. In a further embodiment, R⁴ is fluoroalkyl. In yet another embodiment, R⁴ is sulfonyl. In still another embodiment, R⁴ is fluoroalkylsulfonyl.

In some embodiments, R⁴ is —S(=O)₂Rᵃ, wherein Rᵃ is alkyl or cycloalkyl. In a further embodiment, Rᵃ is C₁-C₄ alkyl, optionally substituted with one or more fluorines. Suitable examples of fluorine-substituted C₁-C₄ alkyl include, but are not limited to, —CH₂F, —CHF₂, —CF₃, —CH₂CF₃, —CH₂CHF₂, —CH₂CH₂F, —CHFCH₃ and —CF₂CH₃. In still a further embodiment, Rᵃ is methyl, optionally substituted with one or more fluorines.

In some embodiments, R⁴ is —S(=O)(=NRᵇ)Rᵃ, wherein Rᵃ is alkyl or cycloalkyl and Rᵇ is hydrogen, cyano or alkyl. In a further embodiment, Rᵃ is C₁-C₄ alkyl, optionally substituted with one or more fluorines. Suitable examples of fluorine-substituted C₁-C₄ alkyl include, but are not limited to, —CH₂F, —CHF₂, —CF₃, —CH₂CF₃, —CH₂CHF₂, —CH₂CH₂F, —CHFCH₃ and —CF₂CH₃.

In some embodiments, R⁴ is —S(=O)₂N(Rᵃ)₂, wherein each Rᵃ is independently hydrogen, alkyl, heteroalkyl, cycloalkyl or heterocycloalkyl, and at least one Rᵃ is hydrogen. In a further embodiment, both Rᵃs are hydrogen. In another further embodiment, one Rᵃ is hydrogen and the other Rᵃ is C₁-C₄ alkyl.

In some embodiments, R⁴ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)

(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, R$^5$ is hydrogen. In some other embodiments, R$^5$ is C$_1$-C$_4$ alkyl or C$_1$-C$_4$ alkoxy. In a further embodiment, R$^5$ is methyl.

In some embodiments, R$^6$ is hydrogen. In some other embodiments, R$^6$ is C$_1$-C$_4$ alkyl or C$_1$-C$_4$ alkoxy. In a further embodiment, R$^6$ is methyl.

In some embodiments, R$^7$ is hydrogen. In some other embodiments, R$^7$ is C$_1$-C$_4$ alkyl or C$_1$-C$_4$ alkoxy. In a further embodiment, R$^7$ is methyl.

In some embodiments, R$^8$ is hydrogen. In some other embodiments, R$^8$ is C$_1$-C$_4$ alkyl or C$_1$-C$_4$ alkoxy. In a further embodiment, R$^8$ is methyl.

In some embodiments, R$^3$ is hydrogen, R$^4$ is —S(=O)$_2$R$^a$ or —S(=O)(=NR$^b$)R$^c$, wherein R$^a$ is fluoroalkyl, R$^b$ is hydrogen, cyano or alkyl and R$^c$ is alkyl. In a further embodiment, R$^1$ is selected from the group consisting of

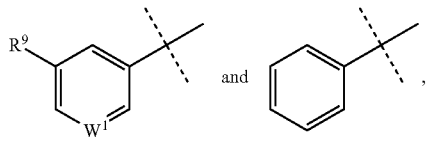

and wherein W$^1$ is N or CR$^{10}$, R$^9$ is cyano, halo, alkyl or alkoxy, and R$^{10}$ is hydrogen, cyano, halo, alkyl or alkoxy; and

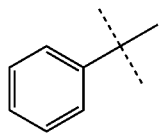

may optionally be substituted with one or more substituents selected from the group consisting of cyano, halo, alkyl and alkoxy. In a further embodiment, the alkyl is C$_1$-C$_4$ alkyl. In another further embodiment, the alkoxy is C$_1$-C$_4$ alkoxy.

In some embodiments, each of R$^2$ and R$^3$ is independently alkyl and R$^4$ is cyano, fluoroalkyl, sulfonamidyl, sulfinyl, sulfonyl, sulfoximinyl or fluoroalkylsulfonyl.

In some embodiments, R$^3$ is —CH$_2$OH. In a further embodiment, R$^4$ is cyano, fluoroalkyl, sulfonamidyl, sulfinyl, sulfonyl, sulfoximinyl or fluoroalkylsulfonyl and R$^5$ is hydrogen. In still a further embodiment, R$^2$ is cyano, halo or alkyl.

In some embodiments, R$^1$ is phenyl or monocyclic heteroaryl; R$^2$ is nitro, halo, cyano or alkyl; R$^3$ is halo, cyano or alkyl; R$^4$ is cyano, fluoroalkyl, sulfonamidyl, sulfinyl, sulfonyl, sulfoximinyl or fluoroalkylsulfonyl. In a further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$. In still a further embodiment, R$^5$ is hydrogen.

In some embodiments, R$^1$ is bicyclic heteroaryl; R$^2$ is nitro, halo, cyano or alkyl; R$^3$ is halo, cyano or alkyl; R$^4$ is cyano, fluoroalkyl, sulfonamidyl, sulfinyl, sulfonyl, sulfoximinyl or fluoroalkylsulfonyl; and R$^5$ is hydrogen.

In some embodiments, R$^1$ is phenyl, monocyclic heteroaryl or bicyclic heteroaryl; R$^2$ is halo, cyano or alkyl; R$^3$ is halo, cyano or alkyl; R$^4$ is cyano, fluoroalkyl, sulfonamidyl, sulfinyl, sulfonyl, sulfoximinyl or fluoroalkylsulfonyl; and R$^5$ is hydrogen.

In some embodiments, R$^2$ and R$^3$ together with the atoms to which they are attached form a 5- or 6-membered carbocycle with at least one sp$^3$ hybridized carbon; R$^4$ is cyano, fluoroalkyl, sulfonamidyl, sulfinyl, sulfonyl, sulfoximinyl or fluoroalkylsulfonyl; and R$^5$ is hydrogen. In a further embodiment, R$^1$ is phenyl or monocyclic heteroaryl. In another further embodiment, R$^1$ is bicyclic heteroaryl.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is S. In further embodiments, Z is CHR$^7$. In yet other embodiments, Z is NR$^8$. In some embodiments, Z is absent.

In another aspect, the disclosure provides a compound of Formula I-A:

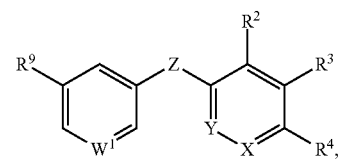

or a pharmaceutically acceptable salt or prodrug thereof, wherein:

X is CR$^5$ or N;

Y is CR$^6$ or N;

Z is S, CHR$^7$, NR$^8$ or absent;

R$^2$ is nitro, carboxaldehyde, carboxylic acid, ester, amido, cyano, halo, sulfonyl or alkyl;

R$^3$ is hydrogen, halo, cyano, alkyl, heteroalkyl, alkenyl, alkynyl, amino, oxime or acyl; or R$^2$ and R$^3$ taken together form a cyclic moiety;

R$^4$ is nitro, halo, cyano, alkyl, sulfinyl, sulfonamidyl, sulfonyl or sulfoximinyl;

R$^5$, R$^6$, R$^7$ and R$^8$ are independently hydrogen, halo, hydroxy, cyano, alkyl or alkoxy;

W$^1$ is N or CR$^{10}$;

R$^9$ is cyano, halo, alkyl or alkoxy; and

R$^{10}$ is hydrogen, cyano, halo, alkyl or alkoxy.

In some embodiments, R$^2$ is cyano, halo or alkyl. In some embodiments, R$^2$ is halo or alkyl. In some embodiments, R$^2$ is fluoro, chloro, bromo or iodo. In some embodiments, R$^2$ is fluoroalkyl. In some further embodiments, R$^2$ is —CH$_2$F, —CHF$_2$ or —CF$_3$.

In some embodiments, R$^3$ is hydrogen, halo, cyano, alkyl, alkenyl, heteroalkyl or acyl; or R$^2$ and R$^3$ taken together form a cyclic moiety. In a further embodiment, R$^3$ is halo, cyano or alkyl. In yet a further embodiment, R$^3$ is —(CH$_2$)$_n$OH, wherein n is 1, 2 or 3. In still a further embodiment, R$^3$ is —CH$_2$OH.

In some embodiments, R$^2$ and R$^3$ taken together with the atoms to which they are attached form a 5- or 6-membered carbocycle with at least one sp$^3$ hybridized carbon. Representative compounds with the carbocycle include, but are not limited to, the following:

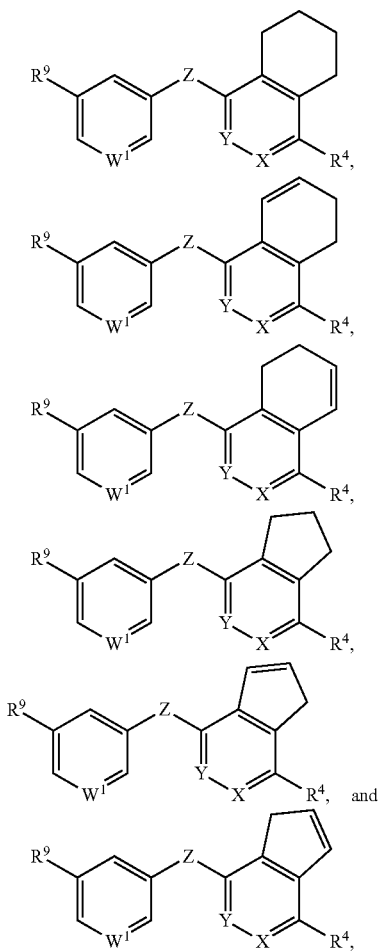

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$$R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=NR$^b$)$R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N($R^a$)$_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^9$ is cyano, halo, $C_1$-$C_4$ alkyl or $C_1$-$C_4$ alkoxy.

In some embodiments, $R^{10}$ is hydrogen, cyano, halo, $C_1$-$C_4$ alkyl or $C_1$-$C_4$ alkoxy.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl.

In some embodiments, $R^3$ is —CH$_2$OH and $R^4$ is cyano, fluoroalkyl, sulfonamidyl, sulfonyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is CH$_2$OH; $R^4$ is cyano, fluoroalkyl, sulfonamidyl, sulfonyl or sulfoximinyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is S. In further embodiments, Z is CHR⁷. In yet other embodiments, Z is NR⁸. In some embodiments, Z is absent.

In another aspect, the disclosure provides a compound of Formula I-B:

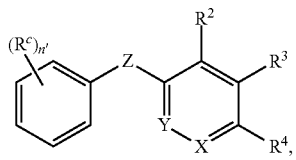

or a pharmaceutically acceptable salt or prodrug thereof, wherein:

X is CR⁵ or N;
Y is CR⁶ or N;
Z is S, CHR⁷, NR⁸ or absent;
R² is nitro, carboxaldehyde, carboxylic acid, ester, amido, cyano, halo, sulfonyl or alkyl;
R³ is hydrogen, halo, cyano, alkyl, heteroalkyl, alkenyl, alkynyl, amino, oxime or acyl; or R² and R³ taken together form a cyclic moiety;
R⁴ is nitro, halo, cyano, alkyl, sulfinyl, sulfonamidyl, sulfonyl or sulfoximinyl;
R⁵, R⁶, R⁷ and R⁸ are independently hydrogen, halo, hydroxy, cyano, alkyl or alkoxy;
R$^c$ is hydrogen, cyano, halo, alkyl or alkoxy; and
n' is 0, 1, 2, 3 or 4.

In some embodiments, R² is cyano, halo or alkyl. In some embodiments, R² is halo or alkyl. In some embodiments, R² is fluoro, chloro, bromo or iodo. In some embodiments, R² is fluoroalkyl. In some further embodiments, R² is —CH₂F, —CHF₂ or —CF₃.

In some embodiments, R³ is hydrogen, halo, cyano, alkyl, alkenyl, heteroalkyl or acyl; or R² and R³ taken together form a cyclic moiety. In a further embodiment, R³ is halo, cyano or alkyl. In yet a further embodiment, R³ is —(CH₂)$_n$OH, wherein n is 1, 2 or 3.

In some embodiments, R² and R³ taken together with the atoms to which they are attached form a 5- or 6-membered carbocycle with at least one sp³ hybridized carbon. Representative compounds with the carbocycle include, but are not limited to, the following:

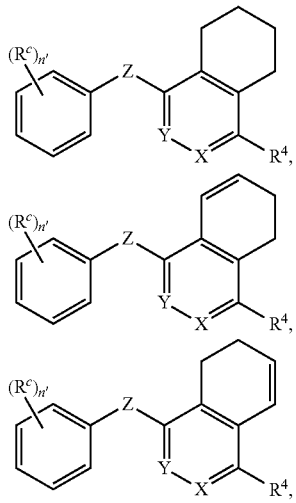

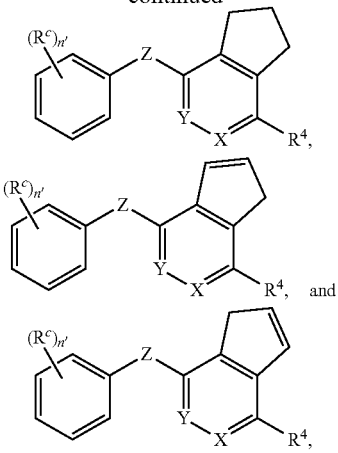

wherein the carbocycle formed by linking R² and R³ may be optionally substituted with fluoro, chloro, hydroxy, alkyl or heteroalkyl. In a further embodiment, the substituent(s) is selected from the group consisting of halo, C₁-C₄ alkyl, C₁-C₄ alkoxy and cyano. In yet other embodiments, the substituent(s) is cycloalkyl or heterocycloalkyl and shares one or more ring atoms with the carbocycle formed by linking R² and R³. In some embodiments, the substituent(s) is C₃-C₅ cycloalkyl or C₃-C₅ heterocycloalkyl. In other embodiments, the substituent is oxo.

In some embodiments, R² and R³ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, C₁-C₄ alkyl, C₁-C₄ alkoxy and cyano.

In some embodiments, R³ is hydrogen, R⁴ is —S(=O)₂R$^a$ or —S(=O)(=NR$^b$)R$^d$, wherein R$^a$ is fluoroalkyl, R$^b$ is hydrogen, cyano or alkyl and R$^d$ is alkyl.

In some embodiments, R⁴ is halo, cyano, fluoroalkyl, sulfinyl, sulfonamidyl, sulfonyl, sulfoximinyl or fluoroalkylsulfonyl. In some embodiments, R⁴ is cyano, fluoroalkyl, sulfonamidyl, sulfinyl, sulfonyl or sulfoximinyl. In some embodiments, R⁴ is fluoroalkyl, sulfonamidyl, sulfonyl or sulfoximinyl. In a further embodiment, R⁴ is fluoroalkyl. In yet another embodiment, R⁴ is sulfonyl. In still another embodiment, R⁴ is fluoroalkylsulfonyl.

In some embodiments, R⁴ is —S(=O)₂R$^a$, wherein R$^a$ is alkyl or cycloalkyl. In a further embodiment, R$^a$ is C₁-C₄ alkyl, optionally substituted with one or more fluorines. Suitable examples of fluorine-substituted C₁-C₄ alkyl include, but are not limited to, —CH₂F, —CHF₂, —CF₃, —CH₂CF₃, —CH₂CHF₂, —CH₂CH₂F, —CHFCH₃ and —CF₂CH₃. In still a further embodiment, R$^a$ is methyl, optionally substituted with one or more fluorines.

In some embodiments, R⁴ is —S(=O)(=NR$^b$)R$^a$, wherein R$^a$ is alkyl or cycloalkyl and R$^b$ is hydrogen, cyano or alkyl. In a further embodiment, R$^a$ is C₁-C₄ alkyl, optionally substituted with one or more fluorines. Suitable examples of fluorine-substituted C₁-C₄ alkyl include, but are not limited to, —CH₂F, —CHF₂, —CF₃, —CH₂CF₃, —CH₂CHF₂, —CH₂CH₂F, —CHFCH₃ and —CF₂CH₃.

In some embodiments, R⁴ is —S(=O)₂—N(R$^a$)₂, wherein each R$^a$ is independently hydrogen, alkyl, heteroalkyl, cycloalkyl or heterocycloalkyl, and at least one R$^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, $R^3$ is —$CH_2OH$ and $R^4$ is fluoroalkyl, sulfonamidyl, sulfonyl, sulfinyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is $CH_2OH$; $R^4$ is fluoroalkyl, sulfonamidyl, sulfonyl, sulfinyl or sulfoximinyl. In a further embodiment, $R^4$ is selected from the group consisting of —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, X is N and Y is $CR^6$. In other embodiments, X is $CR^5$ and Y is N. In still other embodiments, X is N and Y is N. In yet other embodiments, X is $CR^5$ and Y is $CR^6$.

In some embodiments, Z is S. In further embodiments, Z is $CHR^7$. In yet other embodiments, Z is $NR^8$. In some embodiments, Z is absent.

In some embodiments, RC is cyano, halo, $C_1$-$C_4$ alkyl or $C_1$-$C_4$ alkoxy.

In yet another aspect, the disclosure provides a compound of Formula I-C:

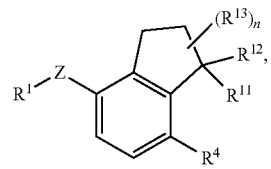

or a pharmaceutically acceptable salt or prodrug thereof, wherein:
Z is S, $CHR^7$, $NR^8$ or absent;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^7$ and $R^8$ are independently hydrogen, halo, hydroxy, cyano, alkyl or alkoxy; $R^{11}$ is hydrogen, hydroxy, alkoxy or amino;
$R^{12}$ is hydrogen, alkyl, alkenyl or alkynyl; or $R^{11}$ and $R^{12}$ in combination form oxo or oxime;
each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and n is 0, 1, 2, 3 or 4.

In some embodiments, for a compound of Formula I-C, $R^1$ is further selected from alkyl, heteroalkyl, cycloalkyl, cycloalkenyl, heterocycloalkyl, aryl, and heteroaryl.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

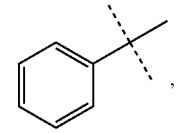

wherein the aryl ring is optionally substituted with one or more substituents selected from the group consisting of cyano, halo, alkyl and alkoxy. In another further embodiment, $R^1$ is

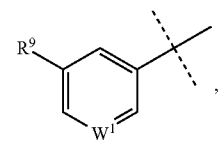

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

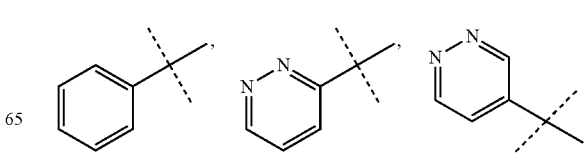

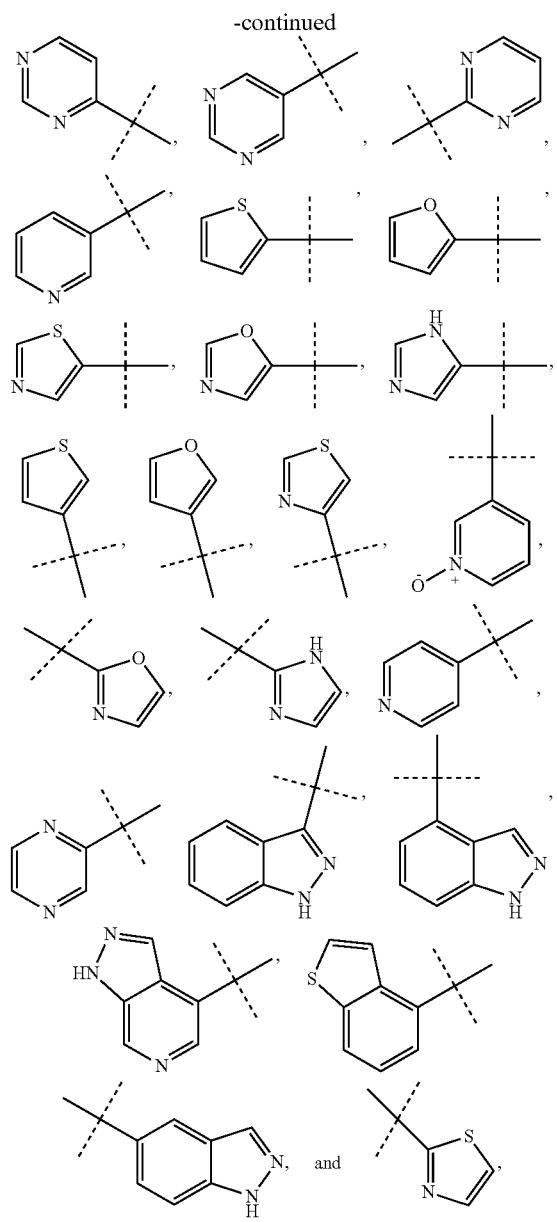

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

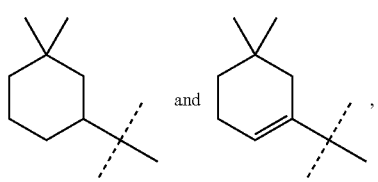

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

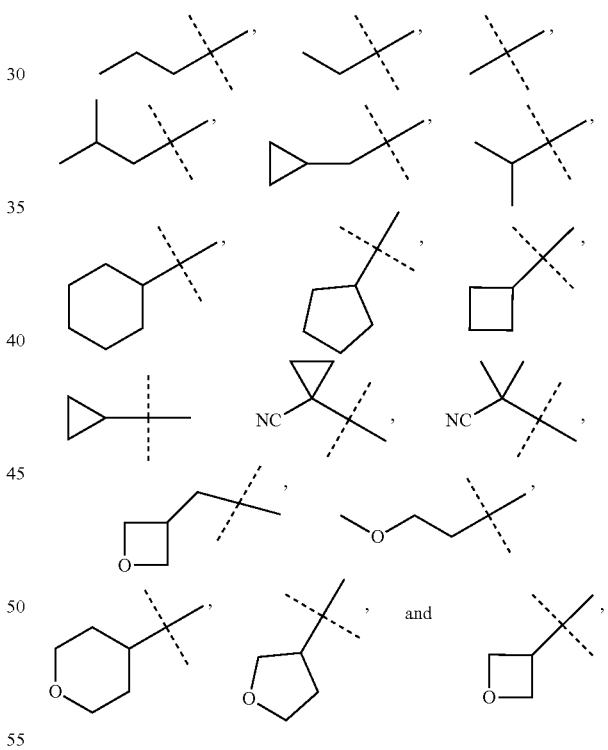

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is $-S(=O)_2R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, $-CH_2F$, $-CHF_2$, $-CF_3$, $-CH_2CF_3$, $-CH_2CHF_2$, $-CH_2CH_2F$, $-CHFCH_3$ and $-CF_2CH_3$. In still a further embodiment, $R^a$ is methyl, optionally substituted with one or more fluorines.

In some embodiments, $R^4$ is $-S(=O)(=NR^b)R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, $-CH_2F$, $-CHF_2$, $-CF_3$, $-CH_2CF_3$, $-CH_2CHF_2$, $-CH_2CH_2F$, $-CHFCH_3$ and $-CF_2CH_3$.

In some embodiments, $R^4$ is $-S(=O)_2N(R^a)_2$, wherein each $R^a$ is independently hydrogen, alkyl, heteroalkyl, cycloalkyl or heterocycloalkyl, and at least one $R^a$ is hydrogen. In another further embodiment, one $R^a$ is hydrogen and the other $R^a$ is $C_1$-$C_4$ alkyl.

In some embodiments, $R^4$ is selected from the group consisting of $-CN$, $-CF_3$, $-S(=O)CH_3$, $-S(=O)_2CH_3$, $-S(=O)_2CH_2F$, $-S(=O)_2CHF_2$, $-S(=O)_2CF_3$, $-S(=O)_2NH_2$, $-S(=O)_2NHCH_3$, $-S(=O)(=NH)CH_3$, $-S(=O)(=NH)CH_2F$, $-S(=O)(=NH)CHF_2$, $-S(=O)(=NH)CF_3$, $-S(=O)(=N-CN)CH_3$, $-S(=O)(=N-CN)CH_2F$, $-S(=O)(=N-CN)CHF_2$ and $-S(=O)(=N-CN)CF_3$.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy or amino. In a further embodiment, $R^{11}$ is hydroxy. In another further embodiment, $R^{11}$ is amino.

In some embodiments, $R^{12}$ is hydrogen. In some other embodiments, $R^{12}$ is alkyl or alkenyl.

In some embodiments, $R^{13}$ is fluoro. In a further embodiment, n is 1, 2 or 3. In a further embodiment, two $R^{13}$s in combination form oxo, oxime or methylene. In still further embodiments, two $R^{13}$s and the carbon atom(s) to which they are attached form a 3- to 8-membered cycloalkyl or heterocycloalkyl moiety.

In some embodiments, $R^1$ is monocyclic aryl or monocyclic heteroaryl and $R^{11}$ is hydroxy or amino. In a further embodiment, $R^{13}$ is fluoro. In still a further embodiment, n is 1, 2 or 3.

In some embodiments, $R^1$ is phenyl or monocyclic heteroaryl, $R^{11}$ is hydroxy or amino, $R^{13}$ is fluoro, n is 1, 2 or 3, and $R^5$ is hydrogen.

In some embodiments, $R^1$ is bicyclic heteroaryl and $R^{11}$ is hydroxy or amino. In a further embodiment, $R^{13}$ is fluoro. In still a further embodiment, n is 1, 2 or 3.

In some embodiments, $R^1$ is bicyclic heteroaryl, $R^{11}$ is hydroxy or amino, $R^{13}$ is fluoro, n is 1, 2 or 3, and $R^5$ is hydrogen.

In some embodiments, $R^4$ is cyano, fluoroalkyl, sulfonamidyl, sulfinyl, sulfonyl, sulfoximinyl or fluoroalkylsulfonyl, and $R^{11}$ is hydroxy or amino. In a further embodiment, $R^{12}$ is hydrogen. In another further embodiment, $R^{13}$ is fluoro. In still a further embodiment, n is 1, 2 or 3.

In some embodiments, $R^4$ is cyano, fluoroalkyl, sulfonamidyl, sulfinyl, sulfonyl, sulfoximinyl or fluoroalkylsulfonyl; $R^{11}$ is hydroxy or amino; $R^{13}$ is fluoro; n is 1, 2 or 3; and $R^5$ is hydrogen. In a further embodiment, $R^{12}$ is hydrogen.

In some embodiments $R^{11}$ is hydroxy or amino and $R^{12}$ is hydrogen. In a further embodiment, $R^{13}$ is fluoro. In still a further embodiment, n is 1, 2 or 3.

In some embodiments $R^{11}$ is hydroxy or amino, $R^{12}$ is hydrogen, $R^{13}$ is fluoro, n is 1, 2 or 3, and $R^5$ is hydrogen. In a further embodiment, $R^4$ is selected from the group consisting of $-CN$, $-CF_3$, $-S(=O)CH_3$, $-S(=O)_2CH_3$, $-S(=O)_2CH_2F$, $-S(=O)_2CHF_2$, $-S(=O)_2CF_3$, $-S(=O)_2NH_2$, $-S(=O)_2NHCH_3$, $-S(=O)(=NH)CH_3$, $-S(=O)(=NH)CH_2F$, $-S(=O)(=NH)CHF_2$, $-S(=O)(=NH)CF_3$, $-S(=O)(=N-CN)CH_3$, $-S(=O)(=N-CN)CH_2F$, $-S(=O)(=N-CN)CHF_2$ and $-S(=O)(=N-CN)CF_3$.

In some embodiments, $R^4$ is fluoroalkyl; n is 0, 1, 2 or 3; $R^{11}$ is hydroxy; and $R^{12}$ is hydrogen.

In some embodiments, $R^4$ is sulfonyl or fluoroalkylsulfonyl; n is 0, 1, 2 or 3; $R^{11}$ is hydroxy; and $R^{12}$ is hydrogen.

In some embodiments, Z is S. In further embodiments, Z is $CHR^7$. In yet other embodiments, Z is $NR^8$. In some embodiments, Z is absent.

In still another aspect, the disclosure provides a compound of Formula I-D, I-E, I-F or I-G:

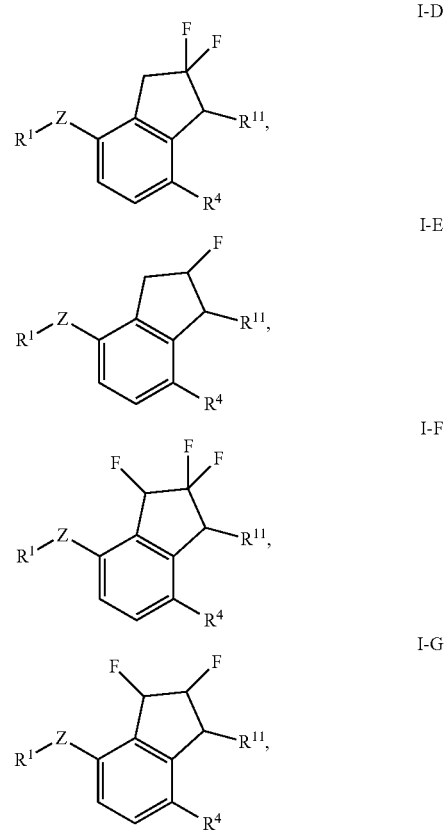

or a pharmaceutically acceptable salt or prodrug thereof, wherein:

Z is S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^7$ and $R^8$ are independently hydrogen, halo, hydroxy, cyano, alkyl or alkoxy; and $R^{11}$ is hydrogen, hydroxy, alkoxy or amino.

In some embodiments, for a compound of Formula I-D, I-E, I-F, or I-G, $R^1$ is further selected from alkyl, heteroalkyl, cycloalkyl, cycloalkenyl, heterocycloalkyl, aryl, and heteroaryl.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

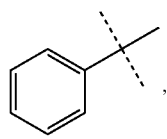

wherein the aryl ring is optionally substituted with one or more substituents selected from the group consisting of cyano, halo, alkyl and alkoxy. In another further embodiment, $R^1$ is

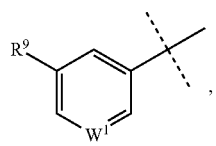

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl having at least one N atom.

In some embodiments, $R^1$ is selected from the group consisting of:

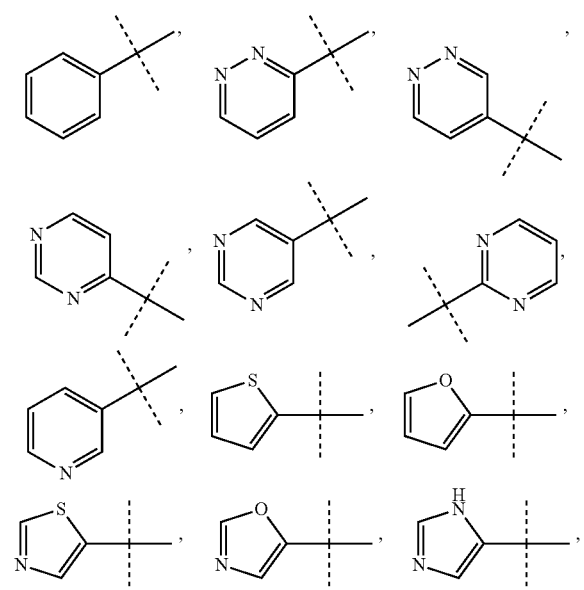

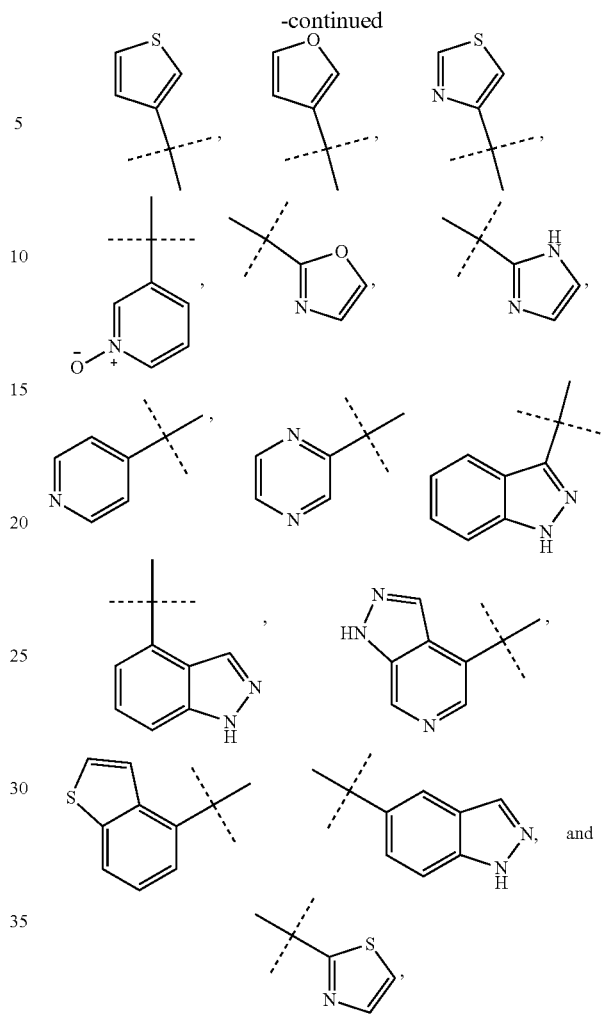

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

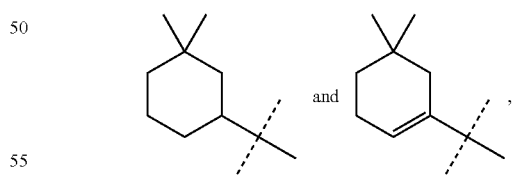

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^t$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

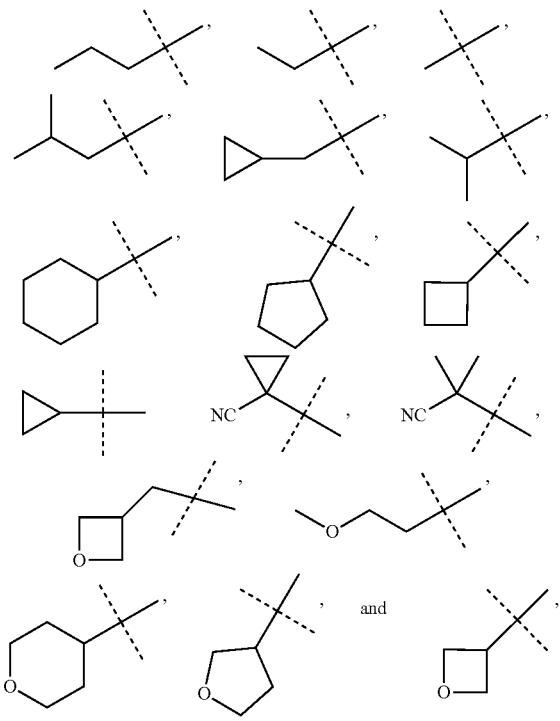

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, option-ally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, both R$^a$s are hydrogen. In a further embodiment, one R$^a$ is hydrogen and the other R$^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino.

In some embodiments $R^1$ is bicyclic heteroaryl and $R^4$ is cyano, fluoroalkyl, sulfinyl, sulfonamidyl, sulfonyl or sulfoximinyl. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N-CN)CF$_3$.

In some embodiments $R^1$ is bicyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is phenyl or monocyclic heteroaryl and $R^4$ is cyano, fluoroalkyl, sulfinyl, sulfonamidyl, sulfonyl or sulfoximinyl. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N-CN)CF$_3$.

In some embodiments $R^1$ is phenyl or monocyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, Z is S. In further embodiments, Z is CHR$^7$. In yet other embodiments, Z is NR$^8$. In some embodiments, Z is absent.

In a further aspect, the disclosure provides a compound of Formula I-H, I-I, I-J or I-K:

I-H
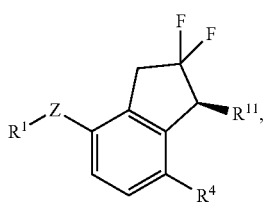

I-I
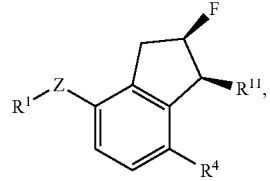

I-J
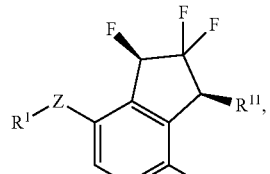

I-K
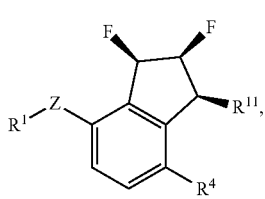

or a pharmaceutically acceptable salt or prodrug thereof, wherein:

Z is S, CHR$^7$, NR$^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^7$ and $R^8$ are independently hydrogen, halo, hydroxy, cyano, alkyl or alkoxy; and $R^{11}$ is hydroxy or amino.

In some embodiments, for a compound of Formula I-H, I-I, I-J, or I-K, $R^1$ is further selected from alkyl, heteroalkyl, cycloalkyl, cycloalkenyl, heterocycloalkyl, aryl, and heteroaryl.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

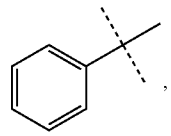

wherein the aryl ring is optionally substituted with one or more substituents selected from the group consisting of cyano, halo, alkyl and alkoxy. In another further embodiment, $R^1$ is

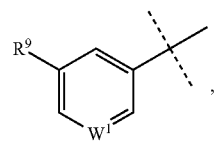

wherein $W^1$ is N or CR$^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

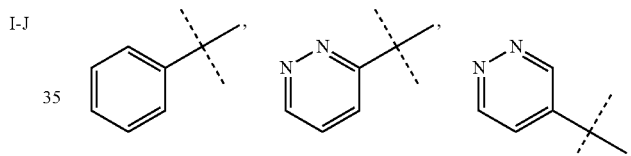

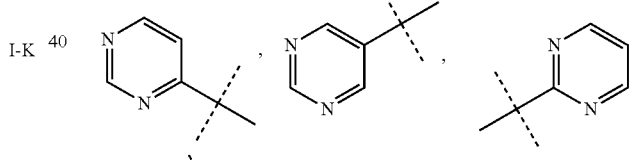

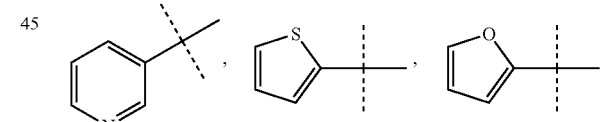

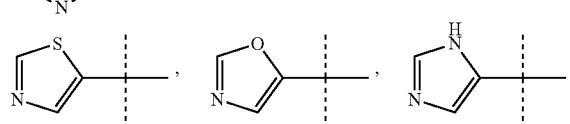

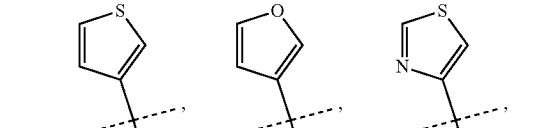

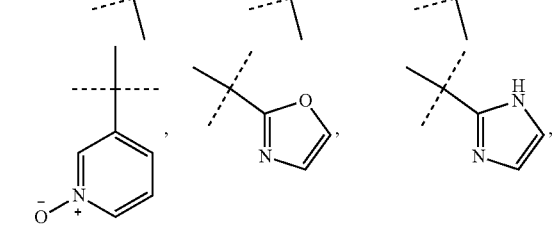

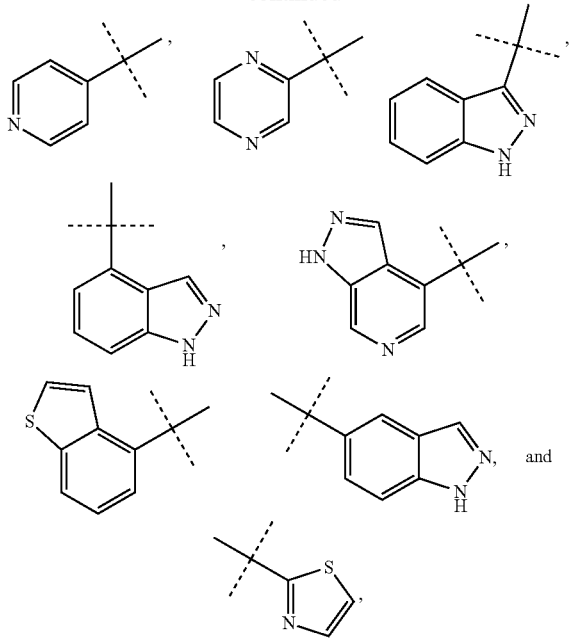

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

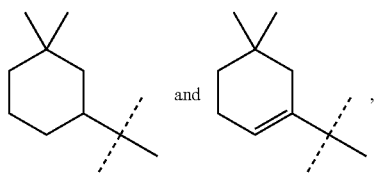

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

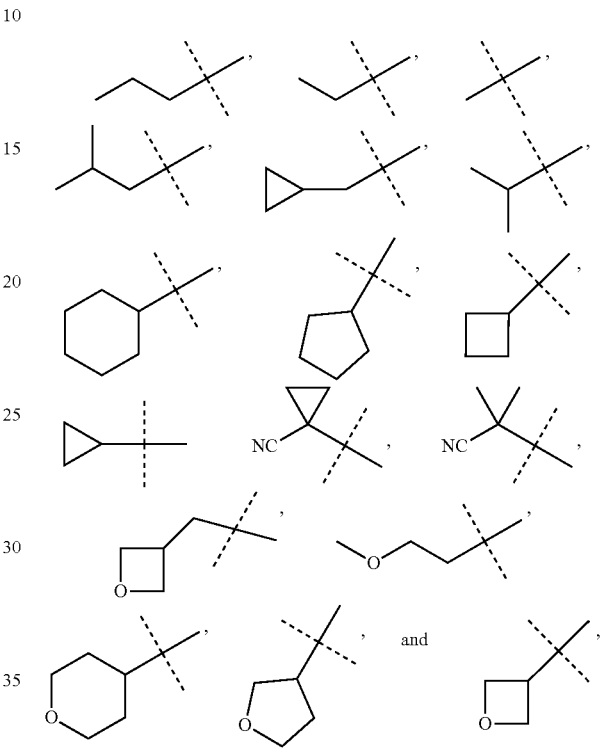

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, both $R^a$s are hydrogen. In a further embodiment, one $R^a$ is hydrogen and the other $R^a$ is $C_1$-$C_4$ alkyl.

In some embodiments, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino.

In some embodiments $R^1$ is bicyclic heteroaryl and $R^4$ is cyano, fluoroalkyl, sulfinyl, sulfonamidyl, sulfonyl or sulfoximinyl. In another further embodiment, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N-CN)$CF_3$.

In some embodiments $R^1$ is bicyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments $R^1$ is phenyl or monocyclic heteroaryl and $R^4$ is cyano, fluoroalkyl, sulfinyl, sulfonamidyl, sulfonyl or sulfoximinyl. In another further embodiment, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N-CN)$CF_3$.

In some embodiments $R^1$ is phenyl or monocyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, Z is S. In further embodiments, Z is $CHR^7$. In yet other embodiments, Z is $NR^8$. In some embodiments, Z is absent.

In some embodiments, a compound of any one of Formulae I-H-I-K may have an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae I—H-I—K may have an enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99%.

In one aspect, the present disclosure provides a compound having the structure of Formula II:

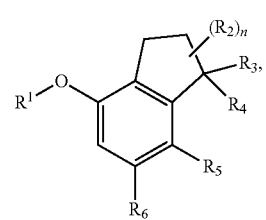

II or a pharmaceutically acceptable salt thereof, wherein:
n is 1, 2, 3 or 4;
$R_1$ is cycloalkyl, alkyl, heteroalkyl or heterocycloalkyl;
each of $R_2$ is hydrogen, alkyl, hydroxy, or halo; or two $R_2$s and the atom(s) to which they are attached form a 3-8 membered cycloalkyl or heterocycloalkyl moiety;
$R_3$ is alkyl, hydrogen, or deuterium and $R_4$ is hydroxy, fluoro, alkylamino, alkoxy, amino, cyano, or amide; or $R_3$ and $R_4$ in combination form oxo or oxime;
$R_5$ is sulfonyl, sulfonamidyl, sulfinyl, sulfoximinyl, nitro, amide, halo, cyano, alkyl, or cycloalkyl; and $R_6$ is hydrogen, halo, or alkyl.

In some embodiments, for a compound of Formula II, $R_1$ is further selected from alkyl, heteroalkyl, cycloalkyl, cycloalkenyl, and heterocycloalkyl.

In some embodiments, for a compound of Formula II, $R_1$ is alkyl. In a further embodiment, the alkyl is substituted with at least one substituent selected from the group consisting of halo, C1-C4 alkyl, C1-C4 alkoxy, and cyano. In another further embodiment, the alkyl is substituted with at least one fluoro.

In some embodiments, for a compound of Formula II, $R_1$ is cycloalkyl. In a further embodiment, the cycloalkyl is cyclobutyl. In still a further embodiment, the cyclobutyl is substituted with at least one substituent selected from the group consisting of halo, C1-C4 alkyl, C1-C4 alkoxy, and cyano. In still another further embodiment, the cyclobutyl is substituted with at least one fluoro.

In some embodiments, for a compound of Formula II, $R_1$ is selected from the group consisting of:

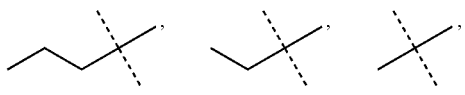

-continued

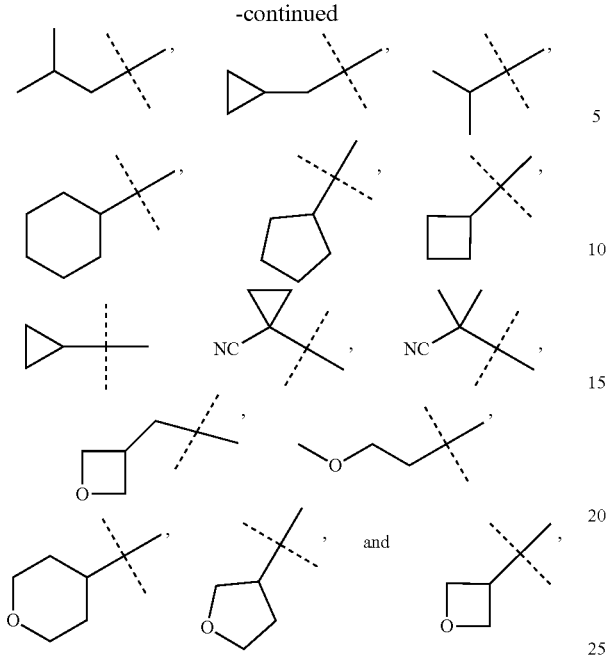

wherein each of the members may optionally be substituted with one or more substituents selected from the group consisting of cyano, halo, alkyl and alkoxy. In a further embodiment, the substituent(s) is selected from the group consisting of fluoro, C1-C4 alkyl, C1-C4 alkoxy, and cyano.

In some embodiments, for a compound of Formula II, n is 1, 2, or 3. In a further embodiment, $R_2$ is fluoro.

In some embodiments, for a compound of Formula II, $R_2$ is halo. In a further embodiment, $R_2$ is fluoro.

In some embodiments, for a compound of Formula II, $R_3$ is hydrogen. In a further embodiment, $R_4$ is hydroxy.

In some embodiments, for a compound of Formula II, $R_4$ is hydroxy. In a further embodiment, $R_6$ is hydrogen.

In some embodiments, for a compound of Formula II, $R_3$ and $R_4$ in combination form oxime.

In some embodiments, for a compound of Formula II, $R_5$ is sulfonyl, alkyl, halo, or cyano. In a further embodiment, $R_5$ is selected from the group consisting of —$CF_3$, —CN, —S(=O)$CH_3$, —S(=O)$_2CH_3$, —S(=O)$_2CH_2F$, —S(=O)$_2CHF_2$, and —S(=O)$_2CF_3$. In still a further embodiment, $R_5$ is —S(=O)$_2CH_3$. In still another further embodiment, $R_5$ is —$CF_3$.

In some embodiments, for a compound of Formula II, $R_6$ is hydrogen.

In some embodiments, for a compound of Formula II, $R_1$ is alkyl or cycloalkyl; n is 1, 2, or 3; and $R_2$ is fluoro. In a further embodiment, $R_3$ is hydrogen. In still a further embodiment, $R_4$ is hydroxy.

In some embodiments, for a compound of Formula II, $R_1$ is alkyl or cycloalkyl; n is 1, 2, or 3; $R_2$ is fluoro; $R_3$ is hydrogen; $R_4$ is hydroxy; and $R_6$ is hydrogen. In a further embodiment, $R_5$ is sulfonyl. In another further embodiment, $R_5$ is fluoroalkyl.

In some embodiments, for a compound of Formula II, $R_1$ is alkyl or cycloalkyl; n is 1, 2, or 3; $R_2$ is fluoro; $R_3$ is hydrogen; $R_4$ is hydroxy; $R_5$ is —S(=O)$_2CH_3$ and $R_6$ is hydrogen.

In some embodiments, for a compound of Formula II, $R_1$ is alkyl or cycloalkyl; n is 1, 2, or 3; $R_2$ is fluoro; $R_3$ is hydrogen; $R_4$ is hydroxy; $R_5$ is —$CF_3$ and $R_6$ is hydrogen.

In another aspect, the present disclosure provides a compound having one of the formulae:

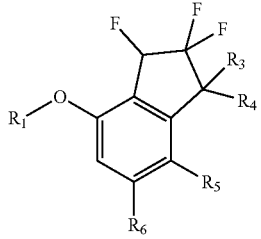

IIa

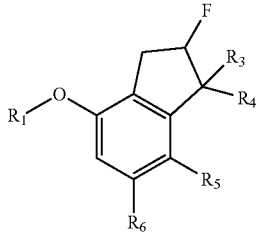

IIb

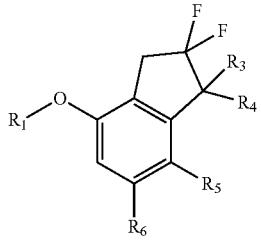

IIc

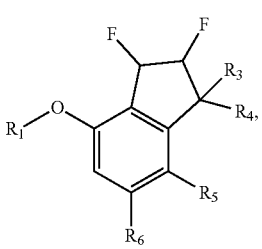

IId or a pharmaceutically acceptable salt thereof, wherein:
$R_1$ is cycloalkyl, alkyl, heteroalkyl or heterocycloalkyl;
$R_3$ is alkyl, hydrogen, or deuterium and $R_4$ is hydroxy, fluoro, alkylamino, alkoxy, amino, cyano, or amide; or $R_3$ and $R_4$ in combination form oxo or oxime;
$R_5$ is sulfonyl, sulfonamidyl, sulfinyl, sulfoximinyl, nitro, amide, halo, cyano, alkyl, or cycloalkyl; and $R_6$ is hydrogen, halo, or alkyl.

In some embodiments, for a compound of Formula IIa, IIb, IIc, or IId, $R_1$ is further selected from alkyl, heteroalkyl, cycloalkyl, cycloalkenyl, and heterocycloalkyl.

In some embodiments, for a compound of Formula IIa, IIb, IIc or IId, $R_1$ is alkyl. In a further embodiment, the alkyl is substituted with at least one substituent selected from the group consisting of halo, C1-C4 alkyl, C1-C4 alkoxy, and cyano. In another further embodiment, the alkyl is substituted with at least one fluoro.

In some embodiments, for a compound of Formula IIa, IIb, IIc or IId, $R_1$ is cycloalkyl. In a further embodiment, the cycloalkyl is cyclobutyl. In still a further embodiment, the cyclobutyl is substituted with at least one substituent selected from the group consisting of halo, C1-C4 alkyl, C1-C4 alkoxy, and cyano. In still another further embodiment, the cyclobutyl is substituted with at least one fluoro.

In some embodiments, for a compound of Formula IIa, IIb, IIc or IId, $R_1$ is selected from the group consisting of:

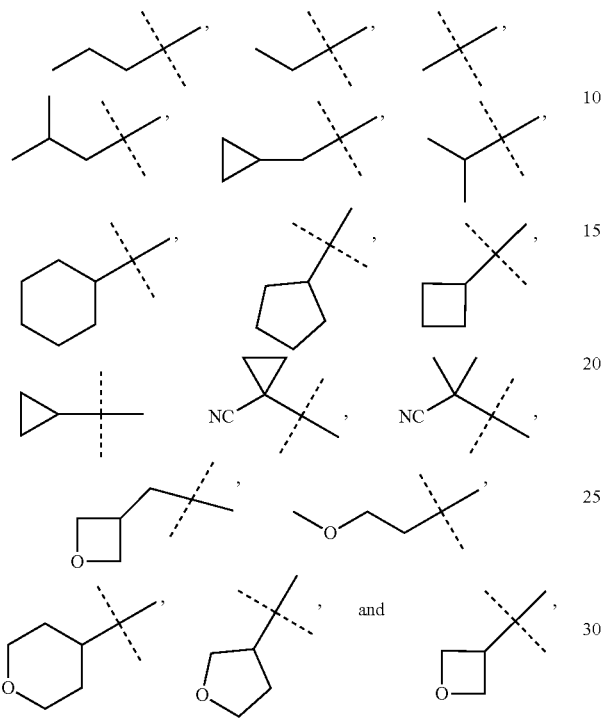

wherein each of the members may optionally be substituted with one or more substituents selected from the group consisting of cyano, halo, alkyl and alkoxy. In a further embodiment, the substituent(s) is selected from the group consisting of fluoro, C1-C4 alkyl, C1-C4 alkoxy, and cyano.

In some embodiments, for a compound of Formula IIa, IIb, IIc or IId, $R_3$ is hydrogen. In a further embodiment, $R_4$ is hydroxy.

In some embodiments, for a compound of Formula IIa, IIb, IIc or IId, $R_4$ is hydroxy. In a further embodiment, $R_6$ is hydrogen.

In some embodiments, for a compound of Formula IIa, IIb, IIc or IId, $R_3$ and $R_4$ in combination form oxime.

In some embodiments, for a compound of Formula IIa, IIb, IIc or IId, $R_5$ is sulfonyl, alkyl, halo, or cyano. In a further embodiment, $R_5$ is selected from the group consisting of —$CF_3$, —CN, —S(=O)$CH_3$, —S(=O)$_2CH_3$, —S(=O)$_2CH_2F$, —S(=O)$_2CHF_2$, and —S(=O)$_2CF_3$. In still a further embodiment, $R_5$ is —S(=O)$_2CH_3$. In still another further embodiment, $R_5$ is —$CF_3$.

In some embodiments, for a compound of Formula IIa, IIb, IIc or IId, $R_6$ is hydrogen.

In some embodiments, for a compound of Formula IIa, IIb, IIc or IId, $R_1$ is alkyl or cycloalkyl; n is 1, 2, or 3; and $R_2$ is fluoro. In a further embodiment, $R_3$ is hydrogen. In still a further embodiment, $R_4$ is hydroxy.

In some embodiments, for a compound of Formula IIa, IIb, IIc or IId, $R_1$ is alkyl or cycloalkyl; n is 1, 2, or 3; $R_2$ is fluoro; $R_3$ is hydrogen; $R_4$ is hydroxy; and $R_6$ is hydrogen. In a further embodiment, $R_5$ is sulfonyl. In another further embodiment, $R_5$ is fluoroalkyl.

In some embodiments, for a compound of Formula IIa, IIb, IIc or IId, $R_1$ is alkyl or cycloalkyl; n is 1, 2, or 3; $R_2$ is fluoro; $R_3$ is hydrogen; $R_4$ is hydroxy; $R_5$ is —S(=O)$_2CH_3$ and $R_6$ is hydrogen.

In some embodiments, for a compound of Formula IIa, IIb, IIc or IId, $R_1$ is alkyl or cycloalkyl; n is 1, 2, or 3; $R_2$ is fluoro; $R_3$ is hydrogen; $R_4$ is hydroxy; $R_5$ is —$CF_3$ and $R_6$ is hydrogen.

In another aspect, the present disclosure provides a compound having one of the formulae:

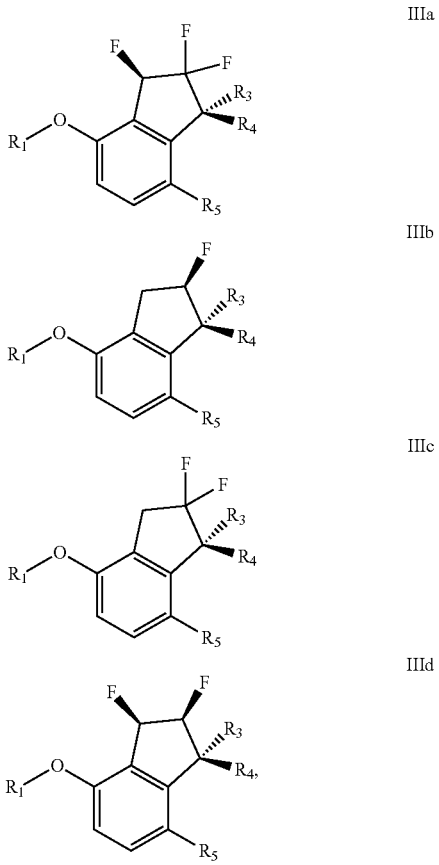

or a pharmaceutically acceptable salt thereof, wherein:

$R_1$ is cycloalkyl, alkyl, heteroalkyl or heterocycloalkyl;

$R_3$ is hydrogen and $R_4$ is hydroxy, alkylamino, alkoxy, amino, or fluoro; or $R_3$ and $R_4$ in combination form oxo or oxime; and $R_5$ is sulfonyl, sulfinyl, sulfonamidyl, sulfoximinyl, nitro, amide, halo, cyano, alkyl, or cycloalkyl.

In some embodiments, for a compound of Formula IIIa, IIIb, IIIc, or IIId, $R_1$ is further selected from alkyl, heteroalkyl, cycloalkyl, cycloalkenyl, and heterocycloalkyl.

In some embodiments, for a compound of Formula IIIa, IIIb, IIIc or IIId, $R_1$ is alkyl. In a further embodiment, the alkyl is substituted with at least one substituent selected from the group consisting of halo, C1-C4 alkyl, C1-C4 alkoxy, and cyano. In another further embodiment, the alkyl is substituted with at least one fluoro.

In some embodiments, for a compound of Formula IIIa, IIIb, IIIc or IIId, $R_1$ is cycloalkyl. In a further embodiment, the cycloalkyl is cyclobutyl. In still a further embodiment, the cyclobutyl is substituted with at least one substituent selected from the group consisting of halo, C1-C4 alkyl, C1-C4 alkoxy, and cyano. In still another further embodiment, the cyclobutyl is substituted with at least one fluoro.

In some embodiments, for a compound of Formula IIIa, IIIb, IIIc or IIId, $R_1$ is selected from the group consisting of:

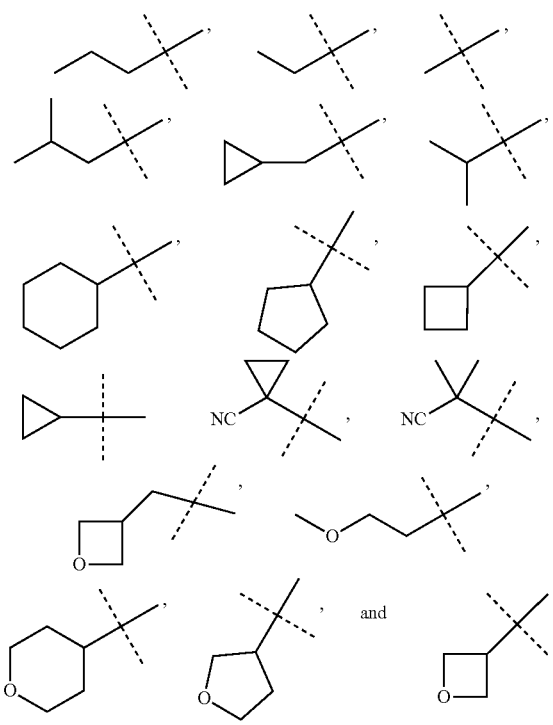

wherein each of the members may optionally be substituted with one or more substituents selected from the group consisting of cyano, halo, alkyl and alkoxy. In a further embodiment, the substituent(s) is selected from the group consisting of fluoro, C1-C4 alkyl, C1-C4 alkoxy, and cyano.

In some embodiments, for a compound of Formula IIIa, IIIb, IIIc or IIId, $R_3$ is hydrogen. In a further embodiment, $R_4$ is hydroxy.

In some embodiments, for a compound of Formula IIIa, IIIb, IIIc or IIId, $R_4$ is hydroxy. In a further embodiment, $R_6$ is hydrogen.

In some embodiments, for a compound of Formula IIIa, IIIb, IIIc or IIId, $R_3$ and $R_4$ in combination form oxime.

In some embodiments, for a compound of Formula IIIa, IIIb, IIIc or IIId, $R_5$ is sulfonyl, alkyl, halo, or cyano. In a further embodiment, $R_5$ is selected from the group consisting of —$CF_3$, —CN, —S(=O)$CH_3$, —S(=O)$_2CH_3$, —S(=O)$_2CH_2F$, —S(=O)$_2CHF_2$, and —S(=O)$_2CF_3$. In still a further embodiment, $R_5$ is —S(=O)$_2CH_3$. In still another further embodiment, $R_5$ is —$CF_3$.

In some embodiments, for a compound of Formula IIIa, IIIb, IIIc or IIId, $R_6$ is hydrogen.

In some embodiments, for a compound of Formula IIIa, IIIb, IIIc or IIId, $R_1$ is alkyl or cycloalkyl; n is 1, 2, or 3; and $R_2$ is fluoro. In a further embodiment, $R_3$ is hydrogen. In still a further embodiment, $R_4$ is hydroxy.

In some embodiments, for a compound of Formula IIIa, IIIb, IIIc or IIId, $R_1$ is alkyl or cycloalkyl; n is 1, 2, or 3; $R_2$ is fluoro; $R_3$ is hydrogen; $R_4$ is hydroxy; and $R_6$ is hydrogen. In a further embodiment, $R_5$ is sulfonyl. In another further embodiment, $R_5$ is fluoroalkyl.

In some embodiments, for a compound of Formula IIIa, IIIb, IIIc or IIId, $R_1$ is alkyl or cycloalkyl; n is 1, 2, or 3; $R_2$ is fluoro; $R_3$ is hydrogen; $R_4$ is hydroxy; $R_5$ is —S(=O)$_2CH_3$ and $R_6$ is hydrogen.

In some embodiments, for a compound of Formula IIIa, IIIb, IIIc or IIId, $R_1$ is alkyl or cycloalkyl; n is 1, 2, or 3; $R_2$ is fluoro; $R_3$ is hydrogen; $R_4$ is hydroxy; $R_5$ is —$CF_3$ and $R_6$ is hydrogen.

In some embodiments, a compound having any one of Formulae IIIa-IIId has enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae IIIa-IIId has enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%.

In one aspect, the present disclosure provides a compound of Formula IV:

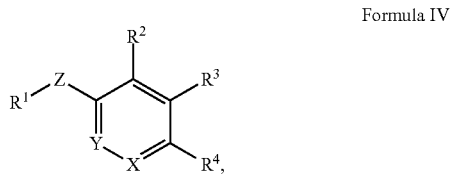

Formula IV or a pharmaceutically acceptable salt or prodrug thereof, wherein:

X is $CR^5$ or N;

Y is $CR^6$ or N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl, heteroaryl, acyl or cyano;

$R^2$ is nitro, carboxaldehyde, carboxyl, ester, amido, cyano, halo, sulfonyl, alkyl, alkenyl, alkynyl or heteroalkyl;

$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and $R^5$, $R^6$, $R^7$ and $R^8$ are independently hydrogen, halo, hydroxy, cyano, alkyl or alkoxy, wherein for a compound or salt of Formula IV, when Z is O, $R^1$ is alkyl, heteroalkyl, cycloalkyl, or heterocycloalkyl.

In some embodiments, for a compound of Formula IV, $R^1$ is further selected from alkyl, heteroalkyl, cycloalkyl, cycloalkenyl, and heterocycloalkyl.

In some embodiments, Z is O, S, $CHR^7$, $NR^8$ or absent. In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano.

In a further embodiment, the substituent(s) is selected from the group consisting of halo, $C_1$-$C_4$ alkyl, $C_1$-$C_4$ alkoxy and cyano.

In some embodiments, $R^1$ is bicyclic heteroaryl. In a further embodiment, the bicyclic heteroaryl is substituted with one or more substituents selected from the group consisting of halo, $C_1$-$C_4$ alkyl, $C_1$-$C_4$ alkoxy and cyano.

In some embodiments, $R^1$ is pyridyl N-oxide. In a further embodiment, the pyridyl N-oxide is substituted with one or more substituents selected from the group consisting of halo, $C_1$-$C_4$ alkyl, $C_1$-$C_4$ alkoxy and cyano.

In some embodiments, $R^1$ is

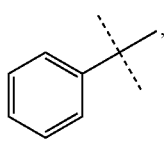

wherein the aryl ring may optionally be substituted with one or more substituents selected from the group consisting of cyano, halo, alkyl and alkoxy. In a further embodiment, the substituent(s) is selected from the group consisting of halo, $C_1$-$C_4$ alkyl, $C_1$-$C_4$ alkoxy and cyano.

In some embodiments, $R^1$ is

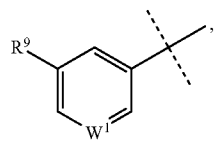

wherein $W^1$ is N or $CR^{10}$, $R^9$ is cyano, halo, alkyl or alkoxy, and $R^{10}$ is hydrogen, cyano, halo, alkyl or alkoxy. In a further embodiment, $R^9$ is cyano, halo, $C_1$-$C_4$ alkyl or $C_1$-$C_4$ alkoxy, and $R^{1'}$ is hydrogen, cyano, halo, $C_1$-$C_4$ alkyl or $C_1$-$C_4$ alkoxy.

In some embodiments, $R^1$ is selected from the group consisting of:

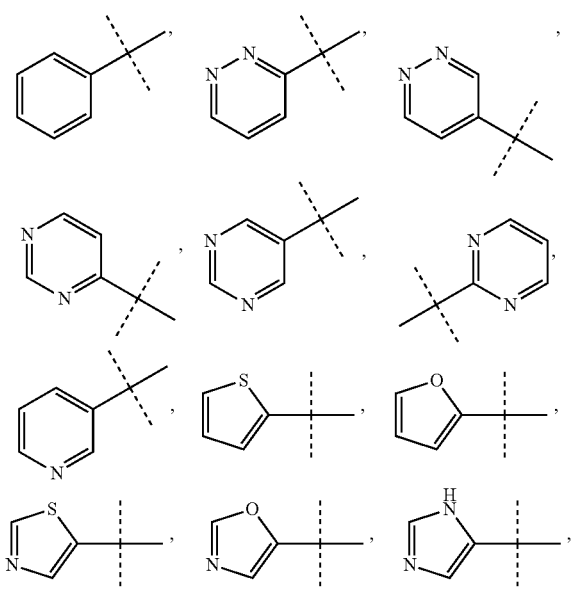

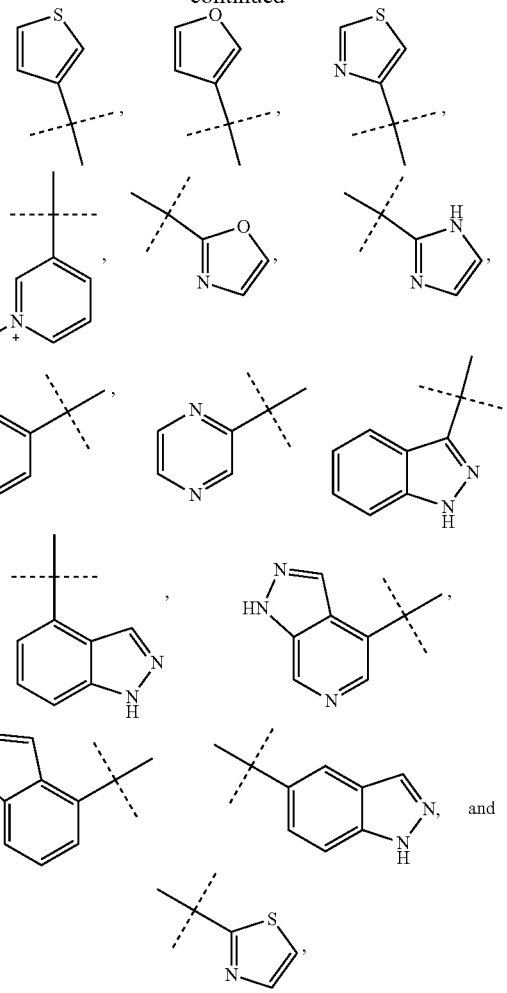

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

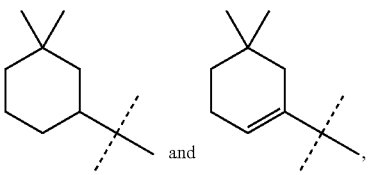

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

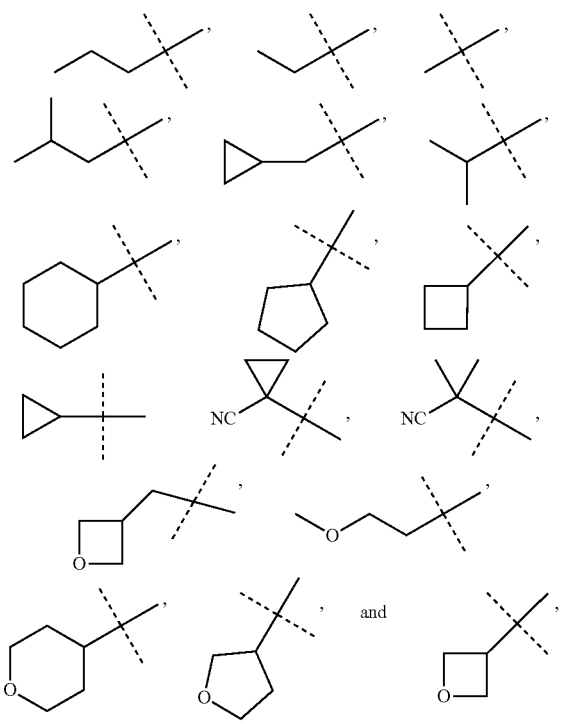

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —$CH_2F$, —$CHF_2$ or —$CF_3$. In another embodiment, $R^2$ is hydrogen. In some other embodiments, $R^2$ is heteroalkyl, alkenyl or alkynyl.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —$(CH_2)_nOH$, wherein n is 1, 2 or 3. In still a further embodiment, $R^3$ is —$CH_2OH$.

In some embodiments, $R^2$ and $R^3$ taken together with the atoms to which they are attached form a 5- or 6-membered carbocycle with at least one sp$^3$ hybridized carbon. Representative compounds with the carbocycle include, but are not limited to, the following:

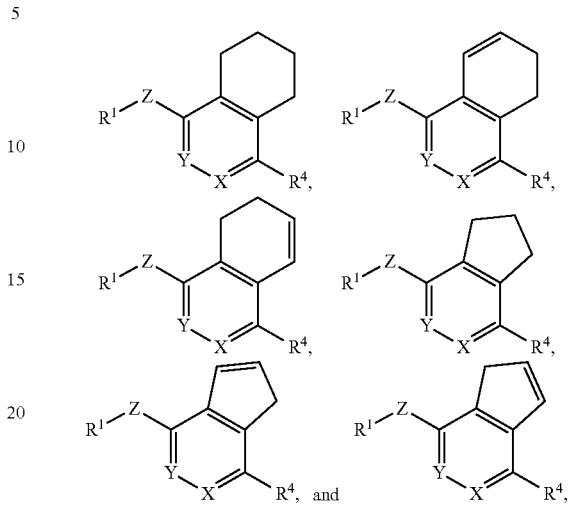

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl, sulfoximinyl or fluoroalkylsulfonyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —$S(=O)_2R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$. In still a further embodiment, $R^a$ is methyl, optionally substituted with one or more fluorines.

In some embodiments, $R^4$ is —$S(=O)(=NR^b)R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$.

In some embodiments, $R^4$ is —S(=O)$_2$N(R$^a$)$_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^3$ is hydrogen, $R^4$ is —S(=O)$_2$R$^a$ or —S(=O)(=NR$^b$)R$^c$, wherein $R^a$ is fluoroalkyl, $R^b$ is hydrogen, cyano or alkyl and RC is alkyl. In a further embodiment, $R^1$ is selected from the group consisting of

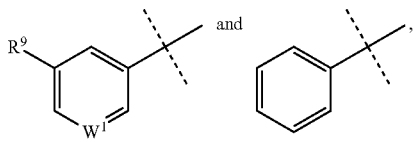

wherein $W^1$ is N or $CR^{10}$, $R^9$ is cyano, halo, alkyl or alkoxy, and $R^{10}$ is hydrogen, cyano, halo, alkyl or alkoxy; and

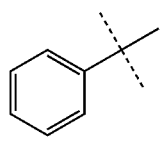

may optionally be substituted with one or more substituents selected from the group consisting of cyano, halo, alkyl and alkoxy. In a further embodiment, the alkyl is $C_1$-$C_4$ alkyl. In another further embodiment, the alkoxy is $C_1$-$C_4$ alkoxy.

In some embodiments, each of $R^2$ and $R^3$ is independently alkyl and $R^4$ is cyano, fluoroalkyl, sulfonamidyl, sulfinyl, sulfonyl, sulfoximinyl or fluoroalkylsulfonyl.

In some embodiments, $R^3$ is —CH$_2$OH. In a further embodiment, $R^4$ is cyano, fluoroalkyl, sulfonamidyl, sulfinyl, sulfonyl, sulfoximinyl or fluoroalkylsulfonyl and $R^5$ is hydrogen. In still a further embodiment, $R^2$ is cyano, halo or alkyl.

In some embodiments, Z is S, CHR$^7$, NR$^8$ or absent; $R^1$ is phenyl or monocyclic heteroaryl; $R^2$ is nitro, halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$. In still a further embodiment, $R^5$ is hydrogen.

In some embodiments, Z is S, CHR$^7$, NR$^8$ or absent; $R^1$ is bicyclic heteroaryl; $R^2$ is nitro, halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl; and $R^5$ is hydrogen.

In some embodiments, Z is S, CHR$^7$, NR$^8$ or absent; $R^1$ is phenyl, monocyclic heteroaryl or bicyclic heteroaryl; $R^2$ is halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl; and $R^5$ is hydrogen.

In some embodiments, $R^2$ and $R^3$ together with the atoms to which they are attached form a 5- or 6-membered carbocycle with at least one sp$^3$ hybridized carbon; $R^4$ is cyano, fluoroalkyl, sulfonamidyl, sulfinyl, sulfonyl, sulfoximinyl or fluoroalkylsulfonyl; and $R^5$ is hydrogen. In a further embodiment, Z is S, CHR$^7$, NR$^8$ or absent; and $R^1$ is phenyl or monocyclic heteroaryl. In another further embodiment, Z is S, CHR$^7$, NR$^8$ or absent; and $R^1$ is bicyclic heteroaryl.

In some embodiments, X is N and Y is $CR^6$. In other embodiments, X is $CR^5$ and Y is N. In still other embodiments, X is N and Y is N. In yet other embodiments, X is $CR^5$ and Y is $CR^6$.

In some embodiments, Z is O. In some embodiments, Z is S. In further embodiments, Z is CHR$^7$. In yet other embodiments, Z is NR$^8$. In some embodiments, Z is absent.

In some embodiments, for a compound of Formula IV, Z is O; X is $CR^5$; Y is $CR^6$; $R^1$ is alkyl or cycloalkyl; and $R^4$ is cyano, fluoroalkyl, sulfonamidyl, sulfinyl, sulfonyl, sulfoximinyl or fluoroalkylsulfonyl. In some embodiments, Z is O; X is CH; Y is CH; $R^1$ is alkyl or cycloalkyl; and $R^4$ is cyano, fluoroalkyl, sulfonamidyl, sulfinyl, sulfonyl, sulfoximinyl or fluoroalkylsulfonyl. In some embodiments, Z is O; X is CH; Y is CH; $R^1$ is alkyl or cycloalkyl; and $R^4$ is sulfonyl or fluoroalkyl, such as $R^4$ is —S(=O)$_2$CH$_3$ or —CF$_3$.

In yet another aspect, the disclosure provides a compound of Formula IV-C:

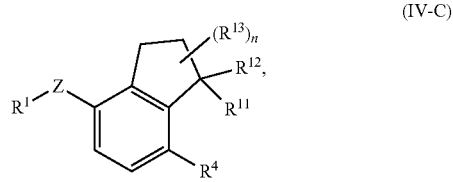

(IV-C)

or a pharmaceutically acceptable salt or prodrug thereof, wherein:

Z is O, S, CHR$^7$, NR$^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^7$ and $R^8$ are independently hydrogen, halo, hydroxy, cyano, alkyl or alkoxy;

$R^{11}$ is hydrogen, hydroxy, alkoxy or amino;

$R^{12}$ is hydrogen, alkyl, alkenyl or alkynyl; or $R^{11}$ and $R^{12}$ in combination form oxo or oxime;

each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and n is 0, 1, 2, 3 or 4, wherein for a compound or salt of Formula IV-C, when Z is O, $R^1$ is alkyl, heteroalkyl, cycloalkyl or heterocycloalkyl.

In some embodiments, for a compound of Formula IV-C, $R^1$ is further selected from alkyl, heteroalkyl, cycloalkyl, cycloalkenyl, and heterocycloalkyl.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

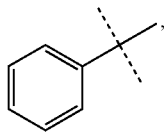

wherein the aryl ring is optionally substituted with one or more substituents selected from the group consisting of cyano, halo, alkyl and alkoxy. In another further embodiment, $R^1$ is

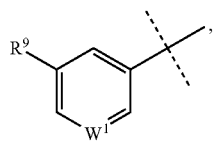

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

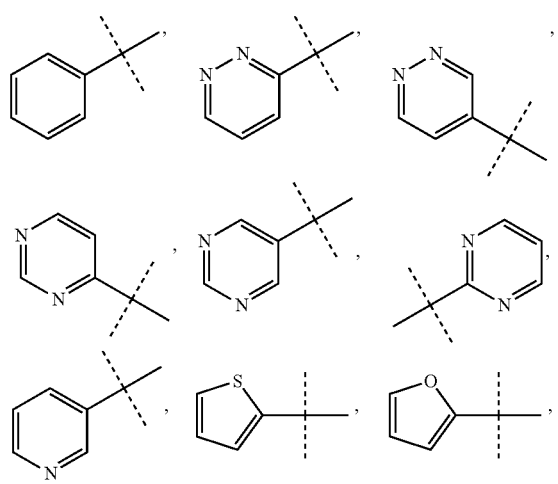

-continued

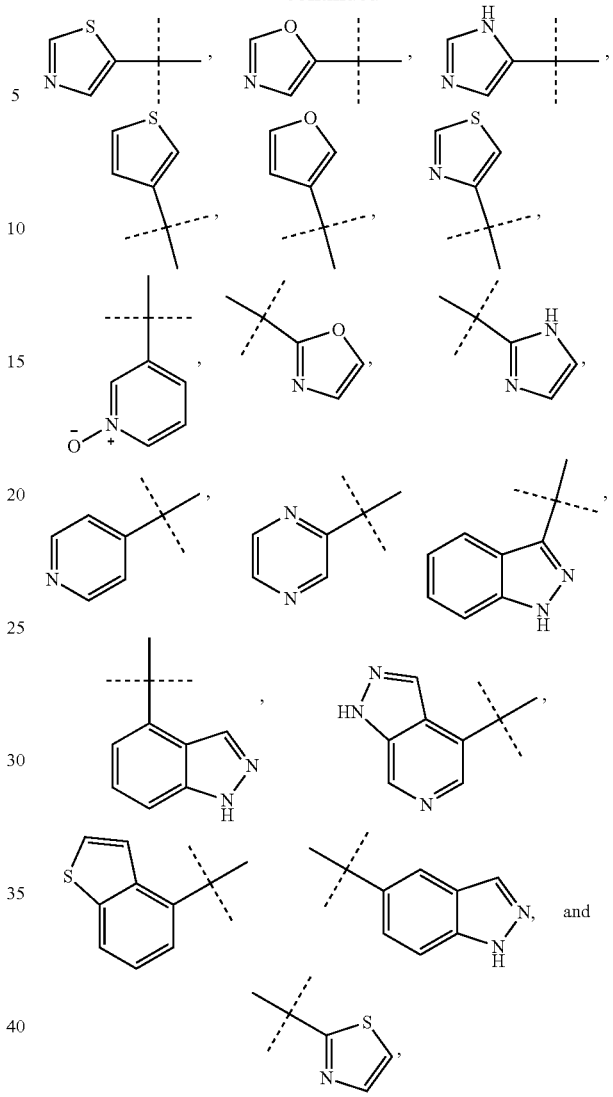

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

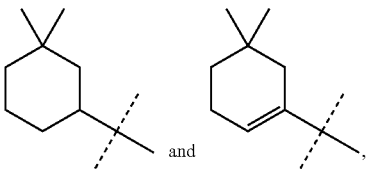

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

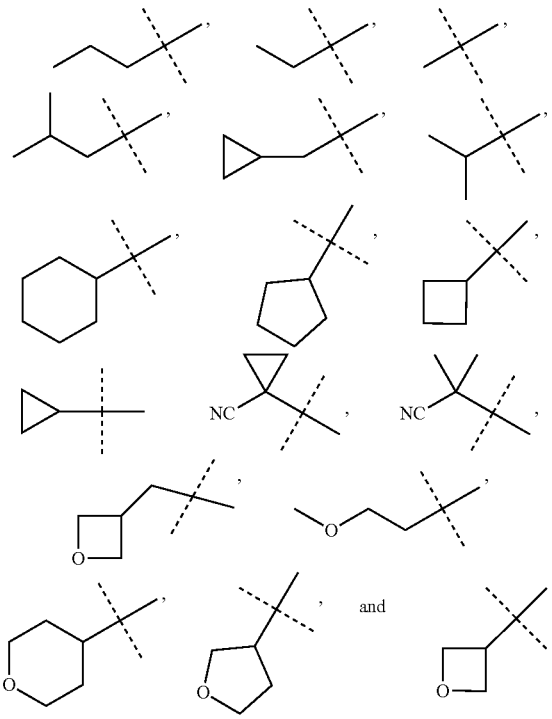

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, one R$^a$ is hydrogen and the other R$^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy or amino. In a further embodiment, $R^{11}$ is hydroxy. In another further embodiment, $R^{11}$ is amino.

In some embodiments, $R^{12}$ is hydrogen. In some other embodiments, $R^{12}$ is alkyl or alkenyl.

In some embodiments, $R^{13}$ is fluoro. In a further embodiment, n is 1, 2 or 3. In a further embodiment, two $R^{13}$s in combination form oxo, oxime or methylene. In still further embodiments, two $R^{13}$s and the carbon atom(s) to which they are attached form a 3- to 8-membered cycloalkyl or heterocycloalkyl moiety.

In some embodiments, Z is S, CHR$^7$, NR$^8$ or absent; $R^1$ is monocyclic aryl or monocyclic heteroaryl; and $R^{11}$ is hydroxy or amino. In a further embodiment, $R^{13}$ is fluoro. In still a further embodiment, n is 1, 2 or 3.

In some embodiments, Z is S, CHR$^7$, NR$^8$ or absent; $R^1$ is phenyl or monocyclic heteroaryl; $R^{11}$ is hydroxy or amino; $R^{13}$ is fluoro; n is 1, 2 or 3; and $R^5$ is hydrogen.

In some embodiments, Z is S, CHR$^7$, NR$^8$ or absent; $R^1$ is bicyclic heteroaryl; and $R^{11}$ is hydroxy or amino. In a further embodiment, $R^{13}$ is fluoro. In still a further embodiment, n is 1, 2 or 3.

In some embodiments, Z is S, CHR$^7$, NR$^8$ or absent; $R^1$ is bicyclic heteroaryl; $R^{11}$ is hydroxy or amino; $R^{13}$ is fluoro; n is 1, 2 or 3; and $R^5$ is hydrogen.

In some embodiments, $R^4$ is cyano, fluoroalkyl, sulfonamidyl, sulfinyl, sulfonyl, sulfoximinyl or fluoroalkylsulfonyl, and $R^{11}$ is hydroxy or amino. In a further embodiment, $R^{12}$ is hydrogen. In another further embodiment, $R^{13}$ is fluoro. In still a further embodiment, n is 1, 2 or 3.

In some embodiments, $R^4$ is cyano, fluoroalkyl, sulfonamidyl, sulfinyl, sulfonyl, sulfoximinyl or fluoroalkylsulfonyl; $R^{11}$ is hydroxy or amino; $R^{13}$ is fluoro; n is 1, 2 or 3; and $R^5$ is hydrogen. In a further embodiment, $R^{12}$ is hydrogen.

In some embodiments $R^{11}$ is hydroxy or amino and $R^{12}$ is hydrogen. In a further embodiment, $R^{13}$ is fluoro. In still a further embodiment, n is 1, 2 or 3.

In some embodiments $R^{11}$ is hydroxy or amino, $R^{12}$ is hydrogen, $R^{13}$ is fluoro, n is 1, 2 or 3, and $R^5$ is hydrogen.

In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^4$ is fluoroalkyl; n is 0, 1, 2 or 3; $R^{11}$ is hydroxy; and $R^{12}$ is hydrogen.

In some embodiments, $R^4$ is sulfonyl or fluoroalkylsulfonyl; n is 0, 1, 2 or 3; $R^{11}$ is hydroxy; and $R^{12}$ is hydrogen.

In some embodiments, Z is O. In some embodiments, Z is S. In further embodiments, Z is CHR$^7$. In yet other embodiments, Z is NR$^8$. In some embodiments, Z is absent.

In some embodiments, for a compound of Formula IV-C, Z is O; $R^1$ is alkyl or cycloalkyl; $R^4$ is cyano, fluoroalkyl, sulfonamidyl, sulfinyl, sulfonyl, sulfoximinyl or fluoroalkylsulfonyl; $R^{11}$ is hydroxy; $R^{12}$ is hydrogen; and $R^{13}$ is fluoro. In some embodiments, Z is O; $R^1$ is alkyl or cycloalkyl; $R^4$ is sulfonyl or fluoroalkyl, such as $R^4$ is —S(=O)$_2$CH$_3$ or —CF$_3$; $R^1$ is hydroxy; $R^{12}$ is hydrogen; and $R^{13}$ is fluoro.

In still another aspect, the disclosure provides a compound of Formula IV-D, IV-E, IV-F or IV-G:

IV-D
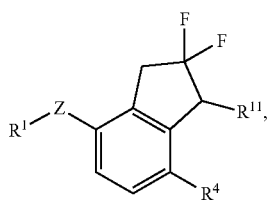

IV-E
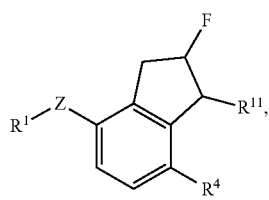

IV-F
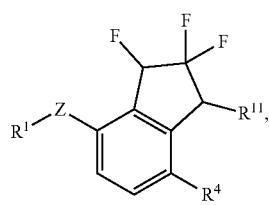

IV-G
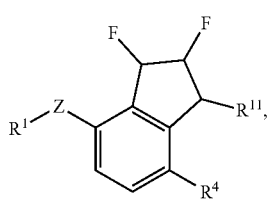

or a pharmaceutically acceptable salt or prodrug thereof, wherein:
Z is O, S, CHR$^7$, NR$^8$ or absent;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^7$ and $R^8$ are independently hydrogen, halo, hydroxy, cyano, alkyl or alkoxy; and
$R^{11}$ is hydrogen, hydroxy, alkoxy or amino,
wherein for a compound or salt of Formula IV-D, IV-E, IV-F or IV-G, when Z is O, $R^1$ is alkyl, heteroalkyl, cycloalkyl or heterocycloalkyl.

In some embodiments, for a compound of Formula IV-D, IV-E, IV-F, or IV-G, $R^1$ is further selected from alkyl, heteroalkyl, cycloalkyl, cycloalkenyl, and heterocycloalkyl.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

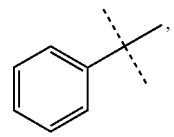

wherein the aryl ring is optionally substituted with one or more substituents selected from the group consisting of cyano, halo, alkyl and alkoxy. In another further embodiment, $R^1$ is

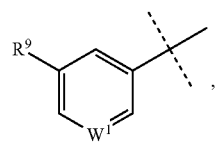

wherein $W^1$ is N or CR$^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl having at least one N atom.

In some embodiments, $R^1$ is selected from the group consisting of:

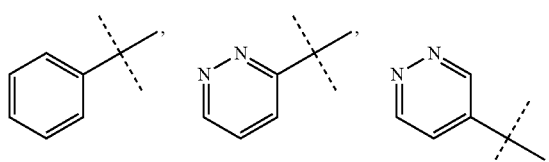

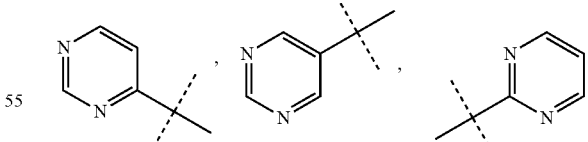

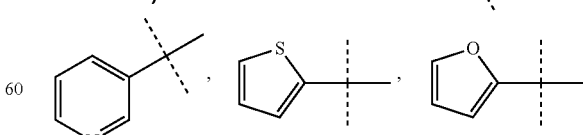

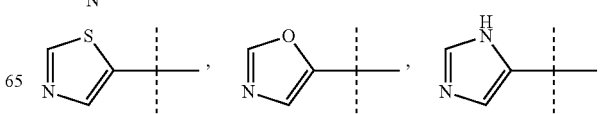

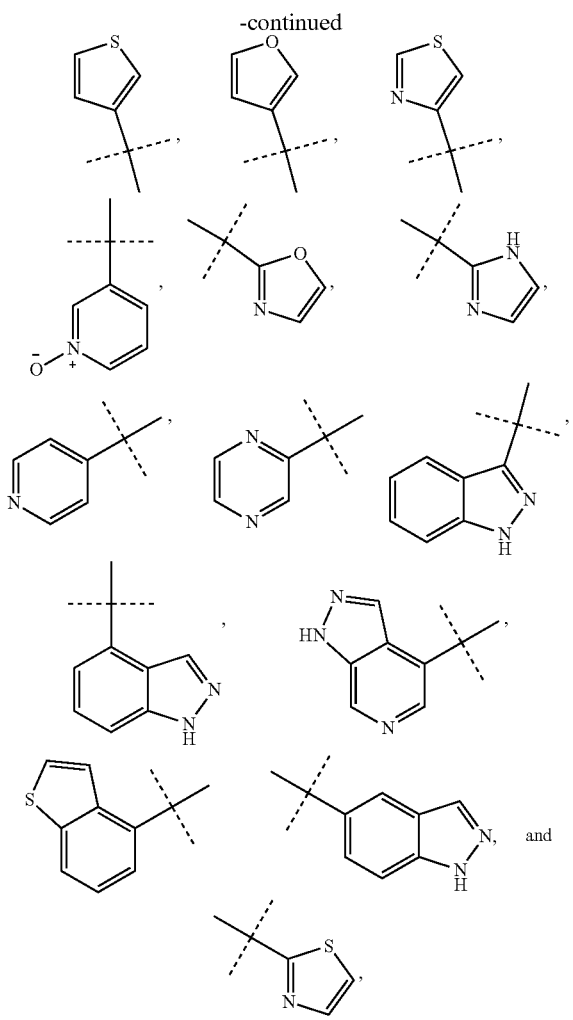

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

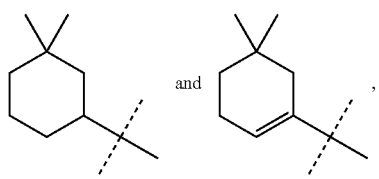

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano, and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

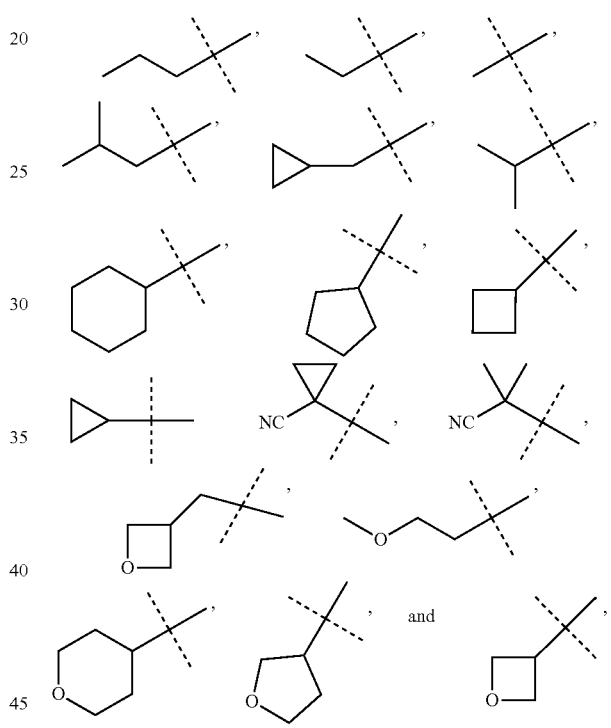

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N($R^a$)$_2$, wherein each $R^a$ is independently hydrogen, alkyl, heteroalkyl, cycloalkyl or heterocycloalkyl, and at least one $R^a$ is hydrogen. In another further embodiment, both $R^a$s are hydrogen. In a further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, Z is S, CHR$^7$, NR$^8$ or absent; $R^1$ is phenyl or monocyclic heteroaryl; and $R^{11}$ is hydroxy or amino.

In some embodiments, Z is S, CHR$^7$, NR$^8$ or absent; $R^1$ is bicyclic heteroaryl; and $R^{11}$ is hydroxy or amino.

In some embodiments, Z is S, CHR$^7$, NR$^8$ or absent; $R^1$ is bicyclic heteroaryl; and $R^4$ is cyano, fluoroalkyl, sulfinyl, sulfonamidyl, sulfonyl or sulfoximinyl. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments Z is S, CHR$^7$, NR$^8$ or absent; $R^1$ is bicyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N-CN)CF$_3$.

In some embodiments, Z is S, CHR$^7$, NR$^8$ or absent; $R^1$ is phenyl or monocyclic heteroaryl; and $R^4$ is cyano, fluoroalkyl, sulfinyl, sulfonamidyl, sulfonyl or sulfoximinyl. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, Z is S, CHR$^7$, NR$^8$ or absent; $R^1$ is phenyl or monocyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, Z is O. In some embodiments, Z is S. In further embodiments, Z is CHR$^7$. In yet other embodiments, Z is NR$^8$. In some embodiments, Z is absent.

In some embodiments, for a compound of Formula IV-D, IV-E, IV-F or IV-G, Z is O; $R^1$ is alkyl or cycloalkyl; $R^4$ is cyano, fluoroalkyl, sulfonamidyl, sulfinyl, sulfonyl, sulfoximinyl or fluoroalkylsulfonyl; and $R^{11}$ is hydroxy. In some embodiments, Z is O; $R^1$ is alkyl or cycloalkyl; $R^4$ is sulfonyl or fluoroalkyl, such as $R^4$ is —S(=O)$_2$CH$_3$ or —CF$_3$; and $R^{11}$ is hydroxy.

In a further aspect, the disclosure provides a compound of Formula IV-H, IV-I, IV-J or IV-K:

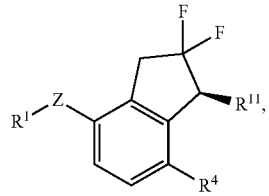

IV-H

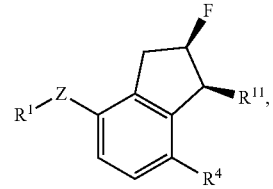

IV-I

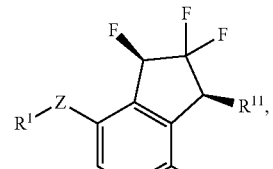

IV-J

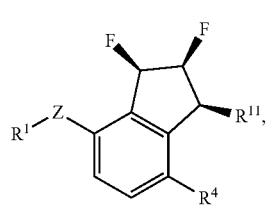

IV-K or a pharmaceutically acceptable salt or prodrug thereof, wherein:

Z is O, S, CHR$^7$, NR$^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^7$ and $R^8$ are independently hydrogen, halo, hydroxy, cyano, alkyl or alkoxy; and $R_{11}$ is hydroxy or amino, wherein for a compound or salt of Formula IV-H, IV-I, IV-J or IV-K, when Z is O, $R^1$ is alkyl, heteroalkyl, cycloalkyl or heterocycloalkyl.

In some embodiments, for a compound of Formula IV-H, IV-I, IV-J or IV-K, $R^1$ is further selected from alkyl, heteroalkyl, cycloalkyl, cycloalkenyl, and heterocycloalkyl.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

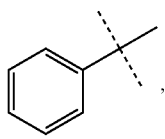

wherein the aryl ring is optionally substituted with one or more substituents selected from the group consisting of cyano, halo, alkyl and alkoxy. In another further embodiment, $R^1$ is

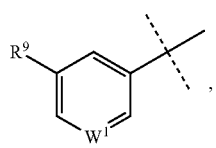

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

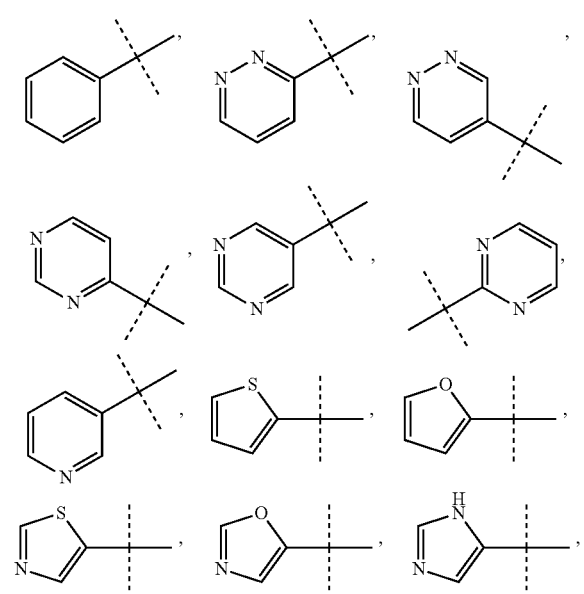

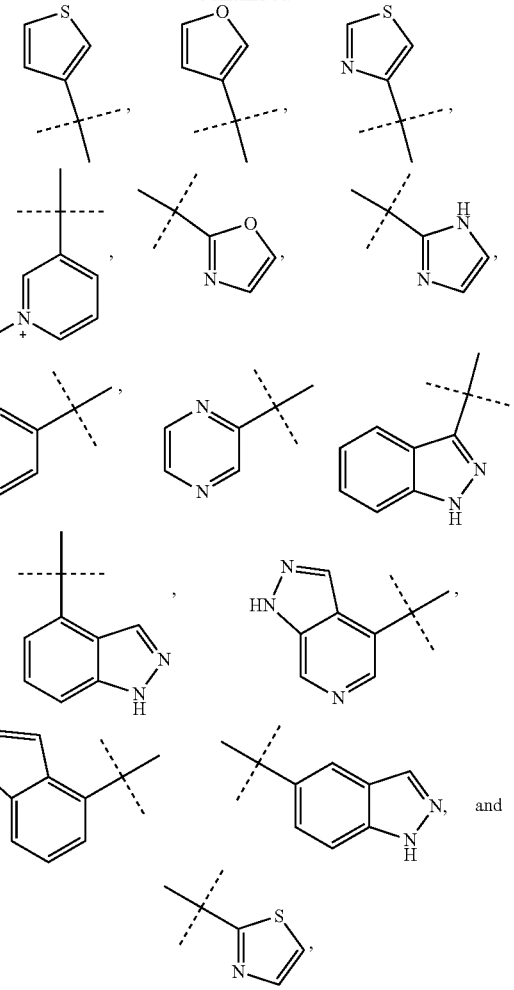

and the rings specified for $R^1$ may optionally be substitute with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiment, $R^1$ is selected from the group consisting of:

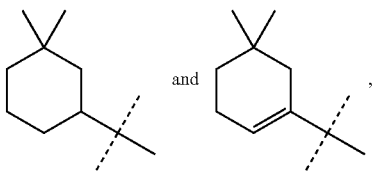

and the rings specified for $R^1$ may optionally be substitute with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

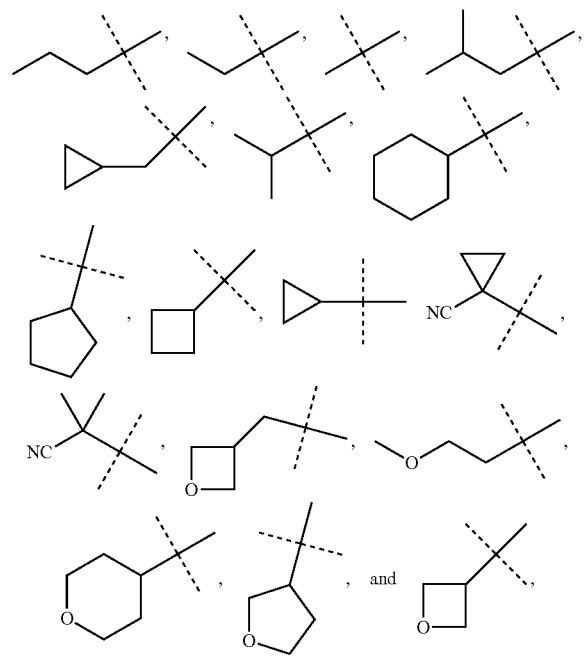

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$$R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=N$R^b$)$R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N($R^a$)$_2$, wherein each $R^a$ is independently hydrogen, alkyl, heteroalkyl, cycloalkyl or heterocycloalkyl, and at least one $R^a$ is hydrogen. In another further embodiment, both $R^a$s are hydrogen. In a further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, Z is S, CHR$^7$, NR$^8$ or absent; $R^1$ is phenyl or monocyclic heteroaryl; and $R^{11}$ is hydroxy or amino.

In some embodiments, Z is S, CHR$^7$, NR$^8$ or absent; $R^1$ is bicyclic heteroaryl; and $R^{11}$ is hydroxy or amino.

In some embodiments, Z is S, CHR$^7$, NR$^8$ or absent; $R^1$ is bicyclic heteroaryl; and $R^4$ is cyano, fluoroalkyl, sulfinyl, sulfonamidyl, sulfonyl or sulfoximinyl. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments Z is S, CHR$^7$, NR$^8$ or absent; $R^1$ is bicyclic heteroaryl; $R^4$ is cyano, fluoroalkyl, sulfinyl, sulfonamidyl, sulfonyl or sulfoximinyl; and $R^{11}$ is hydroxy or amino. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N-CN)CF$_3$.

In some embodiments, Z is S, CHR$^7$, NR$^8$ or absent; $R^1$ is phenyl or monocyclic heteroaryl and $R^4$ is cyano, fluoroalkyl, sulfinyl, sulfonamidyl, sulfonyl or sulfoximinyl. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)

(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, Z is S, CHR$^7$, NR$^8$ or absent; R$^1$ is phenyl or monocyclic heteroaryl; R$^4$ is cyano, fluoroalkyl, sulfinyl, sulfonamidyl, sulfonyl or sulfoximinyl; and R$^{11}$ is hydroxy or amino. In a further embodiment, R$^{11}$ is hydroxy. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, Z is O. In some embodiments, Z is S. In further embodiments, Z is CHR$^7$. In yet other embodiments, Z is NR$^8$. In some embodiments, Z is absent.

In some embodiments, for a compound of Formula IV-H, IV-I, IV-J or IV-K, Z is O; R$^1$ is alkyl or cycloalkyl; R$^4$ is cyano, fluoroalkyl, sulfonamidyl, sulfinyl, sulfonyl, sulfoximinyl or fluoroalkylsulfonyl; and R$^{11}$ is hydroxy. In some embodiments, Z is O; R$^1$ is alkyl or cycloalkyl; R$^4$ is sulfonyl or fluoroalkyl, such as R$^4$ is —S(=O)$_2$CH$_3$ or —CF$_3$; and R$^{11}$ is hydroxy.

In some embodiments, a compound of any one of Formulae IV-H-IV-K may have an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae I-H-I-K may have an enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99%.

In another aspect, the present disclosure provides a compound or pharmaceutically acceptable salt or prodrug thereof, selected from the group consisting of the compounds given in Table 1.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-19, the steps in some cases may be performed in a different order than the order shown in Schemes 1-19. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

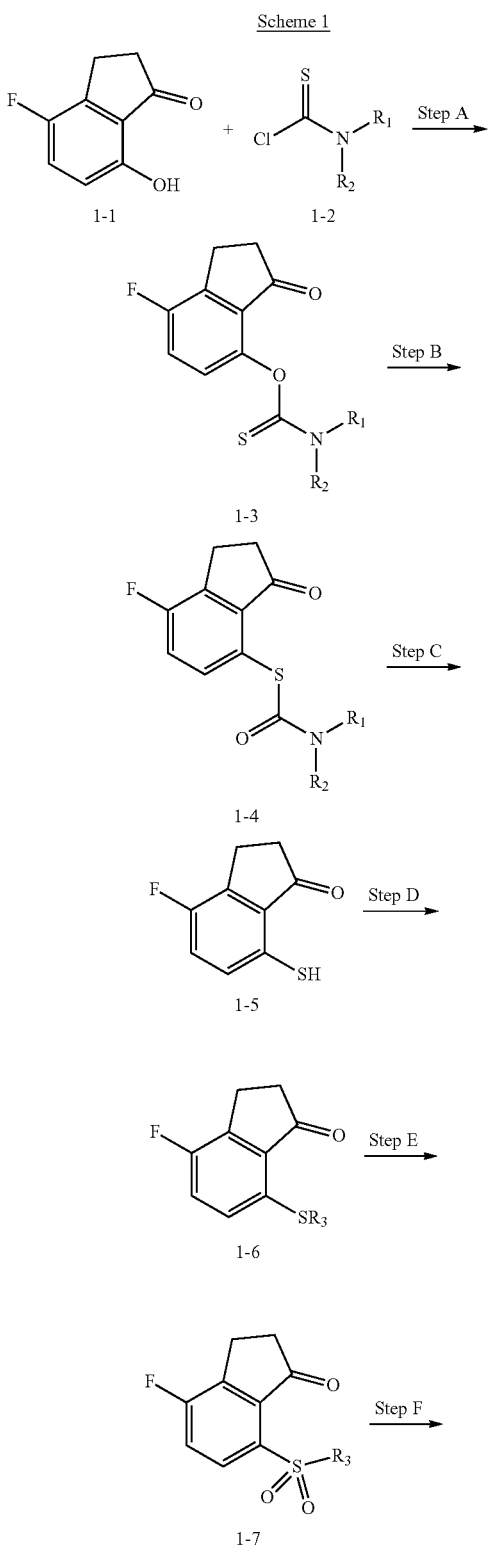

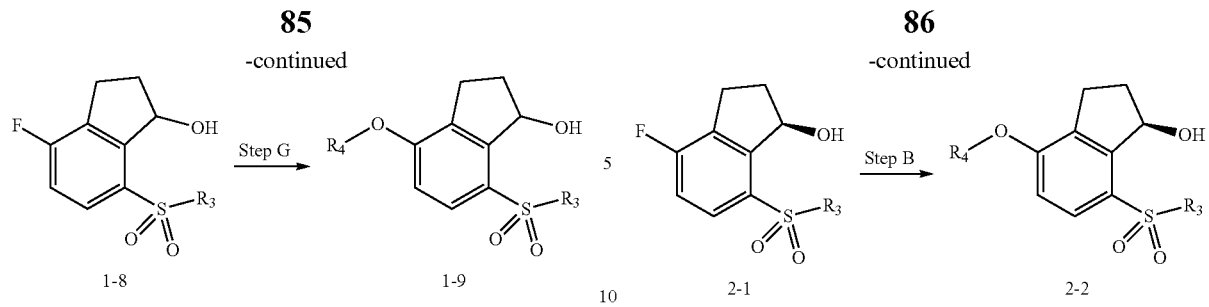

In some embodiments, compounds of Formula 1-9 are prepared according to steps outlined in Scheme 1. The synthesis starts with phenol 1-1. Reaction of 1-1 with chloride 1-2 (wherein $R_1$ and $R_2$ are independently alkyl) provides intermediate 1-3. The reaction may be carried out in a suitable organic solvent in the presence of a base. Suitable bases for the reaction include, but are not limited to, organic bases, for example, triethylamine, N,N-diisopropylethylamine, 1,4-diazabicyclo[2.2.2]octane, and inorganic bases, for example, sodium hydroxide, cesium carbonate, cesium bicarbonate, sodium carbonate, and potassium carbonate. Compound 1-3 is then subjected to a rearrangement reaction to give compound 1-4. Elevated temperature may be needed for the rearrangement to occur. The temperature may be in a range of 100° C. to 300° C. In some embodiments, the temperature is in a range of 180° C. to 240° C. Hydrolysis of compound 1-4 provides thiophenol 1-5, which is alkylated to provide compound 1-6. A variety of alkyl groups may be introduced. In some embodiments, $R_3$ is a C1-C4 alkyl. In a further embodiment, $R_3$ is a C1-C4 fluoroalkyl. Oxidation of compound 1-6 may be accomplished by a variety of methods known in the art, including but are not limited to, $RuCl_3$ catalyzed oxidation in the presence of $NaIO_4$, oxidation with m-chloroperbenzoic acid (mCPBA) and oxidation with Oxone®. The ketone in 1-7 is then reduced to give alcohol 1-8, which then undergoes a nucleophilic aromatic substitution (SNAr) reaction with a suitable substrate $R_4OH$ (wherein $R_4$ is alkyl, cycloalkyl, or heterocycloalkyl) to give compounds of Formula 1-9. Temperature for carrying out the SNAr reaction may depend on the reactivity of both $R_4OH$ and/or compound 1-8. The reaction may be carried out in a temperature range from room temperature to 200° C. In some embodiments, the temperature range is from room temperature to 60° C. In some other embodiments, the temperature range is from 60° C. to 100° C. In some other embodiments, the temperature range is from 100° C. to 200° C.

Scheme 2

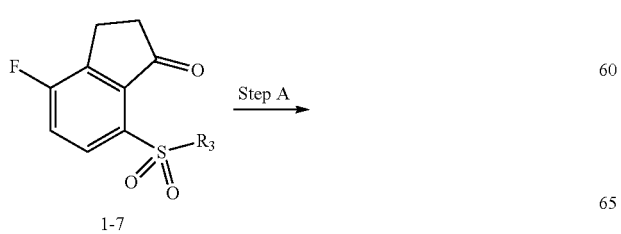

In some other embodiments, compounds of Formula 1-9 are prepared asymmetrically to give compounds of Formula 2-2 (Scheme 2). For example, direct asymmetric reduction of ketone 1-7 (Step A) may be accomplished chemically or enzymatically. For a recent review on enzymatic reduction of ketones, see Moore, et al. *Acc. Chem. Res.* 40: 1412-1419, 2007. Examples of chemical asymmetric reduction of ketone include, but are not limited to, Corey-Bakshi-Shibata (CBS) reduction, asymmetric hydrogenation, and asymmetric transfer hydrogenation. In some embodiments, the asymmetric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R, R configuration):

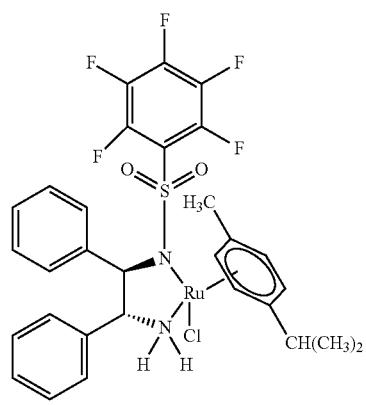

RuCl(FsDPEN)(p-cymene)

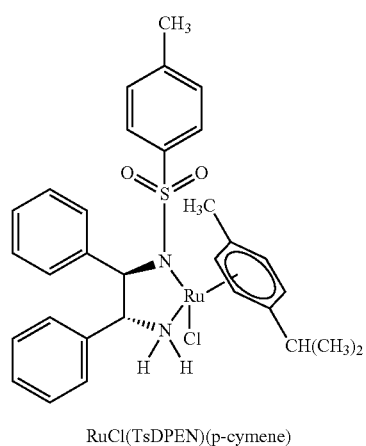

RuCl(TsDPEN)(p-cymene)

-continued

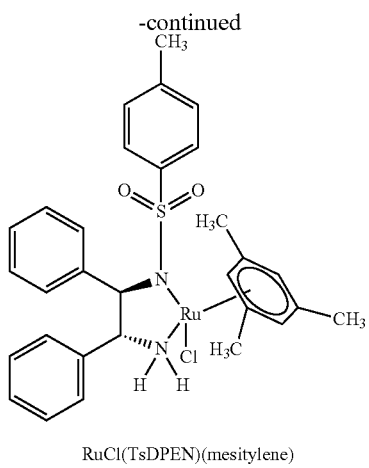

RuCl(TsDPEN)(mesitylene)

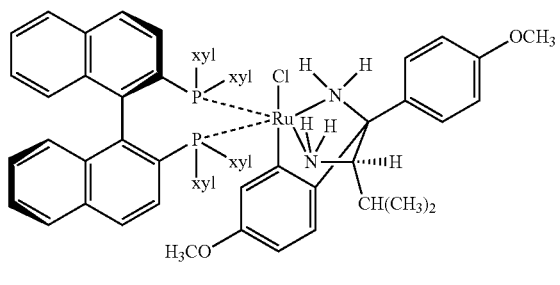

RUCY™

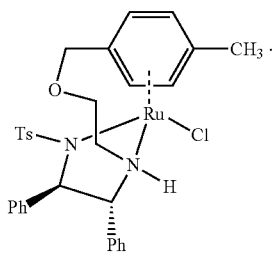

Ts-DENEB

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration. The chiral alcohol 2-1 can be coupled with a suitable substrate to give compounds of Formula 2-2 without significant loss of enantiomeric excess. The loss of enantiomeric excess (ee) in the coupling step for 2-2 may be less than about 1%, less than about 2%, less than about 3%, less than about 4%, less than about 5%, less than about 6%, or less than about 8%.

Scheme 3

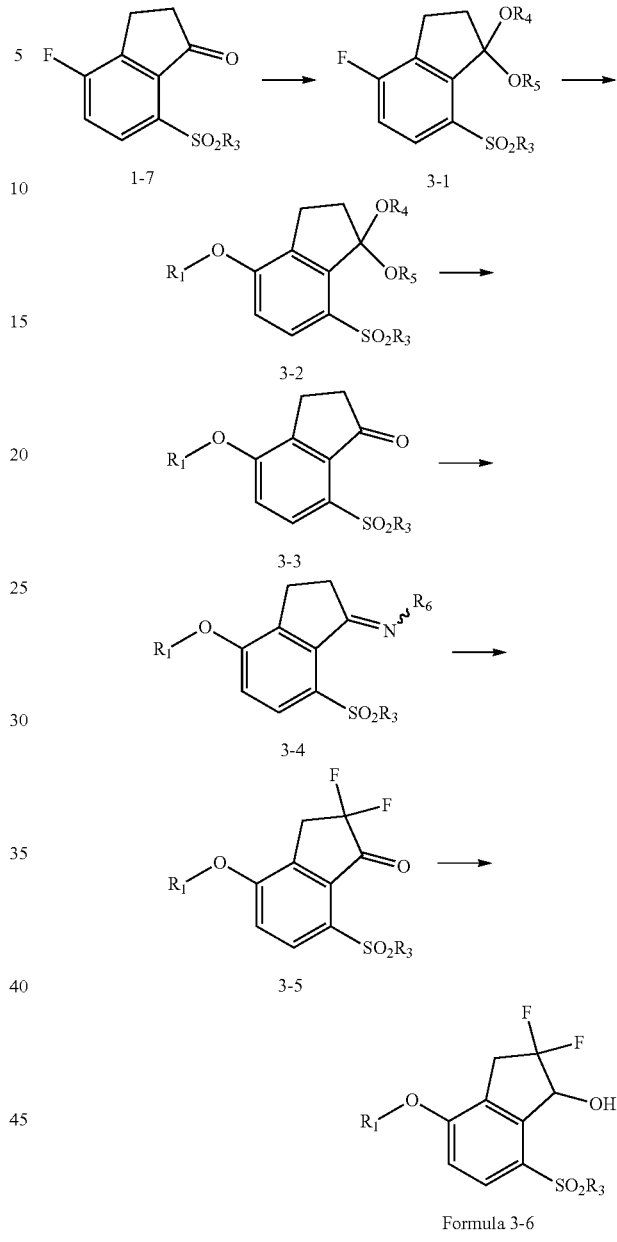

In some embodiments, compounds of Formula 3-6 are prepared according to Scheme 3. The ketone in 1-7 is protected as a ketal to give compound 3-1, wherein each of $R_4$ and $R_5$ is independently an alkyl group. In addition, $R_4$ and $R_5$ may optionally be connected to form a cyclic ketal. Exemplary structures of ketal 3-1 include, but are not limited to, the following:

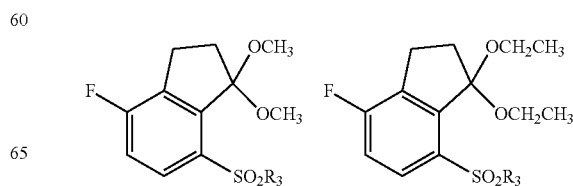

-continued

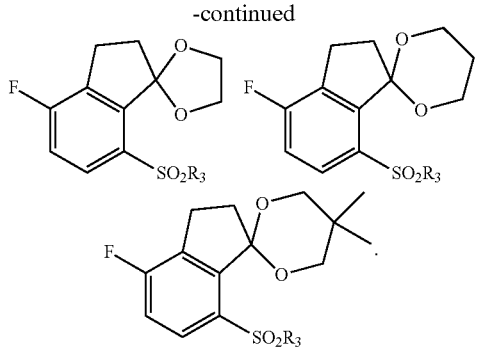

Ketal 3-1 and a suitable substrate R₁OH (wherein R₁ is alkyl, cycloalkyl, or heterocycloalkyl) may undergo a nucleophilic aromatic substitution reaction (SNAr) to give alkyl aryl ether 3-2. Similarly to the SNAr reaction described in Step G of Scheme 1, the reaction temperature may depend on the reactivity of ketal 3-1 and/or R₁OH. Following deprotection of the ketal in 3-2, the resulting ketone 3-3 is condensed with an amine to form imine 3-4, wherein R₆ is alkyl. The imine functional group in 3-4 may exist as a mixture of E, Z isomers. Fluorination of 3-4 can be accomplished with a fluorinating reagent, for example, 1-(chloromethyl)-4-fluoro-1,4-diazoniabicyclo[2.2.2]octane ditetrafluoroborate, to give difluoroketone 3-5 after acid hydrolysis. Finally, reduction of the ketone in 3-5 with a hydride donor gives compounds of Formula 3-6.

Scheme 4

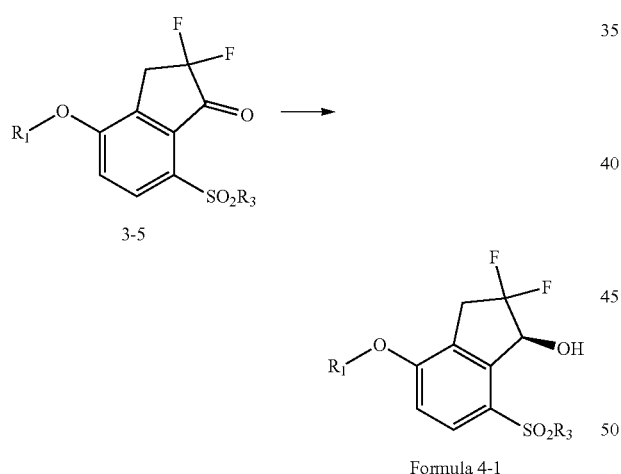

Formula 4-1

Similarly, compounds of Formula 4-1 (wherein R₁ is alkyl, cycloalkyl, or heterocycloalkyl) can be prepared in asymmetric fashion by asymmetric reduction as outlined in Scheme 2. In some embodiments, the asymmetric reduction gives compounds of Formula 4-1 with an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or even higher. The enantiomeric excess of compounds of Formulae 2-2 and 4-1 may be determined by chiral HPLC or Mosher ester analysis. For determination of ee with Mosher ester, see Hoye, et al. *Natural Protocol*, 2: 2451, 2007.

Scheme 5

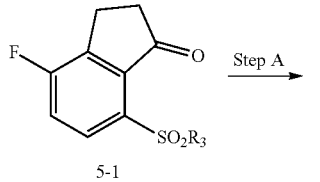
5-1

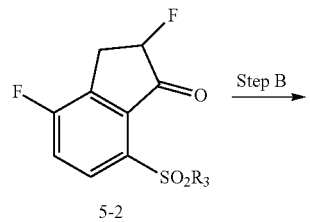
5-2

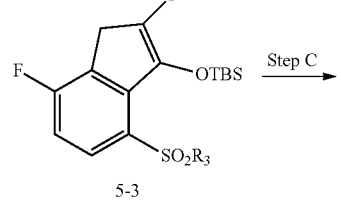
5-3

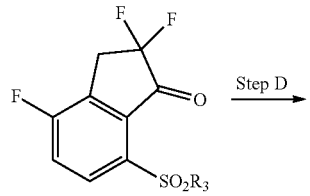
5-4

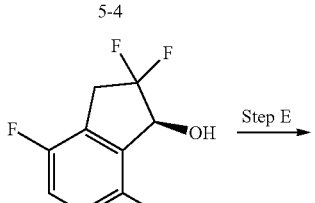
5-5

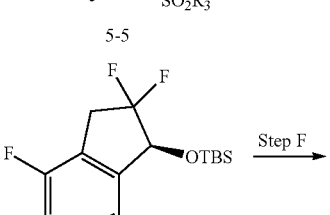
5-6

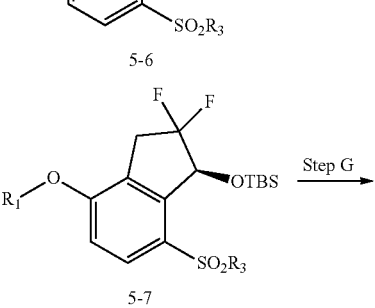
5-7

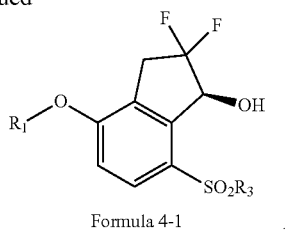

Formula 4-1

Alternatively, compounds of Formula 4-1 are prepared according to Scheme 5. Ketone 5-1 is fluorinated to give monofluoroketone 5-2, which is then converted to a silylenol ether, e.g., TBS enol ether 5-3. Other silyl protecting groups, for example, triisopropylsilyl or diphenyl-t-butylsilyl, may also be used. The resulting enol ether is further fluorinated to give difluoroketone 5-4, which undergoes an asymmetric reduction, such as asymmetric transfer hydrogenation as described herein, to give chiral alcohol 5-5. Protection of the hydroxy moiety, followed by SNAr reaction and then deprotection provides compounds of Formula 4-1.

Scheme 6

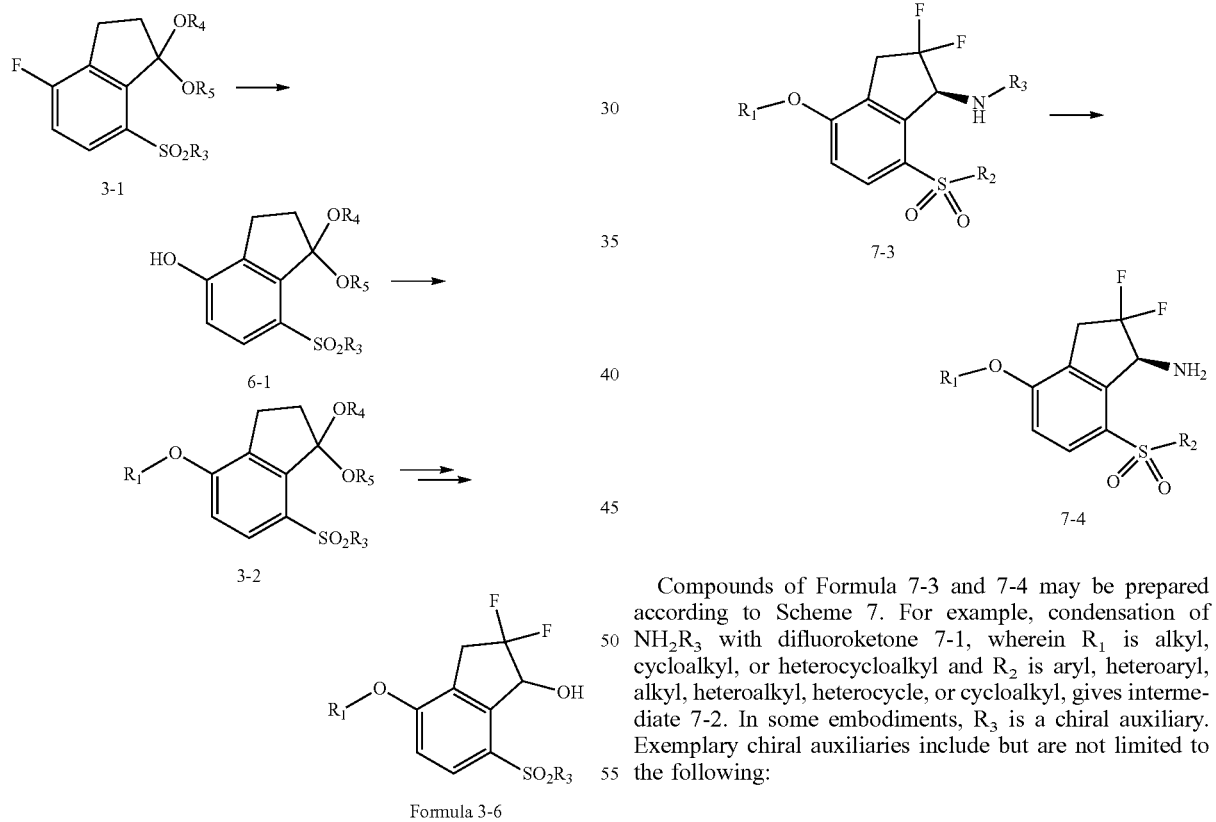

Formula 3-6

Alternatively, compounds of Formula 3-6 are prepared according to Scheme 6. Treatment of aryl fluoro 3-1 with a hydroxide source gives phenol 6-1. Suitable hydroxide sources include, but are not limited to, sodium hydroxide and potassium hydroxide. Suitable solvents for the reaction include, but are not limited to, DMSO, DMA, DMF or EtOH. Phenol 6-1 can react with an alkyl halide, cycloalkyl halide, or a heterocycloalkyl halide via an SN2 displacement reaction or an alcohol via a Mitsunobu reaction to give aryl alkyl ether 3-2, which can be converted to compounds of Formula 3-6 as described in Scheme 3.

Scheme 7

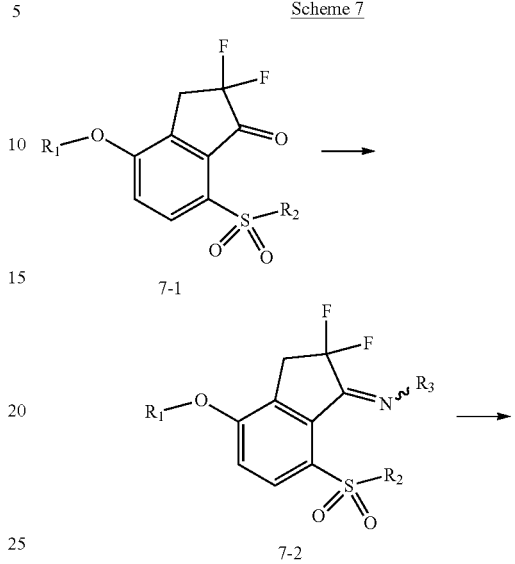

Compounds of Formula 7-3 and 7-4 may be prepared according to Scheme 7. For example, condensation of $NH_2R_3$ with difluoroketone 7-1, wherein $R_1$ is alkyl, cycloalkyl, or heterocycloalkyl and $R_2$ is aryl, heteroaryl, alkyl, heteroalkyl, heterocycle, or cycloalkyl, gives intermediate 7-2. In some embodiments, $R_3$ is a chiral auxiliary. Exemplary chiral auxiliaries include but are not limited to the following:

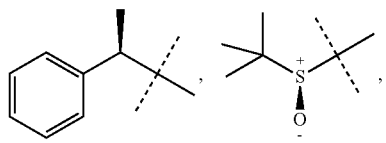

and enantiomers thereof. Hydride reduction of intermediate 7-2 yields 7-3. At this stage, the chiral auxiliary may be cleaved under appropriate conditions, e.g., hydrogenation or acid treatment, to give chiral secondary amine 7-4. In some other embodiments, when compounds of Formula 7-3 are desirable, wherein $R_3$ is not hydrogen, asymmetric hydrogenation or asymmetric transfer hydrogenation is applied on intermediate 7-2 to give compounds of Formula 7-3. For a review on asymmetric hydrogenation and asymmetric transfer hydrogenation, see Iwao Ojima ed. *Catalytic Asymmetric Synthesis*, Wiley-VCH, Inc., 2000, ISBN 0-471-29805-0.

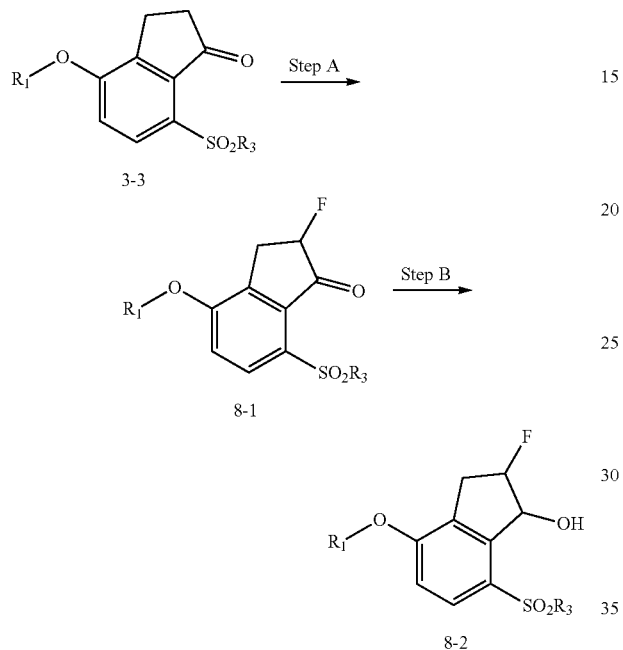

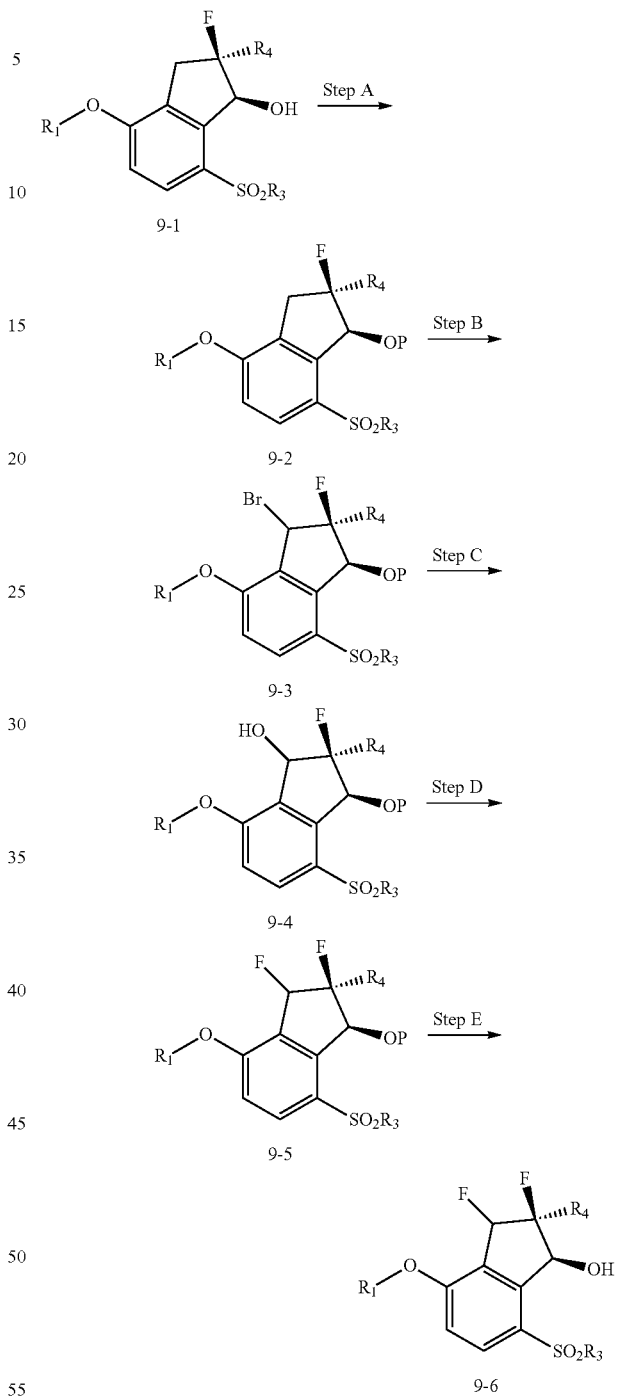

In some embodiments, compounds of Formula 8-2 are prepared according to Scheme 8, wherein $R_1$ is alkyl, cycloalkyl, or heterocycloalkyl. For example, ketones of Formula 3-3 are monofluorinated to give monofluoroketones of Formula 8-1. The monofluorination can be acheived with a variety of fluorinating reagents, e.g., N-Fluoro-o-benzenedisulfonimide, acetyl hypofluorite, Accufluor®, Selectfluor®, Selectfluor® II, or N-Fluorobenzenesulfonimide, in the presence or absence of a base. The compounds of Formula 8-1 are reduced to give compounds of Formula 8-2. In some cases, the reduction is highly diastereoselective to give compounds of Formula 8-2 with greater than 80%, greater than 82%, greater than 84%, greater than 86%, greater than 88%, greater than 90%, greater than 92%, greater than 94%, greater than 96%, or even greater than 96% diastereoselectivity. In some cases, the reduction is highly enantioselective to give compounds of Formula 8-2 with greater than 80%, greater than 82%, greater than 84%, greater than 86%, greater than 88%, greater than 90%, greater than 92%, greater than 94%, greater than 96%, or even greater than 96% enantioselectivity. Reduction conditions to achieve high enantioselectivity include, but are not limited to, asymmetric transfer hydrogenation and enzymatic reduction as described herein.

In some embodiments, compounds of Formula 9-6 are prepared according to Scheme 9, wherein $R_4$ is hydrogen, alkyl or fluoro and $R_1$ is alkyl, cycloalkyl, or heterocycloalkyl. The hydroxy group in compounds of Formula 9-1 may be protected with, e.g., acyl or methoxymethyl ether (MOM), to give compounds of Formula 9-2. Benzylic bromination in Step B may be carried out with a bromide source, e.g., N-bromosuccinimide, in the presence of a radical initiator, e.g., 2,2'-azobis(2-methylpropionitrile) (AIBN) or benzoyl peroxide. The bromide in compounds of Formula 9-3 can be replaced with a hydroxy group in a solvent comprising water in the presence of a silver salt, e.g., $Ag_2CO_3$ or $AgClO_4$ or $AgBF_4$. Finally, fluorination of the hydroxy group in Formula 9-4 followed by deprotection gives compounds of Formula 9-6. In some cases, direct benzylic oxidation may be used for converting compounds of Formula 9-2 to compounds of Formula 9-4, thus bypassing an intermediate bromination step.

Scheme 10

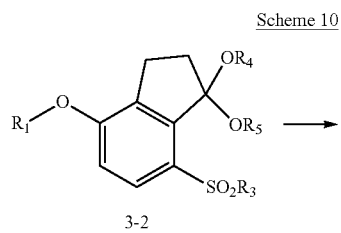

3-2

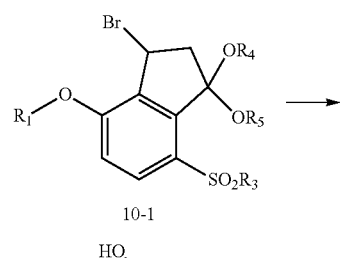

10-1

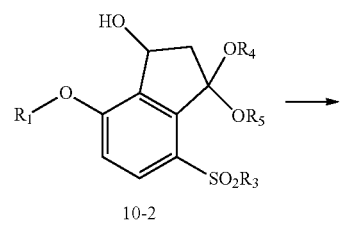

10-2

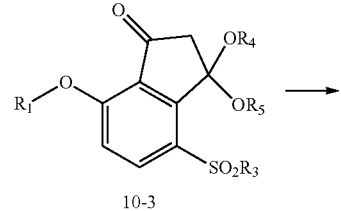

10-3

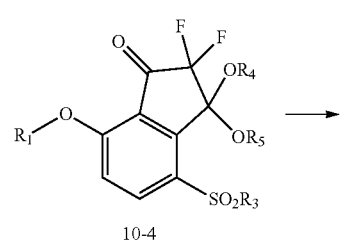

10-4

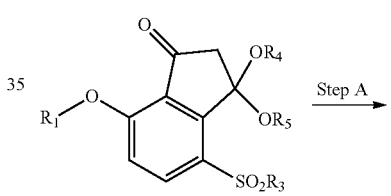

10-5

-continued

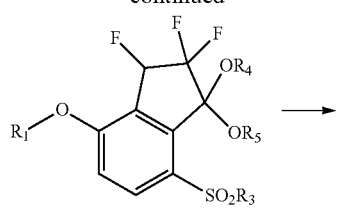

10-6

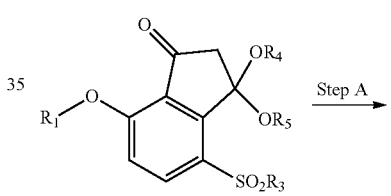

10-7

In some embodiments, compounds of Formula 10-7 are prepared according to Scheme 10, wherein $R_1$ is alkyl, cycloalkyl, or heterocycloalkyl. For example, compounds of Formula 10-3 may be prepared from compounds of Formula 3-2 following a similar sequence as outlined in Scheme 9. Further functional group manipulations lead to compounds of Formula 10-7.

Scheme 11

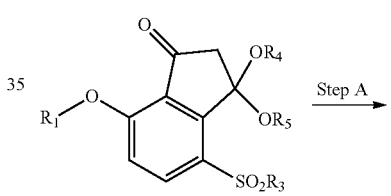

10-3

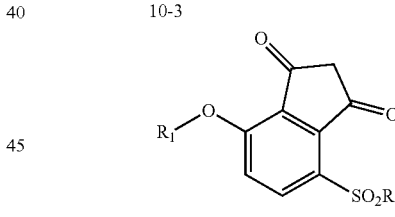

11-1

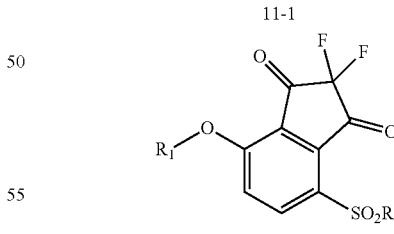

11-2

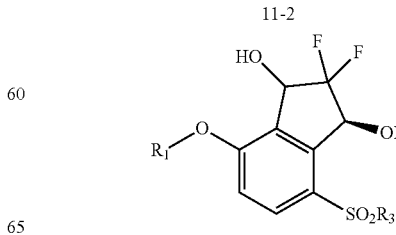

11-3

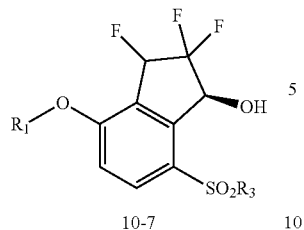

Alternatively, compounds of Formula 10-3 are deprotected to give diketone 11-1, which is fluorinated to give difluoro diketone 11-2. Asymmetric reduction of 11-2 provides diol 11-3. In some embodiments, one of the hydroxy groups is selectively fluorinated to give compounds of Formula 10-7.

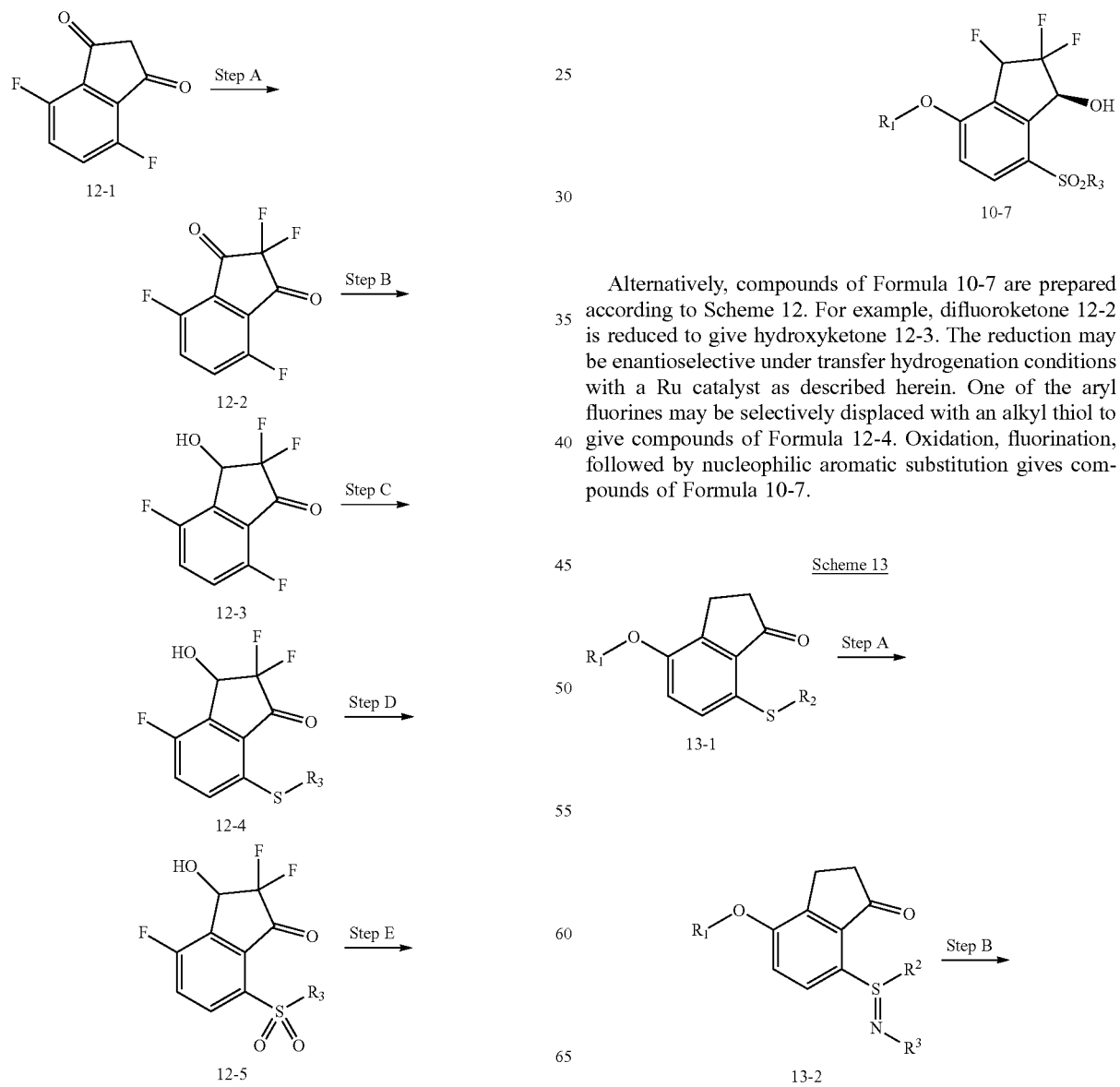

Alternatively, compounds of Formula 10-7 are prepared according to Scheme 12. For example, difluoroketone 12-2 is reduced to give hydroxyketone 12-3. The reduction may be enantioselective under transfer hydrogenation conditions with a Ru catalyst as described herein. One of the aryl fluorines may be selectively displaced with an alkyl thiol to give compounds of Formula 12-4. Oxidation, fluorination, followed by nucleophilic aromatic substitution gives compounds of Formula 10-7.

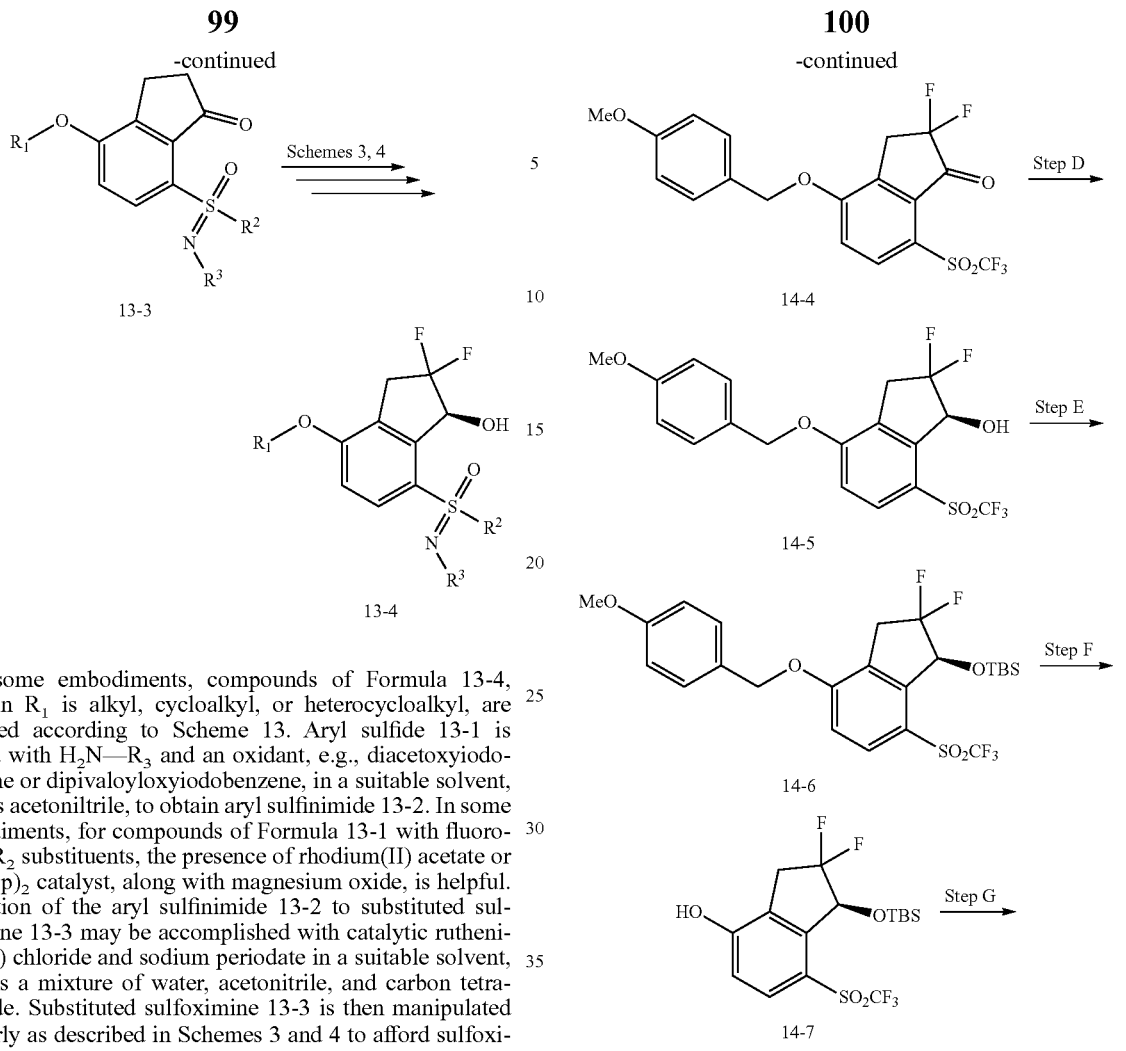

In some embodiments, compounds of Formula 13-4, wherein $R_1$ is alkyl, cycloalkyl, or heterocycloalkyl, are prepared according to Scheme 13. Aryl sulfide 13-1 is treated with $H_2N—R_3$ and an oxidant, e.g., diacetoxyiodobenzene or dipivaloyloxyiodobenzene, in a suitable solvent, such as acetonitrile, to obtain aryl sulfinimide 13-2. In some embodiments, for compounds of Formula 13-1 with fluoroalkyl $R_2$ substituents, the presence of rhodium(II) acetate or $Rh_2(esp)_2$ catalyst, along with magnesium oxide, is helpful. Oxidation of the aryl sulfinimide 13-2 to substituted sulfoximine 13-3 may be accomplished with catalytic ruthenium(III) chloride and sodium periodate in a suitable solvent, such as a mixture of water, acetonitrile, and carbon tetrachloride. Substituted sulfoximine 13-3 is then manipulated similarly as described in Schemes 3 and 4 to afford sulfoximines of Formula 13-4 as a diastereomeric mixture. The diastereomers may be separated by column chromatography.

In some embodiments, compounds of Formula 14-8 are prepared assorting to steps outlined in Scheme 14, wherein $R_3$ is alkyl. The synthesis starts with arylfluoride 14-1, wherein each of $R_1$ and $R_2$ is independently alkyl. In addition, $R_1$ and $R_2$ may optionally be connected to form a cyclic ketal. Exemplary structures of ketals include, but are not limited to, the following:

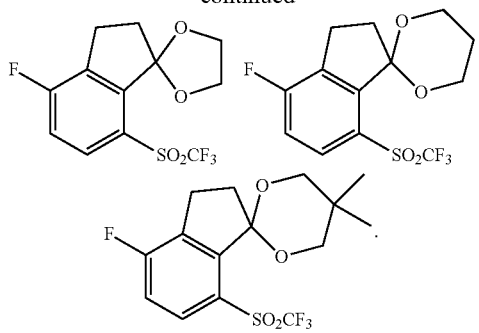

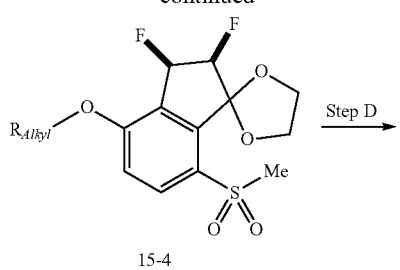

Compounds of Formula 14-1 and a suitable substrate, for example, p-methoxybenzyl alcohol, may undergo a nucleophilic aromatic substitution reaction (SNAr) to give benzyl ether 14-2. The reaction temperature of the SNAr reaction may depend on the reactivity of 14-1 and/or the solvent and base used. Following deprotection of the ketal in 14-2, the resulting ketone 14-3 is condensed with an amine to form an imine intermediate and then fluorinated with an appropriate fluorinating reagent, for example, 1-(chloromethyl)-4-fluoro-1,4-diazoniabicyclo[2.2.2]octane ditetrafluoroborate, to give difluoroketone 14-4 after acid hydrolysis. Asymmetric reduction of the ketone in 14-4 gives compounds of Formula 14-5. The hydroxy group in 14-5 can then be protected, for example, as a TBS ether, to give compound 14-6. Selective deprotection of the PMB ether in 14-6, followed by Mitsunobu reaction with an appropriate alcohol R₃OH and silyl deprotection, provides compounds of Formula 14-8.

Scheme 15

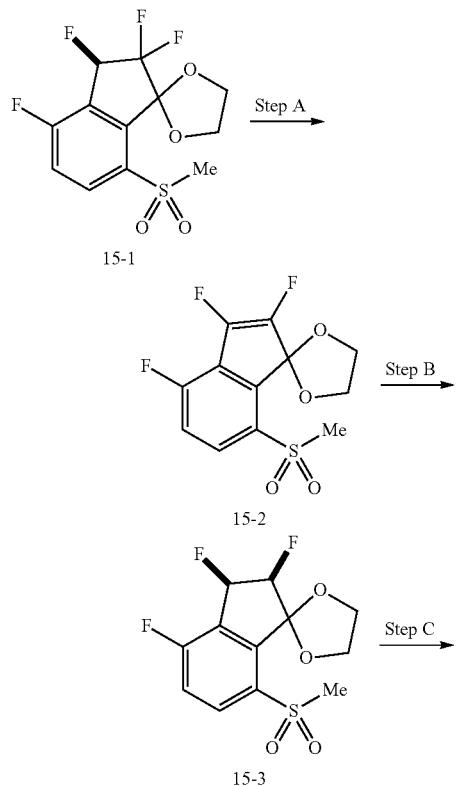

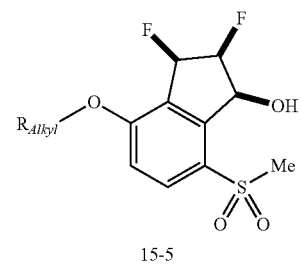

In some embodiments, compounds of Formula 15-5 are synthesized according to Scheme 15. For example, treatment of compound 15-1 with base can provide difluoroalkene 15-2. The amount of base may be about 1 equivalent to avoid byproduct formation. The olefin in 15-2 may be hydrogenated to give compound 15-3 with cis difluoro configuration. At this stage, an alkoxy group can be introduced by displacement of the aryl fluoride in 15-3 by an alcohol in the presence of a base. Finally, deprotection followed by reduction of the resulting ketone provides compounds of Formula 15-5. Intermediate 15-3 may be separated, for example, by chiral column chromatography, to give both enantiomers, each of which can be functionalized as outlined in Scheme 15 to provide either enantiomer of compounds of Formula 15-5.

Scheme 16

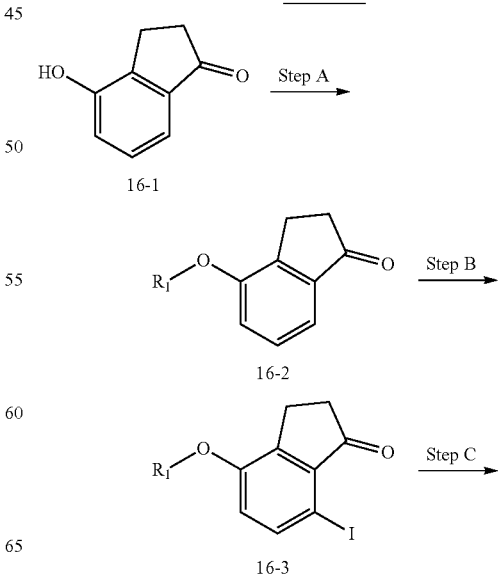

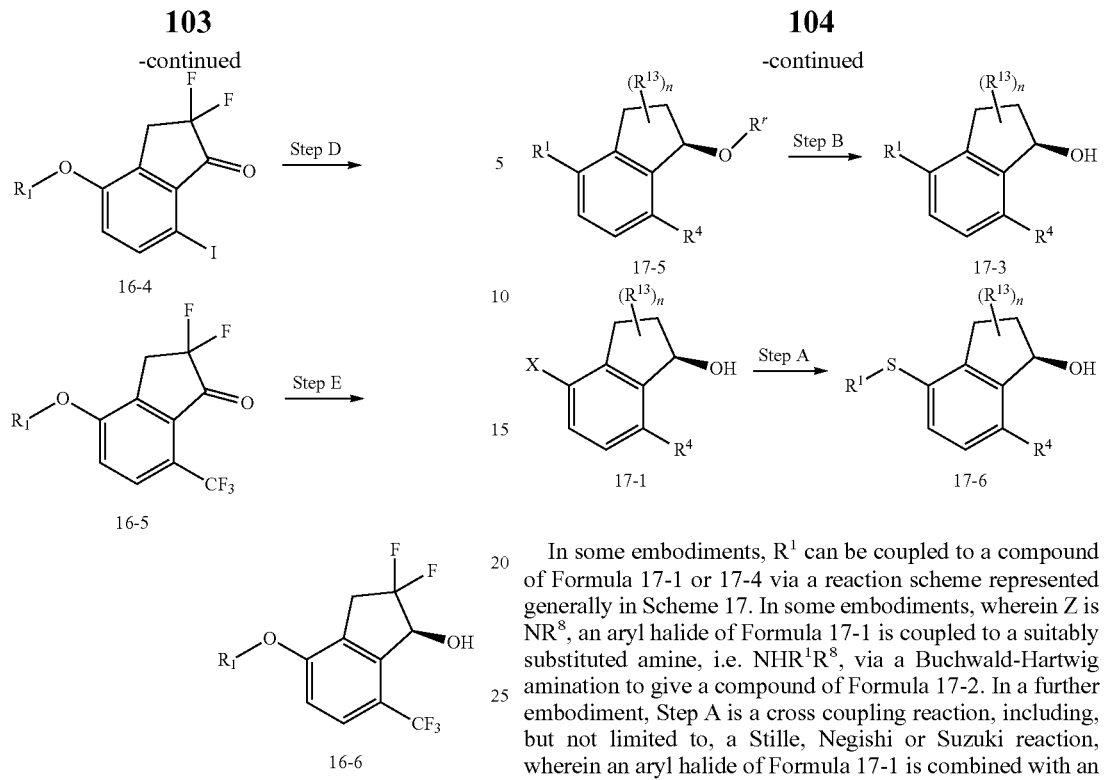

In some embodiments, compounds of Formula 16-6 are synthesized according to Scheme 16. For example, alkylation of compound 16-1 provides compounds of Formula 16-2, wherein $R_1$ is alkyl, cycloalkyl, or heterocycloalkyl. Compounds of Formula 16-2 can be selectively iodinated to give iodide 16-3. Ketone 16-3 can be difluorinated as previously described. Installation of a $CF_3$ group followed by asymmetric reduction provides compounds of Formula 16-6.

In some embodiments, $R^1$ can be coupled to a compound of Formula 17-1 or 17-4 via a reaction scheme represented generally in Scheme 17. In some embodiments, wherein Z is $NR^8$, an aryl halide of Formula 17-1 is coupled to a suitably substituted amine, i.e. $NHR^1R^8$, via a Buchwald-Hartwig amination to give a compound of Formula 17-2. In a further embodiment, Step A is a cross coupling reaction, including, but not limited to, a Stille, Negishi or Suzuki reaction, wherein an aryl halide of Formula 17-1 is combined with an appropriate reactant containing $R^1$ and a suitable catalyst to afford a compound of Formula 17-3. In other embodiments, a compound of Formula 17-4 undergoes an SNAr reaction and a subsequent deprotection to give a compound of Formula 17-3. $R^1$ in a compound of Formula 17-5 may be, for example, morpholine, wherein a C—N bond connects said morpholine to the aryl ring. In still other embodiments, Z is S, and $R^1S$— is attached to a compound of Formula 17-1 via a nucleophilic aromatic substitution (SNAr) reaction to give a compound of Formula 17-6.

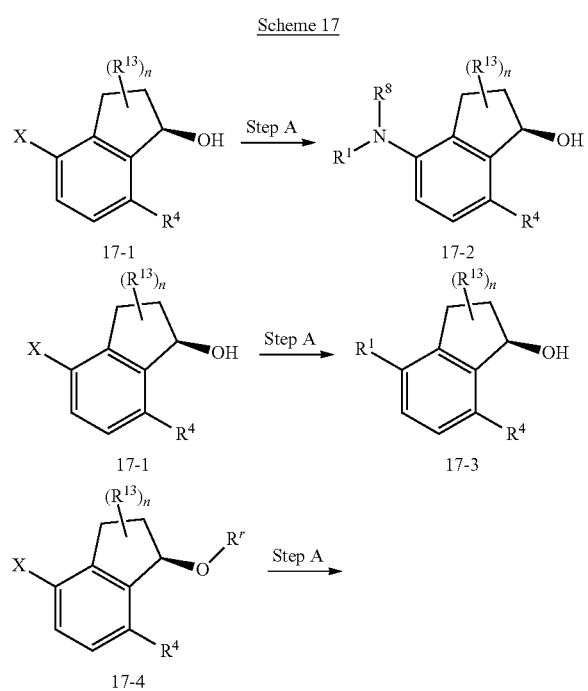

Scheme 17

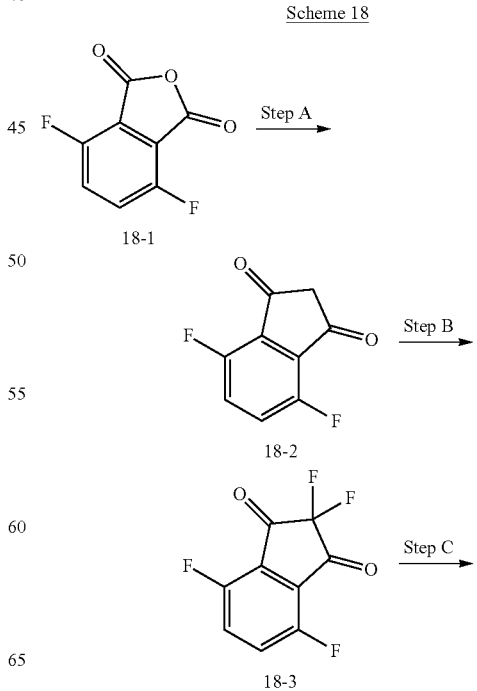

Scheme 18

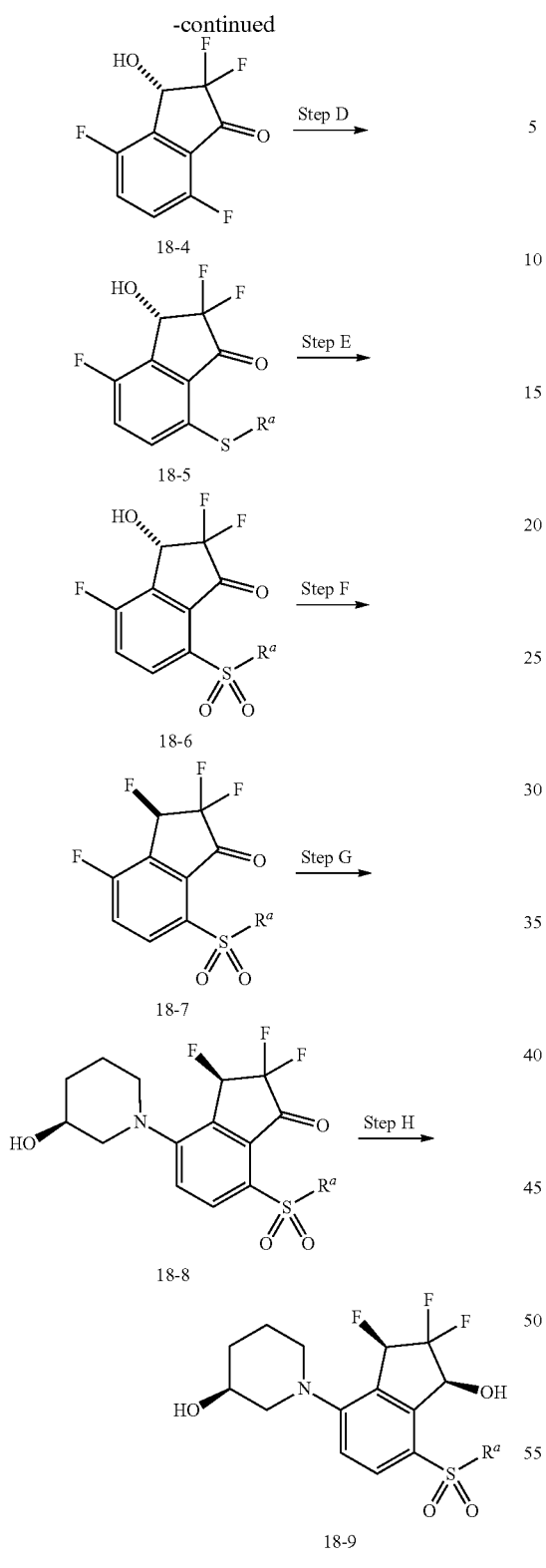

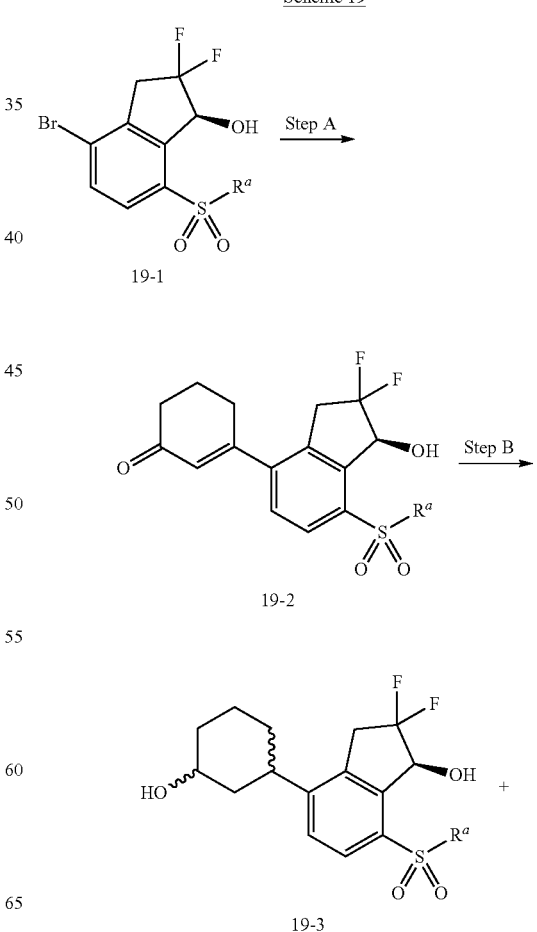

For example, direct asymmetric reduction of ketone 18-3 (Step C) may be accomplished chemically or enzymatically. For a recent review on enzymatic reduction of ketones, see Moore, et al. *Acc. Chem. Res.* 40: 1412-1419, 2007.

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration. Chiral alcohol 18-4 can be coupled with a suitable substrate, for example, an alkyl thiol, to give a compound of Formula 18-5 without significant loss of enantiomeric excess. The loss of enantiomeric excess (ee) in the coupling step for 18-5 may be less than about 1%, less than about 2%, less than about 3%, less than about 4%, less than about 5%, less than about 6% or less than about 8%.

Oxidation of a compound of Formula 18-5 is followed by fluorination, which proceeds with an inversion of stereochemistry at the substituted carbon to give a compound of Formula 18-7. Aryl fluoride 18-7 is then reacted with an amine, e.g. (3S)-3-piperidinol hydrochloride, to give a compound of Formula 18-8. Asymmetric reduction as described above gives a compound of Formula 18-9.

Scheme 19

In some additional embodiments, a compound of Formula 18-9 may be prepared according to steps outlined in Scheme 18. For example, cyclic anhydride 18-1 is converted in two steps to difluoroketone 18-3. In some embodiments, a compound of Formula 18-3 is reduced with a hydride source to give a racemic mixture. In other embodiments, an asymmetric reduction is carried out, affording chiral alcohol 18-4.

-continued

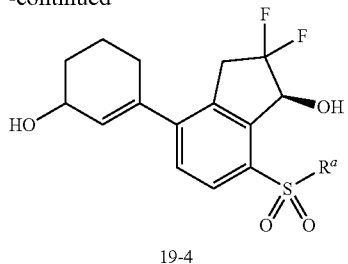

19-4

In some embodiments, a compound of Formula 19-3 or 19-4 can be prepared according to steps outlined in Scheme 19. For example, 19-2 may be prepared via a cross coupling reaction, i.e., a Suzuki reaction with a boronic acid of formula $R^1B(OH)_2$. Hydride reduction of 19-2 gives a mixture of alcohols 19-3 and unsaturated alcohol 19-4.

In some other embodiments, a compound of a formula given in Table 1 is synthesized according to one of the general routes outlined in Schemes 1-19, Examples 1-34 or by methods generally known in the art.

TABLE 1

| No. | Structure | Mass Characterization | $^1$H NMR Data |
|---|---|---|---|
| 1 | 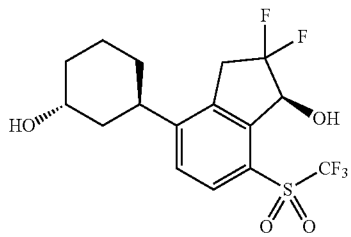 [SMILES: O=S(=O)(c1ccc([C@@H]2CCC[C@@H](O)C2)c2c1[C@H](O)C(F)(F)C2)C(F)(F)F] | (M + HCO$_2$–) 445 | (400 MHz, CDCl$_3$): δ 7.92 (d, 1H), 7.52 (d, 1H), 5.40 (dd, 1H), 4.33-4.28 (m, 1H), 3.59 (ddd, 1H), 3.49 (t, 1H), 3.22-3.13 (m, 2H), 1.97-1.82 (m, 4H), 1.75-1.58 (m, 3H), 1.46 (dd, 1H), 1.42-1.37 (m, 1H) |
| 2 | 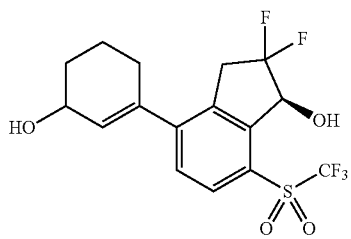 [SMILES: O=S(=O)(c1ccc(C2=CC(O)CCC2)c2c1[C@H](O)C(F)(F)C2)C(F)(F)F] | (M – OH) 381 | (400 MHz, CDCl$_3$): δ 7.93 (d, 1H), 7.50 (d, 1H), 5.91-5.88 (m, 1H), 5.39 (dd, 1H), 4.49-4.43 (m, 1H), 3.64 (ddd, 1H), 3.39 (t, 1H), 3.18 (dd, 1H), 2.49-2.39(m, 1H),2.22-2.11 (m, 1H), 2.09-1.92 (m, 2H), 1.81-1.59 (m, 3H) |
| 3 | 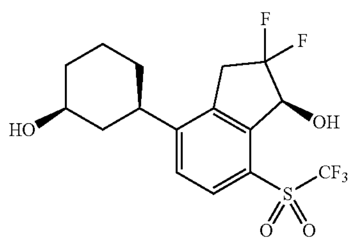 [SMILES: O=S(=O)(c1ccc([C@@H]2CCC[C@H](O)C2)c2c1[C@H](O)C(F)(F)C2)C(F)(F)F] | (M + HCO$_2$–) 445 | (400 MHz, CDCl$_3$): δ 7.94 (d, 1H), 7.55 (d, 1H), 5.41 (dd, 1H), 3.82-3.72 (m, 1H), 3.56 (ddd, 1H), 3.42 (t, 1H), 3.20 (dd, 1H), 2.67 (tt, 1H), 2.17-2.08 (m, 2H), 2.01-1.94 (m, 1H), 1.82-1.75 (m, 1H), 1.60-1.42 (m, 3H), 1.40-1.27 (m, 2H) |
| 4 | 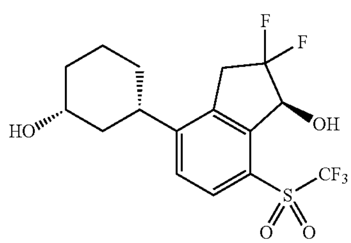 [SMILES: O=S(=O)(c1ccc([C@H]2CCC[C@@H](O)C2)c2c1[C@H](O)C(F)(F)C2)C(F)(F)F] | (M + HCO$_2$–) 445 | (400 MHz, CDCl$_3$): δ 7.94 (d, 1H), 7.55 (d, 1H), 5.41 (dd, 1H), 3.82-3.72 (m, 1H), 3.58 (ddd, 1H), 3.40 (t, 1H), 3.18 (d, 1H), 2.67 (tt, 1H), 2.16-2.06 (m, 2H), 2.02-1.95 (m, 1H), 1.86-1.78 (m, 1H), 1.58-1.28 (m, 5H) |
| 5 | 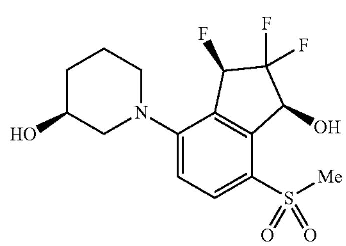 [SMILES: CS(=O)(=O)c1ccc(N2CCC[C@H](O)C2)c2c1[C@H](O)C(F)(F)[C@@H]2F] | 366 (M + H) | |

TABLE 1-continued

| No. | Structure | Mass Characterization | $^1$H NMR Data |
|---|---|---|---|
| 6 | 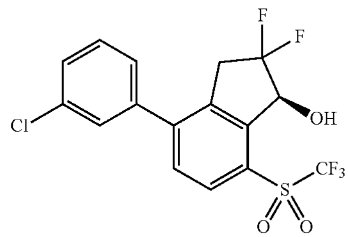 [SMILES: O=S(=O)(c1ccc(-c2cccc(Cl)c2)c2c1[C@H](O)C(F)(F)C2)C(F)(F)F] | (M − H) 411/413 | |
| 7 | 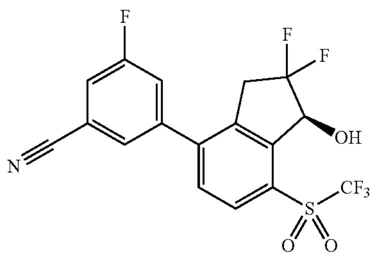 [SMILES: N#Cc1cc(F)cc(-c2ccc(S(=O)(=O)C(F)(F)F)c3c2CC(F)(F)[C@H]3O)c1] | (M − H) 420 | |
| 8 | 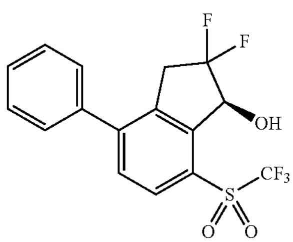 [SMILES: O=S(=O)(c1ccc(-c2ccccc2)c2c1[C@H](O)C(F)(F)C2)C(F)(F)F] | (M − H) 377 | |
| 9 | 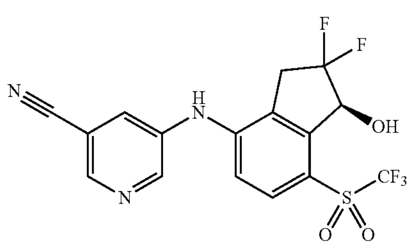 [SMILES: N#Cc1cncc(Nc2ccc(S(=O)(=O)C(F)(F)F)c3c2CC(F)(F)[C@H]3O)c1] | (M + H) 420 | |
| 10 | 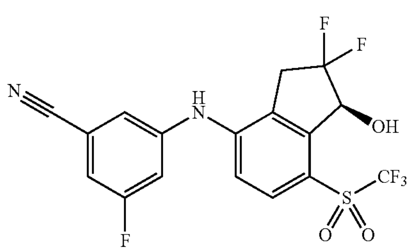 [SMILES: N#Cc1cc(F)cc(Nc2ccc(S(=O)(=O)C(F)(F)F)c3c2CC(F)(F)[C@H]3O)c1] | (M − H) 435 | |
| 11 | 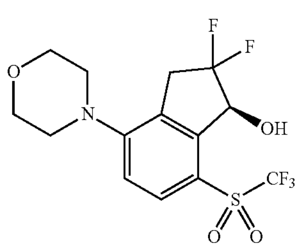 [SMILES: O=S(=O)(c1ccc(N2CCOCC2)c2c1[C@H](O)C(F)(F)C2)C(F)(F)F] | (M + H) 388 | |

TABLE 1-continued

| No. | Structure | Mass Characterization | $^1$H NMR Data |
|---|---|---|---|
| 12 | 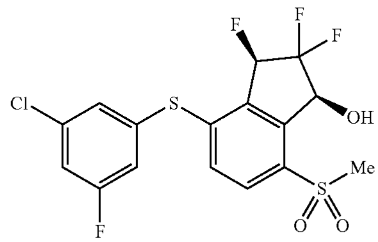 [SMILES: CS(=O)(=O)c1ccc(Sc2cc(F)cc(Cl)c2)c2c1[C@H](O)C(F)(F)[C@@H]2F] | (M + Na) 449 | |
| 13 | 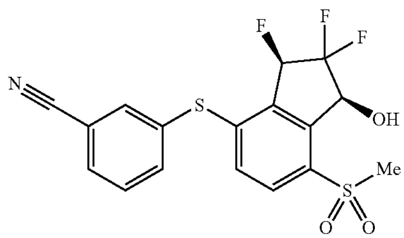 [SMILES: CS(=O)(=O)c1ccc(Sc2cccc(C#N)c2)c2c1[C@H](O)C(F)(F)[C@@H]2F] | (M + Na) 422 | |
| 14 | 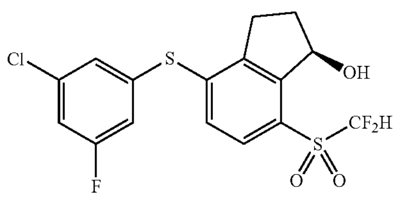 [SMILES: O=S(=O)(c1ccc(Sc2cc(F)cc(Cl)c2)c2c1[C@H](O)CC2)C(F)F] | 453/455 (M + HCO$_2$-) | |
| 15 | 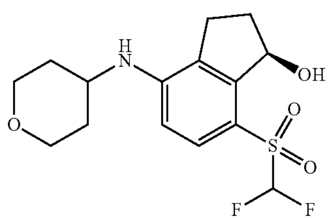 [SMILES: O=S(=O)(c1ccc(NC2CCOCC2)c2c1[C@H](O)CC2)C(F)F] | 346 (M − H) | |
| 16 | 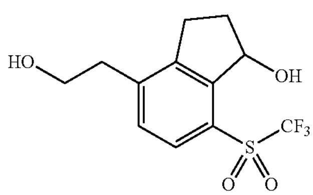 [SMILES: O=S(=O)(c1ccc(CCO)c2c1C(O)CC2)C(F)(F)F] | 309 (M − H) | |
| 17 | 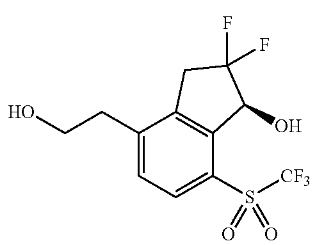 [SMILES: O=S(=O)(c1ccc(CCO)c2c1[C@H](O)C(F)(F)C2)C(F)(F)F] | 345 (M − H) | |
| 18 | 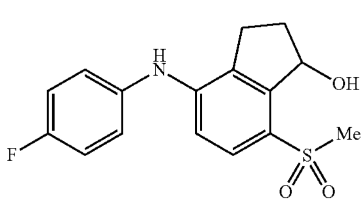 [SMILES: CS(=O)(=O)c1ccc(Nc2ccc(F)cc2)c2c1C(O)CC2] | 320 (M − H) | |

TABLE 1-continued

| No. | Structure | Mass Characterization | ¹H NMR Data |
|---|---|---|---|
| 19 | 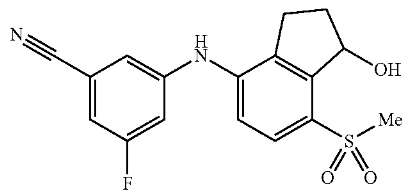 [SMILES: CS(=O)(=O)c1ccc(Nc2cc(F)cc(C#N)c2)c2c1C(O)CC2] | 345 (M − H) | |
| 20 | 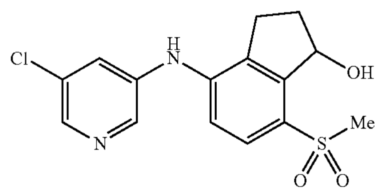 [SMILES: CS(=O)(=O)c1ccc(Nc2cncc(Cl)c2)c2c1C(O)CC2] | 337 (M − H) | |
| 21 | 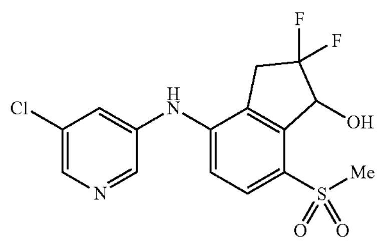 [SMILES: CS(=O)(=O)c1ccc(Nc2cncc(Cl)c2)c2c1C(O)C(F)(F)C2] | 373 (M − H) | |
| 22 | 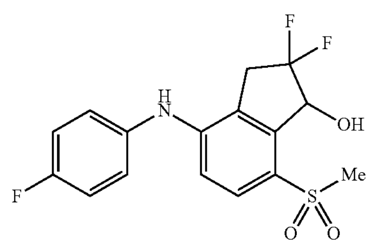 [SMILES: CS(=O)(=O)c1ccc(Nc2ccc(F)cc2)c2c1C(O)C(F)(F)C2] | 356 (M − H) | |
| 23 | 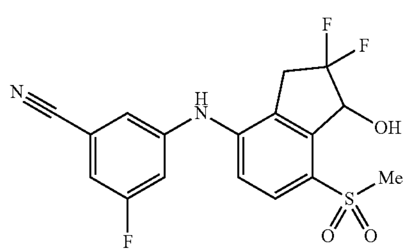 [SMILES: CS(=O)(=O)c1ccc(Nc2cc(F)cc(C#N)c2)c2c1C(O)C(F)(F)C2] | 381 (M − H) | |
| 24 | 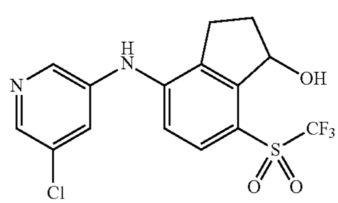 [SMILES: O=S(=O)(c1ccc(Nc2cncc(Cl)c2)c2c1C(O)CC2)C(F)(F)F] | 391 (M − H) | |
| 25 | 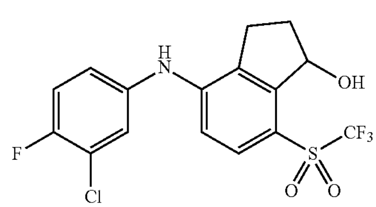 [SMILES: O=S(=O)(c1ccc(Nc2ccc(F)c(Cl)c2)c2c1C(O)CC2)C(F)(F)F] | 408 (M − H) | |

TABLE 1-continued

| No. | Structure | Mass Characterization | ¹H NMR Data |
|---|---|---|---|
| 26 | 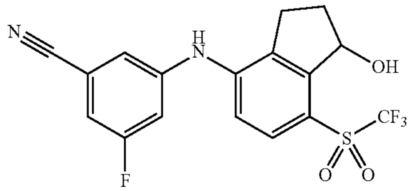 [SMILES: N#Cc1cc(F)cc(Nc2ccc(S(=O)(=O)C(F)(F)F)c3c2CCC3O)c1] | 399 (M − H) | |
| 27 | 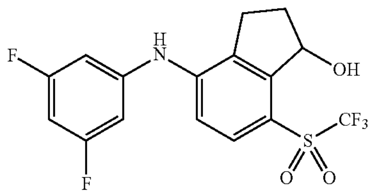 [SMILES: O=S(=O)(c1ccc(Nc2cc(F)cc(F)c2)c2c1C(O)CC2)C(F)(F)F] | 392 (M − H) | |
| 28 | 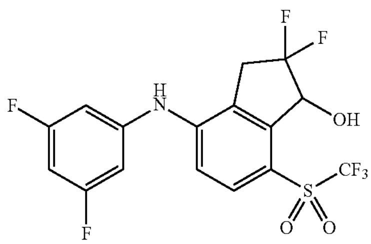 [SMILES: O=S(=O)(c1ccc(Nc2cc(F)cc(F)c2)c2c1C(O)C(F)(F)C2)C(F)(F)F] | | IHNMR (300 MHz, CDCl$_3$): δ 7.83 (d, 1H), 7.30 (d, 1H), 6.77 (m, 2H), 6.67 (m, 1H), 6.10 (s, 1H), 5.36 (m, 1H), 3.45 (m, 1H), 3.27 (m, 2H). |
| 29 | 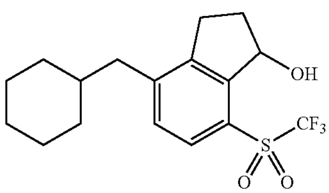 [SMILES: O=S(=O)(c1ccc(CC2CCCCC2)c2c1C(O)CC2)C(F)(F)F] | 361 (M − H) | |
| 30 | 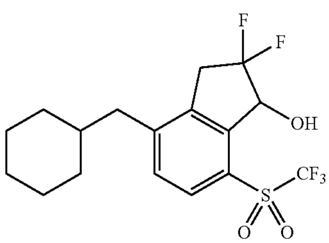 [SMILES: O=S(=O)(c1ccc(CC2CCCCC2)c2c1C(O)C(F)(F)C2)C(F)(F)F] | 397 (M − H) | |
| 31 | 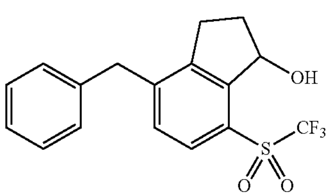 [SMILES: O=S(=O)(c1ccc(Cc2ccccc2)c2c1C(O)CC2)C(F)(F)F] | 355 (M − H) | |
| 32 | 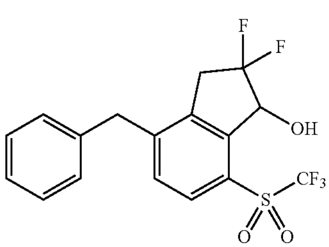 [SMILES: O=S(=O)(c1ccc(Cc2ccccc2)c2c1C(O)C(F)(F)C2)C(F)(F)F] | 391 (M − H) | |

TABLE 1-continued

| No. | Structure | Mass Characterization | ¹H NMR Data |
|---|---|---|---|
| 33 | 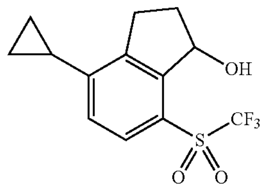 [SMILES: O=S(=O)(c1ccc(C2CC2)c2c1C(O)CC2)C(F)(F)F] | | 1HNMR (300 MHz, CDCl₃): δ 8.76 (d, 1H), 6.97 (d, 1H), 5.62 (m, 1H), 3.29 (m, 1H), 3.09 (m, 1H), 3.05 (m, 1H), 2.36 (m, 2H), L98 (m, 1H), L17 (m, 2H), 0.85 (m, 2H). |
| 34 | 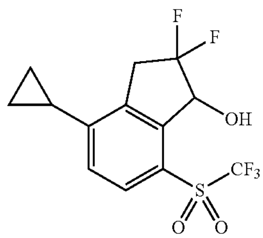 [SMILES: O=S(=O)(c1ccc(C2CC2)c2c1C(O)C(F)(F)C2)C(F)(F)F] | 341 (M − H) | |
| 35 | 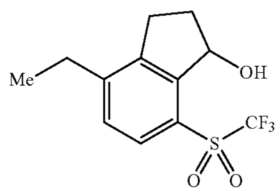 [SMILES: CCc1ccc(S(=O)(=O)C(F)(F)F)c2c1CCC2O] | 294 (M − H) | |
| 36 | 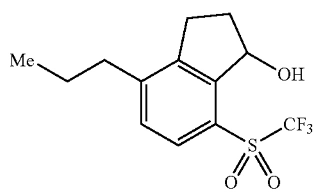 [SMILES: CCCc1ccc(S(=O)(=O)C(F)(F)F)c2c1CCC2O] | 307 (M − H) | |
| 37 | 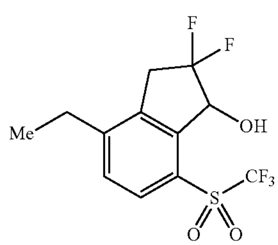 [SMILES: CCc1ccc(S(=O)(=O)C(F)(F)F)c2c1CC(F)(F)C2O] | 329 (M − H) | |
| 38 | 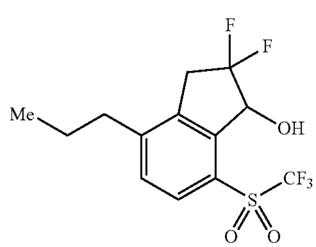 | 343 (M − H) | |
| 39 | 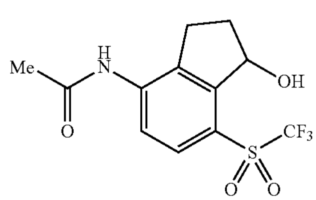 [SMILES: CC(=O)Nc1ccc(S(=O)(=O)C(F)(F)F)c2c1CCC2O] | 322 (M − H) | |

TABLE 1-continued

| No. | Structure | Mass Characterization | $^1$H NMR Data |
|---|---|---|---|
| 40 | 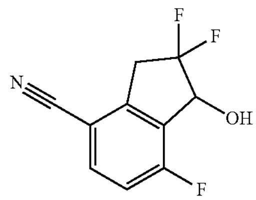 [SMILES: N#Cc1ccc(F)c2c1CC(F)(F)C2O] | 214 (M + H) | |
| 41 | 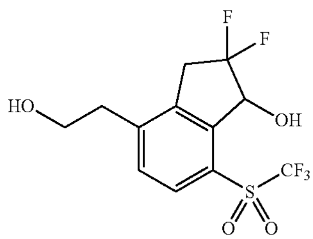 [SMILES: O=S(=O)(c1ccc(CCO)c2c1C(O)C(F)(F)C2)C(F)(F)F] | 345 (M − H) | |
| 42 | 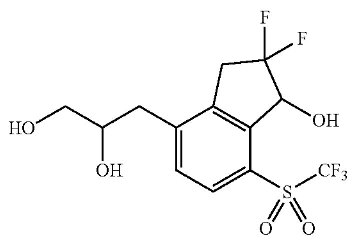 [SMILES: O=S(=O)(c1ccc(CC(O)CO)c2c1C(O)C(F)(F)C2)C(F)(F)F] | 375 (M − H) | |
| 43 | 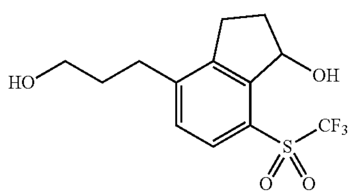 [SMILES: O=S(=O)(c1ccc(CCCO)c2c1C(O)CC2)C(F)(F)F] | 323 (M − H) | |
| 44 | 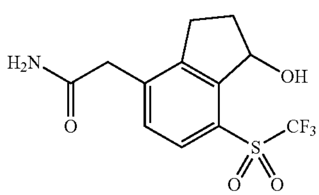 [SMILES: NC(=O)Cc1ccc(S(=O)(=O)C(F)(F)F)c2c1CCC2O] | 322 (M − H) | |
| 45 | 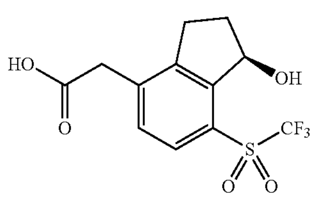 [SMILES: O=C(O)Cc1ccc(S(=O)(=O)C(F)(F)F)c2c1CC[C@H]2O] | 323 (M − H) | |
| 46 | 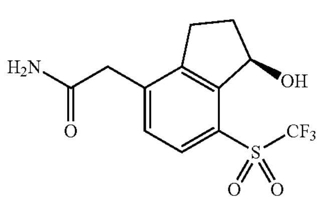 [SMILES: NC(=O)Cc1ccc(S(=O)(=O)C(F)(F)F)c2c1CC[C@H]2O] | 323 (M − H) | |

TABLE 1-continued

| No. | Structure | Mass Characterization | $^1$H NMR Data |
|---|---|---|---|
| 47 | 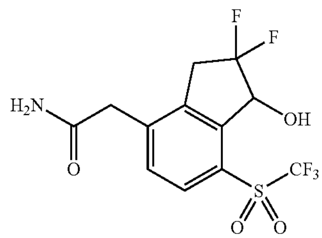 [SMILES: NC(=O)Cc1ccc(S(=O)(=O)C(F)(F)F)c2c1CC(F)(F)C2O] | 360 (M + H) | |
| 48 | 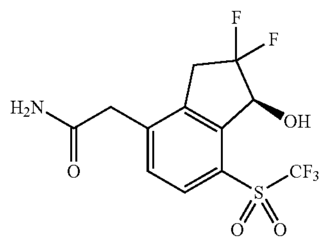 [SMILES: NC(=O)Cc1ccc(S(=O)(=O)C(F)(F)F)c2c1CC(F)(F)[C@H]2O] | 360 (M + H) | |
| 49 | 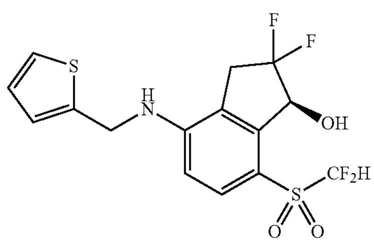 [SMILES: O=S(=O)(c1ccc(NCc2cccs2)c2c1[C@H](O)C(F)(F)C2)C(F)F] | | (400 MHz, CDCl$_3$): δ 7.79 (d, 1H), 7.29 (d, 1 H), 7.07-7.00 (m, 2H), 6.78 (d, 1H), 6.33 (t, 1H), 5.40 (d, 1H), 4.66 (d, 2H), 4.64-4.58 (m, 1H), 3.38-3.24 (m, 2H), 3.14 (t, 1H) |
| 50 | 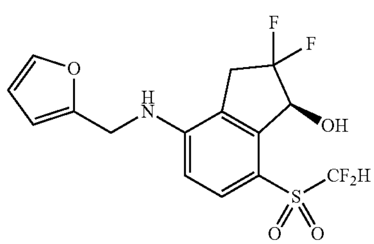 | | (400 MHz, CDCl$_3$): δ 7.79 (d, 1H), 7.40 (s, 1H), 6.80 (d, 1H), 6.46-6.20 (m, 3H), 5.39 (d, 1H), 4.64 (t, 1H), 4.47 (d, 2H), 3.46-3.24 (m, 2H), 3.14 (t, 1H) |
| 51 | 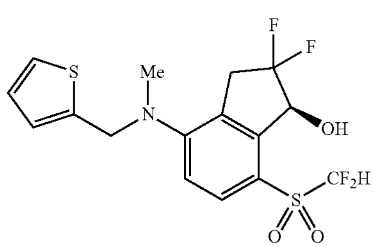 [SMILES: CN(Cc1cccs1)c1ccc(S(=O)(=O)C(F)F)c2c1CC(F)(F)[C@H]2O] | | (400 MHz, CDCl$_3$): δ 7.79 (d, 1H), 7.28 (d, 1H), 7.01-6.94 (m, 3H), 6.35 (t, 1H), 5.38 (d, 1H), 4.61 (m, 2H), 3.70-3.58 (m, 1H), 3.52-3.44 (m, 1H), 3.23 (br s, 1H), 3.00 (s, 3H) |
| 52 | 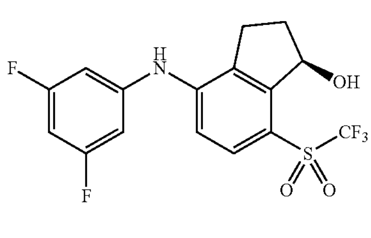 [SMILES: O=S(=O)(c1ccc(Nc2cc(F)cc(F)c2)c2c1[C@H](O)CC2)C(F)(F)F] | [M − H]$^−$ 392 | |

TABLE 1-continued

| No. | Structure | Mass Characterization | ¹H NMR Data |
|---|---|---|---|
| 53 | 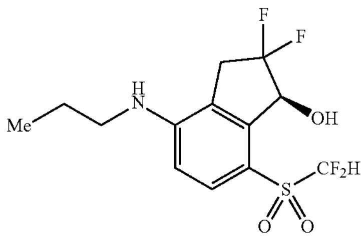 [SMILES: CCCNc1ccc(S(=O)(=O)C(F)F)c2c1CC(F)(F)[C@H]2O] | [M + H]⁺ 343 | |
| 54 | 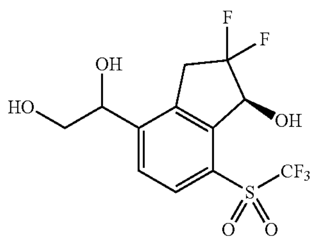 [SMILES: O=S(=O)(c1ccc(C(O)CO)c2c1[C@H](O)C(F)(F)C2)C(F)(F)F] | | (400 MHz, CDCl$_3$): δ 8.00 (dd, 1H), 7.84 (dd, 1H), 5.41 (dd, 1H), 5.00-4.93 (m, 1H), 3.83 (ddd, 1H), 3.72-3.43 (m, 4H) |
| 55 | 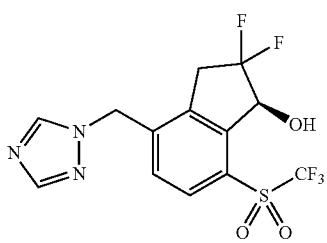 [SMILES: O=S(=O)(c1ccc(Cn2cncn2)c2c1[C@H](O)C(F)(F)C2)C(F)(F)F] | [M − H]⁻ 382 | |
| 56 | 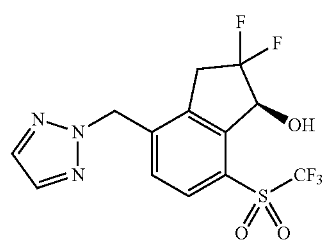 [SMILES: O=S(=O)(c1ccc(Cn2nccn2)c2c1[C@H](O)C(F)(F)C2)C(F)(F)F] | [M − H]⁻ 382 | |
| 57 | 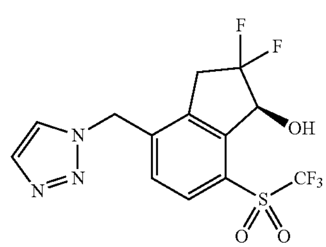 [SMILES: O=S(=O)(c1ccc(Cn2ccnn2)c2c1[C@H](O)C(F)(F)C2)C(F)(F)F] | [M − H]⁻ 382 | |
| 58 | 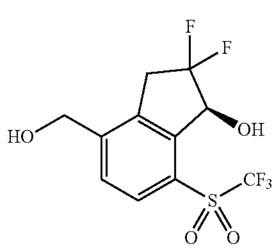 [SMILES: O=S(=O)(c1ccc(CO)c2c1[C@H](O)C(F)(F)C2)C(F)(F)F] | [M − H]⁻ 331 | |

TABLE 1-continued

| No. | Structure | Mass Characterization | ¹H NMR Data |
|-----|-----------|----------------------|-------------|
| 59  | 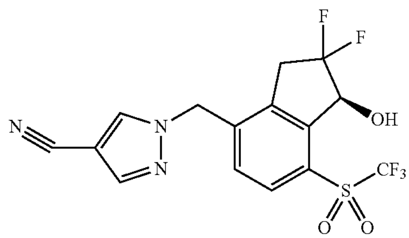 [SMILES: N#Cc1cnn(Cc2ccc(S(=O)(=O)C(F)(F)F)c3c2CC(F)(F)[C@H]3O)c1]          | [M − H]⁻ 406         |             |
| 60  | 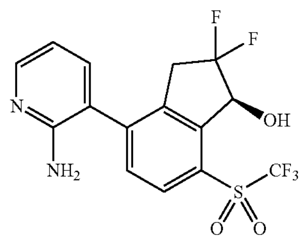 [SMILES: Nc1ncccc1-c1ccc(S(=O)(=O)C(F)(F)F)c2c1CC(F)(F)[C@H]2O]          | [M + H]⁺ 395         |             |
| 61  | 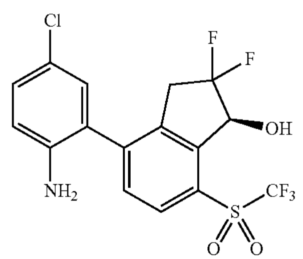 [SMILES: Nc1ccc(Cl)cc1-c1ccc(S(=O)(=O)C(F)(F)F)c2c1CC(F)(F)[C@H]2O]          | [M + H]⁺ 428/430     |             |
| 62  | 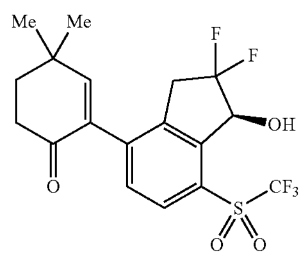 [SMILES: CC1(C)C=C(c2ccc(S(=O)(=O)C(F)(F)F)c3c2CC(F)(F)[C@H]3O)C(=O)CC1]          | [M + H]⁺ 425         |             |
| 63  | 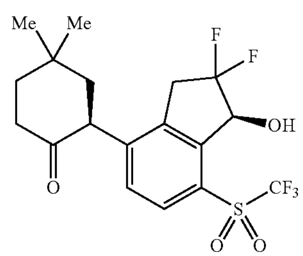 [SMILES: CC1(C)CCC(=O)[C@H](c2ccc(S(=O)(=O)C(F)(F)F)c3c2CC(F)(F)[C@H]3O)C1]          | [M + NH₄]⁺ 444       |             |
| 64  | 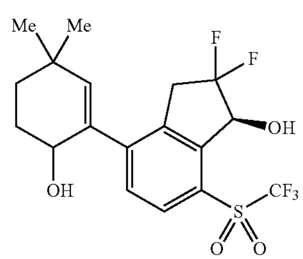 [SMILES: CC1(C)C=C(c2ccc(S(=O)(=O)C(F)(F)F)c3c2CC(F)(F)[C@H]3O)C(O)CC1]          | [M − OH]⁺ 409        |             |

TABLE 1-continued

| No. | Structure | Mass Characterization | ¹H NMR Data |
|---|---|---|---|
| 65 | 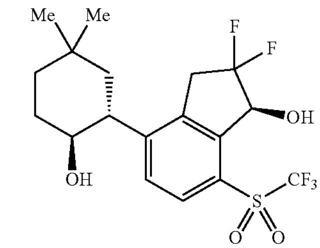 [SMILES: CC1(C)CC[C@H](O)[C@@H](c2ccc(S(=O)(=O)C(F)(F)F)c3c2CC(F)(F)[C@H]3O)C1] | [M + Cl]⁻ 463/465 | |
| 66 | 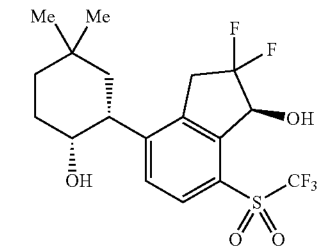 [SMILES: CC1(C)CC[C@@H](O)[C@@H](c2ccc(S(=O)(=O)C(F)(F)F)c3c2CC(F)(F)[C@H]3O)C1] | [M + Cl]⁻ 463/465 | |
| 67 | 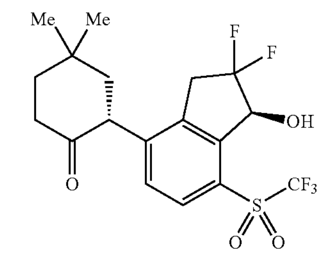 [SMILES: CC1(C)CCC(=O)[C@@H](c2ccc(S(=O)(=O)C(F)(F)F)c3c2CC(F)(F)[C@H]3O)C1] | [M + NH₄]⁺ 444 | |
| 68 | 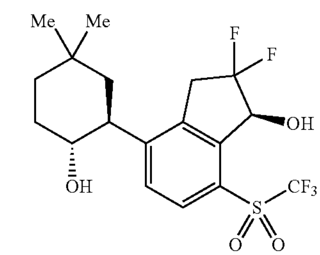 [SMILES: CC1(C)CC[C@@H](O)[C@H](c2ccc(S(=O)(=O)C(F)(F)F)c3c2CC(F)(F)[C@H]3O)C1] | [M + Cl]⁻ 463/465 | |
| 69 | 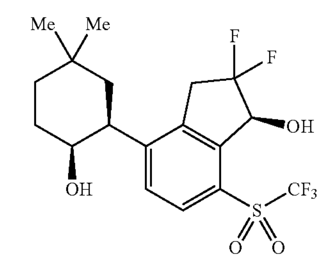 [SMILES: CC1(C)CC[C@H](O)[C@H](c2ccc(S(=O)(=O)C(F)(F)F)c3c2CC(F)(F)[C@H]3O)C1] | [M + NH4]⁺ 446 | |
| 70 | 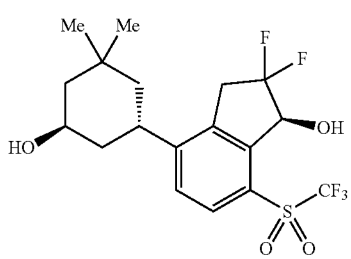 [SMILES: CC1(C)C[C@H](O)C[C@@H](c2ccc(S(=O)(=O)C(F)(F)F)c3c2CC(F)(F)[C@H]3O)C1] | [M + NH4]⁺ 446 | |

TABLE 1-continued

| No. | Structure | Mass Characterization | ¹H NMR Data |
|---|---|---|---|
| 71 | 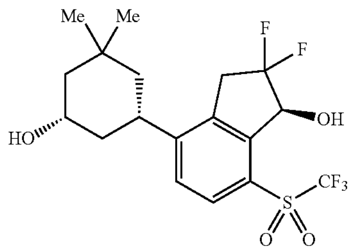 [SMILES: CC1(C)C[C@@H](O)C[C@@H](c2ccc(S(=O)(=O)C(F)(F)F)c3c2CC(F)(F)[C@H]3O)C1] | [M + NH4]⁺ 446 | |
| 72 | 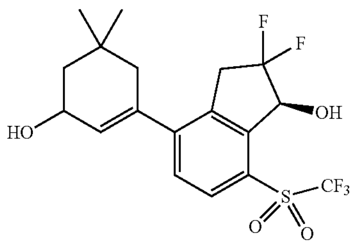 [SMILES: CC1(C)CC(c2ccc(S(=O)(=O)C(F)(F)F)c3c2CC(F)(F)[C@H]3O)=CC(O)C1] | [M − OH]⁺ 409 | |
| 73 | 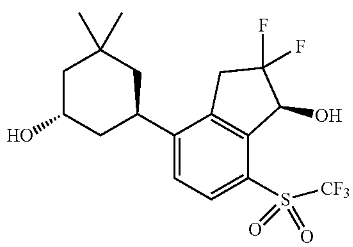 [SMILES: CC1(C)C[C@@H](O)C[C@H](c2ccc(S(=O)(=O)C(F)(F)F)c3c2CC(F)(F)[C@H]3O)C1] | [M + NH4]⁺ 446 | |
| 74 | 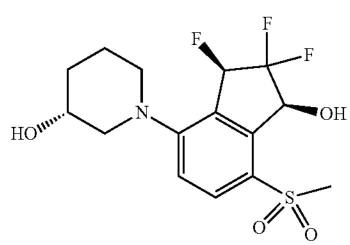 [SMILES: CS(=O)(=O)c1ccc(N2CCC[C@@H](O)C2)c2c1[C@H](O)C(F)(F)[C@@H]2F] | [M + H]⁺ 366 | |
| 75 | 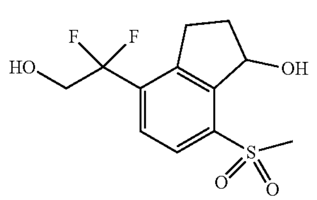 [SMILES: CS(=O)(=O)c1ccc(C(F)(F)CO)c2c1C(O)CC2] | [M + NH$_4$]⁺ 310 | |
| 76 | 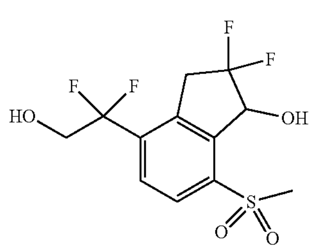 [SMILES: CS(=O)(=O)c1ccc(C(F)(F)CO)c2c1C(O)C(F)(F)C2] | [M + NH$_4$]⁺ 346 | |

TABLE 1-continued

| No. | Structure | Mass Characterization | $^1$H NMR Data |
|---|---|---|---|
| 77 | 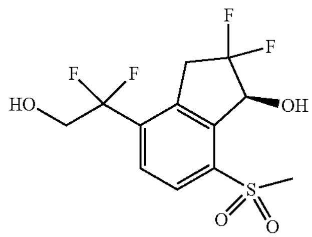 [SMILES: CS(=O)(=O)c1ccc(C(F)(F)CO)c2c1[C@H](O)C(F)(F)C2] | [M + NH$_4$]$^+$ 346 | |
| 78 | 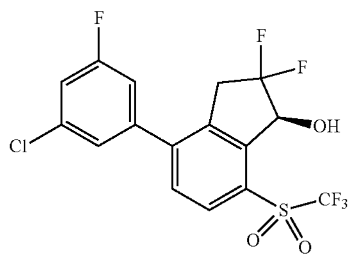 [SMILES: O=S(=O)(c1ccc(-c2cc(F)cc(Cl)c2)c2c1[C@H](O)C(F)(F)C2)C(F)(F)F] | [M + Na]$^+$ 454 | |
| 79 | 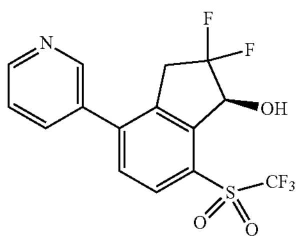 [SMILES: O=S(=O)(c1ccc(-c2cccnc2)c2c1[C@H](O)C(F)(F)C2)C(F)(F)F] | [M + H]$^+$ 380 | |
| 80 | 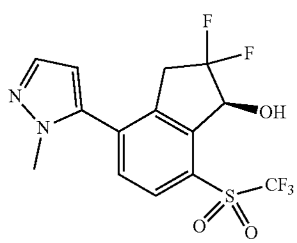 [SMILES: Cn1nccc1-c1ccc(S(=O)(=O)C(F)(F)F)c2c1CC(F)(F)[C@H]2O] | [M + H]$^+$ 383 | |
| 81 | 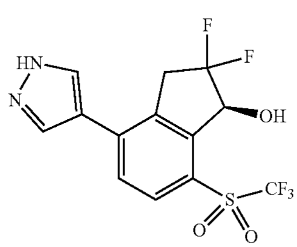 [SMILES: O=S(=O)(c1ccc(-c2cn[nH]c2)c2c1[C@H](O)C(F)(F)C2)C(F)(F)F] | [M + H]$^+$ 369 | |
| 82 | 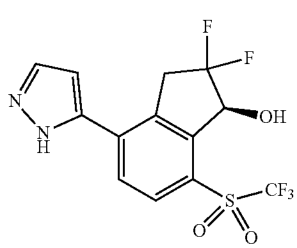 [SMILES: O=S(=O)(c1ccc(-c2ccn[nH]2)c2c1[C@H](O)C(F)(F)C2)C(F)(F)F] | [M + H]$^+$ 369 | |

TABLE 1-continued

| No. | Structure | Mass Characterization | ¹H NMR Data |
|---|---|---|---|
| 83 | 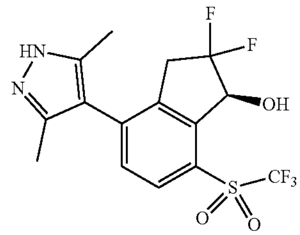 [SMILES: Cc1n[nH]c(C)c1-c1ccc(S(=O)(=O)C(F)(F)F)c2c1CC(F)(F)[C@H]2O] | [M + H]⁺ 397 | |
| 84 | 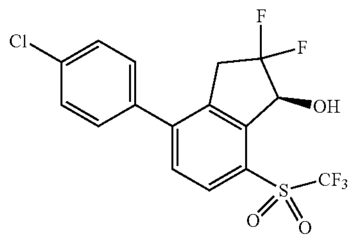 [SMILES: O=S(=O)(c1ccc(-c2ccc(Cl)cc2)c2c1[C@H](O)C(F)(F)C2)C(F)(F)F] | [M + Na]⁺ 436/438 | |
| 85 | 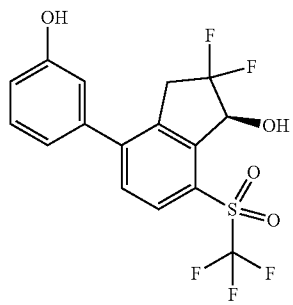 [SMILES: O=S(=O)(c1ccc(-c2cccc(O)c2)c2c1[C@H](O)C(F)(F)C2)C(F)(F)F] | [M − H]⁻ 393 | |
| 86 | 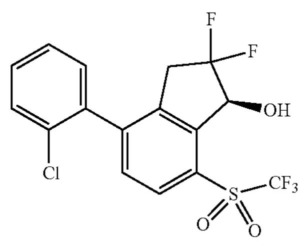 [SMILES: O=S(=O)(c1ccc(-c2ccccc2Cl)c2c1[C@H](O)C(F)(F)C2)C(F)(F)F] | [M + Na]⁺ 436/438 | |
| 87 | 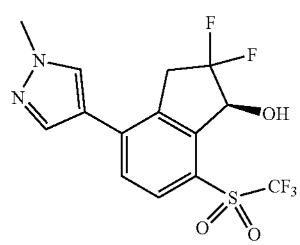 [SMILES: Cn1cc(-c2ccc(S(=O)(=O)C(F)(F)F)c3c2CC(F)(F)[C@H]3O)cn1] | [M + H]⁺ 383 | |
| 88 | 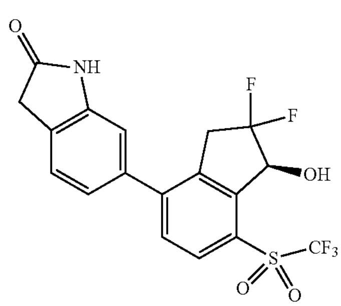 [SMILES: O=C1Cc2ccc(-c3ccc(S(=O)(=O)C(F)(F)F)c4c3CC(F)(F)[C@H]4O)cc2N1] | [M + H]⁺ 434 | |

TABLE 1-continued

| No. | Structure | Mass Characterization | ¹H NMR Data |
|---|---|---|---|
| 89 | 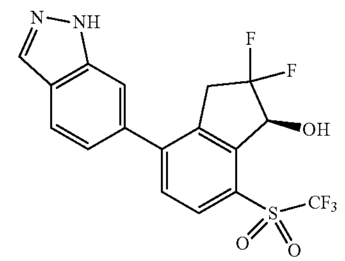 [SMILES: O=S(=O)(c1ccc(-c2ccc3cn[nH]c3c2)c2c1[C@H](O)C(F)(F)C2)C(F)(F)F] | [M + H]⁺ 419 | |
| 90 | 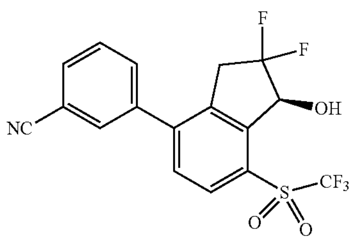 [SMILES: N#Cc1cccc(-c2ccc(S(=O)(=O)C(F)(F)F)c3c2CC(F)(F)[C@H]3O)c1] | [M − H]⁻ 402 | |
| 91 | 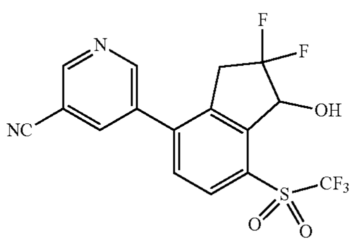 [SMILES: N#Cc1cncc(-c2ccc(S(=O)(=O)C(F)(F)F)c3c2CC(F)(F)C3O)c1] | [M + H]⁺ 405 | |
| 92 | 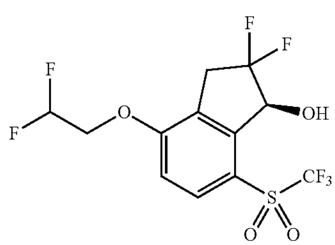 [SMILES: O=S(=O)(c1ccc(OCC(F)F)c2c1[C@H](O)C(F)(F)C2)C(F)(F)F] | [M − H]⁻ 381 | (400 MHz, CDCl₃): δ 8.00 (d, 1H), 7.07 (d, 1H), 6.15 (tt, 1H), 5.38 (dd, 1H), 4.44-4.29 (m, 2H), 3.55-3.39 (m, 2H), 3.16 (d, 1H) |
| 93 | 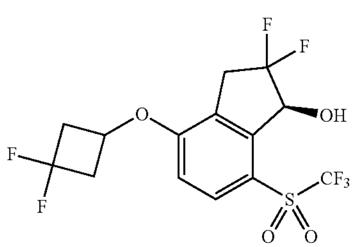 [SMILES: O=S(=O)(c1ccc(OC2CC(F)(F)C2)c2c1[C@H](O)C(F)(F)C2)C(F)(F)F] | [M − H]⁻ 407 | (400 MHz, CDCl₃): δ 7.96 (d, 1H), 6.86 (d, 1H), 5.37 (dd, 1H), 4.86-4.76 (m, 1H), 3.53-3.35 (m, 2H), 3.27-3.14 (m, 3H), 2.92-2.78 (m, 2H) |
| 94 | 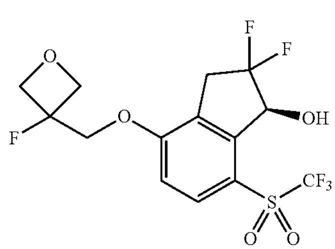 [SMILES: O=S(=O)(c1ccc(OCC2(F)COC2)c2c1[C@H](O)C(F)(F)C2)C(F)(F)F] | [M − H]⁻ 405 | (400 MHz, CDCl₃): δ 8.00 (d, 1H), 7.11 (d, 1H), 5.38 (dd, 1H), 4.92 (dd, 2H), 4.68 (dd, 2H), 4.59-4.46 (m, 2H), 3.54-3.36 (m, 2H), 3.19 (d, 1H) |

TABLE 1-continued

| No. | Structure | Mass Characterization | ¹H NMR Data |
|-----|-----------|----------------------|-------------|
| 95 | 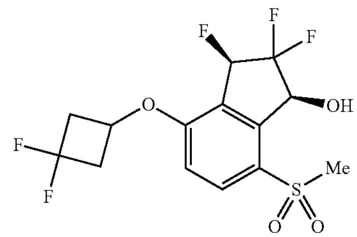 [SMILES: CS(=O)(=O)c1ccc(OC2CC(F)(F)C2)c2c1[C@H](O)C(F)(F)[C@@H]2F] | [M + H]⁺ 373 | (400 MHz, (CD₃)₂CO): δ 8.11 (dd, 1H), 7.33 (d, 1H), 5.87 (dd, 1H), 5.65-5.59 (m, 1H), 5.17-5.08 (m, 1H), 3.40-3.26 (m, 2H), 3.27 (s, 3H), 2.98-2.81 (m, 2H), 2.80 (t, 1H) |
| 96 | 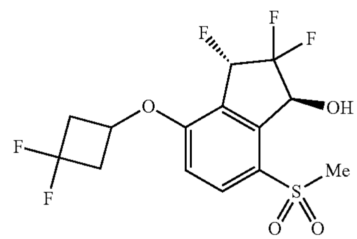 [SMILES: CS(=O)(=O)c1ccc(OC2CC(F)(F)C2)c2c1[C@H](O)C(F)(F)[C@H]2F] | [M + H]⁺ 373 | (400 MHz, CDCl₃): δ 8.06 (dd, 1H), 6.87 (d, 1H), 5.92 (dd, 1H), 5.78 (td, 1H), 4.86-4.76 (m, 1H), 3.98 (d, 1H), 3.25-3.14 (m, 2H), 3.22 (s, 3H), 2.95-2.78 (m, 2H) |
| 97 | 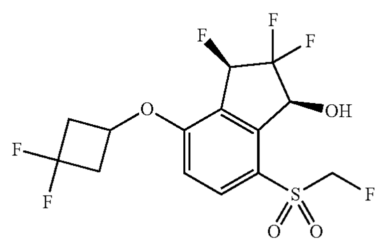 [SMILES: O=S(=O)(CF)c1ccc(OC2CC(F)(F)C2)c2c1[C@H](O)C(F)(F)[C@@H]2F] | [M + H]⁺ 391 | (400 MHz, CDCl₃): δ 8.13 (dd, 1H), 6.93 (d, 1H), 5.76 (dd, 1H), 5.59-5.53 (m, 1H), 5.47 (dd, 1H), 5.18 (dd, 1H), 4.90-4.80 (m, 1H), 3.29-3.16 (m, 2H), 3.16 (d, 1H), 2.97-2.81 (m, 2H) |
| 98 | 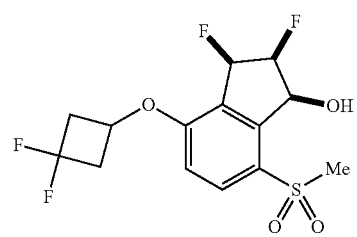 [SMILES: CS(=O)(=O)c1ccc(OC2CC(F)(F)C2)c2c1[C@H](O)[C@H](F)[C@@H]2F] | [M + NH₄]⁺ 372 | (400 MHz, (CD₃)₂CO): δ 8.05 (dd, 1H), 7.25 (d, 1H), 5.99 (dd, 1H), 5.74 (td, 1H), 5.16 (ddt, 1H), 5.13-5.03 (m, 1H), 4.84 (dd, 1H), 3.39-3.25 (m, 2H), 3.28 (s, 3H), 2.95-2.74 (m, 2H) |
| 99 | 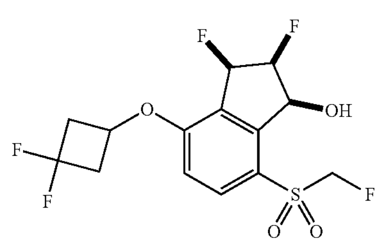 [SMILES: O=S(=O)(CF)c1ccc(OC2CC(F)(F)C2)c2c1[C@H](O)[C@H](F)[C@@H]2F] | [M + NH₄]⁺ 390 | (400 MHz, (CD₃)₂CO): δ 8.09 (dd, 1H), 7.12 (d, 1H), 5.95 (dd, 1H), 5.66 (dd, 1H), 5.61 (td, 1H), 5.34 (dd, 1H), 5.07 (ddt, 1H), 5.03-4.93 (m, 1H), 3.89 (dd, 1H), 3.33-3.18 (m, 2H), 2.95-2.72 (m, 2H) |
| 100 | 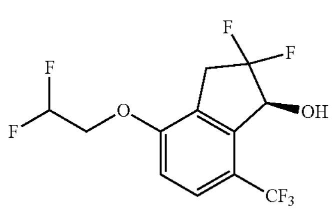 [SMILES: O[C@H]1c2c(C(F)(F)F)ccc(OCC(F)F)c2CC1(F)F] | [M − H + formate]⁻ 363 | (400 MHz, CDCl₃): δ 7.59 (d, 1H), 6.89 (d, 1H), 6.11 (tt, 1H), 5.25-5.20 (m, 1H), 4.33-4.20 (m, 2H), 3.50-3.30 (m, 2H), 2.62-2.59 (m, 1H) |

TABLE 1-continued

| No. | Structure | Mass Characterization | ¹H NMR Data |
|---|---|---|---|
| 101 | 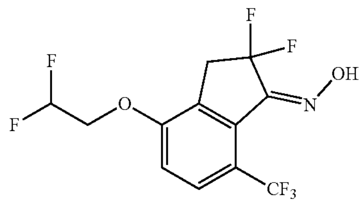 [SMILES: O/N=C1/c2c(C(F)(F)F)ccc(OCC(F)F)c2CC1(F)F] | [M + H]⁺ 332 | (400 MHz, CDCl$_3$): δ 8.13 (s, 1H), 7.69 (d, 1H), 6.90 (d, 1H), 6.12 (II, 1H), 4.34-4.26 (m, 2H), 3.49 (t, 2H) |
| 102 | 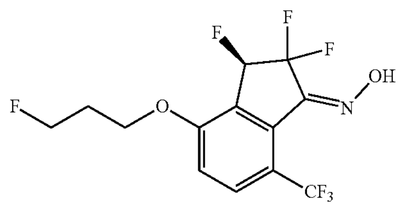 [SMILES: O/N=C1/c2c(C(F)(F)F)ccc(OCCCF)c2[C@@H](F)C1(F)F] | [M − H]⁻ 344 | 344 (400 MHz, CDCl$_3$): δ 8.33 (d, 1H), 7.88-7.84 (m, 1H), 7.04 (d, 1H), 5.82 (dd, 1H), 4.67 (dt, 2H), 4.33-4.24 (m, 2H), 2.32-2.20 (m, 2H) |
| 103 | 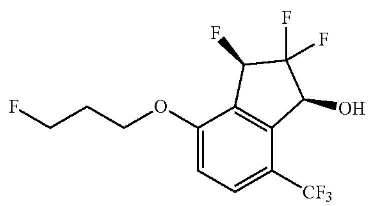 [SMILES: O[C@H]1c2c(C(F)(F)F)ccc(OCCCF)c2[C@@H](F)C1(F)F] | | (400 MHz, CDCl$_3$): δ 7.80-7.77 (m, 1H), 7.05 (d, 1H), 5.74 (dd, 1H), 5.25-5.20 (m, 1H), 4.66 (dt, 2H), 4.33-4.22 (m, 2H), 2.52 (d, 1H), 2.32-2.19 (m, 2H) |
| 104 | 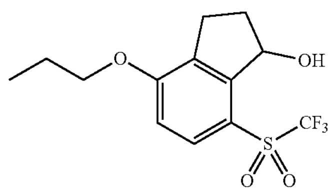 [SMILES: CCCOc1ccc(S(=O)(=O)C(F)(F)F)c2c1CCC2O] | | (300 MHz, CDCl$_3$): δ 7.87 (d, 1H), 6.95 (d, 1H), 5.58 (d, 1H), 4.08 (m, 2H), 2.06-3.17 (m, 2H), 2.84-2.94 (m, 1H), 2.37 (m, 1H), 2.27 (m, 1H), 1.86 (m, 2H), 1.07 (t, 3H) |
| 105 | 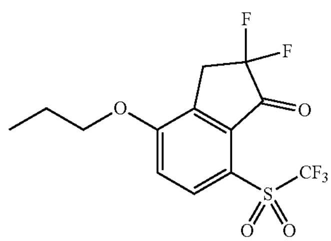 [SMILES: CCCOc1ccc(S(=O)(=O)C(F)(F)F)c2c1CC(F)(F)C2=O] | | (300 MHz, CDC13): δ 8.25 (d, 1H), 7.27 (d, 1H), 4.18 (t, 2H), 3.50 (t, 2H), 1.94 (m, 2H), 1.11 (t, 3H) |
| 106 | 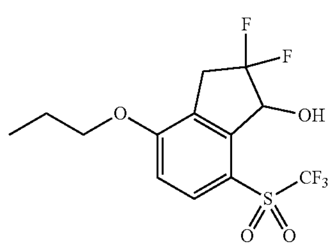 [SMILES: CCCOc1ccc(S(=O)(=O)C(F)(F)F)c2c1CC(F)(F)C2O] | [M − H]⁻ 359 | (300 MHz, CDCl$_3$): δ 7.95 (d, 1H), 7.04 (d, 1H), 5.36 (dd, 1H), 4.10 (m, 2H), 3.45 (m, 1H), 3.39 (m, 1H), 3.20 (m, 1H), 1.88 (m, 2H), 1.07 (t, 3H) |
| 107 | 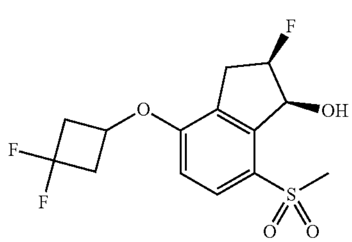 [SMILES: CS(=O)(=O)c1ccc(OC2CC(F)(F)C2)c2c1[C@H](O)[C@H](F)C2] | [M + H]⁺ 337 | |

TABLE 1-continued

| No. | Structure | Mass Characterization | ¹H NMR Data |
| --- | --- | --- | --- |
| 108 | 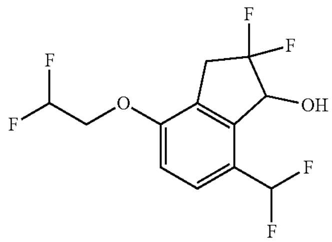 [SMILES: OC1c2c(C(F)F)ccc(OCC(F)F)c2CC1(F)F] | [M − H + HCOOH]⁻ 345 | (300 MHz, CDCl₃): δ 7.57 (d, 1H), 7.00 (t, 1H), 6.85 (t, 1H), 6.13 (t, 1H), 5.32 (m, 1H), 4.24 (t, 2H), 3.25-3.48 (m, 2H), 2.45(d, 1H) |
| 109 | 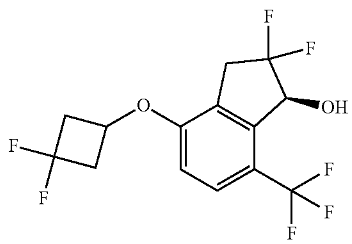 [SMILES: O[C@H]1c2c(C(F)(F)F)ccc(OC3CC(F)(F)C3)c2CC1(F)F] | 389 (M − H + HCOOH) | |
| 110 | 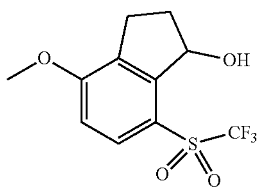 [SMILES: COc1ccc(S(=O)(=O)C(F)(F)F)c2c1CCC2O] | | (300 MHz, CDCl₃): δ 7.90 (d, 1H), 6.97 (d, 1H), 5.58 (m, 1H), 3.97 (s, 3H), 3.17 (m, 1H), 3.12 (m, 1H), 2.87 (m, 1H), 2.37 (m, 1H), 2.27 (m, 1H). |
| 111 | 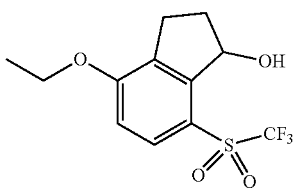 [SMILES: CCOc1ccc(S(=O)(=O)C(F)(F)F)c2c1CCC2O] | | (300 MHz, CDCl₃): δ 7.86 (d, 1H), 6.94 (d, 1H), 5.58 (m, 1H), 4.20 (m, 2H), 3.17 (m, 1H), 3.09 (m, 1H), 2.89 (m, 1H), 2.35 (m, 1H), 2.26 (m, 1H), 1.47 (t, 3H). |
| 112 | 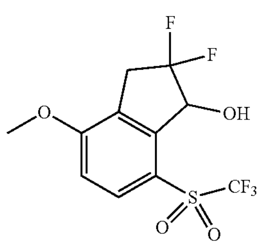 [SMILES: COc1ccc(S(=O)(=O)C(F)(F)F)c2c1CC(F)(F)C2O] | 331 (M − H) | |
| 113 | 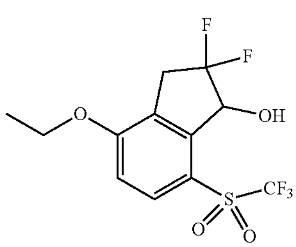 [SMILES: CCOc1ccc(S(=O)(=O)C(F)(F)F)c2c1CC(F)(F)C2O] | 345 (M − H) | |
| 114 | 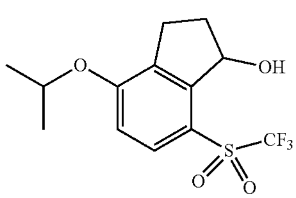 [SMILES: CC(C)Oc1ccc(S(=O)(=O)C(F)(F)F)c2c1CCC2O] | | (300 MHz, CDCl₃): δ 7.85 (d, 1H), 6.94 (d, 1H), 5.57 (m, 1H), 4.72 (m, 1H), 3.18 (m, 1H), 3.11 (m, 1H), 2.86 (m, 1H), 2.35 (m, 1H), 2.25 (m, 1H), 1.41 (d, 6H). |

TABLE 1-continued

| No. | Structure | Mass Characterization | ¹H NMR Data |
|---|---|---|---|
| 115 | 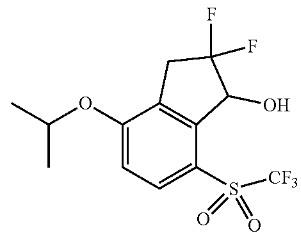 [SMILES: CC(C)Oc1ccc(S(=O)(=O)C(F)(F)F)c2c1CC(F)(F)C2O] | 359 (M − H) | |
| 116 | 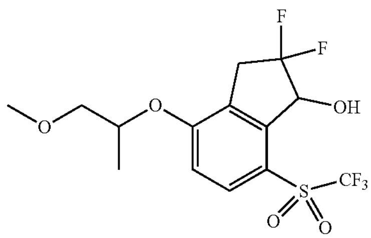 [SMILES: COCC(C)Oc1ccc(S(=O)(=O)C(F)(F)F)c2c1CC(F)(F)C2O] | 389 (M − H) | |
| 117 | 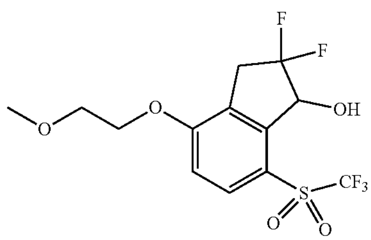 [SMILES: COCCOc1ccc(S(=O)(=O)C(F)(F)F)c2c1CC(F)(F)C2O] | 375 (M − H) | |
| 118 | 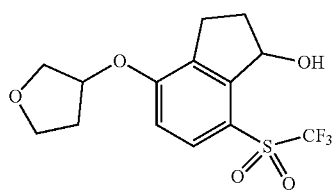 [SMILES: O=S(=O)(c1ccc(OC2CCOC2)c2c1C(O)CC2)C(F)(F)F] | | (300 MHz, CD₃OD): δ 7.89 (d, 1H), 7.28 (d, 1H), 5.44 (m, 1H), 5.27 (m, 1H), 5.14 (d, 1H), 3.77-3.96 (m 4H), 2.93 (m, 1H), 2.76 (m, 1H), 2.29 (m, 1H), 2.15 (m, 1H), 1.97 (m, 2H). |
| 119 | 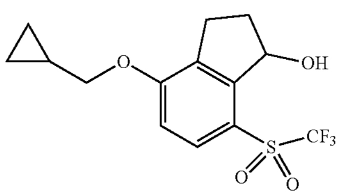 [SMILES: O=S(=O)(c1ccc(OCC2CC2)c2c1C(O)CC2)C(F)(F)F] | | (300 MHz, CDCl₃): δ 7.85 (d, 1H), 6.92 (d, 1H), 5.57 (m, 1H), 3.96 (m, 2H), 3.17 (m, 1H), 3.08 (m, 1H), 2.94 (m, 1H), 2.36 (m, 1H), 2.26 (m, 1H), 1.28 (m, 1H), 0.68 (m, 2H), 0.39 (m, 2H). |
| 120 | 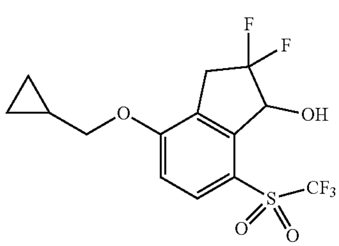 [SMILES: O=S(=O)(c1ccc(OCC2CC2)c2c1C(O)C(F)(F)C2)C(F)(F)F] | 371 (M − H) | |
| 121 | 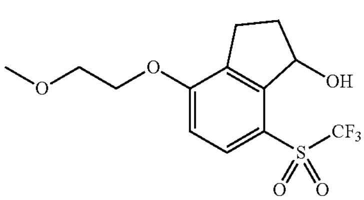 [SMILES: COCCOc1ccc(S(=O)(=O)C(F)(F)F)c2c1CCC2O] | | (300 MHz, CDCl₃): δ 7.87 1H), 6.99 (d, 1H), 5.57 (m, 1H), 4.27 (m, 2H), 3.80 (m, 2H), 3.45 (s, 3H), 3.15 (m, 1H), 3.11 (m, 1H), 2.93 (m, 1H), 2.36 (m, 1H), 2.27 (m, 1H) |

TABLE 1-continued

| No. | Structure | Mass Characterization | ¹H NMR Data |
|---|---|---|---|
| 122 | 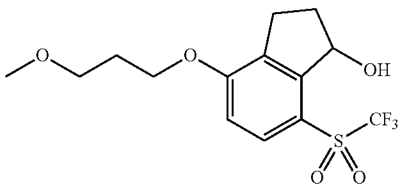 [SMILES: COCCCOc1ccc(S(=O)(=O)C(F)(F)F)c2c1CCC2O] | 372 (M + NH$_4$) | |
| 123 | 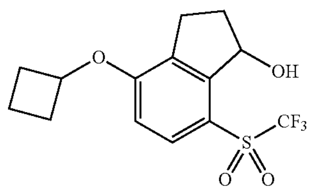 [SMILES: O=S(=O)(c1ccc(OC2CCC2)c2c1C(O)CC2)C(F)(F)F] | | (300 MHz, CDCl$_3$): δ 7.82 (d, 1H), 6.79 (d, 1H), 5.57 (m, 1H), 4.78 (m, 1H), 3.17 (m, 1H), 3.09 (m, 1H), 2.89 (m, 1H), 2.50 (m, 2H), 2.20-2.28 (m, 4H), 1.77 (m, 1H), 1.55 (m, 1H). |
| 124 | 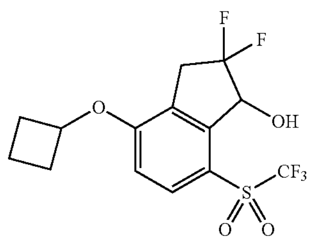 [SMILES: O=S(=O)(c1ccc(OC2CCC2)c2c1C(O)C(F)(F)C2)C(F)(F)F] | 371 (M − H) | |
| 125 | 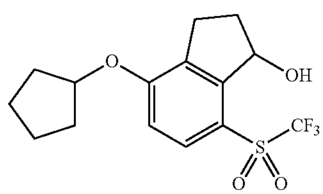 [SMILES: O=S(=O)(c1ccc(OC2CCCC2)c2c1C(O)CC2)C(F)(F)F] | | (300 MHz, CDCl$_3$): δ 7.85 (d, 1H), 6.95 (d, 1H), 5.56 (m, 1H), 4.91 (m, 1H), 3.18 (m, 1H), 3.10 (m, 1H), 2.87 (m, 1H), 2.32 (m, 1 H), 2.25 (m, 1H), 1.56-1.99 (m, 8H). |
| 126 | 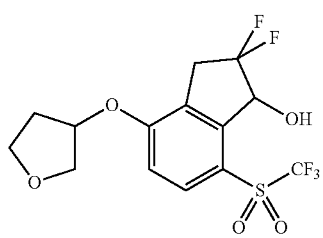 [SMILES: O=S(=O)(c1ccc(OC2CCOC2)c2c1C(O)C(F)(F)C2)C(F)(F)F] | 387 (M − H) | |
| 127 | 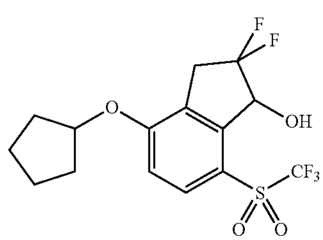 [SMILES: O=S(=O)(c1ccc(OC2CCCC2)c2c1C(O)C(F)(F)C2)C(F)(F)F] | 385 (M − H) | |
| 128 | 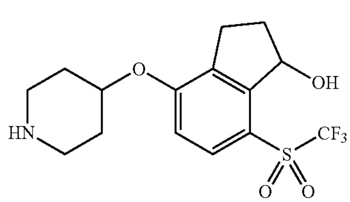 [SMILES: O=S(=O)(c1ccc(OC2CCNCC2)c2c1C(O)CC2)C(F)(F)F] | | (300 MHz, CDCl$_3$): δ 7.92 (d, 1H), 7.04 (d, 1H), 5.36 (d, 1H), 4.60 (m, 1H), 3.46 (m, 1H), 3.39 (m, 1H), 3.14 (m, 2H), 2.80 (m, 2H), 2.05 (m, 2H), 1.76 (m, 2H), 1.55 (m, 4H) |

TABLE 1-continued

| No. | Structure | Mass Characterization | ¹H NMR Data |
|---|---|---|---|
| 129 | 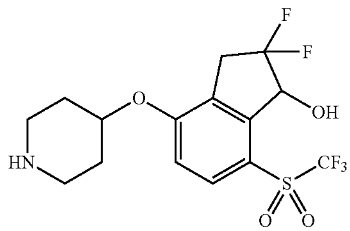 [SMILES: O=S(=O)(c1ccc(OC2CCNCC2)c2c1C(O)C(F)(F)C2)C(F)(F)F] | 402 (M + H) | |
| 130 | 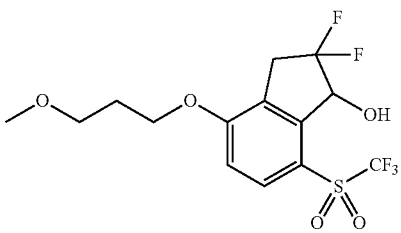 [SMILES: COCCCOc1ccc(S(=O)(=O)C(F)(F)F)c2c1CC(F)(F)C2O] | 389 (M − H) | |
| 131 | 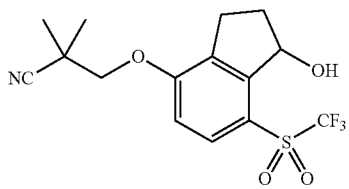 [SMILES: CC(C)(C#N)COc1ccc(S(=O)(=O)C(F)(F)F)c2c1CCC2O] | | (300 MHz, CDCl₃): δ 7.90 (d, 1H), 6.94 (d, 1H), 5.60 (m, 1H), 4.04 (m, 2H), 3.20 (m, 1H), 3.15 (m, 1H), 2.98 (m, 1H), 2.40 (m, 1H), 2.31 (m, 1H), 1.54 (s, 3H), 1.53 (s, 3H) |
| 132 | 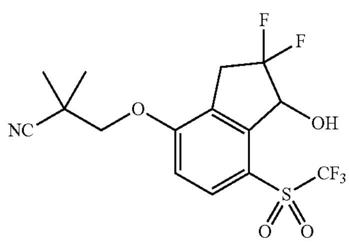 [SMILES: CC(C)(C#N)COc1ccc(S(=O)(=O)C(F)(F)F)c2c1CC(F)(F)C2O] | 398 (M − H) | |
| 133 | 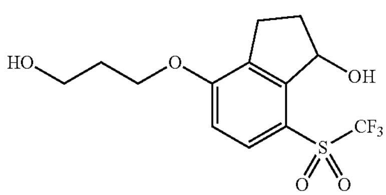 [SMILES: O=S(=O)(c1ccc(OCCCO)c2c1C(O)CC2)C(F)(F)F] | | (300 MHz, CDCl₃): δ 7.90 (d, 1H), 6.94 (d, 1H), 5.60 (m, 1H), 4.04 (m, 2H), 3.20 (m, 1H), 3.15 (m, 1H), 2.98 (m, 1H), 2.40 (m, 1H), 2.31 (m, 1H), 1.54 (s, 3H), 1.53 (s, 3H) |
| 134 | 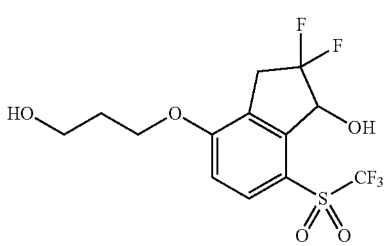 [SMILES: O=S(=O)(c1ccc(OCCCO)c2c1C(O)C(F)(F)C2)C(F)(F)F] | 377 (M + H) | |
| 135 | 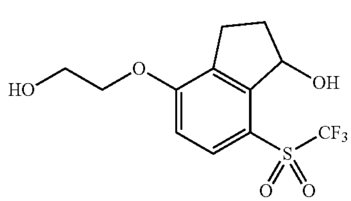 [SMILES: O=S(=O)(c1ccc(OCCO)c2c1C(O)CC2)C(F)(F)F] | 371 (M − H + HCOOH) | |

TABLE 1-continued

| No. | Structure | Mass Characterization | ¹H NMR Data |
|---|---|---|---|
| 136 | 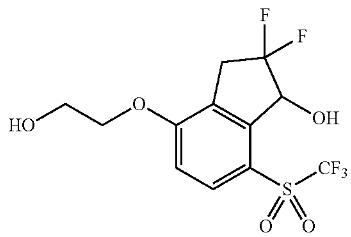 [SMILES: O=S(=O)(c1ccc(OCCO)c2c1C(O)C(F)(F)C2)C(F)(F)F] | 363 (M + H) | |
| 137 | 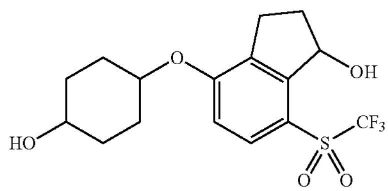 [SMILES: O=S(=O)(c1ccc(OC2CCC(O)CC2)c2c1C(O)CC2)C(F)(F)F] | 425 (M − H + HCOOH) | |
| 138 | 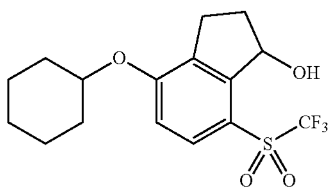 [SMILES: O=S(=O)(c1ccc(OC2CCCCC2)c2c1C(O)CC2)C(F)(F)F] | 382 (M + NH₄⁺) | |
| 139 | 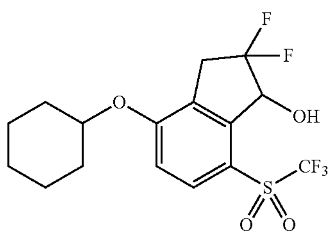 [SMILES: O=S(=O)(c1ccc(OC2CCCCC2)c2c1C(O)C(F)(F)C2)C(F)(F)F] | 399 (M − H) | |
| 140 | 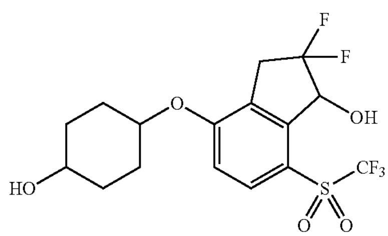 [SMILES: O=S(=O)(c1ccc(OC2CCC(O)CC2)c2c1C(O)C(F)(F)C2)C(F)(F)F] | 415 (M − H) | |
| 141 | 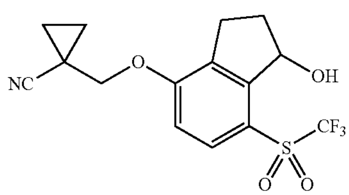 [SMILES: N#CC1(COc2ccc(S(=O)(=O)C(F)(F)F)c3c2CCC3O)CC1] | 406 (M − H + HCOOH) | |
| 142 | 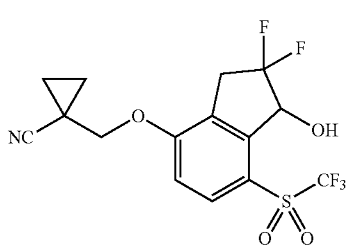 [SMILES: N#CC1(COc2ccc(S(=O)(=O)C(F)(F)F)c3c2CC(F)(F)C3O)CC1] | 398 (M + H) | |

TABLE 1-continued

| No. | Structure | Mass Characterization | ¹H NMR Data |
|---|---|---|---|
| 143 | 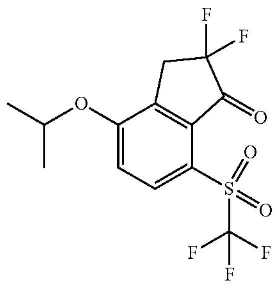 [SMILES: CC(C)Oc1ccc(S(=O)(=O)C(F)(F)F)c2c1CC(F)(F)C2=O] | | (300 MHz, CDCl$_3$): δ 8.23 (d, 1H), 7.25 (d, 1H), 4.83 (m, 1H), 3.47 (t, 2H), 1.48 (d, 6H) |
| 144 | 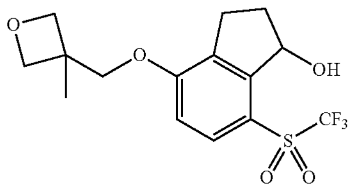 [SMILES: CC1(COc2ccc(S(=O)(=O)C(F)(F)F)c3c2CCC3O)COC1] | 411 (M − H + HCOOH) | |
| 145 | 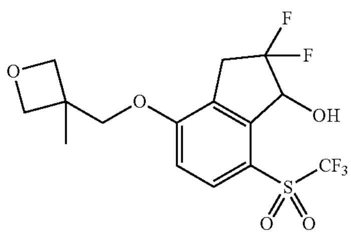 [SMILES: CC1(COc2ccc(S(=O)(=O)C(F)(F)F)c3c2CC(F)(F)C3O)COC1] | 401 (M − H) | |
| 146 | 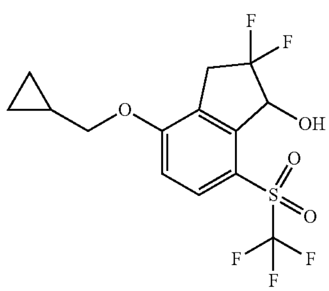 [SMILES: O=S(=O)(c1ccc(OCC2CC2)c2c1C(O)C(F)(F)C2)C(F)(F)F] | | |
| 147 | 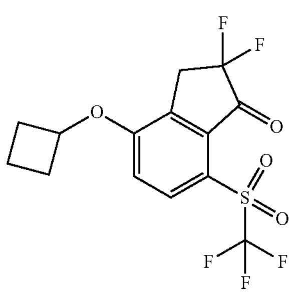 [SMILES: O=C1c2c(S(=O)(=O)C(F)(F)F)ccc(OC3CCC3)c2CC1(F)F] | | |
| 148 | 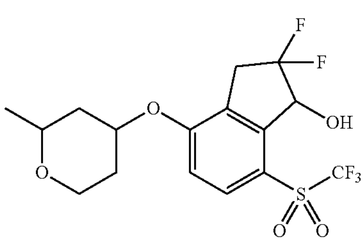 [SMILES: CC1CC(Oc2ccc(S(=O)(=O)C(F)(F)F)c3c2CC(F)(F)C3O)CCO1] | 415 (M − H) | |

TABLE 1-continued

| No. | Structure | Mass Characterization | ¹H NMR Data |
|---|---|---|---|
| 149 | 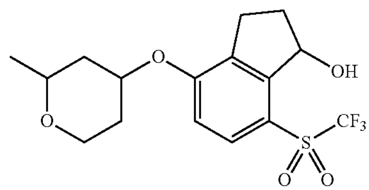 [SMILES: CC1CC(Oc2ccc(S(=O)(=O)C(F)(F)F)c3c2CCC3O)CCO1] | 425 (M − H + HCOOH) | |
| 150 | 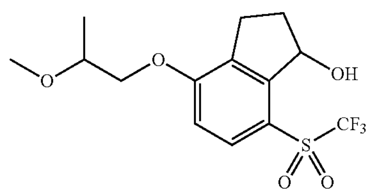 [SMILES: COC(C)COc1ccc(S(=O)(=O)C(F)(F)F)c2c1CCC2O] | 372 (M + NH₄) | |
| 151 | 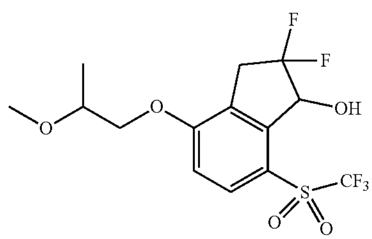 [SMILES: COC(C)COc1ccc(S(=O)(=O)C(F)(F)F)c2c1CC(F)(F)C2O] | 389 (M − H) | |
| 152 | 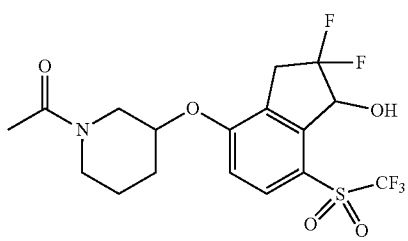 [SMILES: CC(=O)N1CCCC(Oc2ccc(S(=O)(=O)C(F)(F)F)c3c2CC(F)(F)C3O)C1] | 444 (M + H) | |
| 153 | 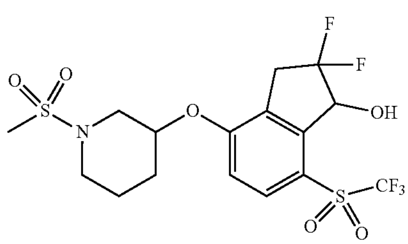 [SMILES: CS(=O)(=O)N1CCCC(Oc2ccc(S(=O)(=O)C(F)(F)F)c3c2CC(F)(F)C3O)C1] | 480 (M + H) | |
| 154 | 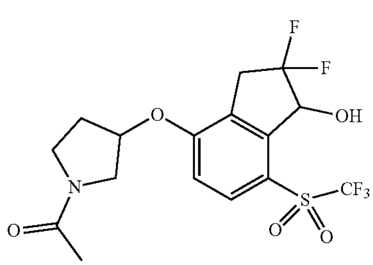 [SMILES: CC(=O)N1CCC(Oc2ccc(S(=O)(=O)C(F)(F)F)c3c2CC(F)(F)C3O)C1] | 430 (M + H) | |

TABLE 1-continued

| No. | Structure | Mass Characterization | ¹H NMR Data |
|---|---|---|---|
| 155 | 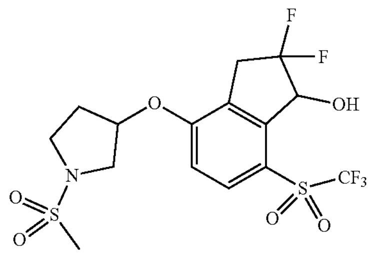 | 446 (M + H) | |
| 156 | 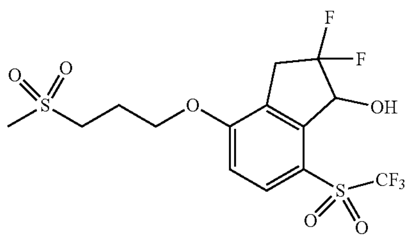 [SMILES: CS(=O)(=O)CCCOc1ccc(S(=O)(=O)C(F)(F)F)c2c1CC(F)(F)C2O] | 439 (M + H) | |
| 157 | 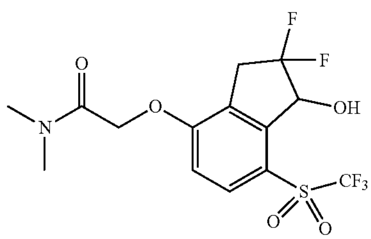 [SMILES: CN(C)C(=O)COc1ccc(S(=O)(=O)C(F)(F)F)c2c1CC(F)(F)C2O] | 404 (M + H) | |
| 158 | 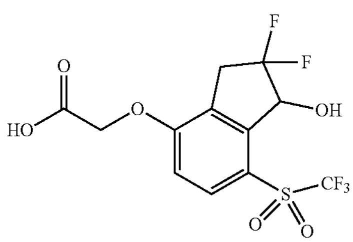 [SMILES: O=C(O)COc1ccc(S(=O)(=O)C(F)(F)F)c2c1CC(F)(F)C2O] | 377 (M + H) | |
| 159 | 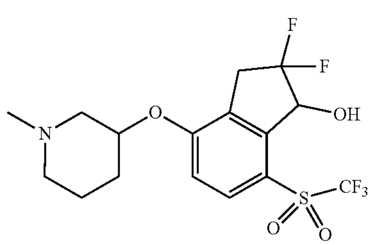 [SMILES: CN1CCCC(Oc2ccc(S(=O)(=O)C(F)(F)F)c3c2CC(F)(F)C3O)C1] | 416 (M + H) | |
| 160 | 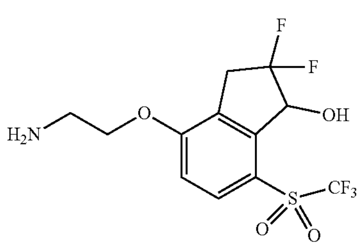 [SMILES: NCCOc1ccc(S(=O)(=O)C(F)(F)F)c2c1CC(F)(F)C2O] | 362 (M + H) | |

TABLE 1-continued

| No. | Structure | Mass Characterization | ¹H NMR Data |
|-----|-----------|----------------------|-------------|
| 161 | 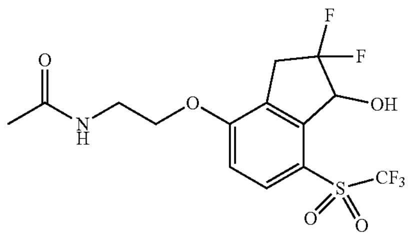 [SMILES: CC(=O)NCCOc1ccc(S(=O)(=O)C(F)(F)F)c2c1CC(F)(F)C2O] | 404 (M + H) | |
| 162 | 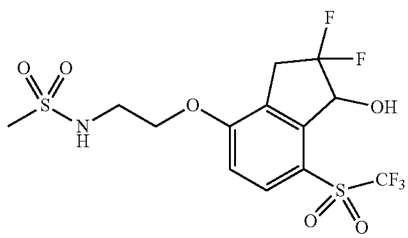 [SMILES: CS(=O)(=O)NCCOc1ccc(S(=O)(=O)C(F)(F)F)c2c1CC(F)(F)C2O] | 440 (M + H) | |
| 163 | 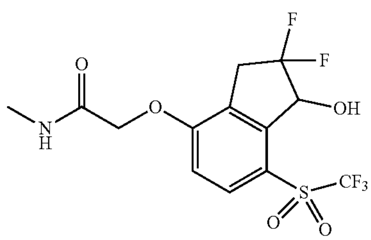 [SMILES: CNC(=O)COc1ccc(S(=O)(=O)C(F)(F)F)c2c1CC(F)(F)C2O] | 390 (M + H) | |
| 164 | 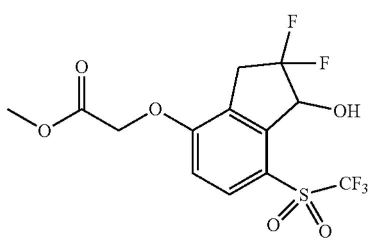 [SMILES: COC(=O)COc1ccc(S(=O)(=O)C(F)(F)F)c2c1CC(F)(F)C2O] | 389 (M − H) | |
| 165 | 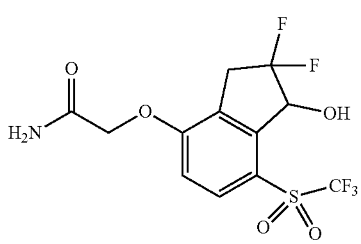 [SMILES: NC(=O)COc1ccc(S(=O)(=O)C(F)(F)F)c2c1CC(F)(F)C2O] | 374 (M − H) | |
| 166 | 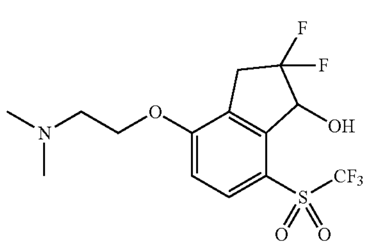 [SMILES: CN(C)CCOc1ccc(S(=O)(=O)C(F)(F)F)c2c1CC(F)(F)C2O] | 390 (M + H) | |

TABLE 1-continued

| No. | Structure | Mass Characterization | ¹H NMR Data |
|---|---|---|---|
| 167 | 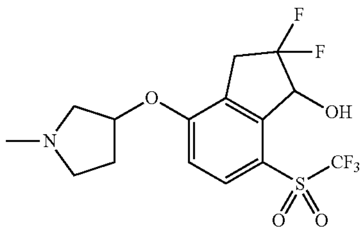 [SMILES: CN1CCC(Oc2ccc(S(=O)(=O)C(F)(F)F)c3c2CC(F)(F)C3O)C1] | | (300 MHz, CDCl$_3$): δ 7.93 (d, 1H), 6.94 (d, 1H), 5.35 (m, 1H), 4.96 (m, 1H), 3.38-3.47 (m, 3H), 2.82-2.92 (m 3H), 2.52 (m, 1H), 2.43 (m 1H), 2.42 (s, 3H), 2.04 (m 1H) |
| 168 | 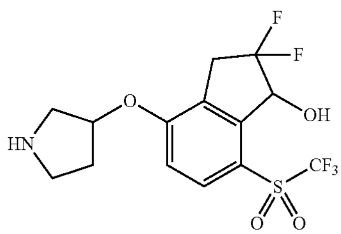 [SMILES: O=S(=O)(c1ccc(OC2CCNC2)c2c1C(O)C(F)(F)C2)C(F)(F)F] | 388 (M + H) | |
| 169 | 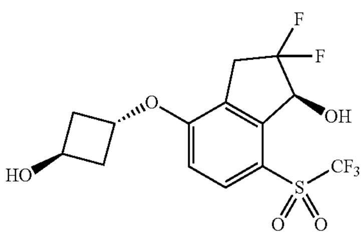 [SMILES: O=S(=O)(c1ccc(O[C@H]2C[C@H](O)C2)c2c1[C@H](O)C(F)(F)C2)C(F)(F)F] | 433 (M − H + HCOOH) | |
| 170 | 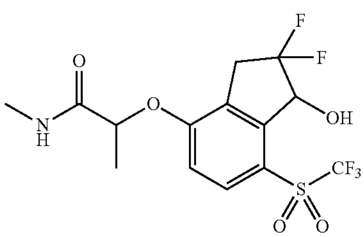 [SMILES: CNC(=O)C(C)Oc1ccc(S(=O)(=O)C(F)(F)F)c2c1CC(F)(F)C2O] | 402 (M − H) | |
| 171 | 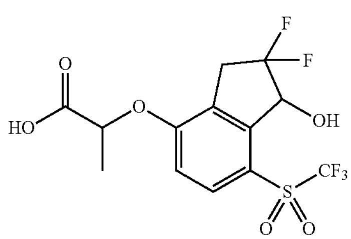 [SMILES: CC(Oc1ccc(S(=O)(=O)C(F)(F)F)c2c1CC(F)(F)C2O)C(=O)O] | 389 (M − H) | |
| 172 | 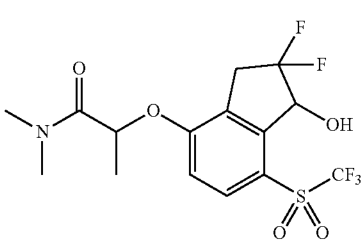 [SMILES: CC(Oc1ccc(S(=O)(=O)C(F)(F)F)c2c1CC(F)(F)C2O)C(=O)N(C)C] | 418 (M + H) | |

TABLE 1-continued

| No. | Structure | Mass Characterization | ¹H NMR Data |
|---|---|---|---|
| 173 | 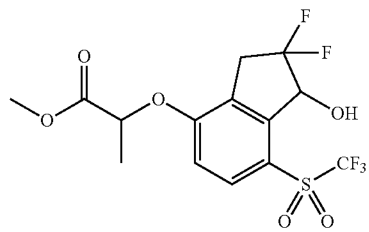 [SMILES: COC(=O)C(C)Oc1ccc(S(=O)(=O)C(F)(F)F)c2c1CC(F)(F)C2O] | | (300 MHz, CDCl₃): δ 7.92 (d, 1H), 6.87 (d, 1H), 5.36 (m, 1H), 4.93 (m, 1H), 3.80 (s, 3H), 3.44-3.60 (m, 2H), 3.22 (m, 1H), 1.71 (d, 3H) |
| 174 | 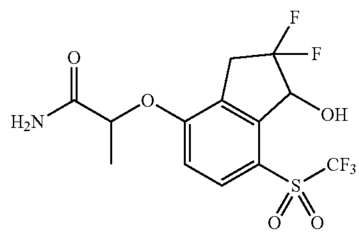 [SMILES: CC(Oc1ccc(S(=O)(=O)C(F)(F)F)c2c1CC(F)(F)C2O)C(N)=O] | 388 (M − H) | |
| 175 | 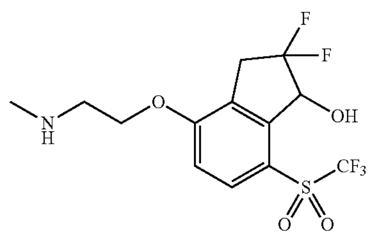 [SMILES: CNCCOc1ccc(S(=O)(=O)C(F)(F)F)c2c1CC(F)(F)C2O] | 376 (M + H) | |
| 176 | 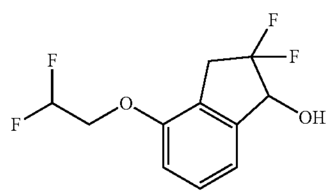 [SMILES: OC1c2cccc(OCC(F)F)c2CC1(F)F] | | (400 MHz, CDCl₃): δ 7.31 (m, 1H), 7.17 (d, 1H), 6.82 (d, 1H), 6.09 (t, 1H), 5.15 (m, 1H), 4.20 (m, 2H), 3.45 (m, 1H), 3.27 (m, 1H), 2.27 (m, 1H) |
| 177 | 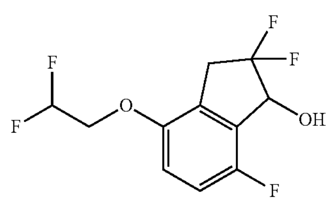 [SMILES: OC1c2c(F)ccc(OCC(F)F)c2CC1(F)F] | 313 (M − H + HCOOH) | |
| 178 | 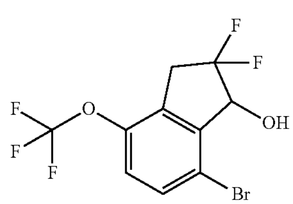 [SMILES: OC1c2c(Br)ccc(OC(F)(F)F)c2CC1(F)F] | | (400 MHz, CDCl₃): δ 7.56 (d, 1H), 7.17 (d, 1H), 5.13 (m, 1H), 3.56 (m, 2H), 2.50 (s, 1H) |
| 179 | 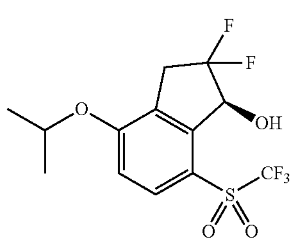 [SMILES: CC(C)Oc1ccc(S(=O)(=O)C(F)(F)F)c2c1CC(F)(F)[C@H]2O] | 359 (M − H) | |

TABLE 1-continued

| No. | Structure | Mass Characterization | ¹H NMR Data |
|---|---|---|---|
| 180 | 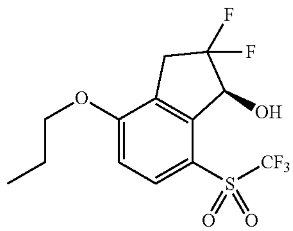 [SMILES: CCCOc1ccc(S(=O)(=O)C(F)(F)F)c2c1CC(F)(F)[C@H]2O] | 359 (M − H) | |
| 181 | 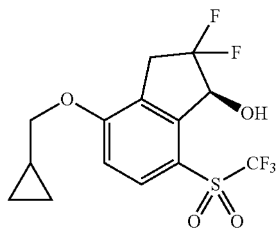 [SMILES: O=S(=O)(c1ccc(OCC2CC2)c2c1[C@H](O)C(F)(F)C2)C(F)(F)F] | 371 (M − H) | |
| 182 | 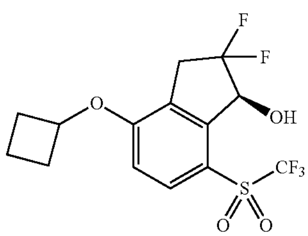 [SMILES: O=S(=O)(c1ccc(OC2CCC2)c2c1[C@H](O)C(F)(F)C2)C(F)(F)F] | 371 (M − H) | |
| 183 | 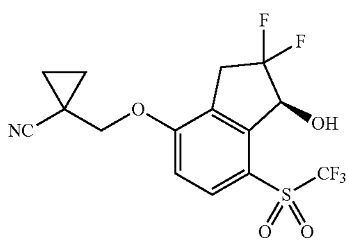 [SMILES: N#CC1(COc2ccc(S(=O)(=O)C(F)(F)F)c3c2CC(F)(F)[C@H]3O)CC1] | 442 (M + HCO$_2^-$) | |
| 184 | 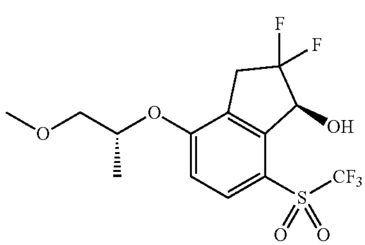 [SMILES: COC[C@@H](C)Oc1ccc(S(=O)(=O)C(F)(F)F)c2c1CC(F)(F)[C@H]2O] | 389 (M − H) | |
| 185 | 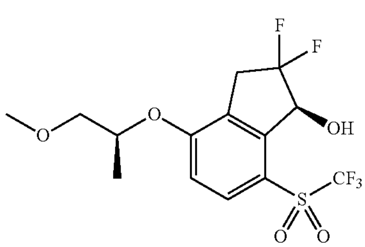 [SMILES: COC[C@H](C)Oc1ccc(S(=O)(=O)C(F)(F)F)c2c1CC(F)(F)[C@H]2O] | 389 (M − H) | |

TABLE 1-continued

| No. | Structure | Mass Characterization | ¹H NMR Data |
|---|---|---|---|
| 186 | 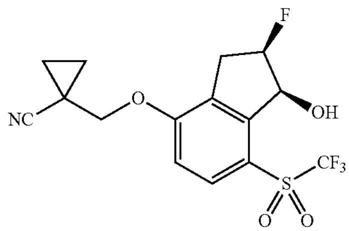 [SMILES: N#CC1(COc2ccc(S(=O)(=O)C(F)(F)F)c3c2C[C@@H](F)[C@H]3O)CC1] | 424 (M + HCO₂⁻) | |
| 187 | 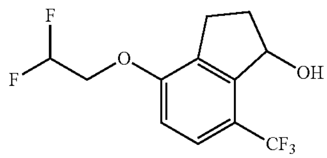 [SMILES: OC1CCc2c(OCC(F)F)ccc(C(F)(F)F)c21] | 265 (M − OH) | |
| 188 | 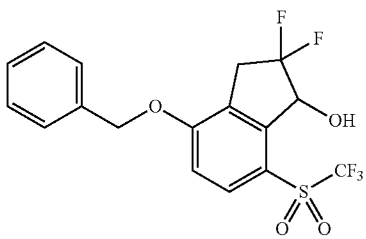 [SMILES: O=S(=O)(c1ccc(OCc2ccccc2)c2c1C(O)C(F)(F)C2)C(F)(F)F] | (M + NH4) 426 | |
| 189 | 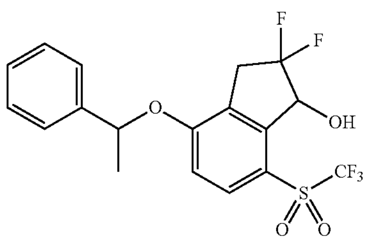 [SMILES: CC(Oc1ccc(S(=O)(=O)C(F)(F)F)c2c1CC(F)(F)C2O)c1ccccc1] | (M − H) 421 | |
| 190 | 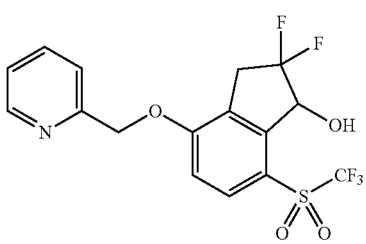 [SMILES: O=S(=O)(c1ccc(OCc2ccccn2)c2c1C(O)C(F)(F)C2)C(F)(F)F] | (M + H) 410 | |
| 191 | 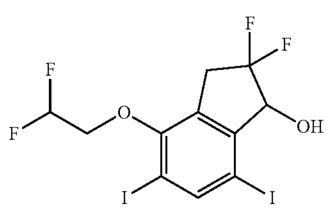 [SMILES: OC1c2c(I)cc(I)c(OCC(F)F)c2CC1(F)F] | | (400 MHz, CDCl₃): δ 8.15 (s, 1H), 6.12 (t, 1H), 4.96-4.87 (1H), 4.22-4.09 (2H), 3.62-3.50 (2H), 2.49 (1H) |
| 192 | 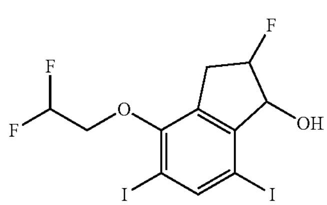 [SMILES: OC1c2c(I)cc(I)c(OCC(F)F)c2CC1F] | (M − OH) 467 | |

TABLE 1-continued

| No. | Structure | Mass Characterization | $^1$H NMR Data |
|---|---|---|---|
| 193 | 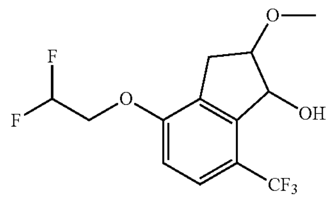 [SMILES: COC1Cc2c(OCC(F)F)ccc(C(F)(F)F)c2C1O] | (M + NH4) 330 | |
| 194 | 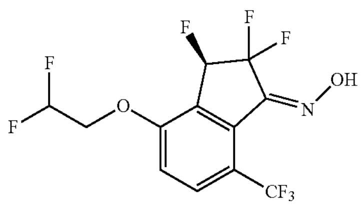 [SMILES: O/N=C1/c2c(C(F)(F)F)ccc(OCC(F)F)c2[C@@H](F)C1(F)F] | (M + H) 350 | |
| 195 | 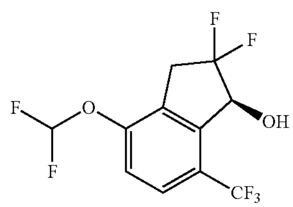 [SMILES: O[C@H]1c2c(C(F)(F)F)ccc(OC(F)F)c2CC1(F)F] | | (400 MHz, CDCl$_3$): δ 7.63 (d, 1H), 7.25 (d, 1H), 6.62 (t, 1H), 5.30-5.25 (m, 1H), 3.58-3.37 (m, 2H), 2.54-2.51 (m, 1H) |
| 196 | 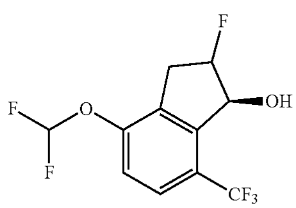 | | (400 MHz, CDCl$_3$): δ 7.59 (d, 1H), 7.18 (d, 1H), 6.60 (t, 1H), 5.40-5.23 (m, 2H), 3.40-3.12 (m, 2H), 2.55-2.51 (m, 1H) |
| 197 | 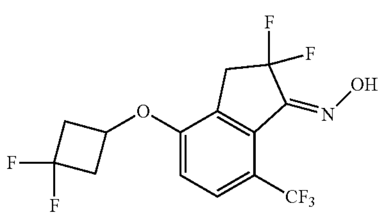 [SMILES: O/N=C1/c2c(C(F)(F)F)ccc(OC3CC(F)(F)C3)c2CC1(F)F] | (M + H) 358 | |
| 198 | 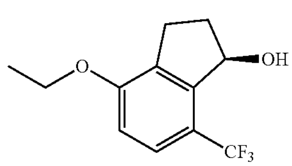 [SMILES: CCOc1ccc(C(F)(F)F)c2c1CC[C@H]2O] | [M − OH]$^+$ 229 | |
| 199 | 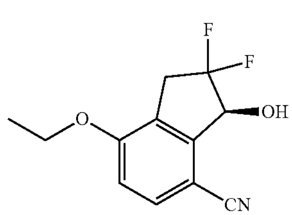 [SMILES: CCOc1ccc(C#N)c2c1CC(F)(F)[C@H]2O] | [M − H + HCOOH]$^-$ 284 | |

TABLE 1-continued

| No. | Structure | Mass Characterization | ¹H NMR Data |
|---|---|---|---|
| 200 | 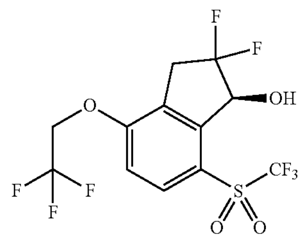 [SMILES: O=S(=O)(c1ccc(OCC(F)(F)F)c2c1[C@H](O)C(F)(F)C2)C(F)(F)F] | [M − H + HCOOH]⁻ 445 | |
| 201 | 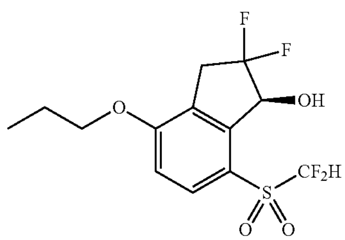 [SMILES: CCCOc1ccc(S(=O)(=O)C(F)F)c2c1CC(F)(F)[C@H]2O] | [M + NH4]⁺ 360 | |
| 202 | 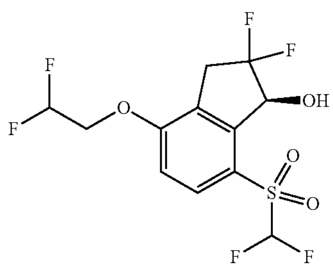 [SMILES: O=S(=O)(c1ccc(OCC(F)F)c2c1[C@H](O)C(F)(F)C2)C(F)F] | [M + NH4]⁺ 382 | |
| 203 | 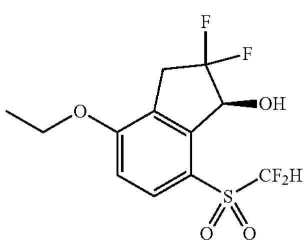 [SMILES: CCOc1ccc(S(=O)(=O)C(F)F)c2c1CC(F)(F)[C@H]2O] | [M + NH4]⁺ 346 | |
| 204 | 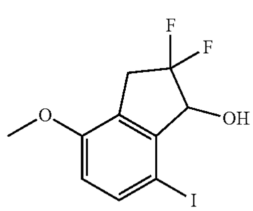 | | (400 MHz, CDCl$_3$): δ 7.62 (d, 1H), 6.63 (d, 1H), 4.94 (dd, 1H), 3.81 (s, 3H), 3.46-3.38 (m, 2H), 2.43-2.40 (m, 1H) |
| 205 | 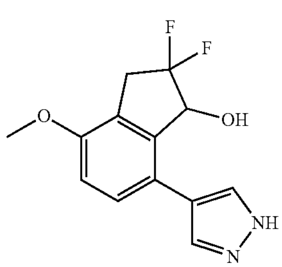 [SMILES: COc1ccc(-c2cn[nH]c2)c2c1CC(F)(F)C2O] | [M + Na]⁺ 289 | |

TABLE 1-continued

| No. | Structure | Mass Characterization | ¹H NMR Data |
|---|---|---|---|
| 206 | 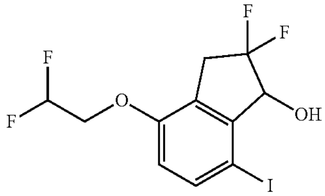 [SMILES: OC1c2c(I)ccc(OCC(F)F)c2CC1(F)F] | | (400 MHz, CDCl₃): δ 7.64 (d, 1H), 6.61 (d, 1H), 6.07 (tt, 1H), 4.94 (d, 1H), 4.19 (td, 2H), 3.50-3.42 (m, 2H), 2.41 (brs, 1H) |
| 207 | 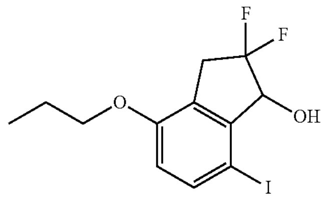 [SMILES: CCCOc1ccc(I)c2c1CC(F)(F)C2O] | | (400 MHz, CDCl₃): δ 7.59 (d, 1H), 6.61 (d, 1H), 4.98-4.91 (m, 1H), 3.92 (td, 2H), 3.48-3.39 (m, 2H), 2.40 (brs, 1H), 1.84-1.76 (m, 2H), 1.02 (t, 3H) |
| 208 | 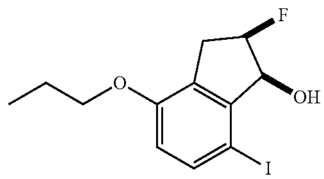 [SMILES: CCCOc1ccc(I)c2c1C[C@@H](F)[C@H]2O] | | (400 MHz, CDCl₃): δ 7.58 (d, 1H), 6.57 (d, 1H), 5.26 (dq, 1H), 5.06-5.01 (m, 1H), 3.91 (t, 2H), 3.21 (dd, 2H), 2.42-2.38 (m, 1H), 1.84-1.74 (m, 2H), 1.03 (t, 3H) |
| 209 | 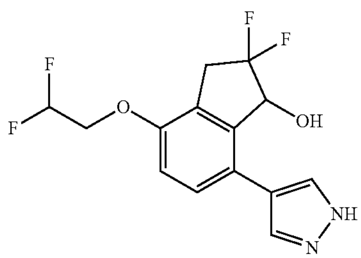 [SMILES: OC1c2c(-c3cn[nH]c3)ccc(OCC(F)F)c2CC1(F)F] | [M + H]⁺ 317 | |
| 210 | 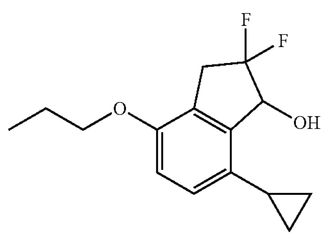 [SMILES: CCCOc1ccc(C2CC2)c2c1CC(F)(F)C2O] | [M + NH4]⁻ 251 | |
| 211 | 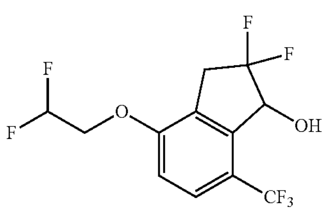 [SMILES: OC1c2c(C(F)(F)F)ccc(OCC(F)F)c2CC1(F)F] | [M − H + HCOOH]⁻ 363 | |
| 212 | 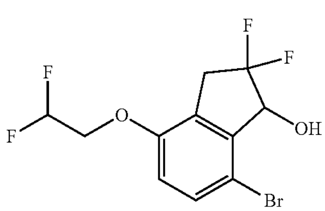 [SMILES: OC1c2c(Br)ccc(OCC(F)F)c2CC1(F)F] | | (400 MHz, CDCl₃): δ 7.42 (d, 1H), 6.73 (d, 1H), 6.07 (tt, 1H), 5.08 (d, 1H), 4.23-4.17 (m, 2H), 3.54-3.35 (m, 2H), 2.49 (brs, 1H) |

TABLE 1-continued

| No. | Structure | Mass Characterization | ¹H NMR Data |
|---|---|---|---|
| 213 | 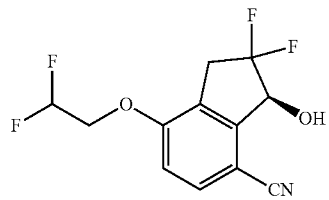 [SMILES: N#Cc1ccc(OCC(F)F)c2c1[C@H](O)C(F)(F)C2] | [M + H]⁺ 276 | |
| 214 | 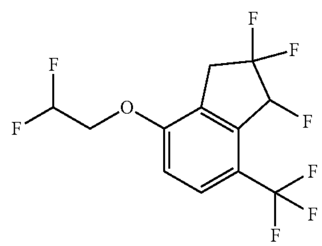 [SMILES: FC(F)COc1ccc(C(F)(F)F)c2c1CC(F)(F)C2F] | | (400 MHz, CDCl$_3$): δ 7.78 (d, 1H), 7.09 (d, 1H), 6.17 (tt, 1H), 5.79 (dd, 1H), 5.24-5.18 (m, 1H), 4.42-4.31 (m, 2H), 2.47-2.44 (m, 1H) |
| 215 | 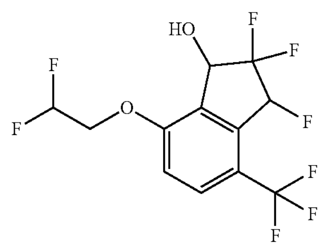 [SMILES: OC1c2c(OCC(F)F)ccc(C(F)(F)F)c2C(F)C1(F)F] | | (400 MHz, CDCl$_3$): δ 7.74 (d, 1H), 7.05 (d, 1H), 6.16 (tt, 1H), 6.02 (dd, 1H), 5.54-5.48 (m, 1H), 4.35 (td, 2H), 2.68 (brd, 1H) |
| 216 | 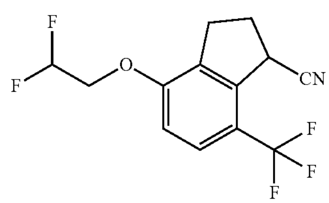 [SMILES: N#CC1CCc2c(OCC(F)F)ccc(C(F)(F)F)c21] | [M − H]⁻ 290 | |
| 217 | 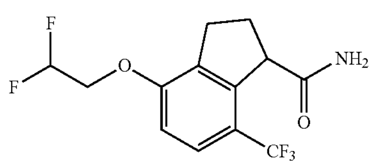 [SMILES: NC(=O)C1CCc2c(OCC(F)F)ccc(C(F)(F)F)c21] | [M + H]⁺ 310 | |
| 218 | 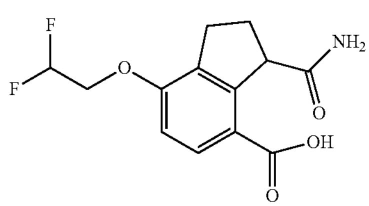 [SMILES: NC(=O)C1CCc2c(OCC(F)F)ccc(C(=O)O)c21] | [M + H]⁺ 286 | |
| 219 | 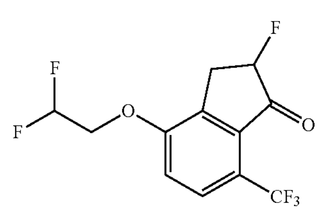 [SMILES: O=C1c2c(C(F)(F)F)ccc(OCC(F)F)c2CC1F] | [M − H + HCOOH]⁻ 343 | |

TABLE 1-continued

| No. | Structure | Mass Characterization | ¹H NMR Data |
|---|---|---|---|
| 220 | 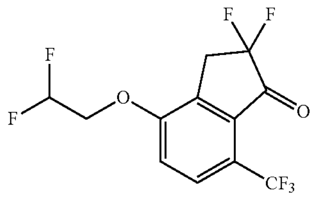 [SMILES: O=C1c2c(C(F)(F)F)ccc(OCC(F)F)c2CC1(F)F] | [M + H]⁺ 317 | |
| 221 | 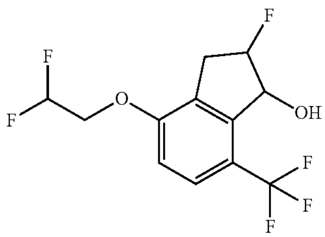 [SMILES: OC1c2c(C(F)(F)F)ccc(OCC(F)F)c2CC1F] | | (400 MHz, CDCl₃): δ 7.56 (d, 1H), 6.84 (d, 1H), 6.11 (tt, 1H), 5.38-5.22 (m, 2H), 4.26 (td, 2H), 3.33-3.07 (m, 2H), 2.52-2.48 (m, 1H) |
| 222 | 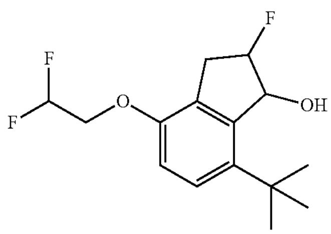 [SMILES: CC(C)(C)c1ccc(OCC(F)F)c2c1C(O)C(F)C2] | | (400 MHz, CDCl₃): δ 7.56 (d, 1H), 6.87 (d, 1H), 6.12 (tt, 1H), 5.49-5.22 (m, 2H), 4.31-4.23 (m, 2H), 3.48-3.06 (m, 2H), 2.48 (brs, 1H) |
| 223 | 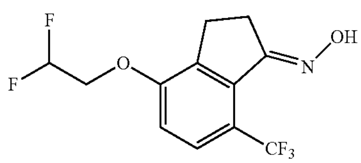 [SMILES: O/N=C1\CCc2c(OCC(F)F)ccc(C(F)(F)F)c21] | | (400 MHz, CDCl₃): δ 7.62 (d, 1H), 7.61 (s, 1H), 6.81 (d, 1H), 6.13 (tt, 1H), 4.28 (td, 2H), 3.09-2.97 (m, 4H) |
| 224 | 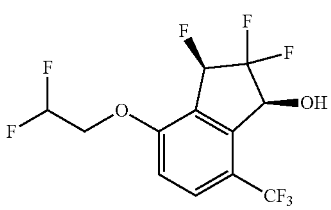 [SMILES: O[C@H]1c2c(C(F)(F)F)ccc(OCC(F)F)c2[C@@H](F)C1(F)F] | [M − H + HCOOH]⁻ 381 | |
| 225 | 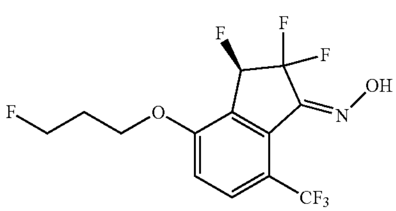 | [M − H]⁻ 344 | |
| 226 | 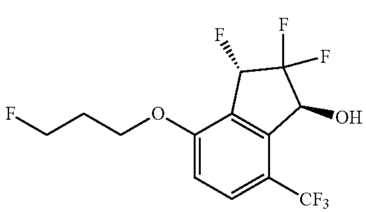 | [M − H + HCOOH]⁻ 377 | |

TABLE 1-continued

| No. | Structure | Mass Characterization | ¹H NMR Data |
|---|---|---|---|
| 227 | 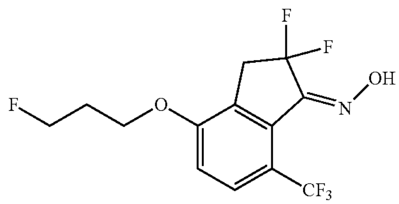 [SMILES: O/N=C1/c2c(C(F)(F)F)ccc(OCCCF)c2CC1(F)F] | [M + H]⁺ 328 | |
| 228 | 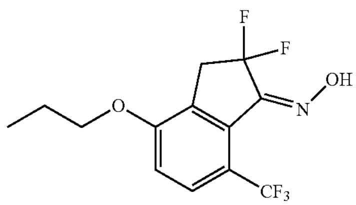 [SMILES: CCCOc1ccc(C(F)(F)F)c2c1CC(F)(F)/C2=N\O] | [M + H]⁺ 310 | |
| 229 | 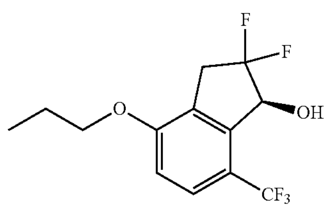 [SMILES: CCCOc1ccc(C(F)(F)F)c2c1CC(F)(F)[C@H]2O] | [M + Na]⁺ 320 | |
| 230 | 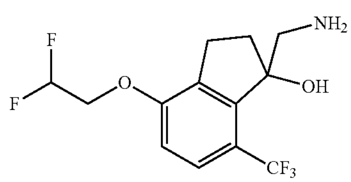 [SMILES: NCC1(O)CCc2c(OCC(F)F)ccc(C(F)(F)F)c21] | [M + H]⁺ 312 | |
| 231 | 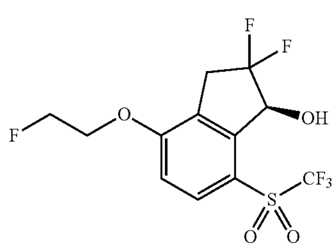 [SMILES: O=S(=O)(c1ccc(OCCF)c2c1[C@H](O)C(F)(F)C2)C(F)(F)F] | 363 (M − H)⁻ | |
| 232 | 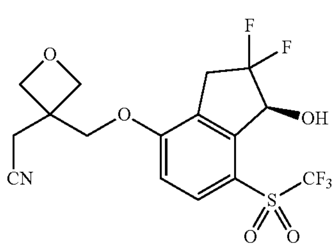 [SMILES: N#CCC1(COc2ccc(S(=O)(=O)C(F)(F)F)c3c2CC(F)(F)[C@H]3O)COC1] | 472 (M + HCO$_2$)⁻ | |
| 233 | 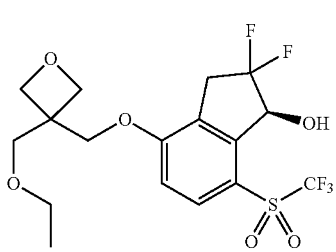 | 491 (M + HCO$_2$)⁻ | |

TABLE 1-continued

| No. | Structure | Mass Characterization | ¹H NMR Data |
|---|---|---|---|
| 234 | 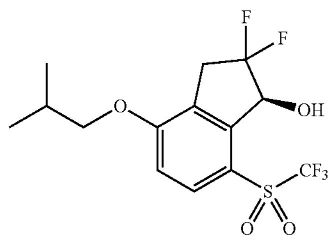 [SMILES: CC(C)COc1ccc(S(=O)(=O)C(F)(F)F)c2c1CC(F)(F)[C@H]2O] | 373 (M − H)⁻ | |
| 235 | 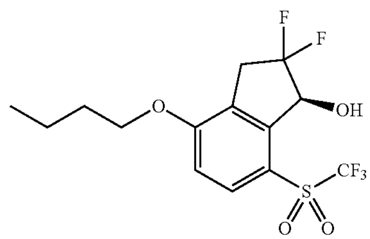 [SMILES: CCCCOc1ccc(S(=O)(=O)C(F)(F)F)c2c1CC(F)(F)[C@H]2O] | 373 (M − H)⁻ | |
| 236 | 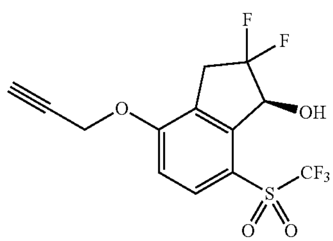 [SMILES: C#CCOc1ccc(S(=O)(=O)C(F)(F)F)c2c1CC(F)(F)[C@H]2O] | 355 (M − H)⁻ | |
| 237 | 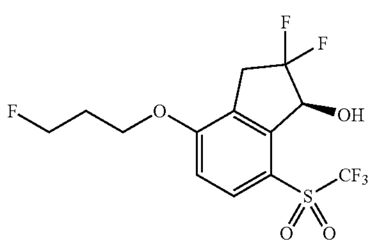 [SMILES: O=S(=O)(c1ccc(OCCCF)c2c1[C@H](O)C(F)(F)C2)C(F)(F)F] | 377 (M − H)⁻ | |
| 238 | 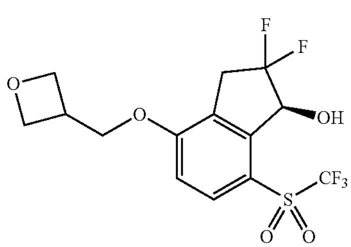 [SMILES: O=S(=O)(c1ccc(OCC2COC2)c2c1[C@H](O)C(F)(F)C2)C(F)(F)F] | 387 (M − H)⁻ | |
| 239 | 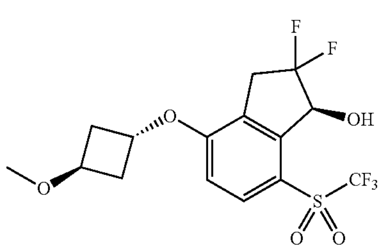 [SMILES: CO[C@H]1C[C@H](Oc2ccc(S(=O)(=O)C(F)(F)F)c3c2CC(F)(F)[C@H]3O)C1] | 401 (M − H)⁻ | |

TABLE 1-continued

| No. | Structure | Mass Characterization | ¹H NMR Data |
|---|---|---|---|
| 240 | 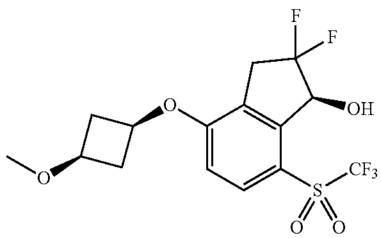 [SMILES: CO[C@H]1C[C@@H](Oc2ccc(S(=O)(=O)C(F)(F)F)c3c2CC(F)(F)[C@H]3O)C1] | 401 (M − H)⁻ | |
| 241 | 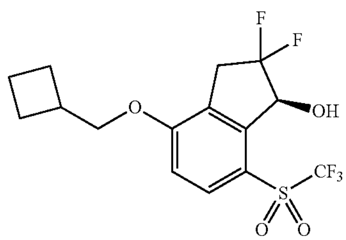 [SMILES: O=S(=O)(c1ccc(OCC2CCC2)c2c1[C@H](O)C(F)(F)C2)C(F)(F)F] | 385 (M − H)⁻ | |
| 242 | 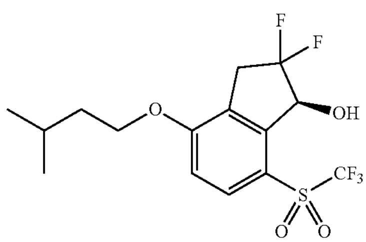 [SMILES: CC(C)CCOc1ccc(S(=O)(=O)C(F)(F)F)c2c1CC(F)(F)[C@H]2O] | 387 (M − H)⁻ | |
| 243 | 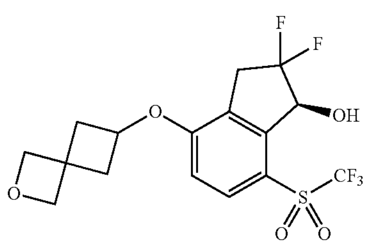 [SMILES: O=S(=O)(c1ccc(OC2CC3(COC3)C2)c2c1[C@H](O)C(F)(F)C2)C(F)(F)F] | 413 (M − H)⁻ | |
| 244 | 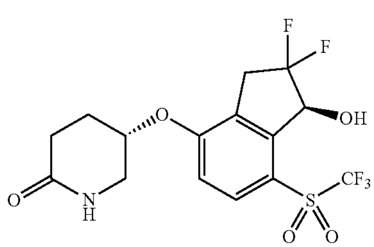 [SMILES: O=C1CC[C@H](Oc2ccc(S(=O)(=O)C(F)(F)F)c3c2CC(F)(F)[C@H]3O)CN1] | 416 (M + H)⁺ | |
| 245 | 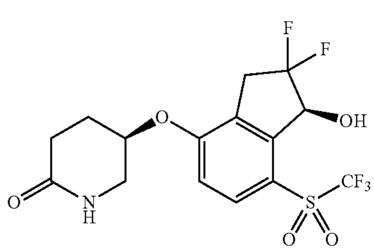 [SMILES: O=C1CC[C@@H](Oc2ccc(S(=O)(=O)C(F)(F)F)c3c2CC(F)(F)[C@H]3O)CN1] | 416 (M + H)⁺ | |

TABLE 1-continued

| No. | Structure | Mass Characterization | $^1$H NMR Data |
|---|---|---|---|
| 246 | 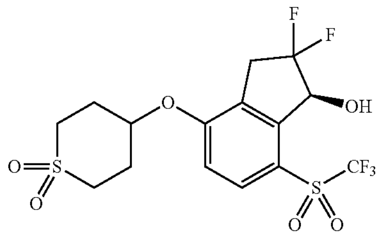 [SMILES: O=S1(=O)CCC(Oc2ccc(S(=O)(=O)C(F)(F)F)c3c2CC(F)(F)[C@H]3O)CC1] | 495 (M + HCO$_2$)$^-$ | |
| 247 | 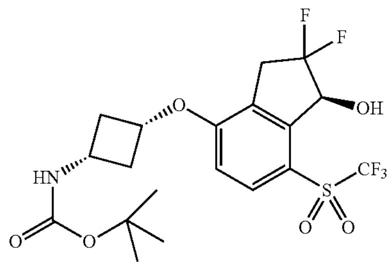 [SMILES: CC(C)(C)OC(=O)N[C@H]1C[C@@H](Oc2ccc(S(=O)(=O)C(F)(F)F)c3c2CC(F)(F)[C@H]3O)C1] | 388 (M + H − CO$_2$—C$_4$H$_8$)$^+$ | |
| 248 | 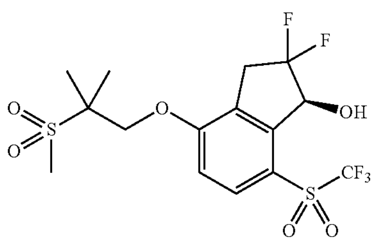 [SMILES: CC(C)(COc1ccc(S(=O)(=O)C(F)(F)F)c2c1CC(F)(F)[C@H]2O)S(C)(=O)=O] | 451 (M − H)$^-$ | |
| 249 | 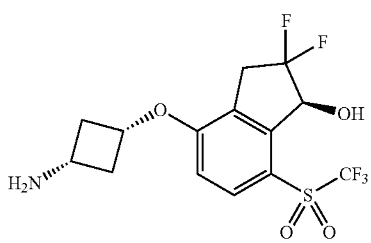 [SMILES: N[C@H]1C[C@@H](Oc2ccc(S(=O)(=O)C(F)(F)F)c3c2CC(F)(F)[C@H]3O)C1] | 388 (M + H)$^+$ | |
| 250 | 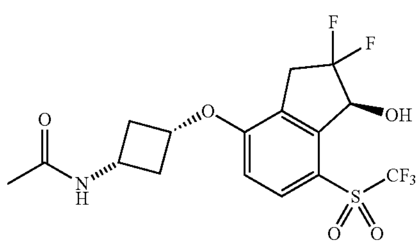 [SMILES: CC(=O)N[C@H]1C[C@@H](Oc2ccc(S(=O)(=O)C(F)(F)F)c3c2CC(F)(F)[C@H]3O)C1] | 430 (M + H)$^+$ | |
| 251 | 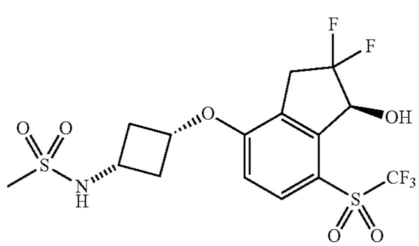 | 510 (M + HCO$_2$)$^-$ | |

TABLE 1-continued

| No. | Structure | Mass Characterization | ¹H NMR Data |
|-----|-----------|----------------------|-------------|
| 252 | 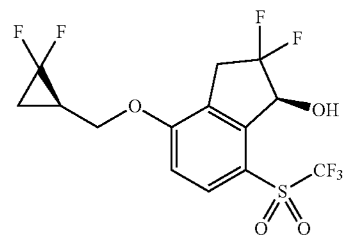 [SMILES: O=S(=O)(c1ccc(OC[C@H]2CC2(F)F)c2c1[C@H](O)C(F)(F)C2)C(F)(F)F] | 407 (M − H)⁻ | |
| 253 | 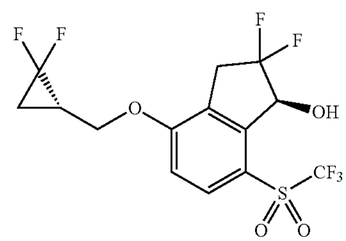 [SMILES: O=S(=O)(c1ccc(OC[C@@H]2CC2(F)F)c2c1[C@H](O)C(F)(F)C2)C(F)(F)F] | 407 (M − H)⁻ | |
| 254 | 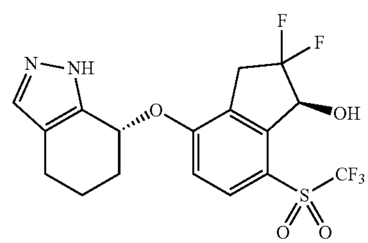 [SMILES: O=S(=O)(c1ccc(O[C@@H]2CCCc3cn[nH]c32)c2c1[C@H](O)C(F)(F)C2)C(F)(F)F] | 439 (M + H)⁺ | |
| 255 | 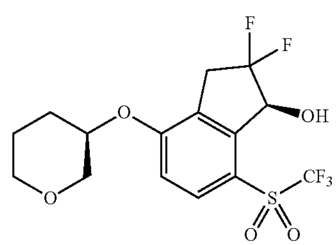 [SMILES: O=S(=O)(c1ccc(O[C@@H]2CCCOC2)c2c1[C@H](O)C(F)(F)C2)C(F)(F)F] | 401 (M − H)⁻ | |
| 256 | 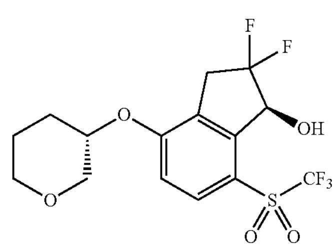 [SMILES: O=S(=O)(c1ccc(O[C@H]2CCCOC2)c2c1[C@H](O)C(F)(F)C2)C(F)(F)F] | 401 (M − H)⁻ | |
| 257 | 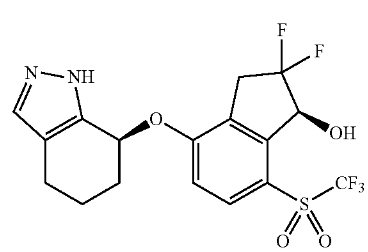 [SMILES: O=S(=O)(c1ccc(O[C@H]2CCCc3cn[nH]c32)c2c1[C@H](O)C(F)(F)C2)C(F)(F)F] | 439 (M + H)⁺ | |

TABLE 1-continued

| No. | Structure | Mass Characterization | ¹H NMR Data |
|---|---|---|---|
| 258 | 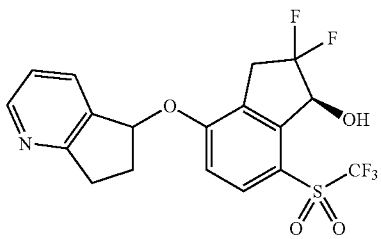 [SMILES: O=S(=O)(c1ccc(OC2CCc3ncccc32)c2c1[C@H](O)C(F)(F)C2)C(F)(F)F] | 436 (M + H)⁺ | |
| 259 | 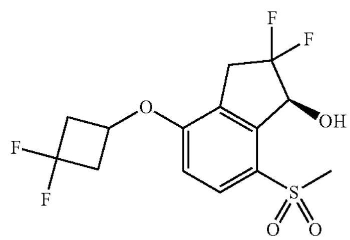 [SMILES: CS(=O)(=O)c1ccc(OC2CC(F)(F)C2)c2c1[C@H](O)C(F)(F)C2] | 355 (M + H)⁺ | |
| 260 | 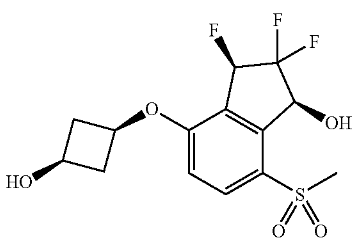 [SMILES: CS(=O)(=O)c1ccc(O[C@H]2C[C@@H](O)C2)c2c1[C@H](O)C(F)(F)[C@@H]2F] | 353 (M + H)⁺ | |
| 261 | 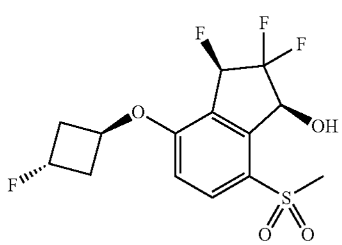 [SMILES: CS(=O)(=O)c1ccc(O[C@H]2C[C@H](F)C2)c2c1[C@H](O)C(F)(F)[C@@H]2F] | 355 (M + H)⁺ | |
| 262 | 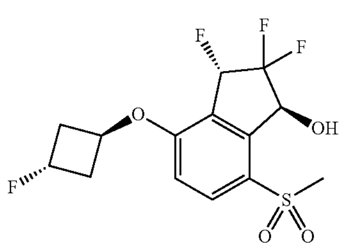 [SMILES: CS(=O)(=O)c1ccc(O[C@H]2C[C@H](F)C2)c2c1[C@H](O)C(F)(F)[C@H]2F] | 355 (M + H)⁺ | |
| 263 | 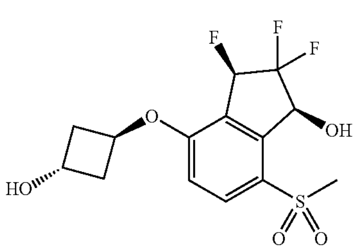 [SMILES: CS(=O)(=O)c1ccc(O[C@H]2C[C@H](O)C2)c2c1[C@H](O)C(F)(F)[C@@H]2F] | 353 (M + H)⁺ | |

TABLE 1-continued

| No. | Structure | Mass Characterization | ¹H NMR Data |
|---|---|---|---|
| 264 | 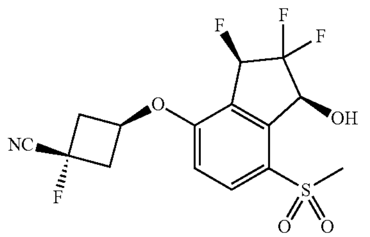 [SMILES: CS(=O)(=O)c1ccc(O[C@H]2C[C@@](F)(C#N)C2)c2c1[C@H](O)C(F)(F)[C@@H]2F] | 402 (M + Na)⁺ | |
| 265 | 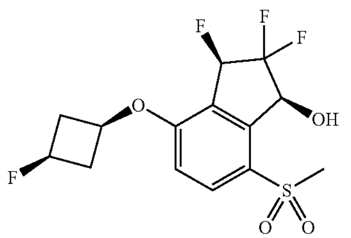 [SMILES: CS(=O)(=O)c1ccc(O[C@H]2C[C@@H](F)C2)c2c1[C@H](O)C(F)(F)[C@@H]2F] | 355 (M + H)⁺ | |
| 266 | 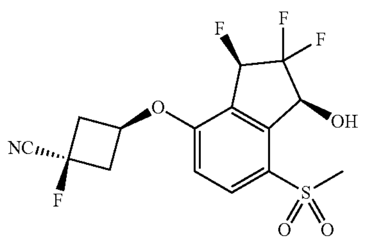 [SMILES: CS(=O)(=O)c1ccc(O[C@H]2C[C@](F)(C#N)C2)c2c1[C@H](O)C(F)(F)[C@@H]2F] | 380 (M + H)⁺ | |
| 267 | 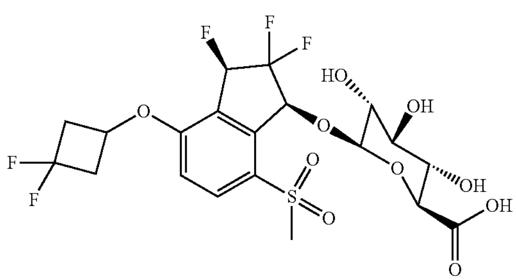 | LCMS ESI(−) m/z: 547 ( (M − H)⁻ | |
| 268 | 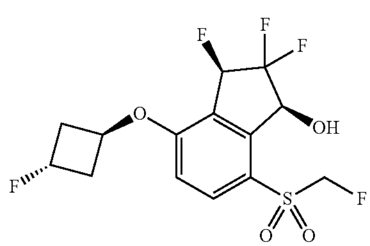 [SMILES: O=S(=O)(CF)c1ccc(O[C@H]2C[C@H](F)C2)c2c1[C@H](O)C(F)(F)[C@@H]2F] | 390 (M + NH₄)⁺ | |
| 269 | 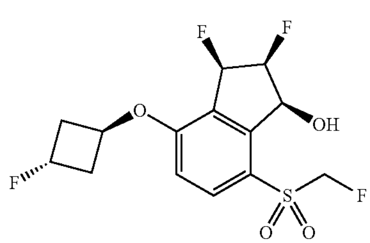 [SMILES: O=S(=O)(CF)c1ccc(O[C@H]2C[C@H](F)C2)c2c1[C@H](O)[C@H](F)[C@@H]2F] | 372 (M + NH₄)⁺ | |

| No. | Structure | Mass Characterization | ¹H NMR Data |
|---|---|---|---|
| 270 | 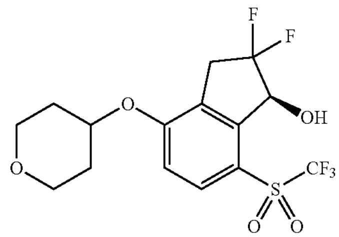 [SMILES: O=S(=O)(c1ccc(OC2CCOCC2)c2c1[C@H](O)C(F)(F)C2)C(F)(F)F] | [M + NH₄]⁺ 420 | |
| 271 | 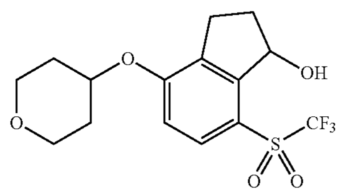 [SMILES: O=S(=O)(c1ccc(OC2CCOCC2)c2c1C(O)CC2)C(F)(F)F] | [M + NH₄]⁺ 384 | |
| 272 | Isomer 1 | | (400 MHz, CDCl₃): δ 8.21 (d, 1H), 7.40 (d, 1H), 4.88-4.83 (m, 1H), 3.67-3.39 (m, 7H), 1.43 (d, 3H) |
| 273 | Isomer 2 | | (400 MHz, CDCl₃): δ 8.13 (d, 1H), 7.34 (d, 1H), 4.82-4.76 (m, 1H), 3.60-3.31 (m, 7H), 1.36 (d, 3H) |
| 274 | 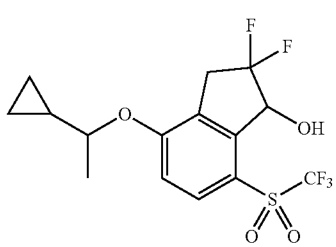 [SMILES: CC(Oc1ccc(S(=O)(=O)C(F)(F)F)c2c1CC(F)(F)C2O)C1CC1] | [M + NH₄]⁺ 404 | |
| 275 | 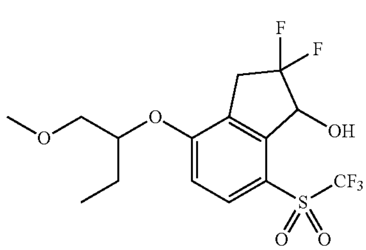 [SMILES: CCC(COC)Oc1ccc(S(=O)(=O)C(F)(F)F)c2c1CC(F)(F)C2O] | [M + NH₄]⁺ 422 | |

TABLE 1-continued

| No. | Structure | Mass Characterization | ¹H NMR Data |
|---|---|---|---|
| 276 | 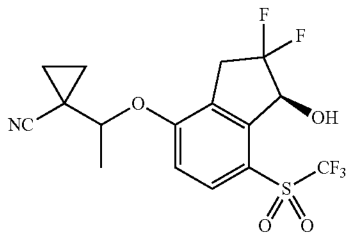 [SMILES: CC(Oc1ccc(S(=O)(=O)C(F)(F)F)c2c1CC(F)(F)[C@H]2O)C1(C#N)CC1] | [M + NH₄]⁺ 429 | |
| 277 | 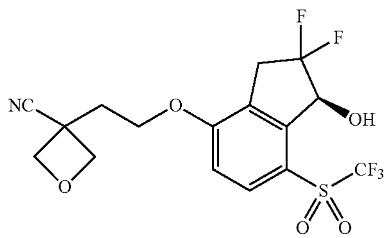 [SMILES: N#CC1(CCOc2ccc(S(=O)(=O)C(F)(F)F)c3c2CC(F)(F)[C@H]3O)COC1] | [M + NH₄]⁺ 445 | |
| 278 | 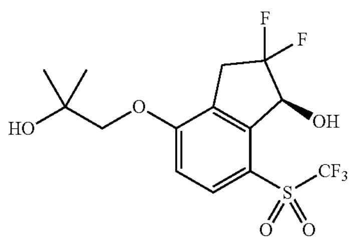 [SMILES: CC(C)(O)COc1ccc(S(=O)(=O)C(F)(F)F)c2c1CC(F)(F)[C@H]2O] | [M + NH₄]⁺ 408 | |
| 279 | 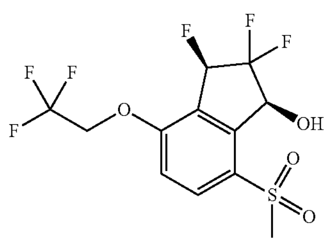 [SMILES: CS(=O)(=O)c1ccc(OCC(F)(F)F)c2c1[C@H](O)C(F)(F)[C@@H]2F] | [M + NH₄]⁺ 382 | |
| 280 | 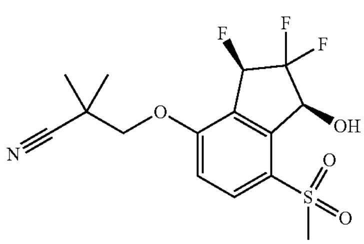 [SMILES: CC(C)(C#N)COc1ccc(S(C)(=O)=O)c2c1[C@@H](F)C(F)(F)[C@H]2O] | [M + NH₄]⁺ 381 | |
| 281 | 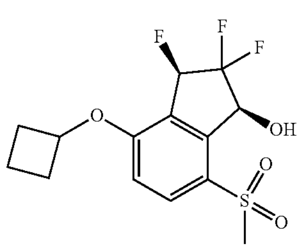 [SMILES: CS(=O)(=O)c1ccc(OC2CCC2)c2c1[C@H](O)C(F)(F)[C@@H]2F] | [M + NH₄]⁺ 354 | |

TABLE 1-continued

| No. | Structure | Mass Characterization | ¹H NMR Data |
|---|---|---|---|
| 282 | 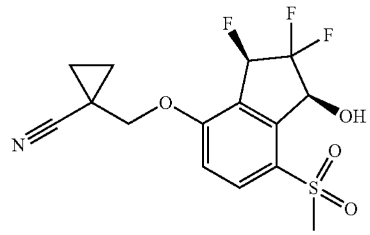 [SMILES: CS(=O)(=O)c1ccc(OCC2(C#N)CC2)c2c1[C@H](O)C(F)(F)[C@@H]2F] | [M + NH₄]⁺ 379 | |
| 283 | 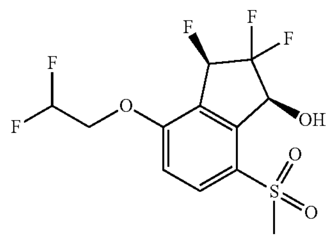 [SMILES: CS(=O)(=O)c1ccc(OCC(F)F)c2c1[C@H](O)C(F)(F)[C@@H]2F] | [M + NH₄]⁺ 364 | |
| 284 | 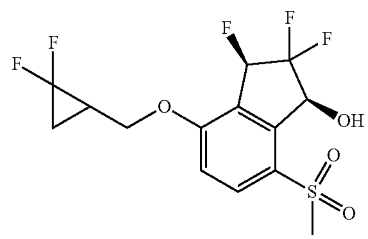 [SMILES: CS(=O)(=O)c1ccc(OCC2CC2(F)F)c2c1[C@H](O)C(F)(F)[C@@H]2F] | [M + NH₄]⁺ 390 | |
| 285 | 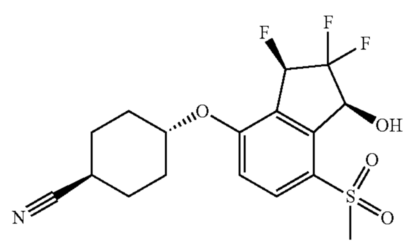 [SMILES: CS(=O)(=O)c1ccc(O[C@H]2CC[C@H](C#N)CC2)c2c1[C@H](O)C(F)(F)[C@@H]2F] | [M + NH₄]⁺ 407 | (400 MHz, CDCl₃): δ 8.09 (d, 1H), 7.07(d, 1H), 5.82-5.66 (m, 1H), 5.61-5.57 (m, 1H), 4.73 (m, 1H), 3.41 (d, 1H), 3.20 (s, 3H), 2.87 (m, 1H), 2.17-1.80 (m, 8H) |
| 286 | 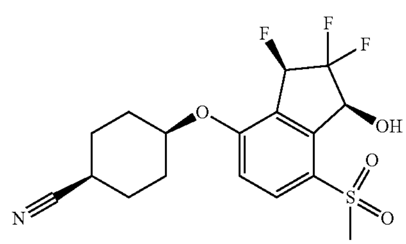 [SMILES: CS(=O)(=O)c1ccc(O[C@H]2CC[C@@H](C#N)CC2)c2c1[C@H](O)C(F)(F)[C@@H]2F] | [M + NH₄]⁺ 407 | (400 MHz, CDCl₃): δ 8.07 (dd, 1H), 7.04(d, 1H), 5.85-5.70 (m, 1H), 5.62-5.58 (m, 1H), 4.65 (m, 1H), 3.25 (d, 1H), 3.20 (s, 3H), 2.76-2.74 (m, 1H), 2.12-1.55 (m, 8H) |
| 287 | 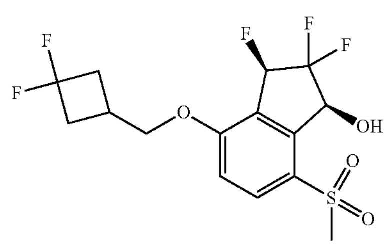 [SMILES: CS(=O)(=O)c1ccc(OCC2CC(F)(F)C2)c2c1[C@H](O)C(F)(F)[C@@H]2F] | [M + NH₄]⁺ 404 | |

| No. | Structure | Mass Characterization | ¹H NMR Data |
|---|---|---|---|
| 288 | 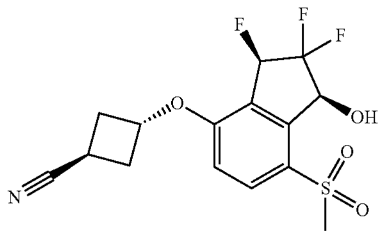 [SMILES: CS(=O)(=O)c1ccc(O[C@H]2C[C@H](C#N)C2)c2c1[C@H](O)C(F)(F)[C@@H]2F] | [M + NH₄]⁺ 379 | (400 MHz, CDCl₃): δ 8.10 (dd, 1H), 6.86(d, 1H), 5.82-5.66 (m, 1H), 5.61-5.58 (m, 1H), 5.17-5.14 (m, 1H), 3.32-3.29 (m, 1H), 3.24 (d, 1H), 3.20 (s, 3H), 2.99-2.93 (m, 2H), 2.76-2.70 (m, 2H) |
| 289 | 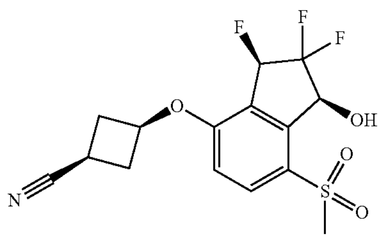 [SMILES: CS(=O)(=O)c1ccc(O[C@H]2C[C@@H](C#N)C2)c2c1[C@H](O)C(F)(F)[C@@H]2F] | [M + NH₄]⁺ 379 | (400 MHz, CDCl₃): δ 8.08 (dd, 1H), 6.84 (d, 1H), 5.85-5.69 (m, IH), 5.62-5.58 (m, 1H), 4.86-4.79 (m, 1H), 3.24 (d, 1H), 3.20 (s, 3H), 3.07-3.00 (m, 2H), 2.96-2.87 (m, 1H), 2.76-2.66 (m, 2H) |
| 290 | 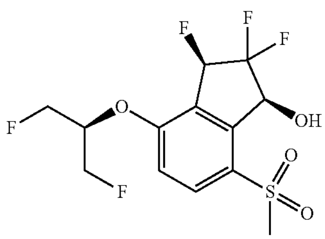 | [M + NH₄]⁺ 378 | |
| 291 | 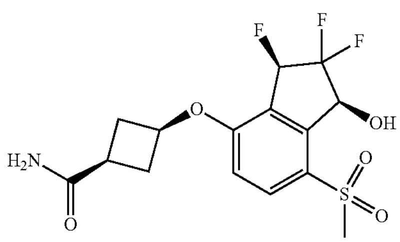 [SMILES: CS(=O)(=O)c1ccc(O[C@H]2C[C@@H](C(N)=O)C2)c2c1[C@H](O)C(F)(F)[C@@H]2F] | [M + NH₄]⁺ 397 | (400 MHz, CDCl₃): δ 8.06 (dd, 1H), 6.90 (d, 1H), 5.85-5.70 (m, IH), 5.59-5.56 (m, 1H), 5.39-5.32 (m, 2H), 4.79-4.76 (m, 1H), 3.24 (d, 1H), 3.20 (s, 3H), 2.83-2.74 (m, 3H), 2.63-2.55 (m, 2H) |
| 292 | 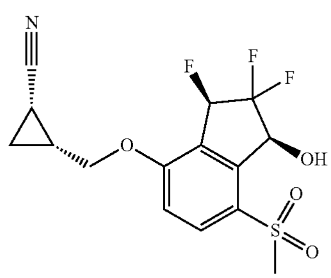 [SMILES: CS(=O)(=O)c1ccc(OC[C@@H]2C[C@@H]2C#N)c2c1[C@H](O)C(F)(F)[C@@H]2F] | [M + NH₄]⁺ 379 | (400 MHz, CDCl₃): δ 8.10 (dd, 1H), 7.09 (d, 1H), 5.91-5.76 (m, 1H), 5.58-5.55 (m, 1H), 4.48-4.44 (m, 1H), 4.14-4.10 (m, 1H), 3.41 (d, 1H), 3.20 (s, 3H), 1.94-1.91 (m, 1H), 1.81-1.76 (m, 1H), 1.46-1.41 (m, 1H), 1.20-1.18 (m, 1H) |
| 293 | 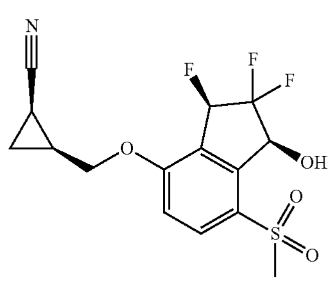 [SMILES: CS(=O)(=O)c1ccc(OC[C@H]2C[C@H]2C#N)c2c1[C@H](O)C(F)(F)[C@@H]2F] | [M + NH₄]⁺ 379 | (400 MHz, CDCl₃): δ 8.12 (dd, 1H), 7.10 (d, IH), 5.91-5.75 (m, 1H), 5.62-5.58 (m, 1H), 4.39-4.29 (m, 2H), 3.26 (d, 1H), 3.21 (s, 3H), 1.90-1.86 (m, 1H), 1.79-1.76 (m, 1H), 1.45-1.39 (m, 1H), 1.26-1.22 (m, 1H) |

TABLE 1-continued

| No. | Structure | Mass Characterization | ¹H NMR Data |
|---|---|---|---|
| 294 | 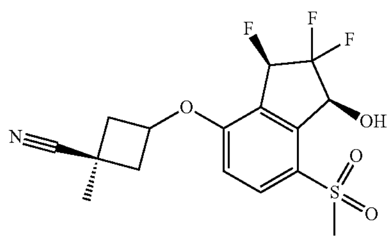 | [M + NH₄]⁺ 393 | (400 MHz, CDCl₃): δ 8.10 (dd, 1H), 6.88 (d, 1H), 5.82-5.66 (m, 1H), 5.61-5.58 (m, 1H), 5.08-5.02 (m, 1H), 3.29 (d, 1H), 3.20 (s, 3H), 3.19-3.14 (m, 2H), 2.42-2.32 (m, 2H), 1.65 (s, 3H) |
| 295 | 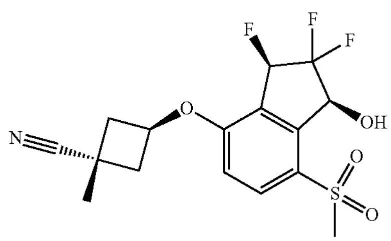 [SMILES: CS(=O)(=O)c1ccc(O[C@H]2C[C@](C)(C#N)C2)c2c1[C@H](O)C(F)(F)[C@@H]2F] | [M + NH₄]⁺ 393 | (400 MHz, CDCl₃): δ 8.05 (d, 1H), 6.81 (d, 1H), 5.87-5.71 (m, 1H), 5.61-5.58 (m, 1H), 4.97-4.91 (m, 1H), 3.25 (d, 1H), 3.20 (s, 3H), 2.92-2.76 (m, 2H), 2.74-2.70 (m, 2H), 1.65 (s, 3H) |
| 296 | 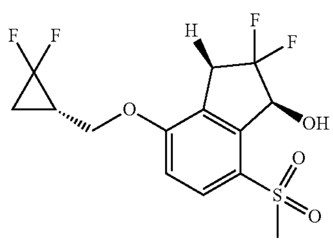 | [M + NH₄]⁺ 390 | (400 MHz, CDCl₃): δ 8.11 (dd, 1H), 7.07 (d, 1H), 5.85-5.69 (m, 1H), 5.62-5.58 (m, 1H), 4.36-4.32 (m, 1H), 4.21-4.17 (m, 1H), 3.27 (d, 1H), 3.20 (s, 3H), 2.18-2.10 (m, 1H), 1.72-1.67 (m, 2H), 1.41-1.33 (m, 1H) |
| 297 | 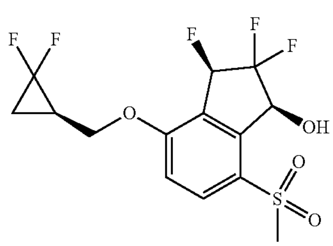 [SMILES: CS(=O)(=O)c1ccc(OC[C@H]2CC2(F)F)c2c1[C@H](O)C(F)(F)[C@@H]2F] | [M + NH₄]⁺ 390 | (400 MHz, CDCl₃): δ 8.11 (dd, 1H), 7.06 (d, 1H), 5.87-5.72 (m, 1H), 5.61-5.57 (m, 1H), 4.25-4.23 (m, 2H), 3.27 (d, 1H), 3.20 (s, 3H), 2.22-2.10 (m, 1H), 1.73-1.70 (m, 2H), 1.39-1.36 (m, 1H) |
| 298 | 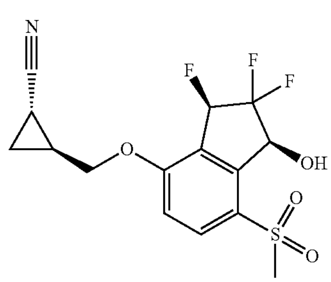 [SMILES: CS(=O)(=O)c1ccc(OC[C@H]2C[C@@H]2C#N)c2c1[C@H](O)C(F)(F)[C@@H]2F] | [M + NH₄]⁺ 379 | (400 MHz, CDCl₃): δ 8.10 (dd, 1H), 7.02 (d, 1H), 5.83-5.67 (m, 1H), 5.61-5.58 (m, 1H), 4.25-4.22 (m, 1H), 4.14-4.09 (m, 1H), 3.32-3.29 (m, 1H), 3.21 (s, 3H), 2.06-2.04 (m, 1H), 1.59-1.55 (m, 1H), 1.47-1.44 (m, 1H), 1.28-1.25 (m, 1H) |
| 299 | 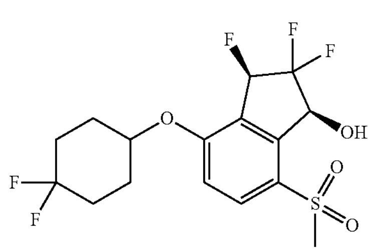 [SMILES: CS(=O)(=O)c1ccc(OC2CCC(F)(F)CC2)c2c1[C@H](O)C(F)(F)[C@@H]2F] | [M + NH₄]⁺ 418 | |

TABLE 1-continued

| No. | Structure | Mass Characterization | ¹H NMR Data |
|-----|-----------|----------------------|-------------|
| 300 | 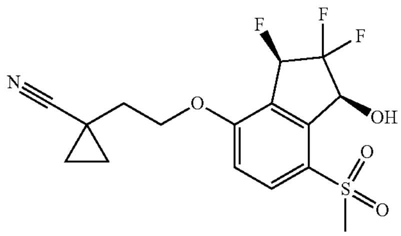 [SMILES: CS(=O)(=O)c1ccc(OCCC2(C#N)CC2)c2c1[C@H](O)C(F)(F)[C@@H]2F] | [M + NH₄]⁺ 393 | |
| 301 | 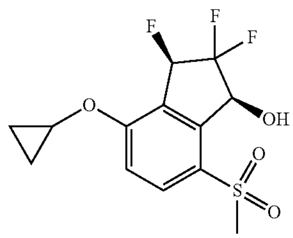 [SMILES: CS(=O)(=O)c1ccc(OC2CC2)c2c1[C@H](O)C(F)(F)[C@@H]2F] | [M + NH₄]⁺ 340 | |
| 302 | 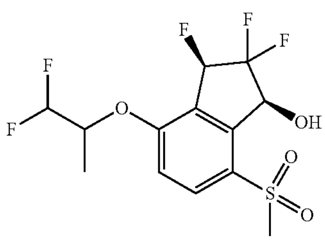 [SMILES: CC(Oc1ccc(S(C)(=O)=O)c2c1[C@@H](F)C(F)(F)[C@H]2O)C(F)F] | [M + NH₄]⁺ 378 | |
| 303 | 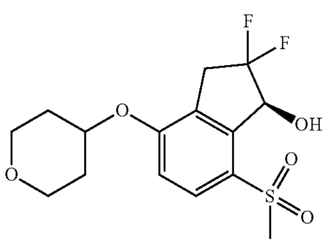 [SMILES: CS(=O)(=O)c1ccc(OC2CCOCC2)c2c1[C@H](O)C(F)(F)C2] | [M + NH₄]⁺ 366 | |
| 304 | 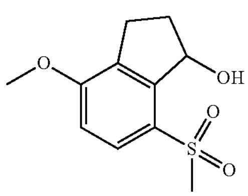 [SMILES: COc1ccc(S(C)(=O)=O)c2c1CCC2O] | [M + NH₄]⁺ 260 | |
| 305 | 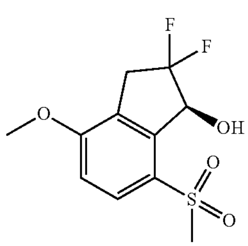 [SMILES: COc1ccc(S(C)(=O)=O)c2c1CC(F)(F)[C@H]2O] | [M + NH₄]⁺ 296 | |

TABLE 1-continued

| No. | Structure | Mass Characterization | ¹H NMR Data |
|---|---|---|---|
| 306 | 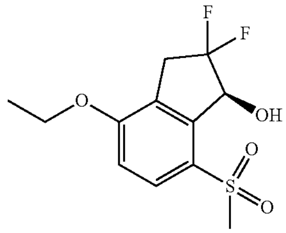 [SMILES: CCOc1ccc(S(C)(=O)=O)c2c1CC(F)(F)[C@H]2O] | [M + NH$_4$]$^+$ 310 | |
| 307 | 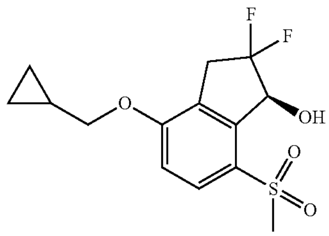 [SMILES: CS(=O)(=O)c1ccc(OCC2CC2)c2c1[C@H](O)C(F)(F)C2] | [M + NH$_4$]$^+$ 336 | |
| 308 | 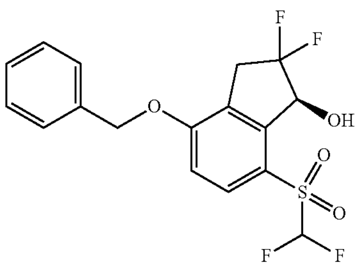 [SMILES: O=S(=O)(c1ccc(OCc2ccccc2)c2c1[C@H](O)C(F)(F)C2)C(F)F] | [M + NH$_4$]$^+$ 408 | |
| 309 | 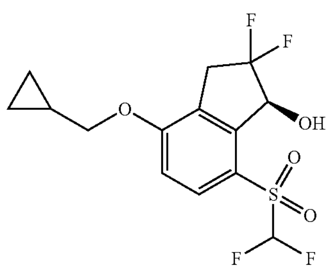 [SMILES: O=S(=O)(c1ccc(OCC2CC2)c2c1[C@H](O)C(F)(F)C2)C(F)F] | [M + NH$_4$]$^+$ 372 | |
| 310 | 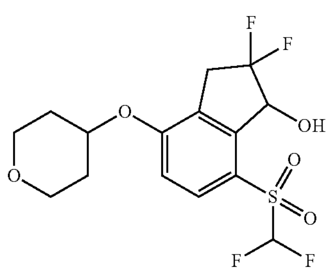 [SMILES: O=S(=O)(c1ccc(OC2CCOCC2)c2c1C(O)C(F)(F)C2)C(F)F] | | (400 MHz, CDCl$_3$): δ 7.89 (d, 1H), 6.98 (d, 1H), 6.55 (t, J =54 Hz, 1H), 5.41 (d, 1H), 4.68 (m, 1H), 3.98-3.88 (m, 2H), 3.66-3.54 (m, 2H), 3.48-3.26 (m, 2H), 1.87-1.74 (m, 2H), 1.62-1.51 (m, 2H) |

Method of Use:

In one aspect, the present disclosure provides a method for treating a proliferative disorder in a subject in need thereof, comprising administering to said subject a HIF-2α inhibitor. In some embodiments, the proliferative disorder is a cancer condition. In some further embodiments, said cancer condition is a cancer selected from the group consisting of lung cancer, head and neck squamous cell carcinoma, pancreatic cancer, breast cancer, ovarian cancer, renal cell carcinoma, prostate cancer, neuroendocrine cancer, gastric cancer, bladder cancer and colon cancer. In another embodiment, the cancer condition is renal cell carcinoma.

In a further embodiment, the present disclosure provides a method of treating a cancer condition, wherein the HIF-2α inhibitor is effective in one or more of inhibiting proliferation of cancer cells, inhibiting metastasis of cancer cells, killing cancer cells and reducing severity or incidence of symptoms associated with the presence of cancer cells. In some other embodiments, said method comprises administering to the cancer cells a therapeutically effective amount of a HIF-2α inhibitor. In some embodiments, the administration takes place in vitro. In other embodiments, the administration takes place in vivo.

In some embodiments, the present invention provides a method of treating a von Hippel-Lindau (VHL) disease, comprising administering to a subject in need thereof an effective amount of a HIF-2α inhibitor described herein. VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2α activity (Maher, et al. *Eur. J. Hum. Genet.* 19: 617-623, 2011). HIF-2α has been linked to cancers of the retina, adrenal gland and pancreas through both VHL disease and activating mutations. Recently, gain-of-function HIF-2α mutations have been identified in erythrocytosis and paraganglioma with polycythemia (Zhuang, et al. *NEJM* 367: 922-930, 2012; Percy, et al. *NEJM* 358: 162-168, 2008; and Percy, et al. *Am. J. Hematol.* 87: 439-442, 2012). Notably, a number of known HIF-2α target gene products (e.g., VEGF, PDGF, and cyclin DI) have been shown to play pivotal roles in cancers derived from kidney, liver, colon, lung, and brain. In fact, therapies targeted against one of the key HIF-2α regulated gene products, VEGF, have been approved for the treatment of these cancers.

As used herein, a therapeutically effective amount of a HIF-2α inhibitor refers to an amount sufficient to effect the intended application, including but not limited to, disease treatment, as defined herein. Also contemplated in the subject methods is the use of a sub-therapeutic amount of a HIF-2α inhibitor for treating an intended disease condition.

The amount of the HIF-2α inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of HIF-2α can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with a HIF-2α inhibitor may be monitored to determine the effectiveness of treatment, and the treatment regimen may be adjusted based on the subject's physiological response to treatment. For example, if inhibition of a biological effect of HIF-2α inhibition is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with a HIF-2α inhibitor is discontinued if inhibition of the biological effect is above or below a threshold, such as in a lack of response or an adverse reaction. The biological effect may be a change in any of a variety of physiological indicators.

In general, a HIF-2α inhibitor is a compound that inhibits one or more biological effects of HIF-2α. Examples of biological effects of HIF-2α include, but are not limited to, heterodimerization of HIF-2α to HIF-1, HIF-2α target gene expression, VEGF gene expression, and VEGF protein secretion. In some embodiments, the HIF-2α inhibitor is selective for HIF-2α, such that the inhibitor inhibits heterodimerization of HIF-2α to HIF-β but not heterodimerization of HIF-1α to HIF-β. Such biological effects may be inhibited by about or more than about 10%, 20%, 30%, 40%, 50%, 60%, 70%, 80%, 90%, 95%, or more.

Hypoxia-inducible factors (HIFs), like HIF-2α, are transcription factors that respond to changes in available oxygen in the cellular environment (e.g. a decrease in oxygen, or hypoxia). The HIF signaling cascade mediates the effects of hypoxia, the state of low oxygen concentration, on the cell. Hypoxia often keeps cells from differentiating. However, hypoxia promotes the formation of blood vessels, and is important for the formation of a vascular system in embryos, and cancer tumors. The hypoxia in wounds also promotes the migration of keratinocytes and the restoration of the epithelium. A HIF-2α inhibitor of the present disclosure may be administered in an amount effective in reducing any one or more of such effects of HIF-2α activity.

HIF-2α activity can be inhibited by inhibiting heterodimerization of HIF-2α to HIF-1β (ARNT), such as with inhibitor compounds disclosed herein. A variety of methods for measuring HIF-2α dimerization are available. In some embodiments, the HIF-2α inhibitor binds the PAS-B domain cavity of HIF-2α.

Inhibition of heterodimerization of HIF-2α to HIF-1p (ARNT) may also be determined by a reduction in HIF-2α target gene mRNA expression. mRNA quantitation can be performed using real-time PCR technology. (Wong, et al, "Real-time PCR for mRNA quantitation", 2005. BioTechniques 39, 1: 1-1.). Yet another method for determining inhibition of heterodimerization of HIF-2α to HIF-1β (ARNT) is by co-immunoprecipitation.

As described herein, HIF-2α is a transcription factor that plays important roles in regulating expression of target genes. Non-limiting examples of HIF-2α target genes include HMOX1, SFTPA1, CXCR4, PAI1, BDNF, hTERT, ATP7A, and VEGF. For instance, HIF-2α is an activator of VEGF. Further non-limiting examples of HIF-2α target genes include HMOX1, EPO, CXCR4, PAI1, CCND1, CLUT1, IL6, and VEGF. A HIF-2α inhibitor of the present disclosure may be administered in an amount effective in reducing expression of any one or more of genes induced by HIF-2α activity. A variety of methods is available for the detection of gene expression levels, and includes the detection of gene transcription products (polynucleotides) and translation products (polypeptides). For example, gene expression can be detected and quantified at the DNA, RNA or mRNA level. Various methods that have been used to quantify mRNA include in situ hybridization techniques, fluorescent in situ hybridization techniques, reporter genes, RNase protection assays, Northern blotting, reverse transcription (RT)-PCR, SAGE, DNA microarray, tiling array, and RNA-seq. Examples of methods for the detection of polynucleotides include, but are not limited to selective colorimetric detection of polynucleotides based on the distance-dependent optical properties of gold nanoparticles, and solution phase detection of polynucleotides using interacting fluorescent labels and competitive hybridization.

Examples for the detection of proteins include, but are not limited to microscopy and protein immunostaining, protein immunoprecipitation, immunoelectrophoresis, western blot, BCA assay, spectrophotometry, mass spectrophotometry and enzyme assay.

In some embodiments, inhibition of HIF-2α is characterized by a decrease in VEGF gene expression. The decrease may be measured by any of a variety of methods, such as those described herein. As a further example, the mRNA expression level of VEGF can be measured by quantitative PCR (QT-PCR), microarray, RNA-seq and nanostring. As another example, an ELISA assay can be used to measure the level VEGF protein secretion.

In some other embodiments, the subject methods are useful for treating a disease condition associated with HIF-2α. Any disease condition that results directly or indirectly from an abnormal activity or expression level of HIF-2α can be an intended disease condition. In some embodiments, the disease condition is a proliferative disorder, such as described herein, including but not limited to cancer. A role of HIF-2α in tumorigenesis and tumor progression has been implicated in many human cancers. Constitutively active HIF-2α may be the result of defective VHL or a low concentration of oxygen in a cancer cell. Rapidly growing tumors are normally hypoxic due to poor vascularization, a condition that activates HIF-2α in support of tumor cell survival and proliferation. Constitutive activation of HIF-2α is emerging as a common theme in diverse human cancers, consequently agents that target HIF-2α have therapeutic value.

The data presented in the Examples herein below demonstrate the anti-cancer effects of a HIF-2α inhibitor. As such, the subject method is particularly useful for treating a proliferative disorder, such as a neoplastic condition. Non-limiting examples of such conditions include but are not limited to acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basal-like carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathy-associated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, glomus tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, non-melanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof.

In some embodiments, the methods of administering a HIF-2α inhibitor described herein are applied to the treatment of cancers of the adrenal glands, blood, bone marrow, brain, breast, cervix, colon, head and neck, kidney, liver, lung, ovary, pancreas, plasma cells, rectum, retina, skin, spine, throat or any combination thereof.

Certain embodiments contemplate a human subject such as a subject that has been diagnosed as having or being at risk for developing or acquiring a proliferative disorder condition. Certain other embodiments contemplate a non-human subject, for example a non-human primate such as a macaque, chimpanzee, gorilla, vervet, orangutan, baboon or other non-human primate, including such non-human subjects that can be known to the art as preclinical models. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present disclosure, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Therapeutic Efficacy:

In some embodiments, therapeutic efficacy is measured based on an effect of treating a proliferative disorder, such as cancer. In general, therapeutic efficacy of the methods and compositions of the disclosure, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some desirable embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the inventive method in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the inventive method can be determined by a number of secondary parameters. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932,412).

In additional desirable embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the disclosure can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, administration of a HIF-2α inhibitor provides improved therapeutic efficacy over treatment with either agent alone. Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold or more, using an appropriate measure (e.g. tumor size reduction, duration of tumor size stability, duration of time free from metastatic events, duration of disease-free survival).

Pharmaceutical Compositions:

A composition of the present disclosure may be formulated in any suitable pharmaceutical formulation. A pharmaceutical composition of the present disclosure typically contains an active ingredient (e.g., a compound of the present disclosure or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants. A composition of the present disclosure may be formulated in any suitable pharmaceutical formulation. In some embodiments, the pharmaceutical acceptable carriers, excipients are selected from the group consisting of water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral intervention administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of each compound administered will be dependent on the mammal being treated, the severity of the disorder or condition, the rate of administration, the disposition of the compound and the discretion of the prescribing physician. However, an effective dosage may be in the range of about 0.001 to about 100 mg per kg body weight per day, in single or divided doses. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the disclosure provides a pharmaceutical composition comprising an amount of a HIF-2α inhibitor formulated for administration to a subject in need thereof. In some embodiments, the pharmaceutical composition comprises between about 0.0001-500 g, 0.001-250 g, 0.01-100 g, 0.1-50 g, or 1-10 g of HIF-2α inhibitor. In some embodiments, the pharmaceutical composition comprises about or more than about 0.0001 g, 0.001 g, 0.01 g, 0.1, 0.5 g, 1 g, 2 g, 3 g, 4 g, 5 g, 6 g, 7 g, 8 g, 9 g, 10 g, 15 g, 20 g, 25 g, 50 g, 100 g, 200 g, 250 g, 300 g, 350 g, 400 g, 450 g, 500 g, or more of a HIF-2α inhibitor. In some embodiments, the pharmaceutical composition comprises between 0.001-2 g of a HIF-2α inhibitor in a single dose. In some embodiments, the pharmaceutical composition comprises an amount between about 50-150 g of a HIF-2α inhibitor. In some embodiments, the therapeutic amount can be an amount between about 0.001-0.1 g of a HIF-2α inhibitor. In some embodiments, the therapeutic amount can be an amount between about 0.01-30 g of a HIF-2α inhibitor.

In some embodiments, a therapeutically effective amount of HIF-2α inhibitor, which can be a daily amount administered over the course of a period of treatment, can sufficiently provide any one or more of the therapeutic effects described herein. As an example, the therapeutic effective amount can be in the range of about 0.001-1000 mg/kg body weight, 0.01-500 mg/kg body weight, 0.01-100 mg/kg body weight, 0.01-30 mg/kg body weight, 0.1-200 mg/kg body weight, 3-200 mg/kg body weight, 5-500 mg/kg body weight, 10-100 mg/kg body weight, 10-1000 mg/kg body weight, 50-200 mg/kg body weight, 100-1000 mg/kg body weight, 200-500 mg/kg body weight, 250-350 mg/kg body weight, or 300-600 mg/kg body weight of a HIF-2α inhibitor. In some embodiments, the therapeutic amount can be about or more than about 0.001 mg/kg body weight, 0.01 mg/kg body weight, 0.1 mg/kg body weight, 0.5 mg/kg body weight, 1 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 15 mg/kg body weight, 20 mg/kg body weight, 25 mg/kg body weight, 50 mg/kg body weight, 100 mg/kg body weight, 200 mg/kg body weight, 250 mg/kg body weight, 300 mg/kg body weight, 350 mg/kg body weight, 400 mg/kg body weight, 450 mg/kg body weight, 500 mg/kg body weight, 600 mg/kg body weight, 800 mg/kg body weight, 1000 mg/kg body weight, or more of a HIF-2a inhibitor. In some embodiments, the effective amount is at least about 0.01 mg/kg body weight of a HIF-2α inhibitor. In some embodiments, the effective amount is an amount between about 0.01-30 mg/kg body weight of a HIF-2α inhibitor. In some embodiments, the therapeutic amount can be an amount between about 50-150 mg/kg body weight of a HIF-2α inhibitor.

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot every second day to once a month or even longer. Most typically and conveniently for the subject, a HIF-2α inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

In some embodiments, the HIF-2α inhibitor can be administered as part of a therapeutic regimen that comprises administering one or more second agents (e.g. 1, 2, 3, 4, 5, or more second agents), either simultaneously or sequentially with the HIF-2α inhibitor. When administered sequentially, the HIF-2α inhibitor may be administered before or after the one or more second agents. When administered simultaneously, the HIF-2α inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising a HIF-2α inhibitor and one or more second agents).

A combination treatment according to the disclosure may be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. The exact dosage will depend upon the agent selected, the route of administration, the form in which the compound is administered, the subject to be treated, the body weight of the subject to be treated, and the preference and experience of the attending physician.

Pharmaceutical Composition for Oral Administration.

In some embodiments, the disclosure provides a pharmaceutical composition for oral administration containing at least one compound of the present disclosure and a pharmaceutical excipient suitable for oral administration. The composition may be in the form of a solid, liquid, gel, semi-liquid, or semi-solid. In some embodiments, the composition further comprises a second agent.

In some embodiments, the disclosure provides a solid pharmaceutical composition for oral administration containing: (i) a HIF-2α inhibitor; and (ii) a pharmaceutical excipient suitable for oral administration. In some embodiments, the composition further contains: (iii) a third agent or even a fourth agent. In some embodiments, each compound or agent is present in a therapeutically effective amount. In other embodiments, one or more compounds or agents is present in a sub-therapeutic amount, and the compounds or agents act synergistically to provide a therapeutically effective pharmaceutical composition.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Composition for Topical (e.g., Transdermal) Delivery.

In some embodiments, the disclosure provides a pharmaceutical composition for transdermal delivery containing a compound of the present disclosure and a pharmaceutical excipient suitable for transdermal delivery. The composition may be in the form of a solid, liquid, gel, semi-liquid, or semi-solid. In some embodiments, the composition further comprises a second agent.

Composition of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Another exemplary formulation for use in the methods of the present disclosure employs transdermal delivery devices ("patches"). Such transdermal patches may be used to provide continuous or discontinuous infusion of a compound of the present disclosure in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Composition for Injection.

In some embodiments, the disclosure provides a pharmaceutical composition for injection containing a compound of the present disclosure and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Composition for Inhalation.

Compositions for inhalation or insufflation include solutions and suspensions in pharmaceutically acceptable, aqueous or organic solvents, or mixtures thereof, and powders. The liquid or solid composition may contain suitable pharmaceutically acceptable excipients as described vide supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Composition.

Pharmaceutical composition may also be prepared from composition described herein and one or more pharmaceutically acceptable excipients suitable for sublingual, buccal, rectal, intraosseous, intraocular, intranasal, epidural, or intraspinal administration. Preparations for such pharmaceutical composition are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

The compounds of the present disclosure can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present disclosure, stabilizers, preservatives, excipients, and the like. The preferred lipids are the phospholipids and phosphatidyl cholines (lecithins), both natural and synthetic. Methods to form liposomes are known in the art. See, for example, Prescott, Ed., "Methods in Cell Biology", Volume XIV, ISBN: 978-

0-12-564114-2, Academic Press, New York, N.W., p. 33 (1976) and Medina, Zhu, and Kairemo, "Targeted liposomal drug delivery in cancer", *Current Pharm. Des.* 10: 2981-2989, 2004. For additional information regarding drug formulation and administration, see "Remington: The Science and Practice of Pharmacy," Lippincott Williams & Wilkins, Philadelphia, ISBN-10: 0781746736, 21$^{st}$ Edition (2005).

The disclosure also provides kits. The kits may include a HIF-2α inhibitor and one or more additional agents in suitable packaging with written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present disclosure and the agent are provided as separate compositions in separate containers within the kit. In some embodiments, the compound of the present disclosure and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Combination Therapies:

The present disclosure also provides methods for further combination therapies in which, in addition to a HIF-2α inhibitor, one or more second agents known to modulate other pathways, or other components of the same pathway, or even overlapping sets of target proteins is used, or a pharmaceutically acceptable salt, ester, prodrug, solvate, hydrate or derivative thereof. In one aspect, such therapy includes but is not limited to the combination of the composition comprising a HIF-2α inhibitor as described herein with one or more of other HIF-2α inhibitors as described herein, chemotherapeutic agents, therapeutic antibodies, and radiation treatment, to provide, where desired, a synergistic or additive therapeutic effect.

Second agents useful in the methods of the disclosure include any agent capable of modulating a target molecule, either directly or indirectly. Non-limiting examples of target molecules modulated by second agents include enzymes, enzyme substrates, products of transitions, antibodies, antigens, membrane proteins, nuclear proteins, cytosolic proteins, mitochondrial proteins, lysosomal proteins, scaffold proteins, lipid rafts, phosphoproteins, glycoproteins, membrane receptors, G-protein-coupled receptors, nuclear receptors, protein tyrosine kinases, protein serine/threonine kinases, phosphatases, proteases, hydrolases, lipases, phospholipases, ligases, reductases, oxidases, synthases, transcription factors, ion channels, RNA, DNA, RNAse, DNAse, phospholipids, sphingolipids, nuclear receptors, ion channel proteins, nucleotide-binding proteins, calcium-binding proteins, chaperones, DNA binding proteins, RNA binding proteins, scaffold proteins, tumor suppressors, cell cycle proteins, and histones.

Second agents may target one or more signaling molecules including but not limited to the following: 4EPB-1, 5-lipoxygenase, A1, Ab1, Acetyl-CoAa Carboxylase, actin, adaptor/scaffold proteins, adenylyl cyclase receptors, adhesion molecules, AFT, Akt1, Akt2, Akt3, ALK, AMPKs, APC/C, ARaf, Arf-GAPs, Arfs, ASK, ASK1, asparagine hydroxylase FIH transferases, ATF2, ATF-2, ATM, ATP citrate lyase, ATR, Auroras, B cell adaptor for PI3-kinase (BCAP), Bad, Bak, Bax, Bcl-2, Bcl-B, Bcl-w, Bcl-XL, Bid, Bik, Bim, BLNK, Bmf, BMP receptors, Bok, BRAF, Btk, Bub, cadherins, CaMKs, Casein kinases, Caspase 2, Caspase 3, Caspase 6, Caspase 7, Caspase 8, Caspase 9, caspases, catenins, cathepsins, caveolins, Cb1, CBP/P300 family, CD45, CDC25 phosphatases, Cdc42, Cdk 1, Cdk 2, Cdk 4, Cdk 6, Cdk 7, Cdks, CENPs, Chk1, Chk2, CLKs, Cot, cRaf, CREB, Crk, CrkL, Csk, Cyclin A, Cyclin B, Cyclin D, Cyclin E, Db1, deacetylases, DLK, DNA methyl transferases, DNA-PK, Dok, Dual Specificity phosphatases (DUSPs), E2Fs, eg5/KSP, Egr-1, eIF4E-binding protein, Elk, elongation factors, endosomal sorting complex required for transport (ESCRT) proteins, Eph receptors, Erks, esterases, Ets, Eyes absent (EYA) tyrosine phosphatases, FAK, Fas associated death domain (FADD), FGF receptors, Fgr, focal adhesion kinase, fodrin, Fos, FOXO, Fyn, GAD, Grb2, Grb2 associated binder (GAB), GSK3α, GSK3β, H-Ras, H3K27, Hdm, HER receptors, HIFs, histone acetylases, histone deacetylases, Histone H3K4 demethylases, HMGA, Hrk, Hsp27, Hsp70, Hsp90s, hydrolases, hydroxylases, IAPs, IGF receptors, IKKs, IL-2, IL-4, IL-6, IL-8, ILK, Immunoglobulin-like adhesion molecules, initiation factors, inositol phosphatases, Insulin receptor, integrins, interferon α, interferon β, IRAKs, Jak1, Jak2, Jak3, JHDM2A, Jnks, K-Ras, Kit receptor, KSR, LAR phosphatase, LAT, Lck, Lim kinase, LKB-1, Low molecular weight tyrosine phosphatase, Lyn, MAP kinase phosphatases (MKPs), MAPKAPKs, MARKs, Mcl-1, Mek 1, Mek 2, MEKKs, MELK, Met receptor, metabolic enzymes, metalloproteinases, MKK3/6, MKK4/7, MLKs, MNKs, molecular chaperones, Mos, mTOR, multi-drug resistance proteins, muscarinic receptors, Myc, MyD88, myosin, myosin binding proteins, myotubularins, MYST family, Myt 1, N-Ras, Nck, NFAT, NIK, nitric oxide synthase, Non receptor tyrosine phosphatases (NPRTPs), Noxa, nucleoside transporters, pI30CAS, p14Arf, p16, p21CIP, p27KIP, p38s, p53, p70S6 Kinase, p90Rsks, PAKs, paxillin, PDGF receptors, PDK1, P-Glycoprotein, phopsholipases, phosphoinositide kinases, PI3-Kinase class 1, Pim1, Pim2, Pim3, Pin1 prolyl isomerase, PKAs, PKCs, PKR, potassium channels, PP1, PP2A, PP2B, PP2C, PP5, PRK, Prks, prolyl-hydroxylases PHD-1, prostaglandin synthases, pS6, PTEN, Puma, RABs, Rac, Ran, Ras-GAP, Rb, Receptor protein tyrosine phosphatases (RPTPs), Rel-A (p65-NFKB), Ret, RHEB, Rho, Rho-GAPs, RIP, RNA polymerase, ROCK 1, ROCK 2, SAPK/JNK1,2,3, SCF ubiquitination ligase complex, selectins, separase, serine phosphatases, SGK1, SGK2, SGK3, Shc, SHIPs, SHPs, sirtuins, SLAP, Slingshot phosphatases (SSH), Smac, SMADs, small molecular weight GTPases, sodium channels, Sos, Sp1, sphingomyelinases, sphingosine kinases, Src, SRFs, STAT1, STAT3, STAT4, STAT5, STAT6, suppressors of cytokine signaling (SOCs), Syk, T-bet, T-Cell leukemia family, TCFs, TGFβ receptors, Tiam, TIE1, TIE2, topoisomerases, Tp1, TRADD, TRAF2, Trk receptors, TSC1,2, tubulin, Tyk2, ubiquitin proteases, urokinase-type plasminogen activator (uPA) and uPA receptor (uPAR) system, UTX, Vav, VEGF receptors, vesicular protein sorting (Vsps), VHL, Wee1, WT-1, WT-1, XIAP, Yes, ZAP70, β-adrenergic receptors and β-catenin.

In one aspect, this disclosure also relates to methods and pharmaceutical compositions for inhibiting abnormal cell growth in a mammal which comprises an amount of a HIF-2α inhibitor, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the disclosure.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens. Non-limiting examples are chemotherapeutic agents, cytotoxic agents, and non-peptide small molecules such as Tykerb/Tyverb (lapatinib), Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include 2,2',2"-trichlorotriethylamine; 2-ethylhydrazide; aceglatone; aldophosphamide glycoside; alkyl sulfonates such as busulfan, improsulfan and piposulfan; alkylating agents such as thiotepa and cyclosphosphamide (CYTOXAN™); aminolevulinic acid; amsacrine; anti-adrenals such as aminoglutethimide, mitotane, trilostane; antibiotics such as anthracyclins, actinomycins and bleomycins including aclacinomysins, actinomycin, anthramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); arabinoside ("Ara-C"); aziridines such as benzodopa, carboquone, meturedopa, and uredopa; bestrabucil; bisantrene; capecitabine; cyclophosphamide; dacarbazine; defofamine; demecolcine; diaziquone; edatraxate; elfomithine; elliptinium acetate; esperamicins; ethylenimines and methylamelamines including altretamine, triethylenemelamine, trietylenephosphoramide, triethylenethiophosphaoramide and trimethylolomelamine; etoglucid; folic acid analogues such as denopterin, methotrexate, pteropterin, trimetrexate; folic acid replenisher such as frolinic acid; gacytosine; gallium nitrate; gemcitabine; hydroxyurea; lentinan; lonidamine; mannomustine; mitobronitol; mitoguazone; mitolactol; mitoxantrone; mopidamol; nitracrine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas; nitrosoureas such as carmustine, chlorozotocin, fotemustine, lomustine, nimustine, ranimustine; oxazaphosphorines; pentostatin; phenamet; pipobroman; pirarubicin; podophyllinic acid; procarbazine; PSK®; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, razoxane; retinoic acid; sizofiran; spirogermanium; taxanes, e.g., paclitaxel (TAXOL™, Bristol-Myers Squibb Oncology, Princeton, N.J.) and docetaxel (TAXOTERE™, Rhone-Poulenc Rorer, Antony, France); tenuazonic acid; thiotepa; triazenes; triaziquone; urethan; vindesine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum or platinum analogs and complexes such as cisplatin and carboplatin; anti-microtubule such as diterpenoids, including paclitaxel and docetaxel, or Vinca alkaloids including vinblastine, vincristine, vinflunine, vindesine, and vinorelbine; etoposide (VP-16); ifosfamide; mitomycin C; mitoxantrone; vincristine; vinorelbine; navelbine; novantrone; teniposide; daunomycin; aminopterin; xeloda; ibandronate; topoisomerase I and II inhibitors including camptothecins (e.g., camptothecin-11), topotecan, irinotecan, and epipodophyllotoxins; topoisomerase inhibitor RFS 2000; epothilone A or B; difluoromethylornithine (DMFO); histone deacetylase inhibitors; compounds which induce cell differentiation processes; gonadorelin agonists; methionine aminopeptidase inhibitors; compounds targeting/decreasing a protein or lipid kinase activity; compounds which target, decrease or inhibit the activity of a protein or lipid phosphatase; anti-androgens; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; temozolomide (TEMODAL®); Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY 142886 from Array PioPharma, AZD6244 from AstraZeneca, PD 181461 or PD0325901 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, and Velcade®.

This disclosure further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the proliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present disclosure can render abnormal cells more sensitive to treatment with radiation for purposes of killing and/or inhibiting the growth of such cells. Accordingly, this disclosure further relates to a method for sensitizing abnormal cells in a mammal to treatment with radiation, which comprises administering to the mammal an amount of a HIF-2α inhibitor or a pharmaceutically acceptable salt, ester, prodrug, solvate, hydrate or derivative thereof, which is effective in sensitizing abnormal cells to treatment with radiation. The amount of the compound in this method can be determined according to the means for ascertaining effective amounts of such compounds described herein.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

In some embodiments, the compositions and methods further comprise administering, separately or simultaneously one or more additional agents (e.g. 1, 2, 3, 4, 5, or more). Additional agents can include those useful in wound healing. Non-limiting examples of additional agents include antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

EXAMPLES

The examples below are intended to be purely exemplary and should not be considered to be limiting in any way. Efforts have been made to ensure accuracy with respect to numbers used (for example, amounts, temperature, etc.) but some experimental errors and deviations should be taken into account.

$^1$H and $^{19}$F NMR analysis of intermediates and exemplified compounds were performed on an Agilent Technologies 400/54 magnet system (operating at 399.85 MHz or 376.24 MHz). Vnmrj VERSION 3.2 software Pulse sequences were selected from the default experiment set. Reference frequency was set using TMS as an internal standard. Typical deuterated solvents were utilized as indicated in the individual examples.

LCMS analysis of intermediates and exemplified compounds was performed on an Agilent Technologies 1200 Series HPLC system coupled to an Agilent Technologies 6150 Quadrapole LC/MS detector. Analytes were detected by UV absorbance at 220 and 254 nm. Analyte ions were detected by mass spectrometry in both negative and positive modes (110-800 amu scan range, API-ES ionization). A long HPLC method was run on a Phenomenex® Kinetex 2.6 μm C18 100 Å, 30×3.00 mm column. The column temperature was set at 40° C. UV absorptions were detected at 220 and 254 nm. Samples were prepared as a solution in about 1:1 (v/v) acetonitrile:water mixture. Flow rate was about 0.80 mL/minute. Elution solvents were acetonitrile and water each containing 0.1% formic acid. In a typical run, a linear gradient starting with 5% acetonitrile and 95% water and ending with 95% acetonitrile and 5% water over 12 minutes was carried out. At the end of each run, the column was washed with 95% acetonitrile and 5% water for 2 minutes.

Enantiomeric excess was determined by Mosher ester analysis or with chiral HPLC. The chiral HPLC analysis was performed on an Agilent Technologies 1200 Series HPLC system. Analytes were detected by UV absorbance at 220 and 254 nm. A detailed description of the analytical method is provided below:

Column: Lux® 5 u Cellulose-4 5.0 μm 1000 Å, 150×4.60 mm
Flow rate: 1.5 mL/min
Mobile phase A: 0.1% Formic acid in water
Mobile phase B: 0.1% Formic acid in Acetonitrile
Strong needle wash: 90% Acetonitrile, 10% Water
Weak needle wash: 10% Water, 90% Acetonitrile
Injection volume: 2 μL
Column temperature: 40° C.
Autosampler temperature: Room temperature
Run time: 5.0 min
Gradient: 60% mobile phase A and 40% mobile phase B Routine chromatographic purification was performed using Biotage Isolera One automated systems running Biotage Isolera One 2.0.6 software (Biotage LLC, Charlotte, N.C.). Flow rates were the default values specified for the particular column in use. Reverse phase chromatography was performed using elution gradients of water and acetonitrile on KP-C18-HS Flash+ columns (Biotage LLC) of various sizes. Typical loading was between 1:50 and 1:1000 crude sample:RP $SiO_2$ by weight. Normal phase chromatography was performed using elution gradients of various solvents (e.g. hexane, ethyl acetate, methylene chloride, methanol, acetone, chloroform, MTBE, etc.). The columns were SNAP Cartridges containing KP-SIL or SNAP Ultra (25 μm spherical particles) of various sizes (Biotage LLC). Typical loading was between 1:10 to 1:150 crude sample:$SiO_2$ by weight.

Compound names were generated with ChemBioDraw Ultra 13.0.0.3015 or OpenEye Scientific Software's mol2nam application.

Example 1: Synthesis of (S)-1-((1S,3R)-2,2,3-trifluoro-1-hydroxy-7-(methylsulfonyl)-2,3-dihydro-1H-inden-4-yl)piperidin-3-ol (Compound 5)

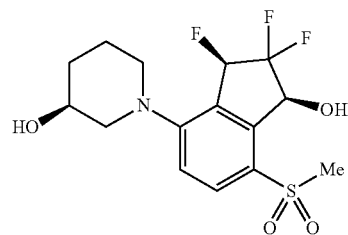 [SMILES: CS(=O)(=O)c1ccc(N2CCC[C@H](O)C2)c2c1[C@H](O)C(F)(F)[C@@H]2F]

Step A: Preparation of 4,7-difluoro-1H-indene-1,3(2H)-dione

A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 hours. The reaction mixture was cooled to 0° C. and treated with 10% hydrochloric acid (65 mL, 211 mmol) by dropwise addition. Once the addition was complete, the ice bath was removed and the mixture stirred at ambient for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL $CH_2Cl_2$. The combined organics were dried with $MgSO_4$, filtered, and concentrated to dryness. The product was used without further purification.

Step B: Preparation of 2,2,4,7-tetrafluoro-1H-indene-1,3(2H)-dione

A solution of the unpurified 4,7-difluoro-1H-indene-1,3 (2H)-dione (4.2 g, 23.1 mmol) in acetonitrile (100 mL) cooled in a 25 OC water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with $MgSO_4$, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. $^1$H NMR (400 MHz, $CDCl_3$): δ 7.70 (t, 2H).

Step C: Preparation of (S)-2,2,4,7-tetrafluoro-3-hydroxy-2,3-dihydro-1H-inden-1-one To a solution of 2,2,4,7-tetrafluoro-1H-indene-1,3(2H)-dione (3.48 g, 16.0 mmol) in dichloromethane (150 mL) at 0° C. was added formic acid (600 μL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The $CH_2Cl_2$ layer was separated and the aqueous layer extracted with ethyl acetate (2×50 mL). The combined organics were dried with $Na_2SO_4$, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. $^1$H NMR (400 MHz, $CDCl_3$): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxide (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over $MgSO_4$, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+) m/z 249 (M+H).

Step E: Preparation of(S)-2,2,4-trifluoro-3-hydroxy-7-(methylsulfonyl)-2,3-dihydro-1H-inden-1-one (S)-2,2,4-trifluoro-3-hydroxy-7-(methylthio)-2,3-dihydro-1H-inden-1-one (400 mg, 1.6 mmol) was dissolved in MeOH (10 mL) and the reaction was treated dropwise with a solution of Oxone® (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over $Na_2SO_4$ and concentrated in vacuo to a yellow solid that was used without further purification (467 mg). LCMS ESI (+) m/z 281.1 (M+H).

Step F: Preparation of (R)-2,2,3,4-tetrafluoro-7-(methylsulfonyl)-2,3-dihydro-1H-inden-1-one (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylaminosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 hours at 0° C. The cold reaction was treated with saturated $NaHCO_3$(10 mL) and stirred vigorously for 20 minutes. The mixture was diluted with additional methylene chloride and the layers were separated. The aqueous was re-extracted with methylene chloride and the combined organic layers were dried over $Na_2SO_4$ and concentrated in vacuo to a yellow solid. The crude material was chromatographed on $SiO_2$(Biotage SNAP Ultra) and eluted with a gradient of ethyl acetate/ hexanes. The desired material was concentrated to a pale yellow solid (258 mg). LCMS ESI (+) m/z 283 (M+H).

Step G: Preparation of (R)-2,2,3-trifluoro-4-((S)-3-hydroxypiperidin-1-yl)-7-(methylsulfonyl)-2,3-dihydro-1H-inden-1-one A solution of (3R)-2,2,3,4-tetrafluoro-7-methylsulfonyl-indan-1-one (28.7 mg, 0.10 mmol) and (3S)-3-piperidinol, hydrochloride (14.0 mg, 0.10 mmol) in DMF (700 µL) was treated with cesium bicarbonate (59.2 mg, 0.31 mmol) and stirred at 35° C. for 3 h. The reaction mixture was poured into 30 mL of water and extracted with 3×10 mL $Et_2O$. The combined organics were rinsed with 10 mL of brine, dried with $MgSO_4$, filtered, and concentrated to dryness. The product was used without further purification. LCMS ESI (+) m/z 364 (M+H).

Step H: Preparation of(S)-1-((1S,3R)-2,2,3-trifluoro-1-hydroxy-7-(methylsulfonyl)-2,3-dihydro-1H-inden-4-yl)piperidin-3-ol (Compound 5)

A solution of (3R)-2,2,3-trifluoro-4-[(3 S)-3-hydroxy-1-piperidyl]-7-methylsulfonyl-indan-1-one (36.3 mg, 0.10 mmol) in dichloromethane (4 mL) was cooled to 0° C. and sparged with nitrogen for 5 min. During this time formic acid (12.1 µL, 0.32 mmol) and triethylamine (27.9 µL, 0.20 mmol) were sequentially added. Once the sparging was complete, RuCl(p-cymene)[(R,R)-Ts-DPEN] (1.3 mg, 2 mol %) was added under a continuous stream of nitrogen. The reaction vessel was sealed and put into the refrigerator to react overnight. Volatiles were removed by concentration under reduced pressure. The residue was purified by chromatography on silica using 45-75% EtOAc/hexane to afford (S)-1-((1S,3R)-2,2,3-trifluoro-1-hydroxy-7-(methylsulfonyl)-2,3-dihydro-1H-inden-4-yl)piperidin-3-ol (Compound 5) as a white solid (23.9 mg, 65%). Retention time HPLC (14 min)=2.63 min; LCMS ESI (+) m/z 366 (M+H); $^1$H NMR (400 MHz, $CDCl_3$): δ 7.97 (dd, 1H), 7.07 (d, 1H), 5.74 (dd, 1H), 5.55 (dd, 1H), 4.01-3.93 (m, 1H), 3.46-3.34 (m, 3H), 3.33 (d, 1H), 3.20-3.13 (m, 1H), 3.18 (s, 3H), 2.01-1.91 (m, 2H), 1.89 (d, 1H), 1.82-1.62 (m, 2H).

Example 2: Synthesis of (S)-2,2-difluoro-4-((1R, 3R)-3-hydroxycyclohexyl)-7-((trifluoromethyl)sulfonyl)-2,3-dihydro-1H-inden-1-ol (Compound 1) and (1S)-2,2-difluoro-4-(3-hydroxycyclohex-1-en-1-yl)-7-((trifluoromethyl)sulfonyl)-2,3-dihydro-1H-inden-1-ol (Compound 2) and (S)-2,2-difluoro-4-((1R,3S)-3-hydroxycyclohexyl)-7-((trifluoromethyl)sulfonyl)-2,3-dihydro-1H-inden-1-ol (Compound 3) and (S)-2,2-difluoro-4-((1S,3R)-3-hydroxycyclohexyl)-7-(methylsulfonyl)-2,3-dihydro-1H-inden-1-ol (Compound 4)

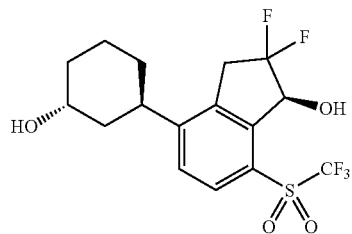

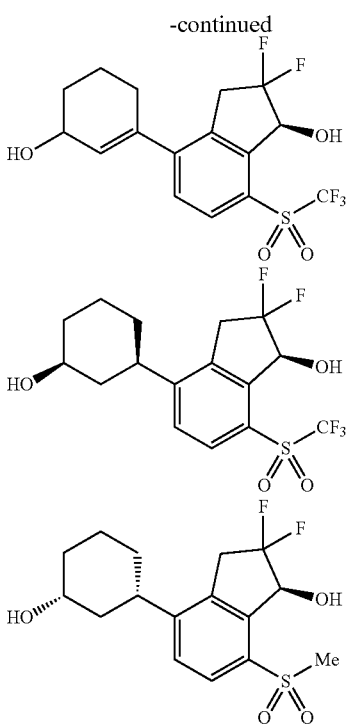

Step A: Preparation of (S)-3-(2,2-difluoro-1-hydroxy-7-((trifluoromethyl)sulfonyl)-2,3-dihydro-1H-inden-4-yl)cyclohex-2-en-1-one A suspension of (1S)-4-bromo-2,2-difluoro-7-(trifluoromethylsulfonyl)indan-1-ol (102.0 mg, 0.27 mmol), 3-(4,4,5,5-tetramethyl-1,3,2-dioxaborolan-2-yl)cyclohex-2-en-1-one (89.2 mg, 0.40 mmol), cesium fluoride (126.0 mg, 0.83 mmol) and bis(di-tert-butyl(4-dimethylaminophenyl)phosphine)dichloropalladium(II) (9.5 mg, 0.013 mmol) in 1,4-dioxane (4.5 mL) was sparged with nitrogen for 3 mins. The vessel was sealed and heated to 80° C. for 1 h. The reaction mixture was poured into 60 mL of water and extracted with 3×20 mL EtOAc. The combined organics were rinsed with 10 mL of brine, dried with MgSO₄, filtered, and concentrated to dryness. Purification was achieved by chromatography on silica using 20-50% EtOAc/hexane. LCMS ESI (−) (M−H) m/z 395.

Step B: Preparation of (S)-2,2-difluoro-4-((1R,3R)-3-hydroxycyclohexyl)-7-((trifluoromethyl)sulfonyl)-2,3-dihydro-1H-inden-1-ol (Compound 1) and (S)-2,2-difluoro-4-(3-hydroxycyclohex-1-en-1-yl)-7-((trifluoromethyl)sulfonyl)-2,3-dihydro-1H-inden-1-ol (Compound 2) and (S)-2,2-difluoro-4-((1R,3S)-3-hydroxycyclohexyl)-7-((trifluoromethyl)sulfonyl)-2,3-dihydro-1H-inden-1-ol (Compound 3) and (S)-2,2-difluoro-4-((1S,3R)-3-hydroxycyclohexyl)-7-(methylsulfonyl)-2,3-dihydro-1H-inden-1-ol (Compound 4)

A solution of 3-[(1S)-2,2-difluoro-1-hydroxy-7-(trifluoromethylsulfonyl)indan-4-yl]cyclohex-2-en-1-one (60.0 mg, 0.15 mmol) in methanol (3.0 mL) at 0° C. was treated with sodium borohydide (11.5 mg, 0.30 mmol) and stirred at 0° C. for 1 h. The reaction mixture was quenched by the addition of 0.5 mL of saturated NH₄Cl. Volatiles were removed by concentration under reduced pressure. The reaction mixture was poured into 30 mL of water and extracted with 3×10 mL EtOAc. The combined organics were rinsed with 10 mL of brine, dried with MgSO₄, filtered, and concentrated to dryness. Initial purification was achieved by chromatography on silica using 10-40% EtOAc/CH₂Cl₂ to isolate 2 components. A second purification was necessary on the first eluting component by chromatography on silica using 20-45% EtOAc/hexanes. Finally, each product was purified individually, as described in the characterization section. Data for (S)-2,2-difluoro-4-((1R,3R)-3-hydroxycyclohexyl)-7-((trifluoromethyl)sulfonyl)-2,3-dihydro-1H-inden-1-ol (Compound 1): Final purification was achieved by chromatography on silica using 30-70% EtOAc/hexanes to afford the desired product as a white solid (1.5 mg, 2%). Retention time HPLC (14 min)=4.69 min; LCMS ESI (−) (M+HCO₂⁻) m/z 445; ¹H NMR (400 MHz, CDCl₃): δ 7.92 (d, 1H), 7.52 (d, 1H), 5.40 (dd, 1H), 4.33-4.28 (m, 1H), 3.59 (ddd, 1H), 3.49 (t, 1H), 3.22-3.13 (m, 2H), 1.97-1.82 (m, 4H), 1.75-1.58 (m, 3H), 1.46 (dd, 1H), 1.42-1.37 (m, 1H). Data for (1S)-2,2-difluoro-4-(3-hydroxycyclohex-1-en-1-yl)-7-((trifluoromethyl)sulfonyl)-2,3-dihydro-1H-inden-1-ol (Compound 2): Final purification was achieved by chromatography on silica using 30-70% EtOAc/hexanes to afford the desired product as a clear solid (3.5 mg, 6%). Retention time HPLC (14 min) =4.70 min; LCMS ESI (+) (M-OH) m/z 381; ¹H NMR (400 MHz, CDCl₃): δ 7.93 (d, 1H), 7.50 (d, 1H), 5.91-5.88 (m, 1H), 5.39 (dd, 1H), 4.49-4.43 (m, 1H), 3.64 (ddd, 1H), 3.39 (t, 1H), 3.18 (dd, 1H), 2.49-2.39 (m, 1H), 2.22-2.11 (m, 1H), 2.09-1.92 (m, 2H), 1.81-1.59 (m, 3H). Data for (S)-2,2-difluoro-4-((R,3S)-3-hydroxycyclohexyl)-7-((trifluoromethyl)sulfonyl)-2,3-dihydro-1H-inden-1-ol (Compound 3): Final purification was achieved by chromatography on silica using 30-70% EtOAc/hexanes to afford the desired product as a clear solid (6.7 mg, 11%). Retention time HPLC (14 min)=4.27 min; LCMS ESI (−) (M+HCO₂⁻) m/z 445; ¹H NMR (400 MHz, CDCl₃): δ 7.94 (d, 1H), 7.55 (d, 1H), 5.41 (dd, 1H), 3.82-3.72 (m, 1H), 3.56 (ddd, 1H), 3.42 (t, 1H), 3.20 (dd, 1H), 2.67 (tt, 1H), 2.17-2.08 (m, 2H), 2.01-1.94 (m, 1H), 1.82-1.75 (m, 1H), 1.60-1.42 (m, 3H), 1.40-1.27 (m, 2H). Data for (S)-2,2-difluoro-4-((1S,3R)-3-hydroxycyclohexyl)-7-(methylsulfonyl)-2,3-dihydro-1H-inden-1-ol (Compound 4): Final purification was achieved by chromatography on silica using 20-60% EtOAc/hexanes to afford the desired product as a white solid (8.6 mg, 14%). Retention time HPLC (14 min)=4.77 min; LCMS ESI (−) (M+HCO₂⁻) m/z 445; ¹H NMR (400 MHz, CDCl₃): δ 7.94 (d, 1H), 7.55 (d, 1H), 5.41 (dd, 1H), 3.82-3.72 (m, 1H), 3.58 (ddd, 1H), 3.40 (t, 1H), 3.18 (d, 1H), 2.67 (tt, 1H), 2.16-2.06 (m, 2H), 2.02-1.95 (m, 1H), 1.86-1.78 (m, 1H), 1.58-1.28 (m, 5H).

Example 3: (S)-3-((2,2-difluoro-1-hydroxy-7-((trifluoromethyl)sulfonyl)-2,3-dihydro-1H-inden-4-yl)amino)-5-fluorobenzonitrile (Compound 10)

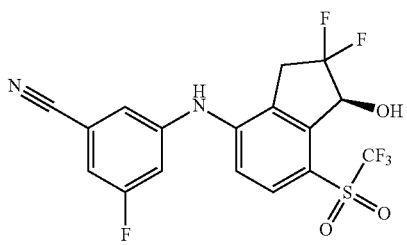 [SMILES: N#Cc1cc(F)cc(Nc2ccc(S(=O)(=O)C(F)(F)F)c3c2CC(F)(F)[C@H]3O)c1]

Step A: Preparation of 4-bromophenyl 3-chloropropanoate

A solution of 4-bromophenol (45.0 g, 260 mmol) in dichloromethane (1.0 L) was cooled to 0° C., treated with triethylamine (44.7 g, 442 mmol). A solution of 3-chloropropionyl chloride (36.3 g, 286 mmol) dissolved in dichloromethane (100 mL) was added dropwise to the reaction vessel. The reaction mixture was allowed to warm to ambient temperature and stirred overnight. Saturated NaCl was added to the reaction mixture, (300 mL). After stirring for 1 hour, the organic layer was separated. The aqueous layer was extracted with dichloromethane. The combined organics were washed with saturated NaCl, dried over $Na_2SO_4$, and concentrated in vacuo. The crude product was used without further purification.

Step B: Preparation of 4-bromo-7-hydroxy-2,3-dihydro-1H-inden-1-one

A flask containing crude (4-bromophenyl) 3-chloropropanoate (68.0 g, 258 mmol) was cooled to 0° C., then treated in several portions with aluminum trichloride (275 g, 2060 mmol). The reaction mixture was then heated at 155° C. under $N_2$ for 3 hours. Stirring became difficult as the reaction proceeded. HCl (g) which was generated from the reaction was trapped by a beaker containing 1 N NaOH. After cooling to ambient temperature, the reaction mixture was further cooled in an ice bath. Water was added very carefully (dropwise initially and then added in small volumes) to the reaction to quench excess $AlCl_3$. The mixture was then extracted with twice with ethyl acetate. The combined organic layers were washed with water and brine, dried and concentrated. The crude product was used without additional purification.

Step C: Preparation of O-(7-bromo-3-oxo-2,3-dihydro-1H-inden-4-yl) dimethylcarbamothioate A mixture of 4-bromo-7-hydroxy-2,3-dihydro-1H-inden-1-one (900 mg, 4.0 mmol) dissolved in DMF (15 mL) was treated with DABCO 33LV (1.3 mL, 12 mmol) and N,N-dimethylcarbamothioyl chloride (1.5 g, 12 mmoil) was stirred overnight at ambient temperature. The reaction was treated with water and ethyl acetate and separated. The aqueous layer was extracted with ethyl acetate then the combined organic layers were washed with water and saturated NaCl. After drying, the organic layer was concentrated in vacuo and purified by chromatography on SiO2 eluting with a gradient of ethyl acetate/hexanes, (670 mg, 54%). $^1$H NMR (400 MHz, $CDCl_3$): δ 7.78-7.76 (d, 1H), 6.97-6.95 (d, 1H), 3.44 (s, 3H), 3.41 (s, 3H), 3.08 (m, 2H), 2.76-2.69 (m, 2H).

Step D: Preparation of S-(7-bromo-3-oxo-2,3-dihydro-1H-inden-4-yl) dimethylcarbamothioate A mixture of O-(7-bromo-3-oxo-2,3-dihydro-1H-inden-4-yl) dimethylcarbamothioate (670 mg, 2.1 mmol) and diphenyl ether (15 mL) was heated at 220° C. under $N_2$ for 30 minutes. After cooling to ambient temperature, the mixture was diluted with hexanes and the mixture was applied to a pad of SiO2 and eluted with hexanes. After removal of the diphenyl ether, the desired product was eluted with ethyl acetate. After concentration in vacuo, the crude product was used without further purification.

Step E: Preparation of 4-bromo-7-mercapto-2,3-dihydro-1H-inden-1-one

A solution of S-(7-bromo-3-oxo-2,3-dihydro-1H-inden-4-yl) dimethylcarbamothioate (670 mg, 2.1 mmol) dissolved in ethanol (25 mL) was treated with 3N sodium hydroxide) 10.7 mL, 32.1 mmol). The mixture was heated to reflux for 1 hour then cooled to 0° C. Aqueous HCl (3M) was added dropwise to neutralize the reaction. Ethanol was removed by concentration in vacuo followed by addition of aqueous HCl (1M) to adjust to pH 3-4. The aqueous was extracted twice with ethyl acetate and the combined organic layers were washed with saturated NaCl, dried and concentrated in vacuo. The crude product was used without further purification.

Step F: Preparation of 4-bromo-7-((trifluoromethyl)thio)-2,3-dihydro-1H-inden-1-one Methyl viologen dichloride hydrate (0.11 g, 0.41 mmol), 4-bromo-7-mercapto-2,3-dihydro-1H-inden-1-one (2.0 g, 8.2 mmol) and triethylamine (1.25 g, 12.3 mmol) were dissolved in DMF (50 mL) and cooled to −50° C. The flask was placed under gentle vacuum then trifluoromethyl iodide (3.2 g, 16 mmol) gas was introduced using a balloon. This reaction was warmed to ambient temperature and stirred at overnight. The reaction mixture was diluted with ethyl acetate and water, filtered through a celite pad, and the layers were partitioned. The organic layer was washed with water, brine, dried over $Na_2SO_4$, filtered, and evaporated. The crude oil was then purified by flash column chromatography on SiO2 eluting with petroleum ether/ethyl acetate, (0.96 g, 51.7%). $^1$H NMR (400 MHz, $CDCl_3$): δ 7.72 (d, 1H), 7.41 (d, 1H), 3.10-3.07 (m, 2H), 2.79-2.77 (m, 2H).

Step G: Preparation of 4-bromo-7-((trifluoromethyl)sulfonyl)-2,3-dihydro-1H-inden-1-one Ruthenium(III) chloride (19 mg, 0.09 mmol) was added to a mixture of 4-bromo-7-((trifluoromethyl)thio)-2,3-dihydro-1H-inden-1-one (0.96 g, 3.1 mmol) and sodium periodate (1.98 g, 9.26 mmol) in a mixture of carbon tetrachloride (20 mL), acetonitrile (20 mL), and water (40 mL). The mixture was stirred at ambient temperature for 3 hours. The reaction mixture was partitioned between dichloromethane and water. The organic layer was washed with brine, dried over $MgSO_4$, filtered, and concentrated in vacuo. The crude product was purified by flash column chromatography on SiO2 eluting with petroleum ether/ethyl acetate, (1.7 g, 79%). $^1$H NMR (400 MHz, $CDCl_3$): δ 8.05-8.02 (m, 2H), 3.21-3.18 (m, 2H), 2.89-2.86 (m, 2H).

Step H: Preparation of 4-bromo-7-((trifluoromethyl)sulfonyl)-2,3-dihydrospiro[indene-1,2'-[1,3]dioxolane]

Trimethylsilyl trifluoromethanesulfonate (177 mg, 0.80 mmol) was added dropwise to a pre-cooled (−78° C.) solution of 4-bromo-7-((trifluoromethyl)sulfonyl)-2,3-dihydro-1H-inden-1-one and trimethyl(2-trimethylsilyloxyethoxy)silane (410 mg, 2.0 mmol) dissolved in dichloromethane (50 mL). The reaction mixture was warmed to ambient temperature and stirred for 2 hours. The reaction was quenched by addition of triethylamine then concentrated in vacuo. The residue was redissolved in ethyl acetate and washed twice with water, and saturated NaCl. The organic layer was separated, dried over $Na_2SO_4$ and concentrated in vacuo. The crude product was purified by chromatography on SiO₂ eluting with ethyl acetate/isohexane, (600 mg, 77%).

Step I: Preparation of 4-bromo-7-((trifluoromethyl)sulfonyl)-2,3-dihydro-1H-inden-1-one 4-Bromo-7-((trifluoromethyl)sulfonyl)-2,3-dihydrospiro[indene-1,2'-[1,3]dioxolane] (3.5 g, 9.1 mmol) was dissolved in THF (72 mL) and treated with 10% aqueous HCl (27 mL, 27 mmol). The mixture was stirred for several minutes then warmed to 60° C. for 2 hours. The mixture was cooled, diluted with diethyl ether and separated. The aqueous was washed with diethyl ether and the combined organics were washed with water, saturated NaHCO₃, saturated NaCl, dried over Na₂SO₄ and concentrated in vacuo to a yellowish solid, (3.09 g, quant.). ¹H NMR (400 MHz, CDCl₃): δ 8.05-8.02 (m, 2H), 3.21-3.18 (m, 2H), 2.89-2.86 (m, 2H).

Step J: Preparation of (E,Z)-3-((4-bromo-7-((trifluoromethyl)sulfonyl)-2,3-dihydro-1H-inden-1-ylidene)amino)propan-1-ol 4-Bromo-7-(trifluoromethylsulfonyl)indan-1-one (3.09 g, 9.02 mmol] was slurried in toluene (35 mL) and cyclohexane (35 mL) then treated with 3-methoxypropylamine (2.15 mL, 27.1 mmol) and pivalic acid (46 mg, 0.45 mmol). The mixture was refluxed through a Dean-Stark trap (sidearm pre-filled with cyclohexane) for 8 hours. The reaction mixture was cooled and concentrated in vacuo. The crude material was taken directly into the fluorination.

Step K: Preparation of 4-bromo-2,2-difluoro-7-((trifluoromethyl)sulfonyl)-2,3-dihydro-1H-inden-1-one Crude (E. Z)-3-((4-bromo-7-((trifluoromethyl)sulfonyl)-2,3-dihydro-1H-inden-1-ylidene)amino)propan-1-ol (3.75 g, 9.1 mmol) was dissolved in dry acetonitrile (23 mL) and added dropwise to a warm (60° C.), suspension of Selectfluor (9.6 g, 27.2 mmol) and sodium sulfate (12.9 g, 90.5 mmol) slurried in acetonitrile (10 mL). After the addition, the mixture was heated to 60° C. for 10 minutes then cooled to ambient temperature and treated with 10% HCl (15 mL) and stirred for 20 minutes. The mixture was adjusted to pH 8 with solid NaHCO₃ then diluted with ethyl acetate and separated. The aqueous was washed with ethyl acetate and the combined organics were washed with saturated NaHCO₃, saturated NaCl, dried over Na₂SO₄ filtered, and concentrated in vacuo to dark oil. The crude material was chromatographed on SiO2 eluting with a gradient of ethyl acetate/hexanes. The desired product was concentrated to a light yellow solid, (2.27 g, 66%). ¹H NMR (400 MHz, CDCl₃): δ 8.22-8.14 (m, 2H), 3.60-3.55 (t, 2H).

Step L: Preparation of (S)-4-bromo-2,2-difluoro-7-((trifluoromethyl)sulfonyl)-2,3-dihydro-1H-inden-1-ol 4-Bromo-2,2-difluoro-7-((trifluoromethyl)sulfonyl)-2,3-dihydro-1H-inden-1-one (1.65 g, 4.35 mmol) was dissolved in isopropanol (21 mL) and treated with triethylamine (1.2 mL, 8.7 mmol), formic acid (0.49 mL, 13.1 mmol) and RuCl(p-cymene)[(R,R)-Ts-DPEN] (27.7 mg, 0.040 mmol). The reaction mixture was stirred at ambient temperature for 4 hours. The solvent was removed in vacuo then the crude material was chromatographed on SiO₂ eluting with a gradient of ethyl acetate/hexanes. The product was isolated as a more pure fraction (1.83 g) and a slightly less pure fraction. Both of these fractions were successfully utilized in the coupling reaction. ¹H NMR (400 MHz, CDCl₃): δ 7.88-7.80 (m, 2H), 5.50-5.45 (m, 1H), 3.66-3.58 (m, 1H), 3.20 (m, 1H).

Step M: Preparation of (S)-3-((2,2-difluoro-1-hydroxy-7-((trifluoromethyl)sulfonyl)-2,3-dihydro-1H-inden-4-yl)amino)-5-fluorobenzonitrile (S)-4-Bromo-2,2-difluoro-7-((trifluoromethyl)sulfonyl)-2,3-dihydro-1H-inden-1-ol (98 mg, 0.26 mmol) was dissolved in 1,4-dioxane (0.80 mL) and treated with benzonitrile, 3-amino-5-fluoro- (42 mg, 0.31 mmol), palladium (II) acetate (2.9 mg, 0.010 mmol), and Xantphos (14.9 mg, 0.030 mmol). The mixture was heated to 120° C. for 1.5 hours in the microwave reactor. The reaction mixture was cooled, diluted with ethyl acetate and water then separated. The aqueous was washed with ethyl acetate and the combined organics were washed with saturated NaHCO₃, saturated NaCl, dried over Na₂SO₄ and concentrated in vacuo. The crude dark oil was chromatographed on SiO₂ eluting with a gradient of ethyl acetate/hexanes. The desired material was recovered in a slightly impure form. This material was re-chromatographed on reversed-phase SiO₂ eluting with a gradient of MeCN/water. A single fraction was collected and to light tan solid, (35 mg, 31%). LCMS ESI (−) m/z (M−H) 435; ¹H NMR (400 MHz, CDCl₃): δ 7.87 (d, 1H), 7.31-7.29 (m, 2H), 7.21-7.19 (m, 2H), 6.18 (m, 1H), 5.42-5.38 (m, 1H), 3.52-3.41 (m, 1H), 3.32-3.24 (m, 1H).

Example 4: Synthesis of (S)-5-((2,2-difluoro-1-hydroxy-7-((trifluoromethyl)sulfonyl)-2,3-dihydro-1H-inden-4-yl)amino)nicotinonitrile (Compound 9)

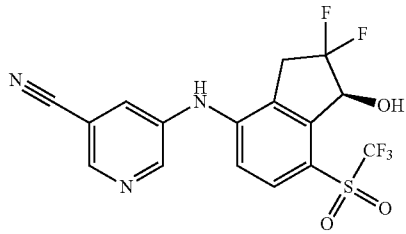 [SMILES: N#Cc1cncc(Nc2ccc(S(=O)(=O)C(F)(F)F)c3c2CC(F)(F)[C@H]3O)c1]

(S)-4-Bromo-2,2-difluoro-7-((trifluoromethyl)sulfonyl)-2,3-dihydro-1H-inden-1-ol (23 mg, 0.060 mmol) was dissolved in 1,4-dioxane (0.20 mL) and treated with 3-pyridinecarbonitrile, 5-amino- (8.6 mg, 0.070 mmol), cesium carbonate (27.5 mg, 0.080 mmol), palladium (II) acetate (0.68 mg, 0.003 mmol), and Xantphos (3.5 mg, 0.010 mmol). After cooling, the mixture was diluted with water and ethyl acetate then separated. This mixture didn't separate well and there was insoluble yellow solid present, which was removed by filtration. The aqueous was washed with ethyl acetate and the combined organics were washed with saturated NaHCO₃, saturated NaCl, dried over Na₂SO₄, and concentrated in vacuo to a dark residue. The crude material was chromatographed on SiO₂ eluting with a gradient of ethyl acetate/hexanes. The product was recovered as light tan solid, (12 mg, 47%). LCMS ESI (+) m/z (M+H) 420; ¹H NMR (400 MHz, CDCl₃ plus CD3OD): δ 8.66 (s, 1H), 8.60

(s, 1H), 7.79-7.75 (m, 2H), 7.22-7.20 (m, 1H), 5.30 (d, 1H), 3.92-3.90 (m, 1H), 3.46-3.32 (m, 1H), 3.31-3.21 (m, 1H).

Example 5: Synthesis of (S)-2,2-difluoro-4-morpholino-7-((trifluoromethyl)sulfonyl)-2,3-dihydro-1H-inden-1-ol (Compound 11)

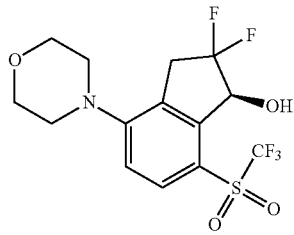 [SMILES: O=S(=O)(c1ccc(N2CCOCC2)c2c1[C@H](O)C(F)(F)C2)C(F)(F)F]

Step A: Preparation of (S)-((4-bromo-2,2-difluoro-7-((trifluoromethyl)sulfonyl)-2,3-dihydro-1H-inden-1-yl)oxy)(tert-butyl)dimethylsilane (S)-4-bromo-2,2-difluoro-7-((trifluoromethyl)sulfonyl)-2,3-dihydro-1H-inden-1-ol (0.30 g, 0.78 mmol) was dissolved in methylene chloride (3.3 mL) and treated with 2,6-lutidine (0.40 mL, 3.1 mmol), cooled to 0° C., followed by treatment with t-butyldimethylsilyl triflate (0.45 mL, 1.9 mmol). The mixture was warmed to ambient temperature and stirred for two hours. The reaction mixture was re-cooled to 0° C. and cold 10% KHSO₄ was added along with additional methylene chloride then the layers were separated. The organic layer was washed with 10% KHSO₄, water, then with one-half saturated NaHCO₃. The organic layer was dried over Na₂SO₄ and concentrated in vacuo to a light yellow oil. The crude product was chromatographed on SiO₂ eluting with a gradient of methylene chloride/hexanes. The product was concentrated to colorless oil, (466 mg, 92%).

Step B: Preparation of (S)-4-(1-((tert-butyldimethylsilyl)oxy)-2,2-difluoro-7-((trifluoromethyl)sulfonyl)-2,3-dihydro-1H-inden-4-yl)morpholine (S)-((4-bromo-2,2-difluoro-7-((trifluoromethyl)sulfonyl)-2,3-dihydro-1H-inden-1-yl)oxy)(tert-butyl)dimethylsilane (0.030 g, 0.060 mmol) was dissolved in DMF (0.25 mL) and treated with sodium acetate (14 mg, 0.17 mmol) followed by morpholine (0.020 mL, 0.17 mmol). The mixture was heated at 120° C. for 1 hour in the microwave reactor. After cooling, the mixture was diluted with ethyl acetate then washed 7 times with water, saturated NaCl, dried over Na₂SO₄ and concentrated in vacuo. The residue was chromatographed on SiO₂ eluting with a gradient of ethyl acetate/hexanes. The product was recovered as a colorless film, (17 mg, 58%). LCMS ESI (+) m/z (M+H) 502.

Step C: Preparation of (S)-2,2-difluoro-4-morpholino-7-((trifluoromethyl)sulfonyl)-2,3-dihydro-1H-inden-1-ol (S)-4-(1-((tert-butyldimethylsilyl)oxy)-2,2-difluoro-7-((trifluoromethyl)sulfonyl)-2,3-dihydro-1H-inden-4-yl)morpholine (0.02 g, 0.04 mmol) was dissolved in THF (0.25 mL) and treated with glacial acetic acid (2 μL, 0.04 mmol) followed by a solution of 1 M tetrabutylammonium fluoride in THF (0.04 mL, 0.04 mmol). The mixture was heated to 60° C. for 45 minutes. The darkened reaction mixture was cooled and added into saturated aqueous NaHCO₃. The mixture was vortexed vigorously then diluted with ethyl acetate and separated. The organic layer was washed with saturated NaHCO₃, saturated NaCl, dried over Na₂SO₄ and concentrated in vacuo. The crude material was chromatographed on SiO₂ eluting with a gradient of ethyl acetate/hexanes. Compound 11 was recovered as light orange oil, (10.8 mg, 78%). LCMS ESI (+) m/z (M+H) 388; ¹H NMR (400 MHz, CDCl₃): δ 7.87 (d, 1H), 7.01 (d, 1H), 5.35-5.31 (m, 1H), 3.93-3.81 (m, 4H), 3.56-3.45 (m, 1H), 3.35-3.23 (m, 3H), 3.16-3.09 (m, 3H).

Example 6: Synthesis of (1S,3R)-4-((3-chloro-5-fluorophenyl)thio)-2,2,3-trifluoro-7-(methylsulfonyl)-2,3-dihydro-1H-inden-1-ol (Compound 12)

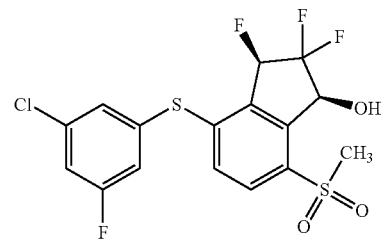 [SMILES: CS(=O)(=O)c1ccc(Sc2cc(F)cc(Cl)c2)c2c1[C@H](O)C(F)(F)[C@@H]2F]

Step A

Preparation of 4,7-difluoro-1H-indene-1,3(2H)-dione (0.52 g, 2.8 mmol) was slurried acetic anhydride (2.5 mL, 27 mmol) and treated with tert-butyl 3-oxobutanoate (0.52 mL, 3.1 mmol) and triethylamine (1.4 mL, 10 mmol). The mixture was stirred at ambient temperature for 60 hours. The reaction was cooled to 0° C. and treated with 10% aqueous hydrochloric acid (8.6 mL, 25 mmol) by dropwise addition. After the addition, the mixture was warmed to ambient temperature then heated to 75° C. for 10 minutes. After cooling, the mixture was diluted with water (20 mL) and extracted three times with methylene chloride (20 mL portions). The combined organics were dried over Na₂SO₄ and concentrated in vacuo to crude orange solid. This material was carried forward without purification.

Step B: Preparation of 2,2,4,7-tetrafluoro-1H-indene-1,3(2H)-dione 4,7-difluoro-1H-indene-1,3(2H)-dione (0.51 g, 2.8 mmol) was dissolved in acetonitrile (27 mL), placed in an ambient temperature water bath then treated with solid sodium carbonate (950 mg, 9.0 mmol) followed by Selectfluor® (2.18 g, 6.2 mmol). The mixture was stirred at ambient temperature for 1 hour. The mixture was filtered to removed undissolved solids, the solids were washed with ethyl acetate and the filtrate was concentrated in vacuo. The residue was redissolved in water (ca. 20 mL) and extracted four times with ethyl acetate (20 mL each). The combined organics were washed with saturated NaCl, dried over Na₂SO₄ and concentrated in vacuo to orange solid. The crude solid was chromatographed on SiO₂ eluting with an aggressive gradient of ethyl acetate/hexanes. The desired material concentrated to orange solid, (493 mg, 81%). ¹H NMR (400 MHz, CDCl₃): δ 7.70-7.65 (2H).

Step C: Preparation of (S)-2,2,4,7-tetrafluoro-3-hydroxy-2,3-dihydro-1H-inden-1-one 2,2,4,7-tetrafluoro-1H-indene-1,3(2H)-dione (5.81 g, 26.6 mmol) was suspended in methylene chloride (260 mL), cooled to 0° C., and treated with formic acid (1.01 mL, 26.6 mmol), triethylamine (2.60 mL, 18.6 mmol), then the reaction mixture was sparged with argon for 5 minutes. RuCl(p-cymene)[(S,S)-Ts-DPEN] (339 mg, 0.530 mmol) was added and the reaction was transferred to the refrigerator and allowed to stand at 4° C. for 20 hours. The cold reaction mixture was poured into cold 1N aqueous HCl (70 mL) and separated. The aqueous was washed twice with ethyl acetate then the combined organic layers were dried over $Na_2SO_4$ and concentrated in vacuo to a brown semi-solid. The crude material was chromatographed on $SiO_2$ eluting with a gradient of ethyl acetate/hexanes. The product was recovered as yellow solid, (3.48 g, 59%). $^1$H NMR (400 MHz, CDCl$_3$): δ 7.86-7.80 (m, 1H), 7.60-7.54 (m, 1H), 5.79-5.74 (m, 1H), 3.23-3.18 (m, 1H).

Step D: Preparation of (S)-2,2,4-trifluoro-3-hydroxy-7-(methylthio)-2,3-dihydro-1H-inden-1-one (S)-2,2,4,7-tetrafluoro-3-hydroxy-2,3-dihydro-1H-inden-1-one (0.40 g, 1.8 mmol) was dissolved in dry acetonitrile (18 mL), cooled to 0° C., and sparged with argon for 5 minutes. The solution was treated in a single portion with sodium thiomethoxide (144 mg, 2.06 mmol) and after 5 minutes, the ice bath was removed and the reaction was stirred at ambient temperature for 3 hours. The reaction mixture was concentrated in vacuo and the residue was redissolved in water and ethyl acetate. After separation, the aqueous was washed twice with ethyl acetate and the combined organics were washed with saturated NaCl, dried over $Na_2SO_4$ and concentrated in vacuo. The orange residue was chromatographed on $SiO_2$ eluting with a gradient of ethyl acetate/hexanes. The desired material was recovered as bright yellow solid, (314 mg, 70%). LCMS ESI (+) m/z (M+H) 249.

Step E: Preparation of (S)-2,2,4-trifluoro-3-hydroxy-7-(methylsulfonyl)-2,3-dihydro-1H-inden-1-one (S)-2,2,4-trifluoro-3-hydroxy-7-(methylthio)-2,3-dihydro-1H-inden-1-one (0.40 g, 1.6 mmol) was dissolved in MeOH (10 mL) and the reaction was treated dropwise with a solution of Oxone® (2.2 g, 3.6 mmol) dissolved in water (10 mL). The mixture was stirred at ambient temperature for 14 hours. The reaction mixture was filtered, the solids were washed with ethyl acetate and the filtrate was concentrated in vacuo to remove volatile solvents. The aqueous filtrate was extracted three times with ethyl acetate then the combined organics were washed with saturated NaCl, dried over $Na_2SO_4$ and concentrated in vacuo to yellow solid, (467 mg, quant.). LCMS ESI (+) m/z (M+H) 281.

Step F: Preparation of (R)-2,2,3,4-tetrafluoro-7-(methylsulfonyl)-2,3-dihydro-1H-inden-1-one (S)-2,2,4-trifluoro-3-hydroxy-7-(methylsulfonyl)-2,3-dihydro-1H-inden-1-one (0.45 g, 1.6 mmol) was dissolved in dichloromethane (16 mL), cooled to 0° C., and treated dropwise with diethylaminosulfur trifluoride (DAST) (0.32 mL, 2.4 mmol) and stirred at 0° C. for 14 hours. The reaction was treated with additional diethylaminosulfur trifluoride (0.32 mL, 2.4 mmol) and stirring continued for 6 hours at 0° C. The cold reaction was treated with saturated $NaHCO_3$ (10 mL) and stirred vigorously for 20 minutes. The mixture was diluted with additional methylene chloride and the layers were separated. The aqueous was re-extracted with methylene chloride and the combined organic layers were dried over $Na_2SO_4$ and concentrated in vacuo to a yellow solid. The crude material was chromatographed on $SiO_2$ eluting with a gradient of ethyl acetate/hexanes. The desired material was recovered as pale yellow solid, (258 mg, 53%). LCMS ESI (+) m/z (M+H) 283.

Step G: Preparation of (1S,3R)-2,2,3,4-tetrafluoro-7-(methylsulfonyl)-2,3-dihydro-1H-inden-1-ol (R)-2,2,3,4-tetrafluoro-7-(methylsulfonyl)-2,3-dihydro-1H-inden-1-one: (0.098 g, 0.35 mmol) was suspended in methylene chloride (3.3 mL), cooled to 0° C., and treated with triethylamine (97 μL, 0.69 mmol), formic acid (39 μL, 1.0 mmol) and RuCl(p-cymene)[(R,R)-Ts-DPEN] (2.2 mg, 0.003 mmol). The solution was allowed to stand at 4° C. in the refrigerator for 60 hours. The reaction mixture was concentrated in a stream of nitrogen gas then chromatographed on $SiO_2$ eluting with a gradient of ethyl acetate/hexanes. The desired fractions were concentrated to colorless film, (53 mg, 53%). LCMS ESI (+) m/z (M+H) 285.

Step H: Preparation of (1S,3R)-4-((3-chloro-5-fluorophenyl)thio)-2,23-trifluoro-7-(methylsulfonyl)-2,3-dihydro-1H-inden-1-ol (1S,3R)-2,2,3,4-tetrafluoro-7-(methylsulfonyl)-2,3-dihydro-1H-inden-1-ol (0.005 g, 0.02 mmol) was treated with cesium bicarbonate (17 mg, 0.090 mmol) and suspended in DMF (0.1 mL) then stirred at ambient temperature for 1 hour. 3-Chloro-5-fluorothiophenol (14 mg, 0.090 mmol) was added and the mixture was stirred at ambient temperature for 18 hours. The reaction was concentrated in a stream of nitrogen gas to remove DMF. The residue was chromatographed on $SiO_2$ eluting with a stepped gradient of ethyl acetate/hexanes. Compound 12 was concentrated to light pink oil, (7 mg, 93%). LCMS ESI (+) m/z (M+Na) 449; $^1$H NMR (400 MHz, CDCl$_3$): δ 7.99-7.95 (m, 1H), 7.33-7.32 (m, 1H), 7.24-7.19 (m, 2H), 7.16-7.13 (m, 1H), 5.75 (dd, 1H), 5.68-5.65 (m, 1H), 3.37-3.36 (m, 1H), 3.23 (s, 3H).

Example 7: Synthesis of 3-(((1S,3R)-2,2,3-trifluoro-1-hydroxy-7-(methylsulfonyl)-2,3-dihydro-1H-inden-4-yl)thio)benzonitrile (Compound 13)

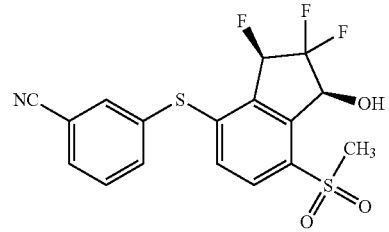 [SMILES: CS(=O)(=O)c1ccc(Sc2cccc(C#N)c2)c2c1[C@H](O)C(F)(F)[C@@H]2F]

(1S,3R)-2,2,3,4-tetrafluoro-7-(methylsulfonyl)-2,3-dihydro-1H-inden-1-ol (0.0073 g, 0.030 mmol) was treated with cesium bicarbonate (25 mg, 0.13 mmol) and suspended in DMF (0.1 mL) then 3-mercapto-benzonitrile (17 mg, 0.13 mmol) was added and the mixture was stirred at ambient temperature for 60 hours. The reaction was concentrated in a stream of nitrogen gas to remove DMF. The residue was chromatographed on SiO$_2$ eluting with a stepped gradient of ethyl acetate/hexanes. The product was concentrated to light oil, (7 mg, 91%). LCMS ESI (+) m/z (M+Na) 422; $^1$H NMR (400 MHz, CDCl$_3$): δ 7.97-7.87 (m, 1H), 7.81 (m, 1H), 7.77-7.74 (m, 2H), 7.61-7.57 (m, 1H), 7.16-7.14 (m, 1H), 5.77 (dd, 1H), 5.69-5.65 (m, 1H), 3.40-3.39 (m, 1H), 3.23 (s, 3H).

Example 8: Synthesis of (S)-4-(3-chlorophenyl)-2,2-difluoro-7-((trifluoromethyl)sulfonyl)-2,3-dihydro-1H-inden-1-ol (Compound 6)

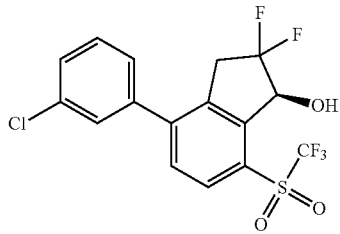 [SMILES: O=S(=O)(c1ccc(-c2cccc(Cl)c2)c2c1[C@H](O)C(F)(F)C2)C(F)(F)F]

Step A: Preparation of 4-((4-methoxybenzyl)oxy)-7-((trifluoromethyl)sulfonyl)-2,3-dihydrospiro[indene-1,2'-[1,3]dioxolane]

A solution of 4'-fluoro-7'-(trifluoromethylsulfonyl)spiro[1,3-dioxolane-2,1'-indane] (1.0 g, 3.07 mmol) and 4-methoxybenzyl alcohol (760 µL, 6.13 mmol) in acetonitrile (9.3 mL) at 25° C. was treated with potassium hydroxide (516 mg, 9.2 mmol) and stirred at 25° C. for 1.5 h. The reaction mixture was poured into 150 mL of water and extracted with 3×40 mL EtOAc. The combined organics were rinsed with 20 mL of brine, dried with MgSO$_4$, filtered, and concentrated to dryness. Purification was achieved by chromatography on silica using 10-25% EtOAc/hexane to afford 4-((4-methoxybenzyl)oxy)-7-((trifluoromethyl)sulfonyl)-2,3-dihydrospiro[indene-1,2'-[1,3]dioxolane] as a solid (1.08 g, 79%). LCMS ESI (+) [M+H]$^+$ m/z 445.

Step B: Preparation of 4-((4-methoxybenzyl)oxy)-7-((trifluoromethyl)sulfonyl)-2,3-dihydro-1H-inden-1-one In a glass pressure vessel, a solution of 4'-[(4-methoxyphenyl)methoxy]-7'-(trifluoromethylsulfonyl)spiro[1,3-dioxolane-2,1'-indane] (1.08 g, 2.43 mmol) in a mixture acetone (20 mL) and water (20 mL) was treated with pyridinium p-toluenesulfonate (122 mg, 0.49 mmol), sealed and stirred at 80° C. overnight. Volatiles were removed by concentration under reduced pressure. The residue was poured into 40 mL of saturated aqueous NaHCO$_3$ and extracted with 3×50 mL EtOAc. The combined organics were rinsed with 30 mL of brine, dried with MgSO$_4$, filtered, and concentrated to dryness. The product was used without further purification. LCMS ESI (+) [M+H]$^+$ m/z 401.

Step C: Preparation of 2,2-difluoro-4-((4-methoxybenzyl)oxy)-7-((trifluoromethyl)sulfonyl)-2,3-dihydro-1H-inden-1-one 2,2-Dimethylpropanoic acid (50 mg, 0.46 mmol) was added to a flask containing a suspension of 4-[(4-methoxyphenyl)methoxy]-7-(trifluoromethylsulfonyl)indan-1-one (922 mg, 2.3 mmol) and 3-methoxypropan-1-amine (0.35 mL, 3.45 mmol) in a mixture of toluene (14 mL) and cyclohexane (14 mL). This was refluxed with a Dean-Stark trap attached at 104° C. After 2.5 h, the reaction mixture was cooled and volatiles removed by concentration under reduced pressure. The residue was dissolved in acetonitrile (24 mL) and treated sequentially with sodium sulfate (850 mg, 6.0 mmol) and 1-(chloromethyl)-4-fluoro-1,4-diazoniabicyclo[2.2.2]octane ditetrafluoroborate (2.13 g, 6.0 mmol). The resulting suspension stirred at 60° C. for 2 h. After cooling to room temperature, the reaction mixture was treated with concentrated hydrochloric acid (600 µL, 7.2 mmol) and water (10 mL). The resulting mixture stirred for 20 min. Volatiles were removed by concentration under reduced pressure. The reaction mixture was poured into 20 mL of water and extracted with 3×30 mL EtOAc. The combined organics were rinsed with 20 mL of brine, dried with MgSO$_4$, filtered, and concentrated to dryness. Purification was achieved by chromatography on silica using 5-40% EtOAc/hexane to afford 2,2-difluoro-4-((4-methoxybenzyl)oxy)-7-((trifluoromethyl)sulfonyl)-2,3-dihydro-1H-inden-1-one as a solid (520 mg, 50%). LCMS ESI (+) [M+H]$^+$ m/z 437.

Step D: Preparation of (S)-2,2-difluoro-4-((4-methoxybenzyl)oxy)-7-((trifluoromethyl)sulfonyl)-2,3-dihydro-1H-inden-1-ol A solution of 2,2-difluoro-4-[(4-methoxyphenyl)methoxy]-7-(trifluoromethylsulfonyl)indan-1-one (520 mg, 1.19 mmol) in dichloromethane (11.9 mL) was cooled to 0° C. and sparged with nitrogen for 5 minutes. During this time, formic acid (130 µL, 3.58 mmol) and triethylamine (330 µL, 2.38 mmol) were sequentially added. Once the sparging was complete, RuCl(p-cymene)[(R,R)-Ts-DPEN](22.8 mg, 0.036 mmol) was added under a continuous stream of nitrogen. The reaction vessel was sealed and put into the refrigerator to react overnight. Once complete, the reaction mixture was poured into 30 mL of saturated aqueous NaHCO$_3$ and extracted with 3×30 mL CH$_2$Cl$_2$. The combined organics were rinsed with 20 mL of brine, dried with MgSO$_4$, filtered, and concentrated to dryness. Purification was achieved by chromatography on silica using 10-40% EtOAc/hexane to afford (S)-2,2-difluoro-4-((4-methoxybenzyl)oxy)-7-((trifluoromethyl)sulfonyl)-2,3-dihydro-1H-inden-1-ol as a solid (370 mg, 71%). LCMS ESI (+) [M+NH$_4$]$^+$ m/z 456.

Step E: Preparation of (S)-tert-butyl((2,2-difluoro-4-((4-methoxybenzyl)oxy)-7-((trifluoromethyl)sulfonyl)-2,3-dihydro-1H-inden-1-yl)oxy)dimethylsilane A solution of (1 S)-2,2-difluoro-4-[(4-methoxyphenyl)methoxy]-7-(trifluoromethylsulfonyl)indan-1-ol (370 mg, 0.84 mmol) and 2,6-lutidine (780 µL, 7.76 mmol) in dichloromethane (8.4 mL) at −78° C. was treated with tert-butyldimethylsilyl trifluoromethanesulfonate (980 µL, 4.22 mmol) and allowed to warm to room temperature over 2 h. The reaction mixture was poured into 30 mL of saturated aqueous NaHCO$_3$ and extracted with 3×20 mL CH$_2$Cl$_2$. The combined organics were rinsed with 10 mL of brine, dried with MgSO$_4$, filtered, and concentrated to dryness. Purification was achieved by chromatography on silica using 5-20% EtOAc/hexane to afford (S)-tert-butyl((2,2-difluoro-4-((4-methoxybenzyl)oxy)-7-((trifluoromethyl)sulfonyl)-2, 3-dihydro-1H-inden-1-yl)oxy)dimethylsilane (460 mg, quant). LCMS ESI (−) [M−H]⁻ m/z 551.

Step F: Preparation of(S)-1-((tert-butyldimethylsilyl)oxy)-2,2-difluoro-7-((trifluoromethyl)sulfonyl)-2,3-dihydro-1H-inden-4-ol A solution of tert-butyl-[(1S)-2,2-difluoro-4-[(4-methoxyphenyl)methoxy]-7-(trifluoromethylsulfonyl)indan-1-yl]oxy-dimethyl-silane (460 mg, 0.83 mmol) in dichloromethane (3.0 mL) at 25° C. was treated with trifluoroacetic acid (3.0 mL) and stirred at 25° C. After 1 h, volatiles were removed by concentration under reduced pressure. To the resulting residue was added 6 mL of toluene and the organic volatiles were once again removed by concentration under reduced pressure. This process was repeated twice. Purification was achieved by chromatography on reverse phase by injection of a DMF solution of the product residue. 40-100% $CH_3CN$/Water was used as eluent. (S)-1-((tert-butyldimethylsilyl)oxy)-2,2-difluoro-7-((trifluoromethyl)sulfonyl)-2,3-dihydro-1H-inden-4-ol was isolated a thick orange oil (236 mg, 89%). LCMS ESI (−) [M−H]⁻ m/z 431.

Step G: Preparation of (S)-2,2-difluoro-1-hydroxy-7-((trifluoromethyl)sulfonyl)-2,3-dihydro-1H-inden-4-yl trifluoromethanesulfonate A solution of (S)-1-((tert-butyldimethylsilyl)oxy)-2,2-difluoro-7-((trifluoromethyl)sulfonyl)-2,3-dihydro-1H-inden-4-ol (215 mg, 0.50 mmol) and 2,6-bis(1,1-dimethylethyl)-4-methyl-pyridine (408 mg, 1.99 mmol) in dichloromethane (10 mL) was cooled to −78° C. and treated with trifluoromethanesulfonic anhydride (0.17 mL, 0.99 mmol). The mixture was stirred at −78° C. for 1 h. The reaction mixture was poured into 20 mL of saturated $NaHCO_3$ and extracted with 3×20 mL EtOAc. The combined organics were rinsed with 10 mL of brine, dried with $MgSO_4$, filtered, and concentrated to dryness. Purification was achieved by chromatography on $SiO_2$ eluting with a gradient of ethyl acetate/hexanes.

Step H: Preparation of tributyl(3-chlorophenyl)stannane

A solution of 3-chlorophenylmagnesium bromide (0.5 M in THF) (1.40 mL, 0.70 mmol) was cooled to −78° C. and treated dropwise with a solution of tributyl(chloro)stannane (230 mg, 0.70 mmol) dissolved in THF (0.5 mL). The solution was stirred for 5 minutes then allowed to warm to ambient temperature slowly without the bath and stirred at ambient temperature for 45 hours. The reaction was quenched by addition of saturated $NH_4Cl$ and water. Diethyl ether was added and the mixture was separated. The aqueous was washed twice with diethyl ether and the combined organics were washed saturated NaCl, dried over $Na_2SO_4$ and concentrated in vacuo. The crude material was chromatographed on $SiO_2$ eluting with cyclohexane. The desired product was concentrated to colorless liquid, (234 mg, 84%). ¹H NMR (400 MHz, CDCl₃): δ 7.58-7.30 (m, 4H), 1.60-1.45 (m, 6H), 1.40-1.28 (m, 6H), 1.17-1.00 (m, 6H), 0.92-0.85 (m, 9H).

Step I: Preparation of(S)-tert-butyl((4-(3-chlorophenyl)-2,2-difluoro-7-((trifluoromethyl)sulfonyl)-2,3-dihydro-1H-inden-1-yl)oxy)dimethylsilane (S)-2,2-difluoro-1-hydroxy-7-((trifluoromethyl)sulfonyl)-2,3-dihydro-1H-inden-4-yl trifluoromethanesulfonate (17 mg, 0.030 mmol) was dissolved in toluene (0.4 mL) then tributyl-(3-chlorophenyl)stannane (23 mg, 0.060 mmol), tetrakis(triphenylphosphine)palladium (1.7 mg, 0.001 mmol), and lithium chloride (4 mg, 0.09 mmol) were added. The reaction mixture was sparged with argon then heated to reflux for 16 hours. After cooling, the mixture was concentrated in a stream of nitrogen gas. The crude material was chromatographed on $SiO_2$ eluting with a gradient of ethyl acetate/hexanes. The less polar UV-active spot was recovered as colorless oil, (9.8 mg, 63%).

Step J: Preparation of(S)-4-(3-chlorophenyl)-2,2-difluoro-7-((trifluoromethyl)sulfonyl)-2,3-dihydro-1H-inden-1-ol (S)-tert-butyl((4-(3-chlorophenyl)-2,2-difluoro-7-((trifluoromethyl)sulfonyl)-2,3-dihydro-1H-inden-1-yl)oxy)dimethylsilane (9.8 mg, 0.020 mmol) was dissolved in THF (0.2 mL) containing glacial acetic acid (3.2 µL, 0.060 mmol) and the mixture was treated with a 1M solution of tetrabutylammonium fluoride in THF (28 µL, 0.030 mmol). The mixture was heated to 60° C. for 2 hours, then the reaction was cooled, treated with one-half saturated $NaHCO_3$, diluted with ethyl acetate and separated. The aqueous was washed twice with ethyl acetate and the combined organics were washed with saturated $NaHCO_3$, saturated NaCl, dried over $Na_2SO_4$ and concentrated in vacuo to dark oil. The crude material was chromatographed on $SiO_2$ eluting with a stepped gradient of ethyl acetate/hexanes. The desired product was concentrated to light yellow solid, (2.5 mg, 32%). LCMS ESI (−) m/z (M−H) 411/413; ¹H NMR (400 MHz, CDCl₃): δ 8.06-8.04 (d, 1H), 7.66-7.64 (d, 1H), 7.48-7.41 (m, 3H), 7.29-7.26 (m, 1H), 5.47-5.43 (m, 1H), 3.78-3.65 (m, 1H), 3.33 (t, 1H), 3.19-3.17 (m, 1H).

Example 9: Synthesis of(S)-2,2-difluoro-4-phenyl-7-((trifluoromethyl)sulfonyl)-2,3-dihydro-1H-inden-1-ol (Compound 8)

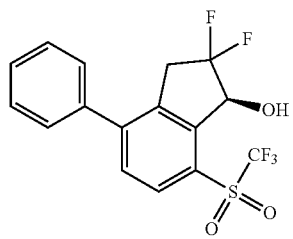 [SMILES: O=S(=O)(c1ccc(-c2ccccc2)c2c1[C@H](O)C(F)(F)C2)C(F)(F)F]

(S)-4-bromo-2,2-difluoro-7-((trifluoromethyl)sulfonyl)-2,3-dihydro-1H-inden-1-ol (20 mg, 0.050 mmol) was dissolved in 1,4-dioxane (0.20 mL) and treated with phenylboronic acid (9.6 mg, 0.080 mmol), Pd(dppf)Cl₂-DCM adduct (3 mg, 0.004 mmol), and potassium fluoride (6.1 mg, 0.10 mmol). The mixture was heated to 100° C. for 10 hours. After cooling, the reaction mixture was concentrated in a stream of nitrogen gas then chromatographed on $SiO_2$ eluting with a gradient of ethyl acetate/hexanes. The desired material was concentrated to white solid, (17 mg, 86%). LCMS ESI (−) m/z (M−H) 377; ¹H NMR (400 MHz, CDCl₃): δ 8.03 (d, 1H), 7.67 (d, 1H), 7.54-7.47 (m, 3H), 7.42-7.39 (m, 2H), 5.47-5.43 (m, 1H), 3.80-3.67 (m, 1H), 3.40-3.31 (t, 1H), 3.22-3.21 (m, 1H).

Example 10: Synthesis of (S)-3-(2,2-difluoro-1-hydroxy-7((trifluoromethyl)sulfonyl)-2,3-dihydro-1H-inden-4-yl)-5-fluorobenzonitrile (Compound (7)

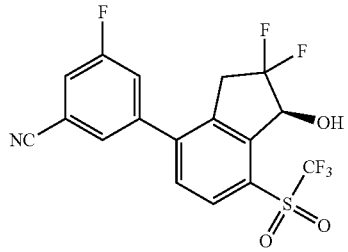 [SMILES: N#Cc1cc(F)cc(-c2ccc(S(=O)(=O)C(F)(F)F)c3c2CC(F)(F)[C@H]3O)c1]

(S)-4-bromo-2,2-difluoro-7-((trifluoromethyl)sulfonyl)-2,3-dihydro-1H-inden-1-ol (20 mg, 0.050 mmol) was dissolved in 1,4-dioxane (0.20 mL) and treated with 3-cyano-5-fluorophenylboronic acid (10 mg, 0.060 mmol), Pd(dppf)Cl$_2$-DCM adduct (3 mg, 0.004 mmol), and potassium fluoride (6.1 mg, 0.10 mmol). The mixture was heated to 100° C. for 10 hours. After cooling, the mixture was concentrated in a stream of nitrogen gas, then directly chromatographed on SiO$_2$ eluting with a gradient of ethyl acetate/hexanes. The desired product was recovered as colorless film, (12 mg, 54%). LCMS ESI (−) m/z (M−H) 420; $^1$H NMR (400 MHz, CDCl$_3$): δ 8.09 (d, 1H), 7.65 (d, 1H), 7.61-7.60 (m, 2H), 7.40-7.37 (m, 1H), 5.49-5.46 (m, 1H), 3.78-3.65 (m, 1H), 3.33-3.25 (t, 1H), 3.20 (m, 1H).

Example 11: Synthesis of (R)-4-((3-chloro-5-fluoro-phenyl)thio)-7-((difluoromethyl)sulfonyl)-2,3-dihydro-1H-inden-1-ol (Compound 14)

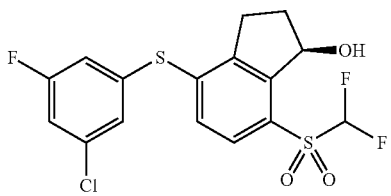 [SMILES: O=S(=O)(c1ccc(Sc2cc(F)cc(Cl)c2)c2c1[C@H](O)CC2)C(F)F]

Sodium bicarbonate (18.9 mg, 0.23 mmol) was added all at once to (1R)-7-(difluoromethylsulfonyl)-4-fluoro-indan-1-ol (20.0 mg, 0.08 mmol) and 3-chloro-5-fluoro-benzenethiol (24.4 mg, 0.15 mmol) in 1-methyl-2-pyrrolidone (0.5 mL) at room temperature then the reaction vial was sealed with a threaded cap. The reaction mixture was then warmed to 90° C. and continued to stir at this temperature until complete as judged by LC-MS (4 h). Cooled to room temperature then purified directly on reverse phase silica gel (25+M, 14 CV, 20-100% MeCN/water) affording (1R)-4-(3-chloro-5-fluoro-phenyl)sulfanyl-7-(difluoromethylsulfonyl)indan-1-ol (25.5 mg, 0.062 mmol, 83% yield). LC-MS ESI (−) m/z 453/455 (M+HCO$_2^-$). $^1$H-NMR (400 MHz, CDCl$_3$): δ 7.84 (d, 1H), 7.19-7.17 (m, 1H), 7.08 (s, 1H), 7.00-6.97 (m, 2H), 5.71-5.68 (m, 1H), 3.64 (d, 1H), 3.21 (s, 3H), 3.12-3.04 (m, 1H), 2.84-2.76 (m, 1H), 2.52-2.43 (m, 1H), 2.27-2.19 (m, 1H).

Example 12: Synthesis of (1R)-7-(difluoromethyl-sulfonyl)-4-(tetrahydropyran-4-ylamino)indan-1-ol (Compound 15)

4-Piperidone (8.4 mg, 0.08 mmol) was added all at once to (1R)-7-(difluoromethylsulfonyl)-4-fluoro-indan-1-ol (22.0 mg, 0.08 mmol) in 1-methyl-2-pyrrolidone (0.5 mL) at room temperature. The reaction mixture was then stirred at 50° C. for 24 h. Additional 4-piperidone (8.4 mg, 0.08 mmol) was added at room temperature and then warmed to 90° C. for an additional 4 h. Cooled to room temperature and added additional 4-piperidone (8.4 mg, 0.08 mmol). Warmed to 90° C. for an additional 4 h. Cooled to room temperature then purified directly on reverse phase silica gel (12+M, 14 CV, 20-100% MeCN/water) affording (1R)-7-(difluoromethylsulfonyl)-4-(tetrahydropyran-4-ylamino)indan-1-ol (15.8 mg, 0.046 mmol, 55% yield). LC-MS ESI (−) m/z 346 (M−H). $^1$H-NMR (400 MHz, CDCl$_3$): δ 7.69 (d, 1H), 6.64 (d, 1H), 6.26 (t, 1H), 5.57-5.56 (m, 1H), 4.14 (d, 1H), 4.06-4.01 (m, 2H), 3.72-3.62 (m, 1H), 3.58-3.51 (m, 2H), 3.32 (d, 1H), 2.95-2.84 (m, 1H), 2.61-2.55 (m, 1 H), 2.47-2.38 (m, 1H), 2.28-2.20 (m, 1H), 2.09-2.03 (m, 2H), 1.62-1.52 (m, 2H).

Example 13: Synthesis of 4-(2-hydroxyethyl)-7-((trifluoromethyl)sulfonyl)-2,3-dihydro-1H-inden-1-ol (Compound 16)

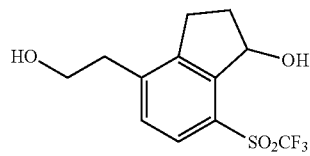

Step A: Preparation of diethyl 2-[7'-(trifluoromethylsulfonyl)spiro[1,3-dioxolane-2,1'-indane]-4'-yl]propanedioate tetrahydrofuran (12.0 ml) was added all at once to sodium hydride (735.6 mg, 18.39 mmol) at 0° C. under nitrogen followed by the slow addition of diethyl malonate (1.86 mL, 12.26 mmol). Stirred for 15 min then a solution of 4'-fluoro-7'-(trifluoromethylsulfonyl)spiro[1,3-dioxolane-2,1'-indane] (1.0 g, 3.07 mmol) in tetrahydrofuran (3.0 mL) was added by syringe over 2 minutes. The reaction mixture was then removed from the cooling bath and stirred at room temperature overnight. Additional sodium hydride (200 mg) was added as well as diethyl malonate (0.5 mL) and stirred an additional 6 h. Cooled to 0° C., quenched with water, extracted with ethyl acetate, washed with brine, dried over sodium sulfate, filtered and concentrated in vacuo. Purified on silica gel (25 g SNAP Ultra, 10-100% ethyl acetate/ hexanes) affording diethyl 2-[7'-(trifluoromethylsulfonyl) spiro[1,3-dioxolane-2,1'-indane]-4'-yl]propanedioate (940.0 mg, 2.01 mmol, 66% yield).

Step B: Preparation of 2-[1-oxo-7-(trifluoromethylsulfonyl)indan-4-yl]acetic acid HCl (4.84 mL, 29.03 mmol) was added to diethyl 2-[7'-(trifluoromethylsulfonyl)spiro[1,3-dioxolane-2,1'-indane]-4'-yl]propanedioate (300.0 mg, 0.64 mmol) then warmed to 100° C. for 6 h. Cooled to room temperature, extracted with MTBE, washed with water, brine, dried over Na$_2$SO$_4$, filtered and concentrated in vacuo affording 2-[1-oxo-7-(trifluoromethylsulfonyl)indan-4-yl]acetic acid (200.0 mg, 0.62 mmol, 96% yield). Used without further purification.

Step C: Preparation of 4-(2-hydroxyethyl)-7-(trifluoromethylsulfonyl)indan-1-ol

Borane dimethylsulfide complex (434.4 µL, 0.87 mmol) was added slowly to 2-[1-oxo-7-(trifluoromethylsulfonyl)indan-4-yl]acetic acid (70.0 mg, 0.22 mmol) in tetrahydrofuran (1.5 mL) at room temperature and stirred for 2 h. Cooled to 0° C. and quenched with 1 N HCl, extracted with ethyl acetate, washed with brine, dried over MgSO$_4$, filtered and concentrated in vacuo. Purified on silica gel (10 g SNAP Ultra, 14 CV, 60-100% ethyl acetate/hexanes) affording 4-(2-hydroxyethyl)-7-(trifluoromethylsulfonyl)indan-1-ol (36.0 mg, 0.12 mmol, 53% yield). Hexanes was added to the clear oil and then cooled to −78° C. with scratching until a white gum was observed, warmed to room temperature and continued scratching until a white powder formed. Hexanes was then removed under a stream of nitrogen to afford Compound 16. LC-MS (−) ESI m/z 309 (M−H). $^1$H-NMR (400 MHz, CDCl$_3$): δ 7.83 (d, 1H), 7.47 (d, 1H), 5.61 (d, 1H), 3.95-3.92 (m, 1H), 3.27-3.18 (m, 1H), 3.10 (s, 1H), 2.99-2.96 (m, 3H), 2.41-2.26 (m, 2H).

Example 14: Synthesis of (S)-2,2-difluoro-4-(2-hydroxyethyl)-7-((trifluoromethyl)sulfonyl)-2,3-dihydro-1H-inden-1-ol (Compound 17)

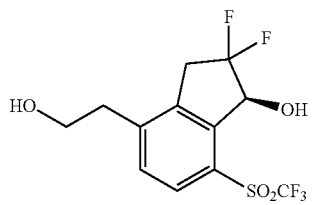

Step A:
Borane dimethylsulfide complex (439.0 µL, 0.88 mmol) was added dropwise to 2-[7'-(trifluoromethylsulfonyl)spiro[1,3-dioxolane-2,1'-indane]-4'-yl]acetic acid (268.0 mg, 0.73 mmol) in tetrahydrofuran (7.0 mL) at 0° C. under nitrogen then slowly warmed to room temperature. Stirred until complete as judged by LC-MS. Quenched carefully with saturated sodium bicarbonate, extracted with ethyl acetate, washed with brine, dried over MgSO$_4$, filtered and concentrated in vacuo. Purified on silica gel (10 g SNAP Ultra, 14 CV, 40-100% ethyl acetate/hexanes) affording 2-[7'-(trifluoromethylsulfonyl)spiro[1,3-dioxolane-2,1'-indane]-4'-yl]ethanol (95.0 mg, 0.27 mmol, 37% yield).

Step B:
HCl (1.0 mL, 1.0 mmol) was added all at once to 2-[7'-(trifluoromethylsulfonyl)spiro[1,3-dioxolane-2,1'-indane]-4'-yl]ethanol (95.0 mg, 0.27 mmol) in acetone (4.0 mL) at room temperature then stirred until complete as judged by LC-MS. Diluted with water, extracted with ethyl acetate, washed with saturated sodium bicarbonate, washed with brine, dried over MgSO$_4$, filtered and concentrated in vacuo. Used without further purification.

Step C:
Tert-Butyldimethylsilyl chloride (46.9 mg, 0.31 mmol) was added all at once to a solution of 4-(2-hydroxyethyl)-7-(trifluoromethylsulfonyl)indan-1-one (80.0 mg, 0.26 mmol) and imidazole (53.0 mg, 0.78 mmol) in dichloromethane (2.0 mL) at room temperature then stirred overnight. Diluted with water, extracted with MTBE, washed with brine, dried over Na$_2$SO$_4$, filtered and concentrated in vacuo. Purified on silica gel (10 g SNAP, 12 CV, 5-60% ethyl acetate/hexanes) affording 4-[2-[tert-butyl(dimethyl)silyl]oxyethyl]-7-(trifluoromethylsulfonyl)indan-1-one (89.0 mg, 0.21 mmol, 81% yield).

Step D:
Pivalic acid (2.2 mg, 0.02 mmol) was added to a mixture of 4-[2-[tert-butyl(dimethyl)silyl]oxyethyl]-7-(trifluoromethylsulfonyl)indan-1-one (89.0 mg, 0.21 mmol) and 3-methoxypropylamine (37.6 mg, 0.42 mmol) in cyclohexane (1.5 mL):toluene (1.5 mL) at room temperature then warmed to reflux with the azeotropic removal of water by Dean-Stark trap. Monitored by $^1$H-NMR. Cooled to room temperature then concentrated in vacuo. Used without further purification.

Step E:
Crude 4-[2-[tert-butyl(dimethyl)silyl]oxyethyl]-N-(3-methoxypropyl)-7-(trifluoromethylsulfonyl)indan-1-imine (103.0 mg, 0.21 mmol) in acetonitrile (1.5 mL) was added to 1-chloromethyl-4-fluoro-1,4-diazoniabicyclo[2.2.2]octane bis(tetrafluoroborate) (184.8 mg, 0.52 mmol) and sodium Sulfate (59.3 mg, 0.42 mmol) in acetonitrile (1.5 mL) at 60° C. and stirred for 1 h. Cooled to room temperature then 1 N HCl (3.0 mL) was added and stirred overnight. Extracted with ethyl acetate, washed with brine, dried over MgSO$_4$, filtered and concentrated in vacuo. Purified on reverse phase silica gel (12+M, 14 CV, 20-100% acetonitrile/water) affording 2,2-difluoro-4-(2-hydroxyethyl)-7-(trifluoromethylsulfonyl)indan-1-one (40.0 mg, 0.12 mmol, 56% yield).

Step F:
Chloro {[(1R,2R)-(−)-2-amino-1,2-diphenylethyl](4-toluenesulfonyl)amido}(p-cymene)ruthenium(II) (1.5 mg, 0.002 mmol) was added all at once to an ice cold solution of 2,2-difluoro-4-(2-hydroxyethyl)-7-(trifluoromethylsulfonyl)indan-1-one (40.0 mg, 0.12 mmol), triethylamine (32.4 µL, 0.23 mmol) and formic acid (13.2 µL, 0.35 mmol) in dichloromethane (1.0 mL) then sealed with a threaded teflon cap and placed in a 4° C. fridge over the weekend. Purified directly on silica gel (10 g SNAP Ultra, 14 CV, 25-100% ethyl acetate/hexanes) affording (1 S)-2,2-difluoro-4-(2-hydroxyethyl)-7-(trifluoromethylsulfonyl)indan-1-ol (Compound 17) (28.0 mg, 0.081 mmol, 70% yield) as a clear oil. Swirled with hexanes to yield a white solid. LC-MS ESI (−) m/z 345 (M−H).

Example 15: Synthesis of 3-(2,2-difluoro-1-hydroxy-7-((trifluoromethyl)sulfonyl)-2,3-dihydro-1H-inden-4-yl)propane-1,2-diol (Compound 42)

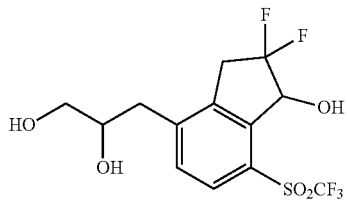

Step A:

Tetrakis(triphenylphosphine)palladium(0) (59.69 mg, 0.0500 mmol) was added all at once to a degassed solution of 4'-bromo-7'-(trifluoromethylsulfonyl)spiro[1,3-dioxolane-2,1'-indane] (200.0 mg, 0.52 mmol) and allyltributyltin (0.19 mL, 0.62 mmol) in DMF (5.0 mL) under nitrogen then warmed to 90° C. until complete as judged by LC-MS. Cooled to room temperature, saturated KF (5.0 mL) was added and stirred for 30 min, extracted with MTBE, washed with brine, dried over MgSO$_4$, filtered and concentrated in vacuo. Purified on silica gel (10 g SNAP Ultra, 14 CV, 5-50% ethyl acetate/hexanes) affording 4'-allyl-7'-(trifluoromethylsulfonyl)spiro[1,3-dioxolane-2,1'-indane] (145.0 mg, 0.42 mmol, 81% yield).

Step B:

HCl (2.0 mL, 2.0 mmol) was added all at once to a solution of 4'-allyl-7'-(trifluoromethylsulfonyl)spiro[1,3-dioxolane-2,1'-indane] (145.0 mg, 0.42 mmol) in acetone (5.0 mL) then stirred overnight at room temperature. Diluted with water, extracted with MTBE, washed with brine, dried over MgSO$_4$, filtered and concentrated in vacuo. Used without further purification.

Step C:

Pivalic acid (2.6 mg, 0.02 mmol) was added all at once to 4-allyl-7-(trifluoromethylsulfonyl)indan-1-one (76.0 mg, 0.25 mmol) and 3-methoxypropylamine (76.4 µL, 0.75 mmol) in cyclohexane (1.5 mL):toluene (1.5 mL) at room temperature then warmed to reflux with azeotropic removal of water via a Dean-Stark trap until complete as judged by $^1$H-NMR. Cooled to room temperature then concentrated in vacuo. Used without further purification.

Step D:

1-chloromethyl-4-fluoro-1,4-diazoniabicyclo[2.2.2]octane bis(tetrafluoroborate) (219.4 mg, 0.62 mmol) was added all at once to crude 4-allyl-N-(3-methoxypropyl)-7-(trifluoromethylsulfonyl)indan-1-imine (93.0 mg, 0.25 mmol) and sodium sulfate (70.4 mg, 0.50 mmol) in acetonitrile (3.0 mL) at 60° C. then stirred for 1 h. Cooled to room temperature, 1 N HCl was added (3.0 mL) and stirred for 15 min, extracted with MTBE, washed with brine, dried over MgSO$_4$, filtered and concentrated in vacuo. Used without further purification.

Step E:

Sodium borohydride (25.0 mg, 0.66 mmol) was added all at once to a solution of 4-allyl-2,2-difluoro-7-(trifluoromethylsulfonyl)indan-1-one (75.0 mg, 0.22 mmol) and 2,2-difluoro-4-[(E)-prop-1-enyl]-7-(trifluoromethylsulfonyl)indan-1-one (75.0 mg, 0.22 mmol) in methanol (2.0 mL) at room temperature and stirred for 30 min. Quenched with 1 N HCl (2.0 mL), diluted with water, extracted with MTBE, washed with brine, dried over Na$_2$SO$_4$, filtered and concentrated in vacuo. Used without further purification.

Step F:

Osmium tetroxide, 4 wt. % solution (27.9 µL, 0.004 4 mmol) was added all at once to a solution of 4-allyl-2,2-difluoro-7-(trifluoromethylsulfonyl)indan-1-ol (75.0 mg, 0.22 mmol), 4-methylmorpholine N-oxide (51.3 mg, 0.44 mmol) in acetone (2.0 mL) then stirred over the weekend in a sealed vial. Diluted with water, extracted with ethyl acetate, washed with brine dried over Na$_2$SO$_4$, filtered and concentrated in vacuo. Purified on silica gel (10 g SNAP Ultra, 14 CV, 50-100% ethyl acetate/hexanes) affording Compound 42 (17.4 mg, 0.046 mmol, 21% yield). LC-MS ESI (−) m/z 375 (M−H)

Example 16: Synthesis of 4-(3-hydroxypropyl)-7-((trifluoromethyl)sulfonyl)-2,3-dihydro-1H-inden-1-ol (Compound 43)

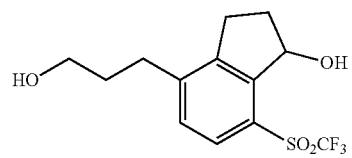

Step A:

3-Ethoxy-3-oxopropylzinc bromide (0.77 mL, 0.39 mmol) was added to a solution of 4'-bromo-7'-(trifluoromethylsulfonyl)spiro[1,3-dioxolane-2,1'-indane] (50.0 mg, 0.13 mmol), palladium(II) acetate (2.9 mg, 0.01 mmol) and SPhos (10.6 mg, 0.03 mmol) in tetrahydrofuran (0.5 mL) at room temperature under nitrogen in a sealed microwave vial then warmed to 60° C. until complete as judged by LC-MS. Cooled to room temperature, quenched with saturated ammonium chloride, extracted with ethyl acetate, washed with brine, dried over MgSO$_4$, filtered and concentrated in vacuo. Purified on silica gel (10 g SNAP Ultra, 14 CV, 5-50% ethyl acetate/hexanes) affording ethyl 3-[7'-(trifluoromethylsulfonyl)spiro[1,3-dioxolane-2,1'-indane]-4'-yl]propanoate (25.0 mg, 0.061 mmol, 47% yield).

Step B:

1 N HCl (1.0 mL, 1.0 mmol) was added all at once to a solution of ethyl 3-[7'-(trifluoromethylsulfonyl)spiro[1,3-dioxolane-2,1'-indane]-4'-yl]propanoate (25.0 mg, 0.06 mmol) in acetone (2.0 mL) then stirred at room temperature until complete as judged by LC-MS (30 min). Diluted with brine, extracted with ethyl acetate, dried over Na$_2$SO$_4$, filtered and concentrated in vacuo. Used without further purification.

Step C:

Lithium borohydride solution (0.2 mL, 0.40 mmol) was added to a solution of crude ethyl 3-[1-oxo-7-(trifluoromethylsulfonyl)indan-4-yl]propanoate (22.0 mg, 0.06 mmol) in tetrahydrofuran (0.50 mL) at room temperature under nitrogen then stirred until complete as judged by LC-MS. Warmed to 75° C. after 5 h at room temperature and held for 3 h. Cooled to room temperature, poured into 1 N HCl, extracted with ethyl acetate, washed with brine, dried over MgSO$_4$, filtered and concentrated in vacuo. Purified on silica gel (10 g SNAP Ultra, 14 CV, 50%-100% EtOAc/hexanes) affording Compound 43 (4.4 mg, 0.014 mmol, 22% yield). LC-MS ESI (−) m/z 323 (M−H).

Example 17: Synthesis of 2-[1-oxo-7-(trifluoromethylsulfonyl)indan-4-yl]acetamide (Compound 44)

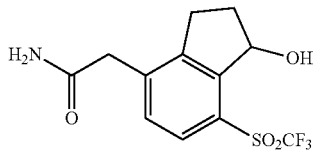

Step A: Preparation of 2-[7'-(trifluoromethylsulfonyl)spiro[1,3-dioxolane-2,1'-indane]-4'-yl]acetic acid Sodium hydroxide (0.55 mL, 1.66 mmol) added by syringe to diethyl 2-[7'-(trifluoromethylsulfonyl)spiro[1,3-dioxolane-2,1'-indane]-4'-yl]propanedioate (515.0 mg, 1.10 mmol) in ethanol 95% (2.2 mL) at room temperature and stirred for 30 min. Warmed to 60° C. for 3 h. Added additional sodium hydroxide (0.55 mL, 1.66 mmol) and stirred until complete as judged by LC-MS. Acidified to pH 2 with 1 N HCl, diluted with brine, extracted with ethyl acetate, dried over $Na_2SO_4$, filtered and concentrated in vacuo affording 2-[7'-(trifluoromethylsulfonyl)spiro[1,3-dioxolane-2,1'-indane]-4'-yl]acetic acid (368 mg, 1.00 mmol, 91% yield). Used without further purification.

Step B: Preparation of 2-[1-oxo-7-(trifluoromethylsulfonyl)indan-4-yl]acetamide

N,N-Diisopropylethylamine (142.7 µL, 0.82 mmol) added all at once to 2-[7'-(trifluoromethylsulfonyl)spiro[1,3-dioxolane-2,1'-indane]-4'-yl]acetic acid (100.0 mg, 0.27 mmol), ammonium chloride (73.0 mg, 1.4 mmol) and HATU (156.1 mg, 0.41 mmol) in DMF (2.0 mL) at room temperature then stirred until complete as judged by LC-MS. Purified directly on reverse phase silica gel (12+M, 14 CV, 20-100% acetonitrile/water) affording 2-[1-oxo-7-(trifluoromethylsulfonyl)indan-4-yl]acetamide (12.0 mg, 0.037 mmol, 14% yield). LC-MS ESI (+) m/z 322 (M+H).

Step C: Preparation of 2-[1-hydroxy-7-(trifluoromethylsulfonyl)indan-4-yl]acetamide Sodium borohydride (4.2 mg, 0.11 mmol) was added all at once to 2-[1-oxo-7-(trifluoromethylsulfonyl)indan-4-yl]acetamide (12.0 mg, 0.04 mmol) in methanol (1.0 mL) at room temperature and stirred for 20 min. Quenched with 1 N HCl, extracted with ethyl acetate, washed with brine, dried over $Na_2SO_4$, filtered and concentrated in vacuo. A portion was purified by preparative TLC (ethyl acetate) affording Compound 44 (1.6 mg, 0.005 mmol, 13% yield). LC-MS ESI (−) m/z 322 (M−H).

Example 18: Synthesis of (R)-2-(1-hydroxy-7-((trifluoromethyl)sulfonyl)-2,3-dihydro-1H-inden-4-yl)acetic acid Compound 45)

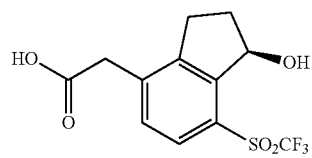

Chloro{[(1R,2R)-(−)-2-amino-1,2-diphenylethyl](4-toluenesulfonyl)amido}(p-cymene)ruthenium(II) (2.0 mg, 0.003 mmol) was added all at once to an ice cold solution of 2-[1-oxo-7-(trifluoromethylsulfonyl)indan-4-yl]acetic acid (102.0 mg, 0.32 mmol), triethylamine (88.2 µL, 0.63 mmol) and formic acid (35.8 µL, 0.95 mmol) in dichloromethane (3.0 mL), sealed with a teflon lined cap and placed in a 4 OC fridge overnight. Warmed to room temperature then stirred for an additional 3 days. Concentrated in vacuo then purified on reverse phase silica gel (25+M, 14 CV, 20-100% acetonitrile/water), diluted with ethyl acetate, washed with 1 N HCl to remove triethylamine, washed with brine, dried over $Na_2SO_4$, filtered and concentrated in vacuo affording 2-[(1R)-1-hydroxy-7-(trifluoromethylsulfonyl)indan-4-yl]acetic acid (45.0 mg, 0.14 mmol, 44% yield). LC-MS ESI (−) m/z 323 (M−H).

Example 19: Synthesis of (S)-4-(2,2-difluoroethoxy)-2,2-difluoro-7-((trifluoromethyl)sulfonyl)-2,3-dihydro-1H-inden-1-ol (Compound 92)

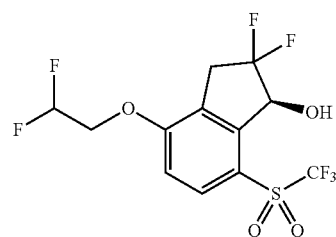 [SMILES: O=S(=O)(c1ccc(OCC(F)F)c2c1[C@H](O)C(F)(F)C2)C(F)(F)F]

Step A: Preparation of 4-((4-methoxybenzyl)oxy)-7-((trifluoromethyl)sulfonyl)-2,3-dihydrospiro[indene-1,2'-[1,3]dioxolane]

A solution of 4'-fluoro-7'-(trifluoromethylsulfonyl)spiro[1,3-dioxolane-2,1'-indane] (1.0 g, 3.07 mmol) and 4-methoxybenzyl alcohol (760 µL, 6.13 mmol) in acetonitrile (9.3 mL) at 25° C. was treated with potassium hydroxide (516 mg, 9.2 mmol) and stirred at 25° C. for 1.5 h. The reaction mixture was poured into 150 mL of water and extracted with 3×40 mL EtOAc. The combined organics were rinsed with 20 mL of brine, dried with $MgSO_4$, filtered, and concentrated to dryness. Purification was achieved by chromatography on silica using 10-25% EtOAc/hexane to afford 4-((4-methoxybenzyl)oxy)-7-((trifluoromethyl)sulfonyl)-2,3-dihydrospiro[indene-1,2'-[1,3]dioxolane] as a solid (1.08 g, 79%). LCMS ESI (+) $[M+H]^+$ m/z 445.

Step B: Preparation of 4-((4-methoxybenzyl)oxy)-7-((trifluoromethyl)sulfonyl)-2,3-dihydro-1H-inden-1-one In a glass pressure vessel, a solution of 4'-[(4-methoxyphenyl)methoxy]-7'-(trifluoromethylsulfonyl)spiro[1,3-dioxolane-2,1'-indane] (1.08 g, 2.43 mmol) in a mixture acetone (20 mL) and water (20 mL) was treated with pyridinium p-toluenesulfonate (122.1 mg, 0.49 mmol), sealed and stirred at 80° C. overnight. Volatiles were removed by concentration under reduced pressure. The residue was poured into 40 mL of saturated aqueous $NaHCO_3$ and extracted with 3×50 mL EtOAc. The combined organics were rinsed with 30 mL of brine, dried with MgSO$_4$, filtered, and concentrated to dryness. The product was used without further purification. LCMS ESI (+) [M+H]$^+$ m/z 401.

Step C: Preparation of 2,2-difluoro-4-((4-methoxybenzyl)oxy)-7-((trifluoromethyl)sulfonyl)-2,3-dihydro-1H-inden-1-one 2,2-Dimethylpropanoic acid (50 mg, 0.46 mmol) was added to a flask containing a suspension of 4-[(4-methoxyphenyl)methoxy]-7-(trifluoromethylsulfonyl)indan-1-one (922 mg, 2.3 mmol) and 3-methoxypropan-1-amine (0.35 mL, 3.45 mmol) in a mixture of toluene (14 mL) and cyclohexane (14 mL). This was refluxed with a Dean-Stark trap attached at 104° C. After 2.5 h, the reaction mixture was cooled and volatiles removed by concentration under reduced pressure. The residue was dissolved in acetonitrile (24 mL) and treated sequentially with sodium sulfate (850 mg, 6.0 mmol) and 1-(chloromethyl)-4-fluoro-1,4-diazoniabicyclo[2.2.2]octane ditetrafluoroborate (2.13 g, 6.0 mmol). The resulting suspension was stirred at 60° C. for 2 h. After cooling to room temperature, the reaction mixture was treated with concentrated hydrochloric acid (600 μL, 7.2 mmol) and water (10 mL). The resulting mixture stirred for 20 minutes. Volatiles were removed by concentration under reduced pressure. The reaction mixture was poured into 20 mL of water and extracted with 3×30 mL EtOAc. The combined organics were rinsed with 20 mL of brine, dried with MgSO$_4$, filtered, and concentrated to dryness. Purification was achieved by chromatography on silica using 5-40% EtOAc/hexane to afford 2,2-difluoro-4-((4-methoxybenzyl)oxy)-7-((trifluoromethyl)sulfonyl)-2,3-dihydro-1H-inden-1-one as a solid (520 mg, 50%). LCMS ESI (+) [M+H]$^+$ m/z 437.

Step D: Preparation of (S)-2,2-difluoro-4-((4-methoxybenzyl)oxy)-7-((trifluoromethyl)sulfonyl)-2,3-dihydro-1H-inden-1-ol A solution of 2,2-difluoro-4-[(4-methoxyphenyl)methoxy]-7-(trifluoromethylsulfonyl)indan-1-one (520 mg, 1.19 mmol) in dichloromethane (11.9 mL) was cooled to 0° C. and sparged with nitrogen for 5 minutes. During this time, formic acid (130 μL, 3.58 mmol) and triethylamine (330 μL, 2.38 mmol) were sequentially added. Once the sparging was complete, RuCl(p-cymene)[(R,R)-Ts-DPEN](22.8 mg, 0.036 mmol) was added under a continuous stream of nitrogen. The reaction vessel was sealed and put into the refrigerator to react overnight. Once complete, the reaction mixture was poured into 30 mL of saturated aqueous NaHCO$_3$ and extracted with 3×30 mL CH$_2$Cl$_2$. The combined organics were rinsed with 20 mL of brine, dried with MgSO$_4$, filtered, and concentrated to dryness. Purification was achieved by chromatography on silica using 10-40% EtOAc/hexane to afford (S)-2,2-difluoro-4-((4-methoxybenzyl)oxy)-7-((trifluoromethyl)sulfonyl)-2,3-dihydro-1H-inden-1-ol as a solid (370 mg, 71%). LCMS ESI (+) [M+NH$_4$]$^+$ m/z 456.

Step E: Preparation of (S)-tert-butyl((2,2-difluoro-4-((4-methoxybenzyl)oxy)-7-((trifluoromethyl)sulfonyl)-2,3-dihydro-1H-inden-1-yl)oxy)dimethylsilane A solution of (1S)-2,2-difluoro-4-[(4-methoxyphenyl)methoxy]-7-(trifluoromethylsulfonyl)indan-1-ol (370 mg, 0.84 mmol) and 2,6-lutidine (780 μL, 7.76 mmol) in dichloromethane (8.4 mL) at −78° C. was treated with tert-butyldimethylsilyl trifluoromethanesulfonate (980 μL, 4.22 mmol) and allowed to warm to room temperature over 2 h. The reaction mixture was poured into 30 mL of saturated aqueous NaHCO$_3$ and extracted with 3×20 mL CH$_2$Cl$_2$. The combined organics were rinsed with 10 mL of brine, dried with MgSO$_4$, filtered, and concentrated to dryness. Purification was achieved by chromatography on silica using 5-20% EtOAc/hexane to afford (S)-tert-butyl((2,2-difluoro-4-((4-methoxybenzyl)oxy)-7-((trifluoromethyl)sulfonyl)-2,3-dihydro-1H-inden-1-yl)oxy)dimethylsilane (460 mg, quant). LCMS ESI (−) [M−H]$^-$ m/z 551.

Step F: Preparation of (S)-1-((tert-butyldimethylsilyl)oxy)-2,2-difluoro-7-((trifluoromethyl)sulfonyl)-2,3-dihydro-1H-inden-4-ol A solution of tert-butyl-[(1S)-2,2-difluoro-4-[(4-methoxyphenyl)methoxy]-7-(trifluoromethylsulfonyl)indan-1-yl]oxy-dimethyl-silane (460 mg, 0.83 mmol) in dichloromethane (3.0 mL) at 25° C. was treated with trifluoroacetic acid (3.0 mL) and stirred at 25° C. After 1 h, volatiles were removed by concentration under reduced pressure. To the resulting residue was added 6 mL of toluene and the organic volatiles were once again removed by concentration under reduced pressure. This process was repeated twice. Purification was achieved by chromatography on reverse phase by injection of a DMF solution of the product residue. 40-100% CH$_3$CN/Water was used as eluent. (S)-1-((tert-Butyldimethylsilyl)oxy)-2,2-difluoro-7-((trifluoromethyl)sulfonyl)-2,3-dihydro-1H-inden-4-ol was isolated a thick orange oil (236 mg, 89%). LCMS ESI (−) [M−H]$^-$ m/z 431.

Step G: Preparation of (S)-4-(2,2-difluoroethoxy)-2,2-difluoro-7-((trifluoromethyl)sulfonyl)-2,3-dihydro-1H-inden-1-ol (Compound 92)

A solution of (1S)-1-[tert-butyl(dimethyl)silyl]oxy-2,2-difluoro-7-(trifluoromethylsulfonyl)indan-4-ol (20.2 mg, 0.047 mmol), triphenylphosphine (25.7 mg, 0.093 mmol), and 2,2-difluoroethanol (11.8 μL, 0.19 mmol) in tetrahydrofuran (0.5 mL) at 25° C. was treated with diisopropyl azodicarboxylate (18.3 μL, 0.093 mmol). After stirring overnight, to the reaction mixture was added sequentially acetic acid (8.0 μL, 0.14 mmol) and tetrabutylammonium fluoride (1.0 M in THF, 7.0 μL, 0.07 mmol). The resulting mixture was heated to 60° C. for 2 h. The reaction mixture was poured into 30 mL of water containing 1 mL of saturated aqueous NaHCO$_3$ and extracted with 3×20 mL EtOAc. The combined organics were rinsed with 10 mL of brine, dried with MgSO$_4$, filtered, and concentrated to dryness. Purification was achieved by chromatography on silica using 1-10% EtOAc/CH$_2$Cl$_2$ to afford Compound 92 as a clear solid (7.1 mg, 40%). Retention time HPLC (14 min)=4.95 min; LCMS ESI (−) [M−H]$^-$ m/z 381; $^1$H NMR (400 MHz, CDCl$_3$): δ 8.00 (d, 1H), 7.07 (d, 1H), 6.15 (tt, 1H), 5.38 (dd, 1H), 4.44-4.29 (m, 2H), 3.55-3.39 (m, 2H), 3.16 (d, 1H).

Example 20: Synthesis of (S)-4-(3,3-difluorocyclobutoxy)-2,2-difluoro-7-((trifluoromethyl)sulfonyl)-2,3-dihydro-1H-inden-1-ol (Compound 93)

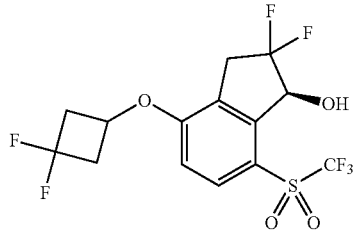

Prepared similarly as described in Example 19, Step G using 3,3-difluorocyclobutan-1-ol in place of 2,2-difluoroethan-1-ol. A first purification was attempted by chromatography on silica using 0-5% EtOAc/CHCl$_3$. A second purification on silica using 10-30% EtOAc/hexane afforded Compound 93 as a white solid (11 mg, 55%). Retention time HPLC (14 min)=5.65 min; LCMS ESI (−) [M−H]$^-$ m/z 407; $^1$H NMR (400 MHz, CDCl$_3$): δ 7.96 (d, 1H), 6.86 (d, 1H), 5.37 (dd, 1H), 4.86-4.76 (m, 1H), 3.53-3.35 (m, 2H), 3.27-3.14 (m, 3H), 2.92-2.78 (m, 2H).

Example 21: Synthesis of (S)-2,2-difluoro-4-((3-fluorooxetan-3-yl)methoxy)-7-((trifluoromethyl)sulfonyl)-2,3-dihydro-1H-inden-1-ol (Compound 94)

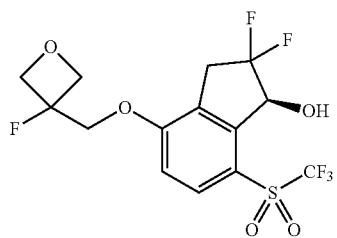 [SMILES: O=S(=O)(c1ccc(OCC2(F)COC2)c2c1[C@H](O)C(F)(F)C2)C(F)(F)F]

Prepared similarly as described in Example 19, Step G using (3-fluorooxetan-3-yl)methanol in place of 2,2-difluoroethan-1-ol. Purification was achieved by chromatography on silica using 20-70% EtOAc/hexane to afford Compound 94 as a clear solid (6.1 mg, 38%). Retention time HPLC (14 min)=4.63 min; LCMS ESI (−) [M−H]$^-$ m/z 405; $^1$H NMR (400 MHz, CDCl$_3$): δ 8.00 (d, 1H), 7.11 (d, 1H), 5.38 (dd, 1H), 4.92 (dd, 2H), 4.68 (dd, 2H), 4.59-4.46 (m, 2H), 3.54-3.36 (m, 2H), 3.19 (d, 1H).

Example 22: Synthesis of (1S,3R)-4-(3,3-difluorocyclobutoxy)-2,2,3-trifluoro-7-(methylsulfonyl)-2,3-dihydro-1H-inden-1-ol (Compound 95) and (1S,3S)-4-(3,3-difluorocyclobutoxy)-2,2,3-trifluoro-7-(methylsulfonyl)-2,3-dihydro-1H-inden-1-ol (Compound 96)

Compound 95

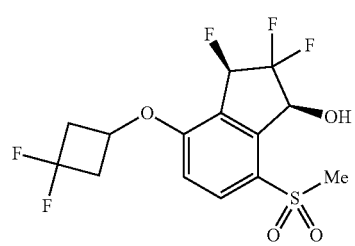

Compound 96

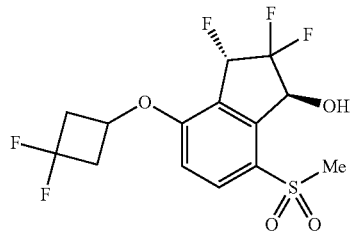

Step A: Preparation of 4,7-difluoro-1H-indene-1,3(2H)-dione

A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 h. The reaction mixture was cooled to 0° C. and treated with 10% hydrochloric acid (65 mL, 211 mmol) by dropwise addition. Once the addition was complete, the ice bath was removed and the mixture stirred at ambient temperature for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL CH$_2$Cl$_2$. The combined organics were dried with MgSO$_4$, filtered, and concentrated to dryness. The product was used without further purification.

Step B: Preparation of 2,2,4,7-tetrafluoro-1H-indene-1,3(2H)-dione

A solution of the unpurified 4,7-difluoro-1H-indene-1,3(2H)-dione (4.2 g, 23.1 mmol) in acetonitrile (100 mL) cooled in a 25° C. water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with MgSO$_4$, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. $^1$H NMR (400 MHz, CDCl$_3$): δ 7.70 (t, 2H).

Step C: Preparation of (S)-2,2,4,7-tetrafluoro-3-hydroxy-2,3-dihydro-1H-inden-1-one To a solution of 2,2,4,7-tetrafluoro-1H-indene-1,3(2H)-dione (3.48 g, 16.0 mmol) in dichloromethane (150 mL) at 0° C. was added formic acid (600 μL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The CH$_2$Cl$_2$ layer was separated and the aqueous layer extracted with ethyl acetate (2×50 mL). The combined organics were dried with Na$_2$SO$_4$, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. $^1$H NMR (400 MHz, CDCl$_3$): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxide (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over MgSO$_4$, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+)[M+H]$^+$ m/z 249.

Step E: Preparation of (S)-2,2,4-trifluoro-3-hydroxy-7-(methylsulfonyl)-2,3-dihydro-1H-inden-1-one (S)-2,2,4-trifluoro-3-hydroxy-7-(methylthio)-2,3-dihydro-1H-inden-1-one (400 mg, 1.6 mmol) was dissolved in MeOH (10 mL) and the reaction was treated dropwise with a solution of Oxone® (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over Na$_2$SO$_4$ and concentrated in vacuo to a yellow solid that was used without further purification (467 mg). LCMS ESI (+) [M+H]$^+$ m/z 281.

Step F: Preparation of (R)-2,2,3,4-tetrafluoro-7-(methylsulfonyl)-2,3-dihydro-1H-inden-1-one (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylaminosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 h at 0° C. The cold reaction was treated with saturated NaHCO$_3$ (10 mL) and stirred vigorously for 20 minutes. The mixture was diluted with additional methylene chloride and the layers were separated. The aqueous was re-extracted with methylene chloride and the combined organic layers were dried over Na$_2$SO$_4$ and concentrated in vacuo to a yellow solid. The crude material was chromatographed on SiO$_2$(Biotage SNAP Ultra) and eluted with a gradient of ethyl acetate/hexane. The desired material was concentrated to a pale yellow solid (258 mg). LCMS ESI (+) [M+H]$^+$ m/z 283.

Step G: Preparation of (R)-2,2,3,4-tetrafluoro-7-(methylsulfonyl)-2,3-dihydrospiro[indene-1,2'-[1,3]dioxolane]

A solution of (3R)-2,2,3,4-tetrafluoro-7-methylsulfonyl-indan-1-one (2.03 g, 7.2 mmol) and 2-bromoethanol (1.53 mL, 21.6 mmol) in DMF (16 mL) at 25° C. was treated with potassium carbonate (2.98 g, 21.6 mmol) and stirred at 25° C. for 30 min. The reaction mixture was poured into 200 mL of water and extracted with 3×50 mL Et$_2$O. The combined organics were rinsed with 30 mL of brine, dried with MgSO$_4$, filtered, and concentrated to dryness. The off-white solid was used without further purification. LCMS ESI (+) [M+H]$^+$ m/z 327.

Step H: Preparation of (R)-4-(3,3-difluorocyclobutoxy)-2,2,3-trifluoro-7-(methylsulfonyl)-2,3-dihydrospiro[indene-1,2'-[1,3]dioxolane]

A solution of (3'R)-2',2',3',4'-tetrafluoro-7'-methylsulfonyl-spiro[1,3-dioxolane-2,1'-indane] (1.95 g, 5.98 mmol) and 3,3-difluoro-cyclobutanol (770 µL, 7.95 mmol) in acetonitrile (30 mL) at 25° C. was treated with potassium hydroxide (402.4 mg, 7.17 mmol) and stirred at 25° C. for 1 h. Excess acetonitrile was removed by concentration under reduced pressure. The reaction mixture was poured into 40 mL of water and extracted with 3×40 mL EtOAc. The combined organics were rinsed with 10 mL of brine, dried with MgSO$_4$, filtered, and concentrated to dryness. Purification was achieved by chromatography on silica using 15-45% EtOAc/hexane to afford a white solid (2.2 g, 89%). LCMS ESI (+) [M+H]$^+$ m/z 415.

Step I: Preparation of (R)-4-(3,3-difluorocyclobutoxy)-2,2,3-trifluoro-7-(methylsulfonyl)-2,3-dihydro-1H-inden-1-one A solution of (3'R)-4'-(3,3-difluorocyclobutoxy)-2',2',3'-trifluoro-7'-methylsulfonyl-spiro[,3-dioxolane-2,1'-indane] (2.2 g, 5.31 mmol) in dichloromethane (30 mL) at 25° C. was treated with perchloric acid (70% in water, 10 mL) and left to stir for 2 days. The reaction mixture was carefully quenched by the addition of 100 mL of saturated aqueous NaHCO$_3$ and extracted with 3×50 mL CH$_2$Cl$_2$. The combined organics were rinsed with 10 mL of brine, dried with MgSO$_4$, filtered, and concentrated to dryness. Purification was achieved by chromatography on silica using 25-65% EtOAc/hexane to afford a solid (1.41 g, 72%). LCMS ESI (+) [M+H]$^+$ m/z 371.

Step J: Preparation of Compound 95 and Compound 96

A solution of (3R)-4-(3,3-difluorocyclobutoxy)-2,2,3-trifluoro-7-methylsulfonyl-indan-1-one (1.41 g, 3.81 mmol) in dichloromethane (40 mL) was cooled to 0° C. and sparged with nitrogen for 5 minutes. During this time formic acid (430 µL, 11.42 mmol) and triethylamine (1.06 mL, 7.62 mmol) were sequentially added. Once the sparging was complete, RuCl(p-cymene)[(R,R)-Ts-DPEN] (48.5 mg, 0.076 mmol) was added under a continuous stream of nitrogen. The reaction vessel was sealed and put into the refrigerator to react overnight. Volatiles were removed by concentration under reduced pressure. The residue was purified by chromatography on silica using 25-55% EtOAc/hexane. Additional purifications by chromatography on silica using 20-50% EtOAc/hexane were necessary to isolate material of sufficient purity. A flash crystallization was performed from CHCl₃. The sample was dissolved in a minimum of refluxing CHCl₃ and then cooled to 0° C. The collected solid was rinsed with CHCl₃ and dried under high vacuum overnight to afford Compound 95 as a white solid (550 mg, 39%). From the repeated purifications, Compound 96 was isolated as a white solid.

Data for Compound 95: LCMS ESI (+) [M+H]⁺ m/z 373; ¹H NMR (400 MHz, (CD3)₂CO): δ 8.11 (dd, 1H), 7.33 (d, 1H), 5.87 (dd, 1H), 5.65-5.59 (m, 1H), 5.17-5.08 (m, 1H), 3.40-3.26 (m, 2H), 3.27 (s, 3H), 2.98-2.81 (m, 2H), 2.80 (t, 1H).

Data for Compound 96: LCMS ESI (+) [M+H]⁺ m/z 373; ¹H NMR (400 MHz, CDCl₃): δ 8.06 (dd, 1H), 6.87 (d, 1H), 5.92 (dd, 1H), 5.78 (td, 1H), 4.86-4.76 (m, 1H), 3.98 (d, 1H), 3.25-3.14 (m, 2H), 3.22 (s, 3H), 2.95-2.78 (m, 2H).

Example 23: Synthesis of (1S,3R)-4-(3,3-difluorocyclobutoxy)-2,2,3-trifluoro-7-((fluoromethyl)sulfonyl)-2,3-dihydro-1H-inden-1-ol (Compound 97)

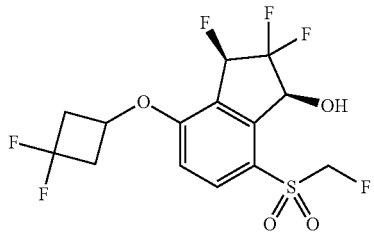 [SMILES: O=S(=O)(CF)c1ccc(OC2CC(F)(F)C2)c2c1[C@H](O)C(F)(F)[C@@H]2F]

Step A: Preparation of (R)-2,2,3,4-tetrafluoro-7-(methylthio)-2,3-dihydro-1H-inden-1-one A solution of (S)-2,2,4-trifluoro-3-hydroxy-7-(methylthio)-2,3-dihydro-1H-inden-1-one (402 mg, 1.62 mmol) in dichloromethane (16.2 mL) at 0° C. was treated with diethylaminosulfur trifluoride (390 μL, 2.92 mmol). The ice bath was removed from the resulting reaction mixture and the reaction mixture was stirred for 2 hours at room temperature. Volatiles were removed by concentration under reduced pressure. The residue was suspended in 30 mL of EtOAc, cooled to 0° C., and quenched by the addition of 20 mL of saturated aqueous NaHCO₃. The reaction mixture was vigorously stirred for 30 minutes and then extracted with 3×20 mL EtOAc. The combined organics were rinsed with 10 mL of brine, dried with MgSO₄, filtered, and concentrated to dryness. The product was used without further purification. LCMS ESI (+) [M+H]⁺ m/z 251.

Step B: Preparation of (R)-2,2,3,4-tetrafluoro-7-((fluoromethyl)thio)-2,3-dihydro-1H-inden-1-one A solution of (R)-2,2,3,4-tetrafluoro-7-(methylthio)-2,3-dihydro-1H-inden-1-one (393 mg, 1.57 mmol) in acetonitrile (15.7 mL) at 0° C. was treated with Selectfluor® (584.3 mg, 1.65 mmol) and stirred at 0° C. for 2 hours. Volatiles were removed by concentration under reduced pressure. The reaction mixture was poured into 30 mL of water and extracted with 3×20 mL EtOAc. The combined organics were rinsed with 10 mL of brine, dried with MgSO₄, filtered, and concentrated to dryness. Purification was achieved by chromatography on silica using 10-30% EtOAc/hexane to afford (R)-2,2,3,4-tetrafluoro-7-((fluoromethyl)thio)-2,3-dihydro-1H-inden-1-one (153 mg, 36%) as a yellow oil. LCMS ESI (+) [M−F]⁺ m/z 249.

Step C: Preparation of (R)-2,2,3,4-tetrafluoro-7-((fluoromethyl)sulfonyl)-2,3-dihydro-1H-inden-1-one A solution of (R)-2,2,3,4-tetrafluoro-7-((fluoromethyl)thio)-2,3-dihydro-1H-inden-1-one (91.8 mg, 0.34 mmol) in a mixture of methanol (3.4 mL) and water (3.4 mL) was treated with Oxone® (252.5 mg, 0.41 mmol). The resulting suspension was heated to 60° C. overnight. Additional Oxone® (252.5 mg, 0.41 mmol) was added and the reaction mixture heated for an additional 6 hours. Volatiles were removed by concentration under reduced pressure. The reaction mixture was poured into 100 mL of water and extracted with 3×25 mL EtOAc. The combined organics were rinsed with 10 mL of brine, dried with MgSO₄, filtered, and concentrated to dryness. Purification was achieved by chromatography on silica using 10-40% EtOAc/hexane to afford (R)-2,2,3,4-tetrafluoro-7-((fluoromethyl)sulfonyl)-2,3-dihydro-1H-inden-1-one as a white solid (73 mg, 71%). LCMS ESI (+) [M+H]⁺ m/z 301.

Step D: Preparation of (1S,3R)-4-(3,3-difluorocyclobutoxy)-2,2,3-trifluoro-7-((fluoromethyl)sulfonyl)-2,3-dihydro-1H-inden-1-ol (Compound 97)

Prepared similarly as described in Example 22, Steps G-J. Purification was achieved by chromatography on silica using 15-30% EtOAc/hexane to afford Compound 97 (29.8 mg, 49%) as a white solid. Retention time HPLC (14 min)=4.63 min; LCMS ESI (+) [M+H]⁺ m/z 391; ¹H NMR (400 MHz, CDCl₃): δ 8.13 (dd, 1H), 6.93 (d, 1H), 5.76 (dd, 1H), 5.59-5.53 (m, 1H), 5.47 (dd, 1H), 5.18 (dd, 1H), 4.90-4.80 (m, 1H), 3.29-3.16 (m, 2H), 3.16 (d, 1H), 2.97-2.81 (m, 2H).

Example 24: Synthesis of (racemic)-4-(3,3-difluorocyclobutoxy)-2,3-difluoro-7-(methylsulfonyl)-2,3-dihydro-1H-inden-1-ol (Compound 98)

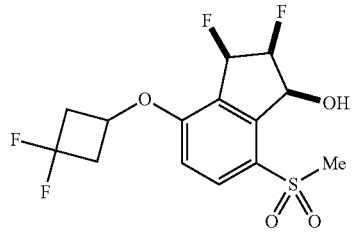 [SMILES: CS(=O)(=O)c1ccc(OC2CC(F)(F)C2)c2c1[C@H](O)[C@H](F)[C@@H]2F]

Step A: Preparation of 2,3,4-trifluoro-7-(methylsulfonyl)spiro[indene-1,2'-[1,3]dioxolane]

A solution of (3'R)-2',2',3',4'-tetrafluoro-7'-methylsulfonyl-spiro[1,3-dioxolane-2,1'-indane] (109 mg, 0.33 mmol) in DMSO (3.3 mL) was treated with 1.0 M aqueous sodium hydroxide (350 μL, 0.35 mmol) and stirred at room temperature for 30 minutes. The reaction mixture was poured into 60 mL of water and extracted with 3×20 mL Et₂O. The combined organics were rinsed with 10 mL of brine, dried with MgSO$_4$, filtered, and concentrated to dryness to afford an off-white solid (88 mg, 86%) that was used without further purification. LCMS ESI (+) [M+H]$^+$ m/z 307.

Step B: Preparation of (racemic)-2,3,4-trifluoro-7-(methylsulfonyl)-2,3-dihydrospiro[indene-1,2'-[1,3]dioxolane]

A solution of 2',3',4'-trifluoro-7'-methylsulfonyl-spiro[1,3-dioxolane-2,1'-indene] (30.0 mg, 0.098 mmol) and palladium on carbon (10 wt. %, 5.2 mg, 0.0049 mmol) in absolute ethanol (2.0 mL) was sparged with nitrogen for 3 minutes. A balloon of hydrogen was then sparged through the solution for 1 minute. After this time, the balloon was directly attached to the reaction vessel and left to stir overnight. The reaction was sparged with nitrogen for 3 minutes and filtered through a pad of celite using EtOAc for washing. The filtrate was concentrated to dryness. Purification was achieved by chromatography on silica using 20-50% EtOAc/hexane to afford a solid (19.7 mg, 64%). LCMS ESI (+) [M+H]$^+$ m/z 309.

Step C: Preparation of (racemic)-4-(3,3-difluorocyclobutoxy)-2,3-difluoro-7-(methylsulfonyl)-2,3-dihydrospiro[indene-1,2'-[1,3]dioxolane]

A solution of racemic-2',3',4'-trifluoro-7'-methylsulfonyl-spiro[1,3-dioxolane-2,1'-indane] (19.3 mg, 0.063 mmol) and 3,3-difluoro-cyclobutanol (9.8 µL, 0.10 mmol) in acetonitrile (1.0 mL) at 25° C. was treated with potassium hydroxide (5.3 mg, 0.094 mmol) and stirred at 25° C. for 1 h. An additional portion of potassium hydroxide (5.3 mg, 0.094 mmol) was added to drive the reaction to completion. Volatiles were removed by concentration under reduced pressure. The reaction mixture was poured into 20 mL of water and extracted with 3×20 mL EtOAc. The combined organics were rinsed with 10 mL of brine, dried with MgSO$_4$, filtered, and concentrated to dryness. An off-white solid (27.2 mg) was isolated and used without further purification. LCMS ESI (+) [M+H]$^+$ m/z 397.

Step D: Preparation of Compound 98

A solution of unpurified (racemic)-4-(3,3-difluorocyclobutoxy)-2,3-difluoro-7-(methylsulfonyl)-2,3-dihydrospiro[indene-1,2'-[1,3]dioxolane] (27.2 mg, 0.063 mmol) in dichloromethane (1.2 mL) at 0° C. was treated with 70% aqueous perchloric acid (120 µL) and stirred at 0° C. for 15 minutes. The reaction mixture was carefully poured onto 20 g of ice, diluted with 5 mL of saturated NaHCO$_3$ and extracted with 3×15 mL CH$_2$Cl$_2$. The combined organics were rinsed with 10 mL of brine, dried with MgSO$_4$, filtered, and concentrated to dryness. The solid residue was used immediately in the next step by suspending in 2 mL of MeOH and cooling to 0° C. The resulting mixture was treated with 2 portions of sodium borohydride (2×2.4 mg, 0.063 mmol) over a 5 minute period. The reaction mixture stirred a further 10 minutes at 0° C. and was then quenched by the addition of 2 mL of aqueous saturated NH$_4$Cl. Volatiles were removed by concentration under reduced pressure. The reaction mixture was poured into 30 mL of water and extracted with 3×15 mL EtOAc. The combined organics were rinsed with 10 mL of brine, dried with MgSO$_4$, filtered, and concentrated to dryness. Purification by chromatography on reverse phase by injection of a DMF solution of the product residue with 5-70% CH$_3$CN/water as eluent afforded Compound 98 as a white solid (4.4 mg, 20%). Retention time HPLC (14 min)=3.06 min; LCMS ESI (+) (M+NH$_4$) m/z 372; $^1$H NMR (400 MHz, (CD3)$_2$CO): δ 8.05 (dd, 1H), 7.25 (d, 1H), 5.99 (dd, 1H), 5.74 (td, 1H), 5.16 (ddt, 1H), 5.13-5.03 (m, 1H), 4.84 (dd, 1H), 3.39-3.25 (m, 2H), 3.28 (s, 3H), 2.95-2.74 (m, 2H).

Example 25: Synthesis of (racemic)-4-(3,3-difluorocyclobutoxy)-2,3-difluoro-7-((fluoromethyl)sulfonyl)-2,3-dihydro-1H-inden-1-ol (Compound 99)

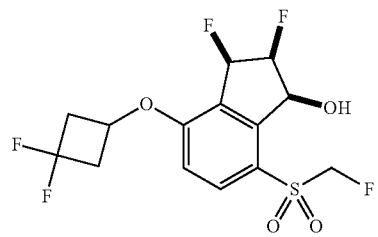 [SMILES: O=S(=O)(CF)c1ccc(OC2CC(F)(F)C2)c2c1[C@H](O)[C@H](F)[C@@H]2F]

Step A: Preparation of 2,3,4-trifluoro-7-((fluoromethyl)sulfonyl)spiro[indene-1,2'-[1,3]dioxolane]

A solution of (3'R)-2',2',3',4'-tetrafluoro-7'-(fluoromethylsulfonyl)spiro[1,3-dioxolane-2,1'-indane] (111.8 mg, 0.32 mmol) in DMSO (2.2 mL) was treated with 1.0 M aqueous sodium hydroxide (420 µL, 0.32 mmol) and stirred at room temperature for 30 minutes. The reaction mixture was poured into 40 mL of water and extracted with 3×30 mL Et$_2$O. The combined organics were rinsed with 10 mL of brine, dried with MgSO$_4$, filtered, and concentrated to dryness. Purification was achieved by chromatography on silica using 10-30% EtOAc/hexanes. The desired product was isolated with ~10% of the trifluoroindane starting material present as a white solid (73.2 mg, 63% yield for olefin). LCMS ESI (+) (M+H) m/z 325.

Step B: Preparation of (racemic)-2,3,4-trifluoro-7-(methylsulfonyl)-2,3-dihydrospiro[indene-1,2'-[1,3]dioxolane]

A solution of 2',3',4'-trifluoro-7'-(fluoromethylsulfonyl)spiro[1,3-dioxolane-2,1'-indene] (77.2 mg, 0.24 mmol) and palladium on carbon (10% by wt., 12.7 mg, 0.012 mmol) in absolute ethanol (4.8 mL) was sparged with nitrogen for 3 mins. A balloon of hydrogen was then sparged through the solution for 1 min. After this time, the balloon was directly attached and the reaction left to stir overnight. The starting material was contaminated with ~10% of the trifluoroindane (starting material for the olefin synthesis). The reaction was sparged with nitrogen for 3 min and filtered through a pad of celite using EtOAc for washing. The filtrate was concentrated to dryness. Purification was achieved by chromatography on silica using 10-40% EtOAc/hexanes to afford a solid (53 mg, 72%). LCMS ESI (+) [M+H]$^+$ m/z 327.

Step C: Preparation of (racemic)-4-(3,3-difluorocyclobutoxy)-2,3-difluoro-7-((fluoromethyl)sulfonyl)-2,3-dihydrospiro[indene-1,2'-[1,3]dioxolane]

A solution of (racemic)-2',3',4'-trifluoro-7'-(fluoromethylsulfonyl)spiro[1,3-dioxolane-2,1'-indane] (13.5 mg, 0.041 mmol) and 3,3-difluoro-cyclobutanol (6.5 µL, 0.066 mmol) in acetonitrile (1.0 mL) at 25° C. was treated with potassium hydroxide (3.5 mg, 0.0600 mmol) and stirred at 25° C. for 1 h. Volatiles were removed by concentration under reduced pressure. The reaction mixture was poured into 20 mL of water and extracted with 3×20 mL EtOAc. The combined organics were rinsed with 10 mL of brine, dried with MgSO$_4$, filtered, and concentrated to dryness. The product was used without further purification. ESI (+) [M+NH$_4$]$^+$ m/z 432.

Step D: Preparation of Compound 99

A solution of (racemic)-4'-(3,3-difluorocyclobutoxy)-2', 3'-difluoro-7'-(fluoromethylsulfonyl)spiro[1,3-dioxolane-2, 1'-indane](16.6 mg, 0.040 mmol) in dichloromethane (1.2 mL) at 0° C. was treated with 70% aqueous perchloric acid (120 µL) and stirred at 0° C. for 1.5 h. The reaction mixture was carefully poured onto 20 g of ice, diluted with 5 mL of saturated NaHCO$_3$ and extracted with 3×15 mL CH$_2$Cl$_2$. The combined organics were rinsed with 10 mL of brine, dried with MgSO$_4$, filtered, and concentrated to dryness. The solid residue was used immediately in the next step by suspending in 1 mL of MeOH and cooling to 0° C. The resulting mixture was treated with 2 portions of sodium borohydride (2×1.5 mg, 0.04 mmol) over a 5 minutes period. The reaction mixture stirred a further 10 minutes at 0° C. and was then quenched by the addition of 1 mL of aqueous saturated NH$_4$Cl. Volatiles were removed by concentration under reduced pressure. The reaction mixture was poured into 30 mL of water and extracted with 3×15 mL EtOAc. The combined organics were rinsed with 10 mL of brine, dried with MgSO$_4$, filtered, and concentrated to dryness. Purification was achieved by chromatography on silica using 15-45% EtOAc/hexane to afford (racemic)-4-(3,3-difluorocyclobutoxy)-2,3-difluoro-7-((fluoromethyl)sulfonyl)-2,3-dihydro-1H-inden-1-ol (Compound 99) (9.2 mg, 62%) as a white solid. Retention time HPLC (14 min)=3.61 min; LCMS ESI (+) [M+NH$_4$]$^+$ m/z 390; $^1$H NMR (400 MHz, (CD3)$_2$CO): δ 8.09 (dd, 1H), 7.12 (d, 1H), 5.95 (dd, 1H), 5.66 (dd, 1H), 5.61 (td, H), 5.34 (dd, 1H), 5.07 (ddt, 1H), 5.03-4.93 (m, 1H), 3.89 (dd, 1H), 3.33-3.18 (m, 2H), 2.95-2.72 (m, 2H).

Example 26: Synthesis of (S)-4-(2,2-difluoroethoxy)-2,2-difluoro-7-(trifluoromethyl)-2,3-dihydro-1H-inden-1-ol (Compound 100)

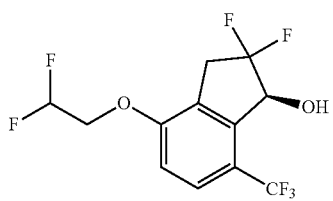

Step A: Preparation of 4-(2,2-difluoroethoxy)-2,3-dihydro-1H-inden-1-one

Diisopropyl azodicarboxylate (0.80 mL, 4.05 mmol) was added dropwise to an ice-cold solution of 4-hydroxyindan-1-one (500 mg, 0.37 mmol), triphenylphosphine (974 mg, 3.71 mmol), and 2,2-difluoroethanol (0.26 mL, 4.05 mmol) in tetrahydrofuran (20 mL). The reaction mixture was allowed to stir overnight at 50° C. The reaction mixture was evaporated and the residue was partitioned between EtOAc and water. The EtOAc was washed with brine, dried over MgSO$_4$, filtered, and evaporated. The residue was chromatographed on a Biotage 100 g SNAP column with a 20% to 80% EtOAc: hexane gradient to afford 4-(2,2-difluoroethoxy)-2,3-dihydro-1H-inden-1-one (610 mg, 2.87 mmol, 85% yield) as a pale yellow crystalline solid.

Step B: Preparation of 4-(2,2-difluoroethoxy)-7-iodo-2,3-dihydro-1H-inden-1-one

1-Chloromethyl-4-fluoro-1,4-diazoniabicyclo[2.2.2]octane bis(tetrafluoroborate) (1020 mg, 2.87 mmol) was added to an ice-cold solution of iodine (802 mg, 3.16 mmol) in acetonitrile (30 mL). This was stirred at 0° C. for a few minutes, then 4-(2,2-difluoroethoxy)-2,3-dihydro-1H-inden-1-one (610 mg, 2.87 mmol) was added. The resulting mixture was stirred at ambient temperature for 4 h. The reaction mixture was evaporated partitioned between EtOAc and dilute aqueous sodium thiosulfate. The EtOAc was washed with aqueous sodium thiosulfate, brine, dried over MgSO$_4$, filtered, and evaporated. The residue was chromatographed on a Biotage 25 g SNAP column with a 5% to 50% EtOAc:hexane gradient to afford 4-(2,2-difluoroethoxy)-7-iodo-2,3-dihydro-1H-inden-1-one (660 mg, 1.95 mmol, 67.9% yield).

Step C: Preparation of (E, Z)-4-(2,2-difluoroethoxy)-7-iodo-N-(3-methoxypropyl)-2,3-dihydro-1H-inden-1-imine Pivalic acid (100 mg, 0.98 mmol) was added to a mixture of 4-(2,2-difluoroethoxy)-7-iodo-2,3-dihydro-1H-inden-1-one (660 mg, 1.95 mmol) and 3-methoxypropylamine (1.00 mL, 9.76 mmol) in cyclohexane (10 mL) and toluene (50 mL). The mixture was refluxed with a Dean-Stark trap attached for a total of 9 h, then stirred at ambient temperature overnight. The reaction mixture was evaporated and the resulting crude (E, Z)-4-(2,2-difluoroethoxy)-7-iodo-N-(3-methoxypropyl)-2,3-dihydro-1H-inden-1-imine was used in the next step.

Step D: Preparation of 4-(2,2-difluoroethoxy)-2,2-difluoro-7-iodo-2,3-dihydro-1H-inden-1-one 1-Chloromethyl-4-fluoro-1,4-diazoniabicyclo[2.2.2]octane bis(tetrafluoroborate) (1493 mg, 4.03 mmol) was added to a mixture of (E, Z)-4-(2,2-difluoroethoxy)-7-iodo-N-(3-methoxypropyl)-2,3-dihydro-1H-inden-1-imine (660 mg, 1.61 mmol) and sodium sulfate (275 mg, 1.94 mmol) in acetonitrile (20 mL). The mixture was heated at 70° C. After 1 h, the cooled reaction mixture was treated with 1M HCl (5.65 mL, 5.65 mmol) and stirred at room temperature for 10 minutes. The reaction mixture was evaporated and the residue was partitioned between EtOAc and water. The EtOAc was washed with brine, dried over MgSO$_4$, filtered, and evaporated. The residue was chromatographed on a Biotage 50 g SNAP column with a 5% to 60% EtOAc: hexane followed by a reverse phase separation on a Biotage 25+ column with a 20% to 80% acetonitrile:water gradient to afford 4-(2,2-difluoroethoxy)-2,2-difluoro-7-iodo-2,3-dihydro-1H-inden-1-one (190 mg, 0.51 mmol, 32% yield over 2 steps).

Step E: Preparation of: 4-(2,2-difluoroethoxy)-2,2-difluoro-7-(trifluoromethyl)-2,3-dihydro-1H-inden-1-one Methyl 2,2-difluoro-2-fluorosulfonyl-acetate (0.10 mL, 0.80 mmol) was added to a vial containing 4-(2,2-difluoroethoxy)-2,2-difluoro-7-iodo-2,3-dihydro-1H-inden-1-one (60.0 mg, 0.160 mmol) and copper(I) iodide (61.1 mg, 0.320 mmol) in DMF (2 mL). The sealed vial was heated at 100° C. After 2 h, the vial was carefully vented, and the reaction mixture was partitioned between EtOAc and water. The EtOAc was washed with 2 portions of brine, dried over MgSO$_4$, filtered, and evaporated to afford 4-(2,2-difluoroethoxy)-2,2-difluoro-7-(trifluoromethyl)-2,3-dihydro-1H-inden-1-one (50 mg, 0.158 mmol, 99% yield). m/z (ES-API-pos) [M+H]$^+$ 317.

Step F: Preparation of Compound 100

To an ice cold solution of 4-(2,2-difluoroethoxy)-2,2-difluoro-7-(trifluoromethyl)-2,3-dihydro-1H-inden-1-one (50 mg, 0.158 mmol) in dichloromethane (10 mL) sparged with nitrogen, was added, formic acid (0.02 mL, 0.630 mmol) and triethylamine (0.06 mL, 0.40 mmol). After more nitrogen sparging, RuCl(p-cymene)[(R,R)-Ts-DPEN] (3.02 mg, 0.0048 mmol) was added, the flask was sealed with a septum, and placed in a 4° C. refrigerator overnight. The reaction mixture was evaporated and the residue was chromatographed on a Biotage 10 g Ultra SNAP column with a 10% to 80% EtOAc:hexane to afford Compound 100 (39.9 mg, 0.125 mmol, 79% yield); $^1$H NMR (400 MHz, CDCl$_3$): δ 7.59 (d, 1H), 6.89 (d, 1H), 6.11 (tt, 1H), 5.25-5.20 (m, 1H), 4.33-4.20 (m, 2H), 3.50-3.30 (m, 2H), 2.62-2.59 (m, 1H); m/z (ES-API-neg) [M−H+formate]$^-$ 363; 83% e.e. by chiral chromatography.

Example 27: Synthesis of 4-(2,2-difluoroethoxy)-2,2-difluoro-7-(trifluoromethyl)-2,3-dihydro-1H-inden-1-one oxime (Compound 101)

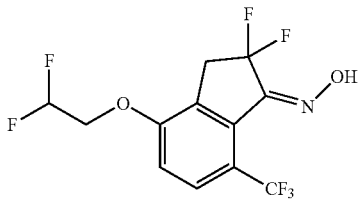

Hydroxylamine hydrochloride (15 mg, 0.20 mmol) was added to a microwave vial containing 4-(2,2-difluoroethoxy)-2,2-difluoro-7-(trifluoromethyl)-2,3-dihydro-1H-inden-1-one (12.3 mg, 0.04 mmol) and pyridine (0.031 mL, 0.40 mmol) in methanol (1 mL). The vial was sealed and heated at 120° C. for 1 h in a microwave. The reaction mixture was evaporated and the residue was chromatographed on a Biotage 10 g Ultra SNAP column with a 10% to 80% EtOAc:hexane gradient to afford Compound 101 (3.7 mg, 0.011 mmol, 29% yield); $^1$H NMR (400 MHz, CDCl$_3$): δ 8.13 (s, 1H), 7.69 (d, 1H), 6.90 (d, 1H), 6.12 (tt, 1H), 4.34-4.26 (m, 2H), 3.49 (t, 2H); m/z (ES-API-pos) [M+H]$^+$ 332.

Example 28: Synthesis of 2,2,3-trifluoro-4-(3-fluoropropoxy)-7-(trifluoromethyl)-2,3-dihydro-1H-inden-1-one oxime (Compound 102)

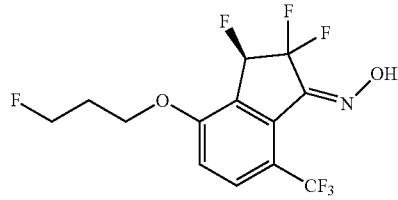

Hydroxylamine hydrochloride (17.3 mg, 0.25 mmol) was added to a microwave vial containing (R)-2,2,3-trifluoro-4-(3-fluoropropoxy)-7-(trifluoromethyl)-2,3-dihydro-1H-inden-1-one (20.5 mg, 0.06 mmol) and pyridine (0.05 mL, 0.62 mmol) in absolute ethanol (2 mL). The vial was sealed and heated for 1.5 h at 120° C. in a microwave. The reaction mixture was evaporated and partitioned between EtOAc and water. The EtOAc was washed with brine, dried over MgSO$_4$, filtered, and evaporated. The residue was chromatographed on a Biotage 10 g ultra SNAP column with a 10% to 80% EtOAc:hexane gradient. Product-containing fractions were evaporated to afford Compound 102 (8.2 mg, 0.024 mmol, 39% yield); 90% e.e. by chiral chromatography; $^1$H NMR (400 MHz, CDCl$_3$): δ 8.33 (d, 1H), 7.88-7.84 (m, 1H), 7.04 (d, 1H), 5.82 (dd, 1H), 4.67 (dt, 2H), 4.33-4.24 (m, 2H), 2.32-2.20 (m, 2H); m/z (ES-API-neg) [M−H]: 344.

Example 29: Synthesis of (1S,3R)-2,2,3-trifluoro-4-(3-fluoropropoxy)-7-(trifluoromethyl)-2,3-dihydro-1H-inden-1-ol (Compound 103)

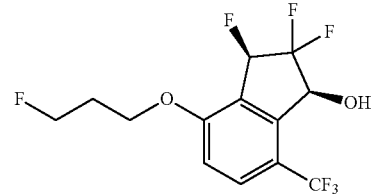

Step A: Preparation of: 4-(3-fluoropropoxy)-2,3-dihydro-1H-inden-1-one

1-Fluoro-3-iodo-propane (0.31 mL, 3.0 mmol) was added to a mixture of 4-hydroxyindan-1-one (300 mg, 2.0 mmol) and potassium carbonate (700 mg, 5.1 mmol) in DMF. The mixture was heated at 70° C. for 3 h, and stirred at ambient temperature overnight. The reaction mixture was partitioned between EtOAc and dilute aqueous NaCl. The EtOAc was washed with 2 portions of brine, dried over MgSO$_4$, filtered, and evaporated. The residue was chromatographed on a Biotage 25 g ultra SNAP column with a 10% to 50% EtOAc:hexane gradient. Product-containing fractions were evaporated to afford 4-(3-fluoropropoxy)-2,3-dihydro-1H-inden-1-one (370 mg, 1.78 mmol, 88% yield) as a colorless oil that crystallized on standing. m/z (ES-API-pos) [M+H]: 209.

Step B: Preparation of: 4-(3-fluoropropoxy)-7-iodo-2,3-dihydro-1H-inden-1-one

1-Chloromethyl-4-fluoro-1,4-diazoniabicyclo[2.2.2]octane bis(tetrafluoroborate) (629 mg, 1.78 mmol) was added to an ice-cold solution of iodine (496 mg, 1.95 mmol) in acetonitrile (10 mL). After 3 minutes, this was poured into a solution of 4-(3-fluoropropoxy)-2,3-dihydro-1H-inden-1-one (370 mg, 1.78 mmol) in acetonitrile (10 mL). The resulting mixture was stirred at 50° C. for 1 h. The reaction mixture was evaporated and the residue was partitioned between EtOAc and dilute aqueous sodium thiosulfate. The EtOAc was washed with sodium thiosulfate, brine, dried over MgSO$_4$, filtered, and evaporated. The residue was chromatographed on a Biotage 50 g ultra SNAP column with a 10% to 80% EtOAc:hexane gradient. Product-containing fractions were evaporated to afford 4-(3-fluoropropoxy)-7-iodo-2,3-dihydro-1H-inden-1-one (498 mg, 1.49 mmol, 84% yield).

Step C: Preparation of: 4-(3-fluoropropoxy)-7-(trifluoromethyl)-2,3-dihydro-1H-inden-1-one Methyl 2,2-difluoro-2-fluorosulfonyl-acetate (0.47 mL, 3.68 mmol) was added to a vial containing 4-(3-fluoropropoxy)-7-iodo-2,3-dihydro-1H-inden-1-one (246 mg, 0.74 mmol) and copper(I) iodide (280 mg, 1.47 mmol) in DMF (5 mL). The sealed vial was heated at 100° C. for 45 min. The reaction mixture was diluted with EtOAc, filtered through celite, and the filtrate was washed with water. The EtOAc was washed with 3 portions of brine, dried over MgSO$_4$, filtered, and evaporated. The residue was chromatographed on a Biotage 25 g Ultra SNAP column with a 20% to 80% EtOAc:hexane gradient. Product-containing fractions were evaporated to afford 4-(3-fluoropropoxy)-7-(trifluoromethyl)-2,3-dihydro-1H-inden-1-one (167 mg, 0.61 mmol, 82% yield). m/z (ES-API-pos) [M+H]: 277.

Step D: Preparation of: 3-bromo-4-(3-fluoropropoxy)-7-(trifluoromethyl)-2,3-dihydro-1H-inden-1-one 2,2'-Azobisisobutyronitrile (9.92 mg, 0.06 mmol) was added to a nitrogen-sparged mixture of 4-(3-fluoropropoxy)-7-(trifluoromethyl)-2,3-dihydro-1H-inden-1-one (167 mg, 0.60 mmol) and N-bromosuccinimide (140 mg, 0.79 mmol) in 1,2-dichloroethane (20 mL). The mixture was heated at 80° C. for 1 h. The reaction mixture was evaporated and the residue was partitioned between EtOAc and water. The EtOAc was washed with brine, dried over MgSO$_4$, filtered, and evaporated. The residue was chromatographed on a Biotage 50 g Ultra SNAP column with a 10% to 80% EtOAc:hexane gradient. Product-containing fractions were evaporated to afford 3-bromo-4-(3-fluoropropoxy)-7-(trifluoromethyl)-2,3-dihydro-1H-inden-1-one (154 mg, 0.434 mmol, 72% yield) as a yellow oil.

Step E: Preparation of: 4-(3-fluoropropoxy)-3-hydroxy-7-(trifluoromethyl)-2,3-dihydro-1H-inden-1-one Silver perchlorate hydrate (195 mg, 0.87 mmol) was added to a solution of 3-bromo-4-(3-fluoropropoxy)-7-(trifluoromethyl)-2,3-dihydro-1H-inden-1-one (154 mg, 0.43 mmol) in 1,2-dimethoxyethane (12 mL) and water (3 mL). The mixture was heated at 50° C. for 30 minutes. The reaction mixture was diluted with EtOAc and dilute NaCl and filtered. The filtrate was partitioned. The EtOAc was washed with brine, dried over MgSO$_4$, filtered, and evaporated. The residue was chromatographed on a Biotage 50 g SNAP column with a 30% to 100% EtOAc:hexane gradient. Product-containing fractions were evaporated to afford 4-(3-fluoropropoxy)-3-hydroxy-7-(trifluoromethyl)-2,3-dihydro-1H-inden-1-one (81.8 mg, 0.28 mmol, 65% yield). m/z (ES-API-neg) [M–H+formate]: 337.

Step F: Preparation of: 4-(3-fluoropropoxy)-7-(trifluoromethyl)-1H-indene-1,3(2H)-dione Dess-Martin periodinane (148 mg, 0.350 mmol) was added to a solution of 4-(3-fluoropropoxy)-3-hydroxy-7-(trifluoromethyl)-2,3-dihydro-1H-inden-1-one (81.8 mg, 0.28 mmol) in dichloromethane (20 mL). The mixture was stirred at ambient temperature for 45 min. The reaction mixture was evaporated and the residue was partitioned between EtOAc and dilute aqueous sodium thiosulfate. The EtOAc was washed with brine, dried over MgSO$_4$, filtered, and evaporated to afford 4-(3-fluoropropoxy)-7-(trifluoromethyl)-1H-indene-1,3(2H)-dione (85.1 mg, 0.293 mmol, quant. yield) as a colorless glass. m/z (ES-API-pos) [M+H]: 291.

Step G: Preparation of: 2,2-difluoro-4-(3-fluoropropoxy)-7-(trifluoromethyl)-1H-indene-1,3(2H)-dione 1-Chloromethyl-4-fluoro-1,4-diazoniabicyclo[2.2.2]octane bis(tetrafluoroborate) (218 mg, 0.61 mmol) was added to a mixture of 4-(3-fluoropropoxy)-7-(trifluoromethyl)-1H-indene-1,3(2H)-dione (81 mg, 0.28 mmol) and sodium carbonate (65.1 mg, 0.61 mmol) in acetonitrile (10 mL). The mixture was stirred at ambient temperature for 40 min. The reaction mixture was evaporated and the residue was partitioned between EtOAc and water. The EtOAc was washed with brine, dried over MgSO$_4$, filtered, and evaporated. The residue was chromatographed on a Biotage 50 g SNAP column with a 20% to 80% EtOAc:hexane gradient. Product-containing fractions were evaporated to afford 2,2-difluoro-4-(3-fluoropropoxy)-7-(trifluoromethyl)-1H-indene-1,3(2H)-dione (76.5 mg, 0.235 mmol, 84% yield) as a colorless glass. m/z (ES-API-neg) [M–H+formate]: 371.

Step H: Preparation of: (S)-2,2-difluoro-4-(3-fluoropropoxy)-3-hydroxy-7-(trifluoromethyl)-2,3-dihydro-1H-inden-1-one To an ice cold solution of 2,2-difluoro-4-(3-fluoropropoxy)-7-(trifluoromethyl)-1H-indene-1,3(2H)-dione (76.5 mg, 0.230 mmol) in dichloromethane (15 mL) sparged with nitrogen, was added triethylamine (0.02 mL, 0.16 mmol). After more nitrogen sparging, formic acid (0.01 mL, 0.23 mmol) was added, followed by RuCl(p-cymene)[(R, R)-TsDPEN] (0.85 mg, 0.001 mmol). The flask was sealed with a septum, and placed in a 4° C. refrigerator overnight. The reaction mixture was evaporated and the residue was chromatographed on a Biotage 25 g ultra SNAP column with a 10% to 80% EtOAc:hexane gradient. Product-containing fractions were evaporated to afford (S)-2,2-difluoro-4-(3-fluoropropoxy)-3-hydroxy-7-(trifluoromethyl)-2,3-dihydro-1H-inden-1-one (53 mg, 0.16 mmol, 69% yield).

Step I: Preparation of: (R)-2,2,3-trifluoro-4-(3-fluoropropoxy)-7-(trifluoromethyl)-2,3-dihydro-1H-inden-1-one Diethylaminosulfur trifluoride (0.04 mL, 0.320 mmol) was added to a solution of (S)-2,2-difluoro-4-(3-fluoropropoxy)-3-hydroxy-7-(trifluoromethyl)-2,3-dihydro-1H-inden-1-one (53 mg, 0.16 mmol) in dichloromethane (10 mL) at −78° C. The mixture was allowed to warm to ambient temperature. After 15 min, the reaction was quenched with some saturated aqueous NaHCO₃ and concentrated. The residue was partitioned between EtOAc and dilute aqueous NaCl. The EtOAc was washed with brine, dried over MgSO₄, filtered, and evaporated. The residue was chromatographed on a Biotage 25 g Ultra SNAP column with a 10% to 80% EtOAc:hexane gradient. Product-containing fractions were evaporated to afford (R)-2,2,3-trifluoro-4-(3-fluoropropoxy)-7-(trifluoromethyl)-2,3-dihydro-1H-inden-1-one (29 mg, 0.088 mmol, 54% yield). m/z (ES-API-neg) [M−H+formate]: 375.

Step J: Preparation of Compound 103

To an ice cold solution of (R)-2,2,3-trifluoro-4-(3-fluoropropoxy)-7-(trifluoromethyl)-2,3-dihydro-1H-inden-1-one (14.7 mg, 0.0400 mmol) in dichloromethane (3 mL) sparged with nitrogen, was added formic acid (0.01 mL, 0.180 mmol) and triethylamine (0.02 mL, 0.110 mmol). After more nitrogen sparging, RuCl(p-cymene)[(R,R)-Ts-DPEN] (0.85 mg, 0.0012 mmol) was added, the flask was sealed with a septum, and placed in a 4° C. refrigerator overnight. The reaction mixture was evaporated and the residue was chromatographed twice on Biotage Ultra SNAP columns, first with a 0% to 50% EtOAc:hexane gradient, then a 50% to 100% DCM:hexane gradient. Product-containing fractions were evaporated to afford Compound 103 (3.8 mg, 0.011 mmol, 26% yield); 92% d.e. by chiral chromatography; ¹H NMR (400 MHz, CDCl₃): δ 7.80-7.77 (m, 1H), 7.05 (d, 1H), 5.74 (dd, 1H), 5.25-5.20 (m, 1H), 4.66 (dt, 2H), 4.33-4.22 (m, 2H), 2.52 (d, 1H), 2.32-2.19 (m, 2H).

Example 30: Synthesis of 4-Propoxy-7-((trifluoromethyl)sulfonyl)-2,3-dihydro-1H-inden-1-ol (Compound 104)

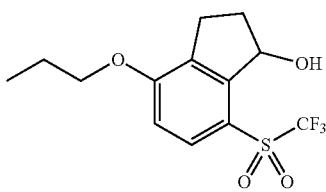 [SMILES: CCCOc1ccc(S(=O)(=O)C(F)(F)F)c2c1CCC2O]

Step A: Preparation of 4-fluoro-7-((trifluoromethyl)thio)-2,3-dihydro-1H-inden-1-one Methyl viologen dichloride hydrate (0.21 g, 0.82 mmol) and 4-fluoro-7-sulfanyl-indan-1-one (3.0 g, 16.5 mmol) were dissolved in DMF (40 mL) in a pressure vessel. The solution was cooled in dry ice/acetone bath under nitrogen and trifluoromethyl iodide (6.45 g, 32.9 mmol) was introduced, then triethylamine (2.5 g, 24.7 mmol) was added and the vial was sealed. The reaction mixture was stirred at ambient temperature for 20 hours. The reaction mixture was diluted with ethyl acetate and water, filtered through a pad of celite. The organic layer was separated, washed with brine, dried (magnesium sulfate), filtered and concentrated under reduced pressure. The residue obtained was purified by flash chromatography on silica gel to give 4-fluoro-7-((trifluoromethyl)thio)-2,3-dihydro-1H-inden-1-one (1.5 g, 36%) as solid.

Step B: Preparation of 4-fluoro-7-((trifluoromethyl)sulfonyl)-2,3-dihydro-1H-inden-1-one Ruthenium(III) chloride (17.4 mg, 0.08 mmol) was added to a mixture of 4-fluoro-7-(trifluoromethylsulfanyl)indan-1-one (0.7 g, 2.8 mmol) and sodium periodate (1.8 g, 8.4 mmol) in carbon tetrachloride (20 mL), acetonitrile (20 mL), and water (40 mL). The mixture was stirred at ambient temperature for 3 hours. DCM (40 mL) was added. The organic layer was separated, washed with brine, dried (MgSO₄), filtered, and concentrated under reduced pressure. The residue obtained was purified by flash column chromatography on silica gel 5:1 petroleum ether/ethyl acetate to give 4-fluoro-7-((trifluoromethyl)sulfonyl)-2,3-dihydro-1H-inden-1-one (0.65 g, 82%) as solid.

Step C: Preparation of 4-fluoro-7-((trifluoromethyl)sulfonyl)-2,3-dihydrospiro[indene-1,2'-[1,3]dioxolane]

Trimethylsilyl trifluoromethanesulfonate (10.6 g, 47.8 mmol) was added dropwise to a solution of 4-fluoro-7-(trifluoromethylsulfonyl)indan-1-one (27.0 g, 95.7 mmol) and trimethyl(2-trimethylsiilyloxyethoxy)silane (23.7 g, 114.8 mmol) in dichloromethane (500 mL) at −78° C. The reaction mixture was allowed to warm to ambient temperature and stirred at ambient temperature for 2 hours. The reaction was then quenched with excess triethyl amine. The volatiles were removed under reduced pressure. The residue was taken up in ethyl acetate (500 mL) and organics were washed with water, brine dried (sodium sulfate), filtered and concentrated under reduced pressure. The residue obtained was purified by flash chromatography on silica gel 4:1 hexane/ethyl acetate to give 4-fluoro-7-((trifluoromethyl)sulfonyl)-2,3-dihydrospiro[indene-1,2'-[,3]dioxolane] (25.0 g, 80%) as solid.

Step D: Preparation of 4-propoxy-7-((trifluoromethyl)sulfonyl)-2,3-dihydrospiro[indene-1,2'-[1,3]dioxolane]

A mixture of 4'-fluoro-7'-(trifluoromethylsulfonyl)spiro[1,3-dioxolane-2,1'-indane] (0.50 g, 1.5 mmol) and KOH (017 g, 3.1 mmol) in propan-1-ol (5.0 mL) was stirred at 100° C. for 10 minutes. After cooling to ambient temperature, the mixture was poured into water (20 mL) and extracted with ethyl acetate. The organic phase was separated, washed with brine, dried (sodium sulfate), filtered and concentrated under reduced pressure to give 4-propoxy-7-((trifluoromethyl)sulfonyl)-2,3-dihydrospiro[indene-1,2'-[1,3]dioxolane] (0.56 g, 100%) as solid.

Step E: Preparation of 4-propoxy-7-((trifluoromethyl)sulfonyl)-2,3-dihydro-1H-inden-1-one To a solution of 4'-propoxy-7'-(trifluoromethylsulfonyl)spiro[1,3-dioxolane-2,1'-indane] (0.56 g, 1.5 mmol) in ACN (10 mL) was added conc. HCl (2.0 mL) and stirred at ambient temperature for 30 minutes. The mixture was poured into water (20 mL) and extracted with ethyl acetate. The organic layer was washed with brine, dried (MgSO₄), filtered and concentrated under reduced pressure. The residue obtained was purified by flash column chromatography 3:1 petroleum ether/ethyl acetate to give 4-propoxy-7-(trifluoromethylsulfonyl)indan-1-one (0.24 g, 49%) as solid.

Step F: Preparation of Compound 104

To a solution of 4-propoxy-7-(trifluoromethylsulfonyl)indan-1-one (0.050 g, 0.16 mmol) in methanol (5 mL) was added sodium borohydride (0.012 g, 0.31 mmol) and stirred at ambient temperature for 10 minutes. The mixture was poured into water (20 mL) and extracted with ethyl acetate. The organic layer were washed with brine, dried (sodium sulfate), filtered and concentrated under reduced pressure to give Compound 104 (0.045 g, 89%) as solid. $^1$HNMR (300 MHz, CDCl$_3$): δ 7.87 (d, 1H), 6.95 (d, 1H), 5.58 (d, 1H), 4.08 (m, 2H), 2.06-3.17 (m, 2H), 2.84-2.94 (m, 1H), 2.37 (m, 1H), 2.27 (m, 1H), 1.86 (m, 2H), 1.07 (t, 3H).

Example 31: Synthesis of 2,2-difluoro-4-propoxy-7-((trifluoromethyl)sulfonyl)-2,3-dihydro-1H-inden-1-one (Compound 105)

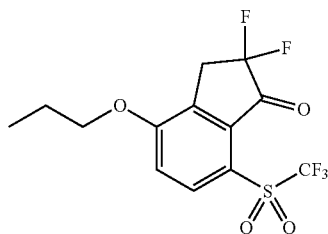 [SMILES: CCCOc1ccc(S(=O)(=O)C(F)(F)F)c2c1CC(F)(F)C2=O]

Step A: Preparation of (E, Z)-N-butyl-4-propoxy-7-((trifluoromethyl)sulfonyl)-2,3-dihydro-1H-inden-1-imine 4-propoxy-7-(trifluoromethylsulfonyl)indan-1-one (0.057 g, 0.18 mmol) in a mixture of solvent of toluene (2 mL) and cyclohexane (2 mL) was added butan-1-amine (1.0 mL) and 2,2,2-trifluoroacetic acid (0.1 mL). The mixture was heated at 100° C. for 2 hours. The solvent was removed under reduced pressure to give (E, Z)-N-butyl-4-propoxy-7-((trifluoromethyl)sulfonyl)-2,3-dihydro-1H-inden-1-imine (0.060 g, 90%) as oil.

Step B: Preparation of Compound 105

N-butyl-4-propoxy-7-(trifluoromethylsulfonyl)indan-1-imine (0.059 g, 0.16 mmol) in acetonitrile (2 mL) was treated with Selectfluor® (0.14 g, 0.39 mmol) and sodium sulfate (0.044 g, 0.31 mmol). The suspension was heated to 60° C. and stirred at this temperature for 1 hour. After cooling to ambient temperature. Water (5 mL) and 1 mL conc. HCl was added, the mixture was stirred at ambient temperature for 30 min. Water (30 mL) was added and extracted with ethyl acetate. The organic layer was separated, dried (sodium sulfate), filtered and concentrated under reduced pressure. The residue obtained was purified by flash column chromatography on silica gel 1:1 petroleum ether/ethyl acetate to give Compound 105 (0.051 g, 91%) as solid. $^1$HNMR (300 MHz, CDCl$_3$): δ 8.25 (d, 1H), 7.27 (d, 1H), 4.18 (t, 2H), 3.50 (t, 2H), 1.94 (m, 2H), 1.11 (t, 3H).

Example 32: Synthesis of 2,2-difluoro-4-propoxy-7-((trifluoromethyl)sulfonyl)-2,3-dihydro-1H-inden-1-ol (Compound 106)

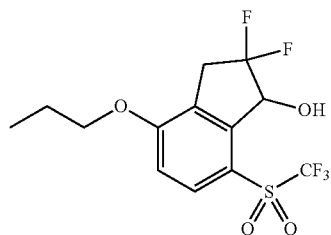

To a solution of 2,2-difluoro-4-propoxy-7-(trifluoromethylsulfonyl)indan-1-one (0.060 g, 0.17 mmol) in methanol (10 mL) was added NaBH$_4$ (0.032 g, 0.84 mmol) at ambient temperature. After stirred at ambient temperature for 1 hour, 50 mL of water was added to the mixture. The mixture was extracted with DCM. The organic layer was separated and concentrated under reduced pressure. The residue obtained was purified by flash column chromatography on silica gel 4:1 petroleum ether/ethyl acetate to give Compound 106 (0.050 g, 83%) as solid. LCMS ESI (−) m/z [M−H]$^-$ 359; $^1$HNMR (300 MHz, CDCl$_3$): δ 7.95 (d, 1H), 7.04 (d, 1H), 5.36 (dd, 1H), 4.10 (m, 2H), 3.45 (m, 1H), 3.39 (m, 1H), 3.20 (m, 1H), 1.88 (m, 2H), 1.07 (t, 3H).

Example 33: Synthesis of (1S,2R)-4-(3,3-difluoro-cyclobutoxy)-2-fluoro-7-(methylsulfonyl)-2,3-dihydro-1H-inden-1-ol (Compound 107)

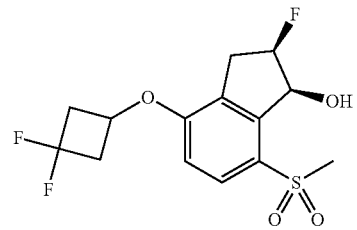 [SMILES: CS(=O)(=O)c1ccc(OC2CC(F)(F)C2)c2c1[C@H](O)[C@H](F)C2]

Step A: Preparation of 4-(3,3-difluorocyclobutoxy)-7-(methylsulfonyl)-2,3-dihydrospiro[indene-1,2'-[1,3]dioxolane]

To a solution of 7'-methylsulfonylspiro[1,3-dioxolane-2,1'-indane]-4'-ol (2.0 g, 7.4 mmol), triphenylphosphine (8.2 g, 31.1 mmol), and 3,3-difluoro-cyclobutanol (1.04 g, 9.6 mmol) in tetrahydrofuran (50 mL) at 60° C. was added diisopropyl azodicarboxylate (2.3 mL, 11.8 mmol). After addition, the reaction mixture was stirred at 60° C. overnight. After cooled to ambient temperature, water (50 mL) and MTBE (50 mL) were added. The organic layer was separated, washed with brine, dried (sodium sulfate), filtered and concentrated under reduced pressure. The residue obtained was purified by flash chromatography on silica gel to give 4'-(3,3-difluorocyclobutoxy)-7'-methylsulfonyl-spiro[1,3-dioxolane-2,1'-indane] (1.0 g, 37%) as solid.

Step B: Preparation of 4-(3,3-difluorocyclobutoxy)-7-(methylsulfonyl)-2,3-dihydro-1H-inden-1-one 1 N HCl (3.3 mL, 3.3 mmol) was added all at once to a solution of 4'-(3,3-difluorocyclobutoxy)-7'-methylsulfonylspiro[1,3-dioxolane-2,1'-indane] (1.0 g, 2.8 mmol) in acetone (10 mL) at ambient temperature. The reaction mixture was stirred at ambient temperature for 30 minutes. Acetone was removed under reduced pressure. Water (10 mL) and ethyl acetate (40 mL) were added. The organic layer was separated, washed with brine, dried (sodium sulfate), filtered and concentrated under reduce pressure. The resulting solid was suspended in MTBE (20 mL) and stirred at ambient temperature for 10 minutes. The solid formed was collected by filtration, washed with MTBE and dried to give 4-(3,3-difluorocyclobutoxy)-7-methylsulfonyl-indan-1-one (0.66 g, 75%) as a white solid.

Step C: Preparation of 4-(3,3-difluorocyclobutoxy)-2-fluoro-7-(methylsulfonyl)-2,3-dihydro-1H-inden-1-one 1-chloromethyl-4-fluoro-1,4-diazoniabicyclo[2.2.2]octane bis(tetrafluoroborate) (1.02 g, 2.9 mmol) was added all at once to 4-(3,3-difluorocyclobutoxy)-7-methylsulfonyl-indan-1-one (0.65 g, 2.1 mmol) in methanol (20 mL) at room temperature then warmed to reflux for 18 hours. After cooling to ambient temperature, water (30 mL) was added. Methanol was removed under reduced pressure. Water (20 ml) and ethyl acetate (40 mL) were added. The organic layer was separated, washed with brine, dried (sodium sulfate) and concentrated under reduced pressure. The residue obtained was purified by flash chromatography on silica gel 1:1 hexane/ethyl acetate to give 4-(3,3-difluorocyclobutoxy)-2-fluoro-7-methylsulfonyl-indan-1-one (0.62 g, 90%) as solid.

Step D: Preparation of (1S,2R)-4-(3,3-difluorocyclobutoxy)-2-fluoro-7-(methylsulfonyl)-2,3-dihydro-1H-inden-1-ol Formic acid (0.22 mL, 5.8 mmol) was added to dichloromethane (20 mL) at 0° C., followed by triethylamine (0.54 mL, 3.9 mmol). 4-(3,3-difluorocyclobutoxy)-2-fluoro-7-methylsulfonyl-indan-1-one (0.65 g, 1.9 mmol) was added and followed by RuCl(p-cymene)[(R,R)-TsDPEN] (0.02 g, 0.04 mmol) at 0° C. The reaction mixture was put in 4° C. refrigerator for 18 hours. Saturated sodium bicarbonate (50 mL) was added. The organic layer was separated, dried (sodium sulfate), filtered and concentrated under reduced pressure. The residue obtained was purified by flash chromatography on silica gel 1:1 hexane/ethyl acetate to give a solid. It was suspended in methanol (20 mL) and stirred at ambient temperature for 30 minutes. Solid was collected by filtration and dried to give Compound 107 (0.03 g, 4%) as solid. LCMS ESI (+) m/z 337 (M+H).

Example 34: Synthesis of 4-(2,2-difluoroethoxy)-7-(difluoromethyl)-2,2-difluoro-2,3-dihydro-1H-inden-1-ol (Compound 108)

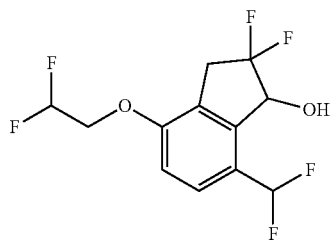 [SMILES: OC1c2c(C(F)F)ccc(OCC(F)F)c2CC1(F)F]

Step A: Preparation of 7-(2,2-difluoroethoxy)-3-oxo-2,3-dihydro-1H-indene-4-carbonitrile A mixture of 4-(2,2-difluoroethoxy)-7-iodo-indan-1-one (1.5 g, 4.4 mmol) and copper cyanide (0.52 g, 5.8 mmol) in 1-methyl-2-pyrrolidone (15 mL) was heated at 175° C. for 45 minutes in a microwave. The reaction mixture was diluted with ethyl acetate and water, filtered through a pad of celite. The organic layer was separated, washed with brine, dried (sodium sulfate), filtered and concentrated under reduced pressure. The residue obtained was purified by flash chromatography on silica gel 1:1 hexane/ethyl acetate to give 7-(2,2-difluoroethoxy)-3-oxo-indane-4-carbonitrile (1.0 g, 95%) as solid.

Step B: Preparation of 7-(2,2-difluoroethoxy)-3-((3-methoxypropyl)imino)-2,3-dihydro-1H-indene-4-carbonitrile A suspension of 7-(2,2-difluoroethoxy)-3-oxo-indane-4-carbonitrile (1.0 g, 4.2 mmol), 3-methoxypropan-1-amine (0.64 mL, 6.3 mmol) and 2,2-dimethylpropanoic acid (0.04 g, 0.42 mmol) in benzene (50 mL) was warmed to reflux with the azeotropic removal of water via a Dean-Stark trap for 6 hours. After cooling to ambient temperature, solvent was concentrated under reduced pressure to give 7-(2,2-difluoroethoxy)-3-(3-methoxypropylimino)indane-4-carbonitrile (1.29 g, 99%) which was used directly for the next step without further purification.

Step C: Preparation of 7-(2,2-difluoroethoxy)-2,2-difluoro-3-oxo-2,3-dihydro-1H-indene-4-carbonitrile A suspension of Selectfluor® (3.74 g, 10.0 mmol) and sodium sulfate (0.59 g, 4.2 mmol) in acetonitrile (30 mL) was warmed to 78° C. (bath) and stirred at 78° C. (bath) for 5 minutes. 7-(2,2-Difluoroethoxy)-3-(3-methoxypropylimino)indane-4-carbonitrile (1.29 g, 4.2 mmol) in acetonitrile (10 mL) was added dropwise (ca. 5 minutes). After addition, the reaction mixture was stirred at 78° C. for 30 minutes. After cooling to ambient temperature, 3 N HCl (5.9 mL, 16.7 mmol) was added and then stirred for 30 minutes at ambient temperature. Acetonitrile was removed under reduced pressure. Water (50 mL) and ethyl acetate (30 mL) were added, The organic layer was separated, washed with brine, dried (sodium sulfate), filtered and concentrated under reduced pressure to give 7-(2,2-difluoroethoxy)-2,2-difluoro-3-oxo-indane-4-carbonitrile (1.1 g, 96%) as oil.

Step D: Preparation of 4-(2,2-difluoroethoxy)-2,2-difluoro-2,3-dihydrospiro[indene-1,2'-[1,3]dioxolane]-7-carbonitrile To a suspension of 7-(2,2-difluoroethoxy)-2,2-difluoro-3-oxo-indane-4-carbonitrile (1.1 g, 4.0 mmol) and potassium carbonate (0.83 g, 6.0 mmol) in N,N-dimethylformamide (10 mL) was added 2-bromoethanol (0.43 mL, 6.0 mmol) at ambient temperature. The mixture was stirred at ambient temperature for 2 hours. Water (50 mL) and MTBE (100 mL) were added. The organic layer was separated, washed with brine, dried (sodium sulfate), filtered and concentrated under reduced pressure. The residue obtained was purified by flash chromatography on silica gel 5:1 hexane/ethyl acetate to give 7'-(2,2-difluoroethoxy)-2',2'-difluoro-spiro[1,3-dioxolane-2,3'-indane]-4'-carbonitrile (0.97 g, 75%) as solid.

Step E: Preparation of 4-(2,2-difluoroethoxy)-2,2-difluoro-2,3-dihydrospiro[indene-1,2'-[1,3]dioxolane]-7-carbaldehyde To a solution of 7-(2,2-difluoroethoxy)-2,2-difluoro-3-oxo-indane-4-carbonitrile (0.2 g, 0.63 mmol) in dichloromethane (2 mL) was added 1.0 M diisobutylaluminum hydride solution (0.95 mL, 0.95 mmol) at −40° C. The reaction mixture was stirred at −40° C. for 3 hours, quenched with methanol, Rochelle's solution and acidified with 1 N HCl. DCM (20 mL) was added. The organic layer was separated, washed with brine, dried (sodium sulfate), filtered and concentrated under reduced pressure. The residue obtained was purified by flash chromatography on silica gel 2:1 hexane/ethyl acetate to give 4-(2,2-difluoroethoxy)-2,2-difluoro-2,3-dihydrospiro[indene-1,2'-[1,3]dioxolane]-7-carbaldehyde (0.14 g, 68%) as solid.

Step F: Preparation of 4-(2,2-difluoroethoxy)-7-(difluoromethyl)-2,2-difluoro-2,3-dihydrospiro[indene-1,2'-[1,3]dioxolane]

A solution of 7'-(2,2-difluoroethoxy)-2',2'-difluoro-spiro[1,3-dioxolane-2,3'-indane]-4'-carbaldehyde (0.07 g, 0.23 mmol) in dichloromethane (5 mL) was treated with DEOXO-FLUOR (0.1 mL, 0.55 mmol) and ethanol (0.002 g, 0.05 mmol) at ambient temperature. The reaction mixture was stirred at 40° C. for 2 days. The reaction mixture was cooled to 0° C. and quenched by the addition of 10 mL of saturated aqueous NaHCO$_3$. The reaction mixture was vigorously stirred for 30 min. DCM (10 mL) was added. The organic layer was separated, washed with brine, dried (sodium sulfate), filtered and concentrated under reduced pressure. The residue obtained was purified by flash chromatography on silica gel 3:1 hexane/ethyl acetate to give 4'-(2,2-difluoroethoxy)-7'-(difluoromethyl)-2',2'-difluoro-spiro[1,3-dioxolane-2,1'-indane] (0.05 g, 63%) as solid.

Step G: Preparation of 4-(2,2-difluoroethoxy)-7-(difluoromethyl)-2,2-difluoro-2,3-dihydro-1H-inden-1-one A solution of 4'-(2,2-difluoroethoxy)-7'-(difluoromethyl)-2',2'-difluoro-spiro[1,3-dioxolane-2,1'-indane] (0.05 g, 0.14 mmol) in dichloromethane (0.4 mL) at ambient temperature was treated with 70% perchloric acid (0.17 mL, 2.8 mmol) and left to stir for 3 hours. The reaction mixture was carefully added to 20 mL of saturated sodium bicarbonate solution and extracted with MTBE. The organic layer was separated, washed with brine, dried (sodium sulfate), filtered and concentrated under reduced pressure to give 4-(2,2-difluoroethoxy)-7-(difluoromethyl)-2,2-difluoro-indan-1-one (0.041 g, 98%) as oil.

Step H: Preparation of Compound 108

To a solution of 4-(2,2-difluoroethoxy)-7-(difluoromethyl)-2,2-difluoro-indan-1-one (0.040 g, 0.14 mmol) in methanol (0.5 mL) was added sodium borohydride (0.01 g, 0.14 mmol) at ambient temperature. After stirred at ambient temperature for 30 minutes, water (0.2 mL) was added and stirred for 10 minutes. It was directly purified by C18 reverse phase flash chromatography (Biotage Isolera One unit, C18 Flash 25+M column, 5-90% CH3CN/water, 10 CV) to give Compound 108 (0.029 g, 70% yield) as solid. LCMS ESI (−)[M−H+HCOOH]$^-$ m/z 345. $^1$HNMR (300 MHz, CDCl$_3$): δ 7.57 (d, 1H), 7.00 (t, 1H), 6.85 (t, 1H), 6.13 (t, 1H), 5.32 (m, 1H), 4.24 (t, 2H), 3.25-3.48 (m, 2H), 2.45 (d, 1H).

Example 35: Synthesis of N-(3-Chlorophenyl-4,6-t$_2$)-4-nitrobenzo[c][1,2,5]oxadiazol-5-amine

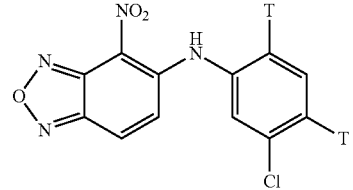

Step A: Synthesis of 3-chlorobenzen-4,6-t$_2$-amine

3-Chloro-4,6-diiodoaniline (100 mg,) was dissolved in methanol (3 mL) and added with triethylamine (0.1 mL) and submitted for overnight tritiation using 50 Ci of tritium gas, at room temperature. Labile tritium was removed by dissolving the crude reaction mixture in methanol (3 mL) and bringing to dryness under vacuum. Labile removal was done in duplicate. The crude tritiated material was purified by preparative TLC (Silica gel, 1000μ) using hexane:ethyl acetate:AcOH (85:14:1). The product band was eluted with ethyl acetate to give 3-chlorobenzen-4,6-t$_2$-amine (yield=600 mCi, radiochemical purity was >98%).

Step B: Synthesis of N-(3-Chlorophenyl-4,6-t$_2$)-4-nitrobenzo[c][1,2,5]oxadiazol-5-amine A stirred mixture of 5-chloro-4-nitro-2,1,3-benzoxadiazole (20 mg, 0.1 mmol), 3-chlorobenzen-4,6-t$_2$-amine (600 mCi) and Cs$_2$CO$_3$ (65 mg, 0.20 mmol) in DMF (1 mL) was heated at 60° C. for 1 h. After cooling, the reaction mixture was partitioned between EtOAc and water. The aqueous layer was extracted with EtOAc. The combined organic layers were washed with water and brine, dried and concentrated. The residue was purified by preparative HPLC on an ACE-5 C18 Semi-prep column, 250×10 mm, 100 Å. Elution was carried out isocratically using 0.1% TFA in water/Acetonitrile (35:65) to give the title compound (478 mCi, 80%).

Example 36: HIF-2α Scintillation Proximity Assay (SPA)

The total assay volume was about 100 μL in the following configuration: 2 μL compound in 100% DMSO, 88 μL buffer with protein and probe and 10 μL of SPA beads. The compound was diluted in a master plate consisting of a 10-point dose response with a 3-fold compound dilution from 100 μM to 5 nM. Assays were run on a 96-well plate in which one column, designated as the high signal control, contained DMSO with no compound and another column, designated as the low signal control, contained no protein. Prior to plating out of compound, a buffer solution, consisting of 25 mM TRIS pH 7.5 (Sigma), 150 mM NaCl (Sigma), 15% Glycerol (Sigma), 0.15% BSA (Sigma), 0.001% Tween-20 (Sigma), 150 nM N-(3-Chlorophenyl-4,6-t$_2$)-4-nitrobenzo[c][1,2,5]oxadiazol-5-amine and 100 nM HIF-2α HIS TAG-PASB Domain, was made and allowed to equilibrate for 30 minutes. Compounds that were to be tested were then plated in to a 96-well white clear bottom Isoplate-96 SPA plate (Perkin Elmer). To the compounds was added 88 µL of the buffer solution, then the plate covered with a plastic cover and aluminum foil, placed onto a shaker and equilibrated for 1 hour. After equilibration, 10 µL of a 2 mg/mL solution of YSi Cu His tagged SPA beads (Perkin Elmer) were then added to each well of the plate, covered and equilibrated for another 2 hours. The plates were then removed from the shaker, placed into a 1450 LSC and luminescence counter MicroBeta Trilux (Perkin Elmer) to measure the extent of probe displacement. The percent inhibition was determined and $IC_{50}$ values were calculated using the Dotmatics system based on the following equation: % inhibition=[(high control−sample)/(high control−low control)]×100.

Example 37: VEGF ELISA Assay

Figure 3:
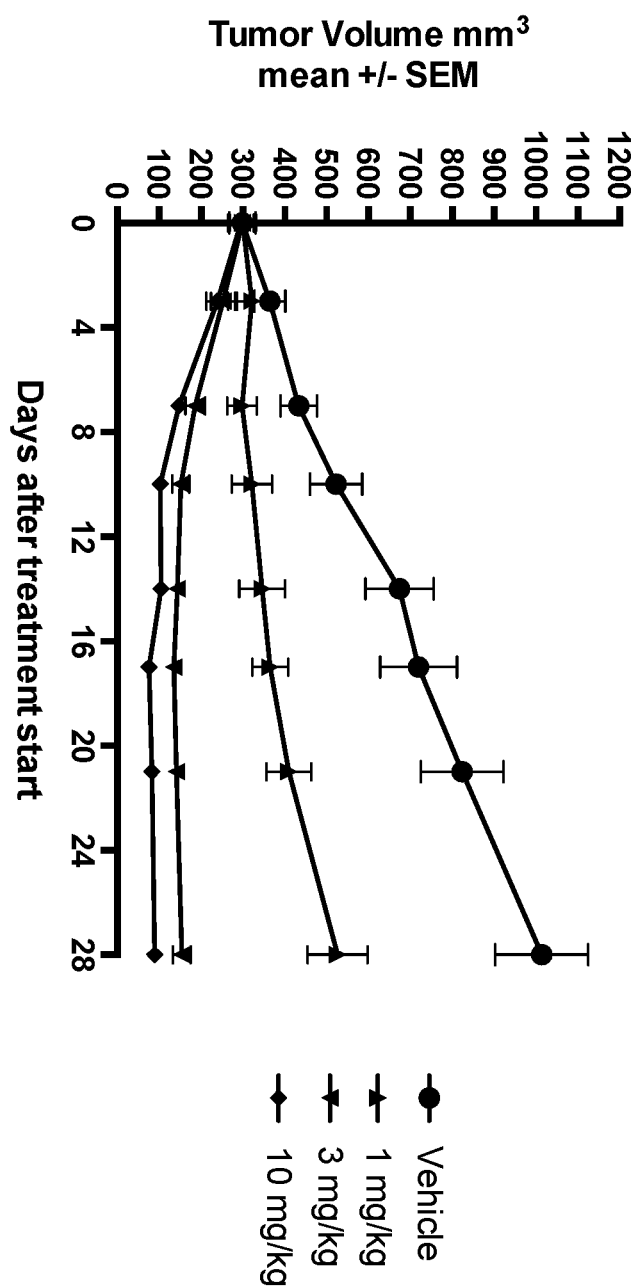
FIG. 3 shows treatment of 786-O xenograft bearing mice at 0 mg/kg (denoted as "Vehicle"), 1 mg/kg, 3 mg/kg, and 10 mg/kg of Compound 95 QD (once a day) for 28 days.
Figure 4:
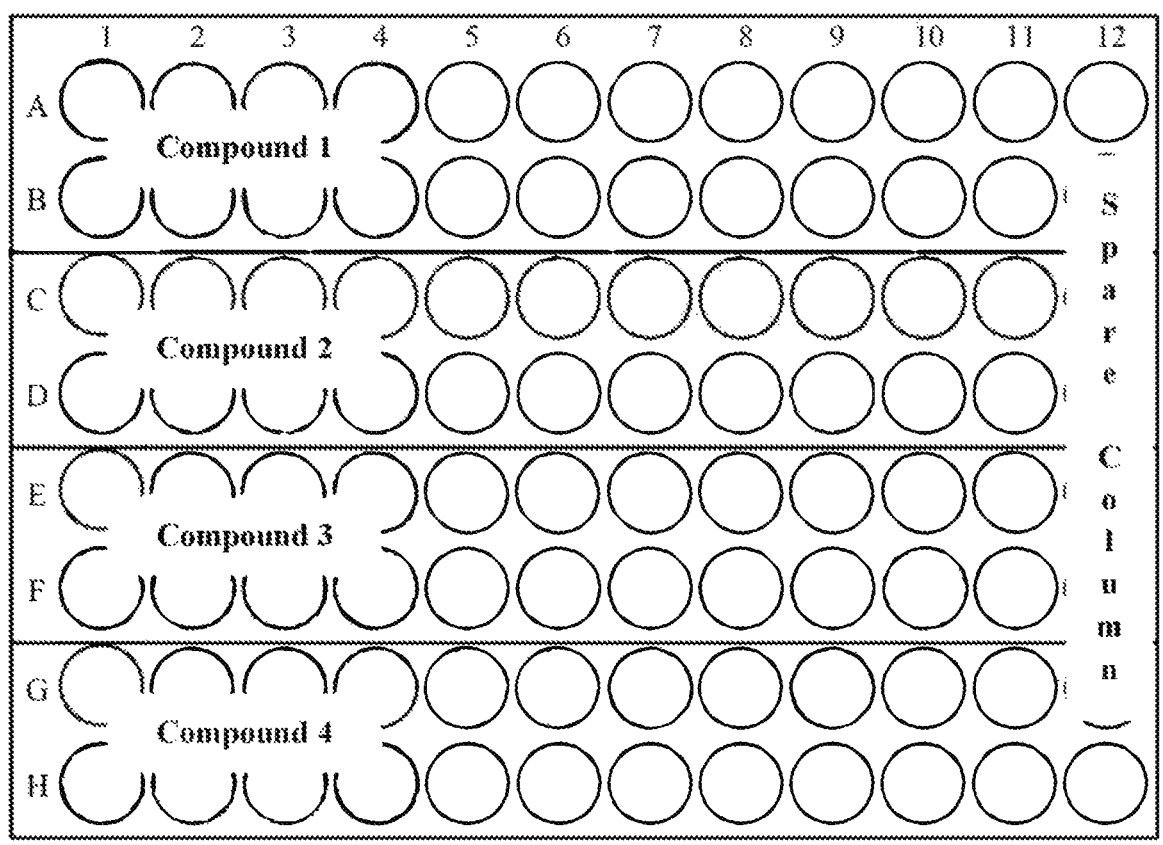
FIG. 4 depicts a 96-well plate layout of an ELISA assay.

About 7500 786-0 cells in 180 µL of growth medium were seeded into each well of a 96-well, white, clear bottom plate (07-200-566, Fisher Scientific) on day one in the layout presented in FIG. 3.
Four hours later, serial dilutions of 10× compound stocks were made in growth medium from 500× DMSO stocks, and 20 µL of those 10× stocks were added to each well to make final concentrations as follows (1 µM): 20, 6.67, 2.22, 0.74, 0.25, 0.082, 0.027, 0.009, 0.003, 0.001, and 0. Each concentration was plated in duplicate. About 20 hours later, medium was removed by suction and each well was supplied with 180 µL of growth medium. About 20 µL freshly-made 10× compound stocks were added to each well. About 24 hours later, cell culture medium was removed and the VEGF concentration determined using an ELISA kit purchased from R&D systems, following the manufacturer's suggested method. The $EC_{50}$ was calculated by GraphPad Prism using the dose-response-inhibition (four parameter) equation. The cell-seeded plate was then subjected to CellTiter-Glo luminescence cell viability assay (Promega) by adding 50 µL of Celltiter Glo reagent into each well and shaking the plate for 8 minutes at 550 rpm (Thermomixer R, Eppendorf) then the luminescence signal immediately read in a plate reader (3 second delay, 0.5 second/well integration time, Synergy 2 multi Detection Microplate reader).

Example 38: Luciferase Assay

Figure 5:
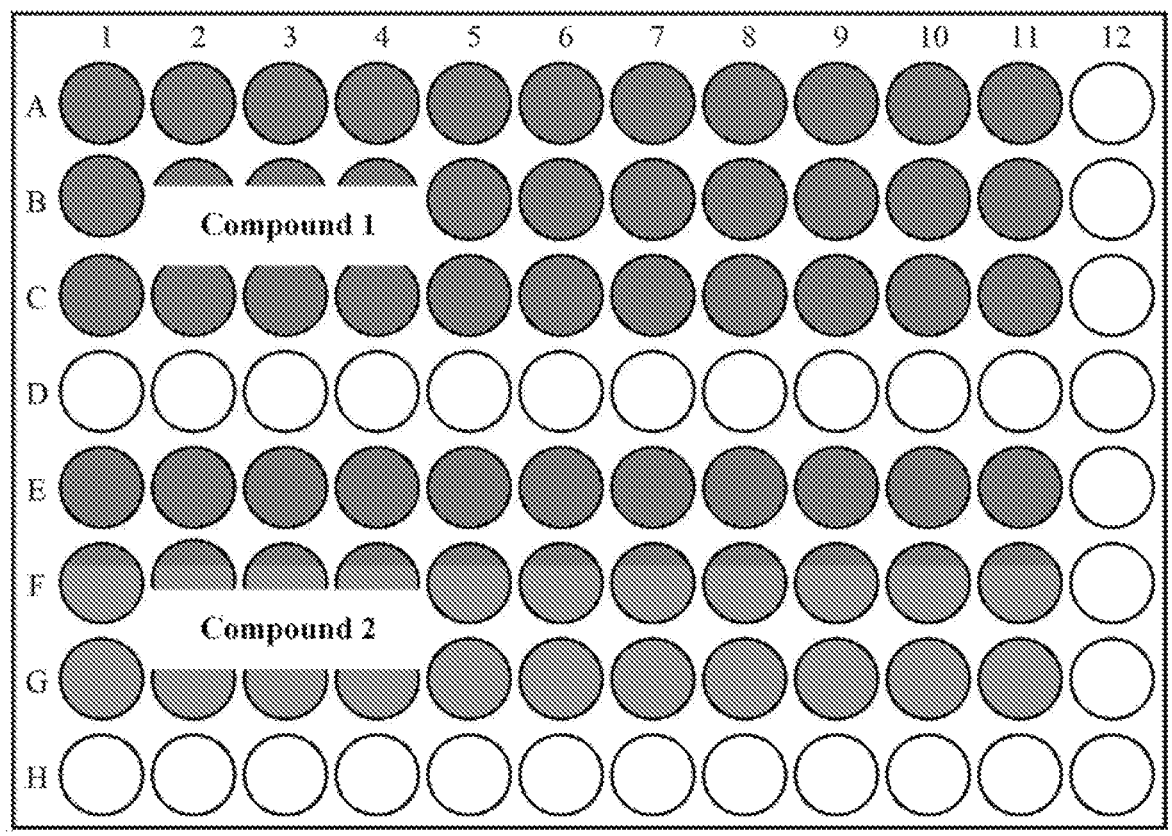
FIG. 5 depicts a 96-well plate layout of a luciferase assay.

786-O-Hif-Luc single clone cells were obtained by infecting 786-O cells (ATCC® CRL-1932™) with commercial lentivirus that delivers a luciferase gene driven by multiple HIF responsive elements (Cignal Lenti HIF Reporter (luc): CLS-007L, Qiagen) at Multiplicity of Infection (MOI) of 25 for 24 hours. The cells were replenished with fresh medium (Dulbecco's Modified Eagle's Medium (DMEM, D5796, Sigma) supplemented with 10% FBS (F6178, Sigma), 100 units penicillin and 100 µg streptomycin/mL (P4333, Sigma)) for another 24 hours. A pool of infected cells were then selected against 2 µg/mL of puromycin (P8833, Sigma) for 10 days followed by limited dilution to select single clones. The clones were tested for their response to HIF-2 inhibitors and the ones that showed the biggest dynamic range (786-0-Hif-Luc) were expanded and used for the luciferase assay. For the luciferase assay, about 7500 786-O-Hif-Luc cells in 90 µL growth medium were seeded into each well of a 96-well white opaque plate (08-771-26, Fisher scientific) a day before treatment with the layout presented in FIG. 5.
On treatment day, serial dilutions of 10× compound stocks were made in growth medium from 500× DMSO stocks, and 10 µL of the 10× stocks were added to each well to make final concentrations as follows (µM): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. $EC_{50}$ were calculated using Dotmatics software.
Table 2 shows biological activities of selected compounds in Luciferase, VEGF ELISA and Scintillation Proximity assays. Compound numbers correspond to the numbers and structures provided in Table 1 and Examples 1-34.

TABLE 2

| | Less than 50 nM (++++) | 50 nM to 249 nM (+++) | 250 nM to 1000 nM (++) | Greater than 1000 nM (+) |
|---|---|---|---|---|
| Scintillation Proximity Assay $IC_{50}$ (nM) | 4, 6, 7, 10, 12, 28, 30, 53, 70, 71, 78, 92, 93, 94, 95, 97, 98, 99, 100, 102, 103, 107, 109, 115, 116, 124, 127, 129, 130, 132, 139, 142, 148, 151, 179, 180, 181, 182, 183, 184, 186, 200, 202, 224, 229, 234, 235, 237, 238, 239, 240, 241, 252, 253, 256, 261, 264, 265, 266, 268, 269, 270, 274, 281, 284, 287, 288, 289, 294, 302, 306, 311, 314, 315, 317, 318, 322, 324, 329 | 1, 9, 38, 66, 68, 72, 75, 84, 90, 106, 108, 113, 120, 126, 131, 136, 138, 185, 188, 194, 197, 201, 206, 207, 211, 221, 222, 225, 226, 231, 242, 243, 255, 259, 262, 275, 279, 283, 296, 297, 299, 310, 312, 316, 323, 327 | 2, 3, 8, 17, 26, 27, 32, 34, 43, 44, 52, 63, 96, 101, 117, 123, 125, 134, 145, 162, 169, 173, 203, 228, 232, 236, 260, 276, 277, 278, 282, 290, 293, 298, 303, 309 | 5, 11, 13, 14, 15, 16, 18, 19, 20, 21, 22, 23, 24, 25, 29, 31, 33, 35, 36, 37, 39, 40, 41, 42, 45, 46, 47, 48, 49, 50, 51, 54, 55, 56, 57, 58, 59, 60, 61, 62, 64, 65, 67, 69, 73, 74, 76, 77, 79, 80, 81, 82, 83, 85, 86, 87, 88, 89, 91, 104, 110, 111, 112, 114, 118, 119, 121, 122, 128, 133, 135, 137, 140, 141, 144, 149, 150, 152, 153, 154, 155, 156, 157, 158, 159, 160, 161, 163, 164, 165, 166, 167, 168, 170, 171, 172, 174, 175, 176, 177, 178, |

TABLE 2-continued

| Less than 50 nM (++++) | 50 nM to 249 nM (+++) | 250 nM to 1000 nM (++) | Greater than 1000 nM (+) |
|---|---|---|---|
| | | | 187, 189, 190, 191, 192, 193, 195, 196, 198, 199, 204, 205, 208, 209, 210, 212, 213, 214, 215, 216, 217, 218, 219, 220, 223, 227, 230, 233, 244, 245, 246, 247, 248, 249, 250, 251, 254, 257, 258, 263, 271, 280, 285, 286, 291, 292, 295, 300, 301, 304, 305, 307, 308, 313, 319, 320, 321, 325, 328 |
| Mean VEGF ELISA EC$_{50}$ (nM): 10, 92, 93, 97, 100, 109, 139, 179, 180, 181, 182, 183, 234, 237, 268, 270 | 28, 95, 99, 127, 132, 142, 184, 231, 235, 238, 261, 265, 269, 288, 289, 311, 312, 329 | 16, 98, 259 | |
| Mean Luciferase EC$_{50}$ (nM): 10, 92, 93, 94, 97, 100, 103, 106, 109, 124, 127, 139, 148, 179, 180, 181, 182, 183, 184, 186, 200, 229, 234, 235, 237, 241, 252, 253, 261, 268, 269, 270, 274, 311, 314, 315, 317, 318, 322 | 1, 7, 9, 28, 44, 68, 70, 95, 99, 115, 116, 120, 126, 132, 142, 151, 201, 202, 206, 211, 221, 222, 224, 231, 238, 240, 242, 255, 256, 259, 265, 281, 288, 289, 309, 310, 312, 323, 329 | 3, 4, 26, 38, 52, 53, 71, 78, 84, 90, 98, 107, 113, 117, 130, 138, 145, 169, 185, 188, 194, 203, 207, 232, 236, 239, 243, 275, 276, 278, 284, 287, 290, 294, 296, 297, 299, 302, 303, 316, 324, 327 | 2, 6, 8, 12, 13, 16, 17, 27, 30, 32, 34, 37, 55, 59, 63, 66, 72, 75, 79, 86, 91, 96, 101, 102, 108, 123, 125, 129, 131, 134, 136, 140, 141, 162, 164, 190, 195, 197, 208, 217, 225, 226, 228, 246, 247, 248, 249, 250, 251, 260, 262, 264, 266, 277, 279, 280, 282, 283, 292, 293, 295, 298, 306, 307, 308 |

Example 39: In Vivo PK/PD Study

PK/PD study for Compound 95: Compound 95 was formulated with 10% absolute ethanol, 30% PEG400, 60% water containing 0.5% methyl cellulose and 0.5% Tween80®. About 5×10$^6$ renal cell carcinoma 786-O tumor cells (ATCC® CRL-1932™, VHL and HIF-1α null cell line) in PBS and Matrigel (1:1 in volume) were injected subcutaneously at the right flanks of SCID/Biege mice at 6-7 weeks of age for xenograft development. When the xenografts reached about 400 mm$^3$ in size, the tumor bearing mice were randomly divided into 2 groups (n=3). Plasma was collected prior to treatment by retro-orbital bleeding. The animals were treated with either vehicle or Compound 95 at 3 mg/kg by oral gavage (six times at 12 hour intervals). All animals were sacrificed at 12 hours post last dose. Tumor, kidney, and plasma samples were collected from each animal. Total RNA was extracted from the tumors and kidneys. The mRNA levels of several genes were determined by qRT-PCR (FIG. 1).

Total RNA was extracted from the tumors, and the expressions of putative HIF-1α and HIF-2α regulated genes were determined by qRT-PCR. Two of HIF-2α specific target genes (PAI-1 and CCND1) and two genes regulated by both HIF-1α and HIF-2α (VEGFA and GLUT1) displayed a significant reduction in response to Compound 95 treatment. The HIF-1α specific target gene PGK1 exhibited no significant change in response to Compound 95 treatment. These data indicated that Compound 95 selectively inhibited the expressions of HIF-2α specific target genes in the 786-O xenograft model.

The level of human VEGFA was determined by ELISA assay. Compound 95 treatment led to a significant reduction of human VEGFA in the plasma reflecting the inhibition of HIF-2α in the 786-O xenografts.

Example 40: In Vivo Efficacy Study

Compound 95 was formulated with 10% absolute ethanol, 30% PEG400, 60% water containing 0.5% methylcellulose and 0.5% Tween80®. 5×10$^6$ tumor cells in PBS and Matrigel (1:1 in volume) were inoculated subcutaneously at right flank for each SCID/Biege mouse at 6-7 weeks of age for tumor development. When the xenografts reached about 300 mm$^3$ in size, the tumor bearing mice were randomly grouped into four groups (n=8) and treatment was started with vehicle QD and Compound 95 at 1, 3 and 10 mg/kg QD, respectively, for twenty eight days. Tumor sizes were measured twice weekly in two dimensions using a caliper and the volumes were expressed in mm$^3$ using the formula V=0.5×a×b$^2$ where a and b were the long and short diameters of the tumor, respectively. All data were displayed as Mean and the standard error of the mean (SEM). As shown in FIG. 3 and Table 3, Compound 95 treatment led to a statistically significant reduction of tumor sizes for all treatment groups in renal cell carcinoma 786-O xenograft model.

TABLE 3

Compound 95 786-O Xenograft Study:
Tumor sizes after 28 days of dosing

| Treatment group | Vehicle | 1 mg/kg | 3 mg/kg | 10 mg/kg |
|---|---|---|---|---|
| Tumor size (mm$^3$) Mean ± SEM | 1013.93 ± 110.97 | 525.72 ± 71.48 | 154.52 ± 21.04 | 89.45 ± 8.63 |

What is claimed is:

1. A compound of Formula IV-C:

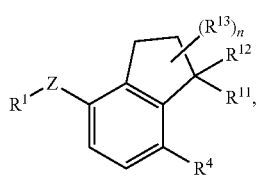

Formula IV-C or a pharmaceutically acceptable salt or prodrug thereof, wherein:
Z is O, S, CHR$^7$, NR$^8$ or absent;
R$^1$ is alkyl, cycloalkyl, heterocycloalkyl, aryl or heteroaryl;
R$^4$ is cyano, alkyl, cycloalkyl, heteroaryl, sulfonyl, or fluoroalkylsulfonyl;
R$^7$ and R$^8$ are independently hydrogen, halo, hydroxy, cyano, alkyl or alkoxy;
R$^{11}$ is hydroxy, alkoxy or amino;
R$^{12}$ is hydrogen or alkyl; or R$^{11}$ and R$^{12}$ in combination form oxo or oxime;
R$^{13}$ is fluoro; and
n is 0, 1, 2, 3 or 4,
wherein for a compound or a pharmaceutically acceptable salt or prodrug thereof, of Formula IV-C, when Z is O, R$^1$ is alkyl, cycloalkyl or heterocycloalkyl.

2. The compound of claim 1, or a pharmaceutically acceptable salt or prodrug thereof wherein Z is O.

3. The compound of claim 1, or a pharmaceutically acceptable salt or prodrug thereof, wherein R$^1$ is cyclobutyl, cyclopentyl or cyclohexyl.

4. The compound of claim 1, or a pharmaceutically acceptable salt or prodrug thereof wherein R$^1$ is phenyl or pyridyl.

5. The compound of claim 1, or a pharmaceutically acceptable salt or prodrug thereof, wherein R$^1$ is substituted with at least one substituent selected from the group consisting of halo, C$_1$-C$_4$ alkyl, C$_1$-C$_4$ alkoxy and cyano.

6. The compound of claim 5, or a pharmaceutically acceptable salt or prodrug thereof, wherein R$^1$ is substituted with at least one fluoro.

7. The compound of claim 1, or a pharmaceutically acceptable salt or prodrug thereof, wherein R$^4$ is selected from the group consisting of —CF$_3$, —CN, —S(═O)$_2$CH$_3$, —S(═O)$_2$CH$_2$F, —S(═O)$_2$CHF$_2$, and —S(═O)$_2$CF$_3$.

8. The compound of claim 1, or a pharmaceutically acceptable salt or prodrug thereof, wherein R$^{11}$ is hydroxy.

9. The compound of claim 1, or a pharmaceutically acceptable salt or prodrug thereof, wherein:
R$^4$ is cyano, fluoroalkyl, or sulfonyl;
R$^{11}$ is hydroxy or amino; and
R$^{12}$ is hydrogen.

10. The compound of claim 1, or a pharmaceutically acceptable salt or prodrug thereof, wherein n is 1, 2 or 3.

11. The compound of claim 1, or a pharmaceutically acceptable salt or prodrug thereof, wherein
Z is O;
R$^1$ is cycloalkyl or alkyl;
R$^4$ is sulfonyl, fluoroalkyl, or cyano;
R$^{11}$ is hydroxy;
R$^{12}$ is hydrogen; and
n is 1, 2, or 3.

12. The compound of claim 1, or a pharmaceutically acceptable salt or prodrug thereof, wherein the compound is a compound of Formula IV-D, IV-E, IV-F or IV-G:

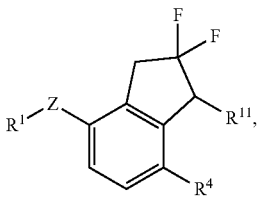

IV-D

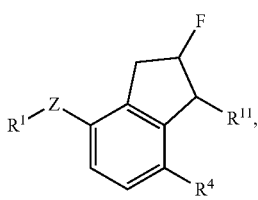

IV-E

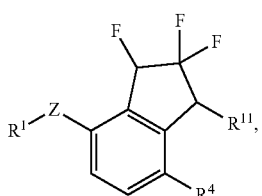

IV-F

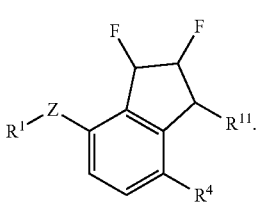

IV-G

13. A compound, or a pharmaceutically acceptable salt or prodrug thereof, selected from the group consisting of:

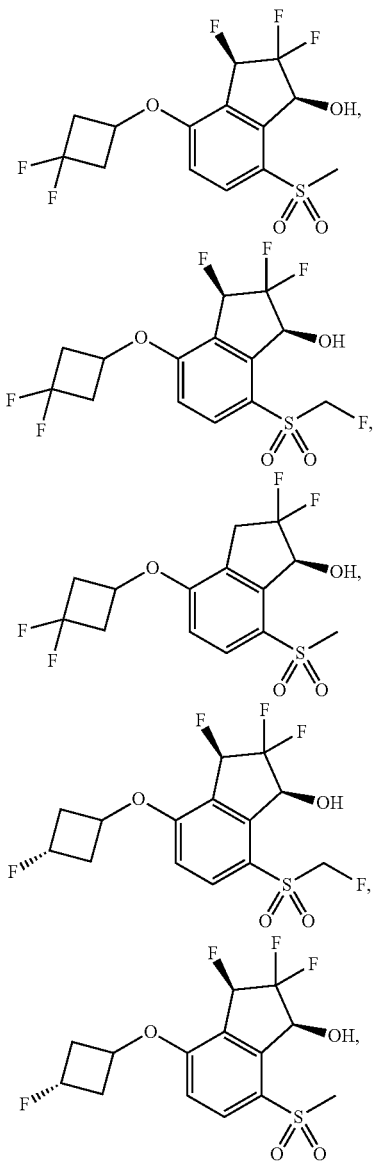

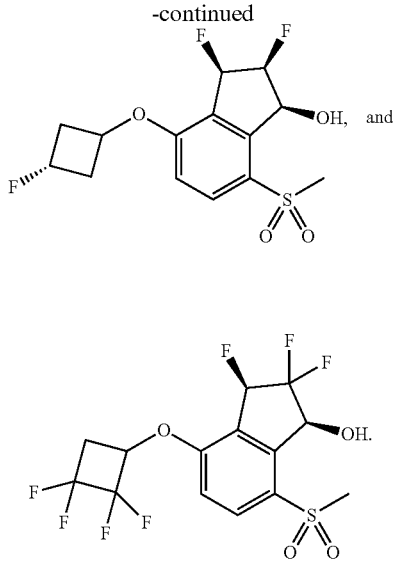

14. A pharmaceutical composition comprising the compound of claim 1, or a pharmaceutically acceptable salt or prodrug thereof, and a pharmaceutically acceptable carrier.

15. A method of inhibiting HIF-2α signaling output, comprising contacting HIF-2α with an effective amount of the compound of claim 1, or a pharmaceutically acceptable salt or prodrug thereof.

16. A method of treating von Hippel-Lindau (VHL) disease, comprising administering to a subject in need thereof an effective amount of the compound of claim 1, or a pharmaceutically acceptable salt or prodrug thereof.

17. A method of treating renal cell carcinoma, comprising administering to a subject in need thereof a therapeutically effective amount of the compound of claim 1, or a pharmaceutically acceptable salt or prodrug thereof.

18. The method of claim 17, wherein said renal cell carcinoma is clear cell renal cell carcinoma (ccRCC).

* * * * *